United States Patent
Green et al.

(10) Patent No.: US 10,457,934 B2
(45) Date of Patent: Oct. 29, 2019

(54) METHODS FOR GENOME ASSEMBLY, HAPLOTYPE PHASING, AND TARGET INDEPENDENT NUCLEIC ACID DETECTION

(71) Applicant: Dovetail Genomics, LLC, Santa Cruz, CA (US)

(72) Inventors: Richard E. Green, Santa Cruz, CA (US); Paul Hartley, San Jose, CA (US); Christopher Troll, Santa Cruz, CA (US); Ei Ei Min, Capitola, CA (US)

(73) Assignee: Dovetail Genomics, LLC, Scotts Valley, CA (US)

( * ) Notice: Subject to any disclaimer, the term of this patent is extended or adjusted under 35 U.S.C. 154(b) by 0 days.

(21) Appl. No.: 15/649,268

(22) Filed: Jul. 13, 2017

(65) Prior Publication Data

US 2017/0314014 A1 Nov. 2, 2017

Related U.S. Application Data

(63) Continuation of application No. PCT/US2016/057557, filed on Oct. 18, 2016.
(Continued)

(51) Int. Cl.
*C12N 15/10* (2006.01)
*G16B 30/00* (2019.01)
(Continued)

(52) U.S. Cl.
CPC ....... *C12N 15/1065* (2013.01); *C12Q 1/6806* (2013.01); *C12Q 1/6809* (2013.01);
(Continued)

(58) Field of Classification Search
None
See application file for complete search history.

(56) References Cited

U.S. PATENT DOCUMENTS

| 3,817,837 A | 6/1974 | Rubenstein et al. |
| 3,850,752 A | 11/1974 | Schuurs et al. |
(Continued)

FOREIGN PATENT DOCUMENTS

| EP | 0476014 A1 | 3/1992 |
| EP | 0624059 A1 | 11/1994 |
(Continued)

OTHER PUBLICATIONS

Adams, et al. The Genome Sequence of *Drosophila melanogaster*. Science Mar. 24, 2000, 287.5461: 2185-2195 DOI: 10.1126/science.287.5461.2185.
(Continued)

*Primary Examiner* — Joseph Woitach
(74) *Attorney, Agent, or Firm* — Wilson Sonsini Goodrich & Rosati

(57) ABSTRACT

The disclosure provides methods to assemble genomes of eukaryotic or prokaryotic organisms. The disclosure provides methods for haplotype phasing and meta-genomics assemblies. The disclosure provides a streamlined method for accomplishing these tasks, such that intermediates need not be labeled by an affinity label to facilitate binding to a solid surface. The disclosure also provides methods and compositions for the de novo generation of scaffold information, linkage information, and genome information for unknown organisms in heterogeneous metagenomic samples or samples obtained from multiple individuals. Practice of the methods can allow de novo sequencing of entire genomes of uncultured or unidentified organisms in heterogeneous samples, or the determination of linkage informa-
(Continued)

tion for nucleic acid molecules in samples comprising nucleic acids obtained from multiple individuals.

23 Claims, 32 Drawing Sheets

Specification includes a Sequence Listing.

Related U.S. Application Data

(60) Provisional application No. 62/294,198, filed on Feb. 11, 2016, provisional application No. 62/255,953, filed on Nov. 16, 2015, provisional application No. 62/243,591, filed on Oct. 19, 2015, provisional application No. 62/243,576, filed on Oct. 19, 2015.

(51) Int. Cl.
*G16B 50/00* (2019.01)
*C12Q 1/6874* (2018.01)
*C12Q 1/6806* (2018.01)
*C12Q 1/6809* (2018.01)
*C12Q 1/6869* (2018.01)

(52) U.S. Cl.
CPC ......... *C12Q 1/6869* (2013.01); *C12Q 1/6874* (2013.01); *G16B 30/00* (2019.02); *G16B 50/00* (2019.02)

(56) References Cited

U.S. PATENT DOCUMENTS

| | | | |
|---|---|---|---|
| 3,939,350 A | 2/1976 | Kronick et al. |
| 3,996,345 A | 12/1976 | Ullman et al. |
| 4,275,149 A | 6/1981 | Litman et al. |
| 4,277,437 A | 7/1981 | Maggio |
| 4,366,241 A | 12/1982 | Tom et al. |
| 4,988,617 A | 1/1991 | Landegren et al. |
| 5,143,854 A | 9/1992 | Pirrung et al. |
| 5,234,809 A | 8/1993 | Boom et al. |
| 5,242,794 A | 9/1993 | Whiteley et al. |
| 5,348,853 A | 9/1994 | Wang et al. |
| 5,476,930 A | 12/1995 | Letsinger et al. |
| 5,494,810 A | 2/1996 | Barany et al. |
| 5,567,583 A | 10/1996 | Wang et al. |
| 5,571,639 A | 11/1996 | Hubbell et al. |
| 5,593,839 A | 1/1997 | Hubbell et al. |
| 5,705,628 A | 1/1998 | Hawkins |
| 5,780,613 A | 7/1998 | Letsinger et al. |
| 5,786,146 A | 7/1998 | Herman et al. |
| 5,837,832 A | 11/1998 | Chee et al. |
| 5,989,823 A | 11/1999 | Jayasena et al. |
| 5,994,056 A | 11/1999 | Higuchi |
| 6,033,854 A | 3/2000 | Kurnit et al. |
| 6,110,709 A | 8/2000 | Ausubel et al. |
| 6,117,635 A | 9/2000 | Nazarenko et al. |
| 6,171,785 B1 | 1/2001 | Higuchi |
| 6,174,670 B1 | 1/2001 | Wittwer et al. |
| 6,225,109 B1 | 5/2001 | Juncosa et al. |
| 6,287,766 B1 | 9/2001 | Nolan et al. |
| 6,326,145 B1 | 12/2001 | Whitcombe et al. |
| 6,416,950 B1 | 7/2002 | Lohse et al. |
| 6,449,562 B1 | 9/2002 | Chandler et al. |
| 6,582,938 B1 | 6/2003 | Su et al. |
| 6,787,308 B2 | 9/2004 | Balasubramanian et al. |
| 6,833,246 B2 | 12/2004 | Balasubramanian |
| 6,897,023 B2 | 5/2005 | Fu et al. |
| 6,969,488 B2 | 11/2005 | Bridgham et al. |
| 7,001,724 B1 | 2/2006 | Greenfield |
| 7,361,468 B2 | 4/2008 | Liu et al. |
| 7,414,117 B2 | 8/2008 | Saito et al. |
| 7,425,415 B2 | 9/2008 | Pfeifer et al. |
| 7,709,179 B2 | 5/2010 | Iwashita |
| 7,709,197 B2 | 5/2010 | Drmanac |
| 7,901,891 B2 | 3/2011 | Drmanac |
| 7,985,546 B2 | 7/2011 | Church et al. |
| 8,058,004 B2 | 11/2011 | Oleinikov |
| 8,071,296 B2 | 12/2011 | Ruan et al. |
| 8,076,070 B2 | 12/2011 | Chen et al. |
| 8,153,373 B2 | 4/2012 | De Laat et al. |
| 8,278,112 B2 | 10/2012 | Shokat et al. |
| 8,367,322 B2 | 2/2013 | Barany et al. |
| 8,642,295 B2 | 2/2014 | De Laat et al. |
| 8,673,562 B2 | 3/2014 | Drmanac |
| 8,741,577 B2 | 6/2014 | Graneli et al. |
| 9,411,930 B2 | 8/2016 | Green, Jr. et al. |
| 9,434,985 B2 | 9/2016 | Dekker et al. |
| 2002/0012930 A1 | 1/2002 | Rothberg et al. |
| 2002/0190663 A1 | 12/2002 | Rasmussen |
| 2003/0022207 A1 | 1/2003 | Balasubramanian et al. |
| 2003/0044781 A1 | 3/2003 | Korlach et al. |
| 2003/0064398 A1 | 4/2003 | Barnes |
| 2003/0068629 A1 | 4/2003 | Rothberg et al. |
| 2003/0100102 A1 | 5/2003 | Rothberg et al. |
| 2003/0148344 A1 | 8/2003 | Rothberg et al. |
| 2003/0228627 A1 | 12/2003 | Emerson et al. |
| 2004/0106110 A1 | 6/2004 | Balasubramanian et al. |
| 2004/0197779 A1 | 10/2004 | Apffel et al. |
| 2004/0248161 A1 | 12/2004 | Rothberg et al. |
| 2005/0079510 A1 | 4/2005 | Berka et al. |
| 2005/0100932 A1 | 5/2005 | Lapidus et al. |
| 2005/0124022 A1 | 6/2005 | Srinivasan et al. |
| 2005/0130161 A1 | 6/2005 | Fraser et al. |
| 2005/0260625 A1 | 11/2005 | Wang |
| 2006/0012784 A1 | 1/2006 | Ulmer |
| 2006/0012793 A1 | 1/2006 | Harris |
| 2006/0024678 A1 | 2/2006 | Buzby |
| 2006/0024711 A1 | 2/2006 | Lapidus et al. |
| 2006/0078909 A1 | 4/2006 | Srinivasan et al. |
| 2006/0078937 A1 | 4/2006 | Korlach et al. |
| 2006/0252061 A1 | 11/2006 | Zabeau et al. |
| 2007/0172839 A1 | 7/2007 | Smith et al. |
| 2007/0231817 A1 | 10/2007 | De Laat et al. |
| 2007/0277251 A1 | 11/2007 | Wartiovaara et al. |
| 2009/0111115 A1 | 4/2009 | Drmanac et al. |
| 2009/0191598 A1 | 7/2009 | Ruan et al. |
| 2009/0233291 A1 | 9/2009 | Chen et al. |
| 2009/0269771 A1 | 10/2009 | Schroeder |
| 2009/0298064 A1 | 12/2009 | Batzoglou et al. |
| 2010/0062947 A1 | 3/2010 | De Laat et al. |
| 2010/0081141 A1 | 4/2010 | Chen et al. |
| 2010/0093986 A1 | 4/2010 | Zwick et al. |
| 2010/0130373 A1 | 5/2010 | Dekker et al. |
| 2011/0033854 A1 | 2/2011 | Drmanac et al. |
| 2011/0256593 A1 | 10/2011 | Hsieh et al. |
| 2011/0287947 A1 | 11/2011 | Chen et al. |
| 2011/0300537 A1 | 12/2011 | Slepnev |
| 2011/0306504 A1 | 12/2011 | Xiao et al. |
| 2012/0197533 A1 | 8/2012 | Nazarenko et al. |
| 2012/0302449 A1 | 11/2012 | Dong et al. |
| 2012/0330559 A1 | 12/2012 | Jiang et al. |
| 2013/0005585 A1 | 1/2013 | Anderson et al. |
| 2013/0045872 A1 | 2/2013 | Zhou et al. |
| 2013/0096009 A1 | 4/2013 | Dekker et al. |
| 2013/0183672 A1 | 7/2013 | De Laat et al. |
| 2013/0203605 A1 | 8/2013 | Shendure et al. |
| 2013/0310548 A1 | 11/2013 | Park |
| 2014/0031241 A1 | 1/2014 | Nicol et al. |
| 2014/0141982 A1 | 5/2014 | Jacobson et al. |
| 2014/0220587 A1 | 8/2014 | Green, Jr. et al. |
| 2015/0363550 A1 | 12/2015 | Green, Jr. et al. |
| 2016/0246922 A1 | 8/2016 | Putnam |

FOREIGN PATENT DOCUMENTS

| | | | |
|---|---|---|---|
| EP | 0717113 A2 | 6/1996 |
| EP | 0728520 A1 | 8/1996 |
| EP | 1967582 A1 | 9/2008 |
| EP | 2083090 A1 | 7/2009 |
| WO | WO-9015070 A1 | 12/1990 |
| WO | WO-9210092 A1 | 6/1992 |
| WO | WO-9309668 A1 | 5/1993 |
| WO | WO-9511995 A1 | 5/1995 |

(56) References Cited

FOREIGN PATENT DOCUMENTS

| WO | WO-9729212 A1 | 8/1997 |
|---|---|---|
| WO | WO-9841651 A1 | 9/1998 |
| WO | WO-0014281 A2 | 3/2000 |
| WO | WO-02088382 A2 | 11/2002 |
| WO | WO-02103046 A2 | 12/2002 |
| WO | WO-03020968 A2 | 3/2003 |
| WO | WO-03031947 A2 | 4/2003 |
| WO | WO-03042657 A2 | 5/2003 |
| WO | WO-2005001113 A2 | 1/2005 |
| WO | WO-2005005655 A1 | 1/2005 |
| WO | WO-2005005657 A1 | 1/2005 |
| WO | WO-2005044836 A2 | 5/2005 |
| WO | WO-2006040550 A1 | 4/2006 |
| WO | WO-2007093819 A2 | 8/2007 |
| WO | WO-2008024473 A2 | 2/2008 |
| WO | WO-2008127281 A2 | 10/2008 |
| WO | WO-2008143903 A2 | 11/2008 |
| WO | WO-2009053039 A1 | 4/2009 |
| WO | WO-2009147386 A1 | 12/2009 |
| WO | WO-2010036323 A1 | 4/2010 |
| WO | WO-2011056872 A2 | 5/2011 |
| WO | WO-2012005595 A2 | 1/2012 |
| WO | WO-2012045012 A2 | 4/2012 |
| WO | WO-2012047726 A1 | 4/2012 |
| WO | WO-2012054873 A2 | 4/2012 |
| WO | WO-2012106546 A2 | 8/2012 |
| WO | WO-2012142531 A2 | 10/2012 |
| WO | WO-2012142611 A2 | 10/2012 |
| WO | WO-2012150317 A1 | 11/2012 |
| WO | WO-2013078470 A2 | 5/2013 |
| WO | WO-2014012010 A1 | 1/2014 |
| WO | WO-2014047561 A1 | 3/2014 |
| WO | WO-2014121091 A1 | 8/2014 |
| WO | WO-2015089243 A1 | 6/2015 |
| WO | WO-2016019360 A1 | 2/2016 |
| WO | WO-2016044313 A1 | 3/2016 |
| WO | WO-2016061517 A2 | 4/2016 |
| WO | WO-2016207647 A1 | 12/2016 |
| WO | WO-2016207653 A1 | 12/2016 |
| WO | WO-2016207661 A1 | 12/2016 |

OTHER PUBLICATIONS

Adey, A. et al. In vitro, long-range sequence information for 19 de novo genome assembly via transposase contiguity. Genome Res., 24(12):2041-2049, Dec. 2014.

Alkan, C. et al. Limitations of next-generation genome sequence assembly. Nat. Methods, 8(1):61-65, Jan. 2011.

Allison (2007) Fundamental Molecular Biology. Wiley-Blackwell, Chapter 8, pp. 1-15.

Amini, S. et al. Haplotype-resolved whole-genome sequencing by contiguity-preserving transposition and combinatorial indexing. Nat. Genet., 46(12):1343-1349, Dec. 2014.

Ausubel, et al., eds. 1993. Current Protocols in Molecular Biology. Part 1: *E. coli*, plasmids, and bacteriophages, pp. 1-15.

Blander, G. et al. SIRT1 Shows No Substrate Specificity in Vitro. Journal of biological Chemistry (2005) vol. 280, p. 9780-9785.

Blecher-Gonen, Ronnie et al. High-throughput chromatin immunoprecipitation for genome-wide mapping of in vivo protein-DNA interactions and epigenomic states. Nature Protocols, 8(3):539-554 (Feb. 21, 2013).

Bolger, A.M. et al. Trimmomatic: a flexible trimmer for Illumina sequence data. Bioinformatics, 30(15):2114-2120, Aug. 2014.

Bradnam, K.R. et al. Assemblathon 2: evaluating de novo methods of genome assembly in three vertebrate species. Gigascience, 2(1):10, 2013.

Burton, et al. Chromosome-scale scaffolding of de novo genome assemblies based on chromatin interactions. Nat. Biotechnol. 2013, 31: 1119-1125.

Cai et al., SATB1 packages densely looped transcriptionally active chromatin for coordinated expression of cytokine genes, Nature Genetics, 2006, vol. 38, No. 11, pp. 1278-1288.

Chapman, et al. Meraculous: de novo genome assembly with short paired-end reads. PloS one. 2011, 6.8: e23501.

Constans, A. Microarrays in Microtubes, The Scientist Magazine: Technology, Sep. 22, 2003, pp. 1-3; 17.13:36.

International Application No. PCT/US2014/014184 International Search Report and Written Opinion dated Apr. 23, 2014.

Cortese, J. Array of options: Instrumentation for Microarray production and Analysis. The Scientists Magazine. May 29, 2000. 14.11: 26.

Cortese J., The array of today. Scientist, 2000 14.17: 25.

de Koning, A.P. et al. Repetitive elements may comprise over two-thirds of the human genome. PLoS Genet., 7(12):e1002384, Dec. 2011.

Dekker et al., A closer look at long-range chromosomal interactions. Trends in Biochemical Science (Jun. 2003) 28(6):277-280.

Dekker et al., Capturing chromosome conformation, Science, Feb. 15, 2002, vol. 295, pp. 1306-1311.

Dixon, J. R. et al. Topological domains in mammalian genomes identified by analysis of chromatin interactions. Nature, 485(7398):376-380, May 2012.

Dostie et al., Chromosome Conformation Capture Carbon Copy (5C): a massively parallel solution for mapping interaction between genomic elements, Genome research, 2006, vol. 16, No. 10, pp. 1299-1309.

Dower, et al. Recombinant and synthetic randomized peptide libraries. Ann. Rep. Med. Chem. 1991, 26:271-280.

Drmanac, et al. Human Genome Sequencing Using Unchained Base Reads on Self-Assembling DNA Nanoarrays. Science Jan. 1, 2010, 327.5961: 78-81 DOI:10.1126/science.1181498.

Ekins, R. et al. Microarrays: Their Origins and applications. Trends in Biotechnology, 17(6); 217-218 (Jun. 1999).

Fan et al. A versatile assay for high-throughput gene expression profiling on universal array matrices. Genome Research, 2004, vol. 14 No. 5 pp. 878-885.

Fangman, et al. Activation of replication origins within yeast chromosomes, Annual Review of Cell Biology, 7(1); 375-402 (1991).

Flot, JF et al. Contact genomics: scaffolding and phasing (meta) genomes using chromosome 3D physical signatures. FEBS Letters 589 (2015) 2966-2974.

Fodor, et al. Light-directed, spatially addressable parallel chemical synthesis. Science. Feb. 15, 1991, 251.4995: 767-773; DOI: 10.1126/science.1990438.

Fullwood, et al. ChIP-Based Methods for the Identification of Long-Range Chromatin Interactions Journal of Cellular Biochemistry, vol. 107, No. 1, pp. 30-39, May 2009.

Fullwood, MJ. et al. Chromatin interaction analysis using paired-end tag sequencing. Jan. 2010 Curr. Prot. In Mol. Biol. Chapter 21; unit 21, 15:1-25. doi: 10.1002/0471142727.mb2115s89.

Fyodorov, et al. Chromatin assembly in vitro with purified recombinant ACF and NAP-1. Methods in enzymology. 2002, 371: 499-515.

Garaj et al., Graphene as a sub-nanometer trans-electrode membrane, Nature, Sep. 9, 2010, 467(7312): 190-193.

GE Healthcare: Instructions 71-7106-00AF Activated Thiol Sepharose 4B (pp. 1-12) (Jul. 2008).

Gilmour, David S., et al. Detecting protein-DNA interactions in vivo: distribution of RNA polymerase on specific bacterial genes. Proceedings of the National Academy of Sciences. (1984) 81(14): 4275-4279.

Gnerre, S. et al. High-quality draft assemblies of mammalian genomes from massively parallel sequence data. Proc. Natl. Acad. Sci. USA, 108(4)1513-1518 (Jan. 2011).

Goodwin, S. et al. Oxford nanopore sequencing and de novo assembly of a eukaryotic genome. bioRxiv, pp. 1-28 (Jul. 15, 2015).

Green R.E. et al. Three crocodilian genomes reveal ancestral patterns of evolution among archosaurs. Science, 346(6215):1254449 (1-11) (Dec. 12, 2014).

Grunenwald, H. et al. Rapid, high-throughput library preparation for next-generation sequencing. Nature Methods, 7:1-2 (Aug. 2010).

Gwynne, P. et al. Mioroarray analysis: the next revolution in molecular biology. Science. pp. 1-6 (Aug. 6, 1999).

(56) References Cited

OTHER PUBLICATIONS

Haussler, D. et al. Genome 10K: a proposal to obtain whole-genome sequence for 10,000 vertebrate species. J. Hered., 100(6):659-674, (Nov. 5, 2009).
Heid, C.A. et al. Real time quantitative PCR. Genome Research, 6(10): 986-994 (1996).
Herschleb, J. et al. Pulsed-field gel electrophoresis. Pulsed-field gel electrophoresis. Nature Protocols 2(3):677-84 (Mar. 29, 2007).
Hesselberth, Jay R. et al. Global mapping of protein-DNA interaction in vivo by digital genomic foot printing, Nature Methods 6(4): 283-289 (Apr. 2009).
Kalhor, R. et al. Genome architectures revealed by tethered chromosome conformation capture and population-based modeling, Nature Biotechnology, 30(1): 90-98 (Jan. 2012).
Kaplan, N. et al. High-throughput genome scaffolding from in vivo DNA interaction frequency. Nat. Biotechnol., 31(12):1143-1147 (Dec. 2013).
Kidd, J.M. et al. Mapping and sequencing of structural variation from eight human genomes. Nature, 453(7191):56-64, May 2008.
Kitzman, Jacob O. et al. Haplotype-resolved genome sequencing of a Gujarati Indian individual, Nature Biotechnology, 29(1):59-63 (Jan. 2011).
Koren, S. et al. Hybrid error correction and de novo assembly of single-molecule sequencing reads. Nature biotechnology, 30(7):693-700, 2012.
Kotoulas, S. et al. The chipping forecast. Special supplement to Nature Genetics vol. 21; pp. 1-6 (1999).
Kundu, Tapas K. et al. Activator-dependent transcription from chromatin in vitro involving targeted histone acetylation by p300. Molecular cell. 6(3): 551-561 (Sep. 2000).
Lasken, Roger S. et al. Mechanism of chimera formation during the Multiple Displacement Amplification reaction. BMC biotechnology 7(19):1-11 (Apr. 12, 2007).
Lee, T.I. et al. Chromatin immunoprecipitation and microarray-based analysis of protein location, Nature Protocols 1(2): 729-748 (2006).
Lemieux, B. et al. Overview of DNA chip technology. Molecular Breeding 4: 277-289 (1998).
Levene, M.J. et al. Zero-Mode Waveguides for Single-Molecule Analysis at High Concentrations, Science, 299(5607):682-686 (Jan. 31, 2003).
Lieberman-Aiden, E. et al. Comprehensive mapping of long-range interactions reveals folding principles of the human genome. Science, 326(5950):289-293 (Oct. 9, 2009).
Liu, B. et al. COPE: n accurate k-mer-based pair-end reads connection tool to facilitate genome assembly, Bioinformatics, 28(22); 2870-2874 (Oct. 8, 2012).
Lupski, James R. et al. Whole-genome sequencing in a patient with Charcot-Marie-Tooth neuropathy. New England Journal of Medicine, 362(13): 1181-1191 (Apr. 1, 2010).
Lusser, Alexandra et al. Strategies for the reconstitution of chromatin. Nature Methods, 1(1):19-26 (Oct. 2004).
Ma, H. et al. Application of Real-time Polymerase Chain Reaction (RT-PCR), The Journal of American Science, 2 (3):1-15 (Aug. 10, 2006).
Maniatis et al. Molecular Cloning: A Laboratory Manual, Cold Spring Harbor, N.Y., pp. 280-281 (1982).
Margulies, M. et al. Genome sequencing in open microfabricated high density picolitre reactors. Nature 437(7057):376-380 (Sep. 15, 2005).
Marie-Nelly, H. et al. High-quality genome (re)assembly using chromosomal contact data. Nature Communications 5:5695 (Dec. 17, 2014).
Marshall, A. et al. DNA chips: an array of possibilities. Nature Biotechnology, 16(1): 27-31 (Jan. 1998).
Mary, I. et al. Metaproteomic and metagenomic analyses of defined oceanic microbial populations using microwave cell fixation and flow cytometric sorting. FEMS Microbiol Ecol. 74(1):10-18 (Oct. 2010). E-Pub. Jul. 5, 2010.

Meyer, M. et al. Illumina sequencing library preparation for highly multiplexed target capture and sequencing. Cold Spring Harb Protoc, 2010(6):pdb.prot5448 (Jun. 2010).
Miller, S.A. et al. A Simple salting out procedure for extracting DNA from human nucleated cells. Nucleic Acids Research 16(3):1215 (Feb. 11, 1988).
Morrison, A.J. et al. Retinoblastoma Protein Transcriptional Repression through Histone Deacetylation of a Single Nucleosome. Molecular and Cellular biology 22(3);856-865 (Feb. 2002).
Myers, E.W. et al. A Whole-Genome Assembly of *Drosohila*. Science, 287(5461):2196-2204 (Mar. 24, 2000).
Nazarenko, I.A. et al. A closed tube format for amplification and detection of DNA based on energy transfer. Nucleic acids research, 25(12):2516-2521 (Jun. 15, 1997).
Nickitas-Etienne, A. International Preliminary Report on Patentability and Written Opinion, PCT/US2014/069642, The International Bureau of WIPO, dated Jun. 23, 2016.
Peng, Z. et al. Generation of long insert pairs using a Cre-LoxP Inverse PCR approach, PLoS One, 7(1): e29437 (2012) E-Pub Jan. 9, 2012.
Peters, B.A. et al. Accurate whole-genome sequencing and haplotyping from 10 to 20 human cells. Nature, 487(7406):190-195 (Jul. 11, 2012).
Putnam, N. H. et al. Supplemental Material—Chromosome-scale shotgun assembly using an in vitro method for long-range likage. Genome Research 26:342-350 (2016). E-Pub Feb. 4, 2016.
Putnam, N.H. et al. Chromosome-scale shotgun assembly using an in vitro method for long-range linkage. arXiv:1502.05331[q-bio. GN] pp. 1-25. Feb. 18, 2015 (Retrieved from the Internet Oct. 8, 2015).
Quail, M.A. et al. A tale of three next generation sequencing platforms: comparison of Ion Torrent, Pacific Biosciences and Illumina MiSeq sequencers. BMC Genomics, 13:341 (Jul. 24, 2012).
Rios, J. et al. Identification by whole-genome resequencing of gene defect responsible for severe hypercholesterolemia. Human Molecular Genetics, 19(22): 4313-4318 (Nov. 15, 2010). E-Pub Aug. 18, 2010).
Rozowsky, J. et al. AlleleSeq: analysis of allele-specific expression and binding in a network framework. Mol. Syst. Biol., 7:522; pp. 1-15 (Aug. 2, 2011).
Salzberg, S.L. et al. GAGE: A critical evaluation of genome assemblies and assembly algorithms. Genome Res., 22(3):557-567 (Mar. 2012). E-Pub Jan. 6, 2012.
Sambrook, et al. Mixed Oligonucleotide-primed Amplification of cDNA (MOPAC). Cold Spring Harbor Protocols, pp. 1-30 (2006).
Schena, Mark et al. Genes, genomes, and chips. DNA microarrays: A practical approach. Oxford University Press, pp. 1-18 (1999): ISBN-10: 1881299376 ISBN-13: 978-1881299370.
Schena, M. et al. PCR applications: protocols for functional genomics. Chapter 28: Parallel analysis with biological chips. Eds. Michael A. Innis, David H. Gelfand, John J. Sninsky. Academic Press. ISBN: 0-12-372185-7. pp. 445-456 (1999).
Schloss, P.D. et al. A statistical toolbox for metagenomics: assessing functional diversity in microbial communities, BMC Bioinformatics 9(34):1-15 (Jan. 23, 2008).
Schmidt, D. et al. ChIP-seq: using high-throughput sequencing to discover protein-DNA interactions. Methods 48(3): 240-248(Jul. 2009).
Schwartz, D.C. et al. Separation of yeast chromosome-sized DNAs by pulsed field gradient gel electrophoresis. Cell 37(1): 67-75 (May 1984).
Selvaraj, S. et al. Whole-genome haplotype reconstruction using proximity-ligation and shotgun sequencing. Nature Biotechnology, 31(12):1111-1118 (Dec. 2013).
Selvaraj, S. et al. Complete haplotype phasing of the MHC and KIR loci with targeted HaploSeq. BMC Genomics 16:900, pp. 1-7 (Nov. 5, 2015).
Shalon, D. et al. A DNA microarray system for analyzing complex DNA samples using two-color fluorescent probe hybridization. Genome research, 6(7): 639-645 (Jul. 1996).

(56) References Cited

OTHER PUBLICATIONS

Shedlock, A.M. et al. Phylogenomics of nonavian reptiles and the structure of the ancestral amniote genome. Proc. Natl. Acad. Sci. U.S.A., 104(8):2767-2772 (Feb. 20, 2007). E-Pub Feb. 16, 2007.
Sheridan, C. Milestone approval lifts Illumina's NGS from research into clinic. Nature Biotechnology, 32(2):111-112 (Feb. 2014).
Shiio Y., et al. Quantitative proteome analysis using isotope-coded affinity tags and mass spectrometry. Nature Protocols, 1(1): 139-145 (2006).
Sigma Protein A immobilized product sheet, pp. 1-4 (Published Mar. 2001) accessed on Apr. 14, 2016.
Simpson, J.T. et al. Efficient de novo assembly of large genomes using compressed data structures. Genome Res, 22(3): 549-556 (Mar. 2012). E-Pub Dec. 7, 2011. doi: 10.1101/gr.126953.111.
Solomon, M.J. et al. Formaldehyde-mediated DNA-protein crosslinking: a probe for in vivo chromatin structures. Proceedings of the National Academy of Sciences, 82(19): 6470-6474 (Oct. 1985).
Solomon, M.J. et al. Mapping protein-DNA interactions in vivo with formaldehyde: evidence that histone H4 is retained on a highly transcribed gene. Cell, 53(6):937-947 (Jun. 17, 1988).
Soni, et al. Progress toward ultrafast DNA sequencing using solid-state nanopores. Clin Chem, 53(11)1996-2001 (Nov. 2007). E-Pub. Sep. 21, 2007.
Splinter, E. 3C Technology: Analyzing the Spatial Organization of Genomic Loci In Vivo Methods in Enzymology, 375:493-507 (2004).
Storek, Michael J. et al. High-resolution footprinting of sequence-specific protein-DNA contacts, Nature Biotechnology, 20(2):183-186 (Feb. 1, 2002).
Syed, F. et al. Optimized library preparation method for next-generation sequencing. Application Note Abstract, Nature Methods 6:i-ii (Oct. 2009).
Tanizawa, H. et al., Mapping of long-range associations throughout the fission yeast genome reveals global genome organization linked to transcriptional regulation. Nucleic Acid Research, 38(22):8164-8177 (Dec. 2010). Epub Oct. 28, 2010.
Teague, B. et al. High-resolution human genome structure by single-molecule analysis. Proceedings of the National Academy of Sciences, 107(24): 10848-10853 (Jun. 15, 2010).
Torjensen, I. Genomes of 100,000 people will be sequenced to create an open access research resource. BMJ, 347:f6690 (Nov. 6, 2013).
Tuzun, E. et al. Fine-scale structural variation of the human genome. Nat. Genet., 37(7):727-732 (Jul. 2005). Epub May 15, 2005.
Tyagi, S. et al. Molecular beacons: probes that fluoresce upon hybridization. Nature Biotechnology, 14(3):303-308 (Mar. 1996).
Umbarger, M.A. Chromosome conformation capture assays in bacteria. Methods 58(3):212-220 (Nov. 2012). Epub Jul. 6, 2012. doi: 10.1016/j.ymeth.2012.06.017.
Venter, J.C. et al. The sequence of the human genome. Science, 291(5507):1304-1351 (Feb. 16, 2001).
Voskoboynik, A. et al. The genome sequence of the colonial chordate, Botryllus schlosseri. eLife, 2:e00569 (2013). doi: 10.7554/eLife.00569. Epub Jul. 2, 2013.
Weisenfeld N.I., et al. Comprehensive variation discovery in single human genomes. Nat. Genet. 46(12):1350-1355 (Dec. 2014). doi: 10.1038/ng.3121. Epub Oct. 19, 2014.
Whitcombe, D. et al. Detection of PCR Products Using Self-probing Amplicons and Fluorescence. Nature Biotechnology, 17(8):804-807 (Aug. 1999).
Williams, L.J. Paired-end sequencing of Fosmid libraries by Illumina. Genome Res., 22(11):2241-2249 (Nov. 2012). Epub Jul. 16, 2012.
Wing, R.D., et al. An improved method of plant megabase DNA isolation in agarose microbeads suitable for physical mapping and YAC cloning. The Plant Journal, 4(5):893-898 (1993).
Wu, T.D. et al. GMAP: a genomic mapping and alignment program for mRNA and EST sequences. Bioinformatics, 21(9):1859-1875, May 1, 2005. Epub Feb. 22, 2005.
Wu, C.C. et al. Long-span, mate-pair scaffolding and other methods for faster next-generation sequencing library creation. Nat. Methods, 9(9; Advertising Feature):i-ii (Sep. 2012).
Zhou, S. et al. A single molecule scaffold for the maize genome. PLoS Genetics, 5(11): e1000711; pp. 1-14 (Nov. 20, 2009).
Zinchenko, A. et al. Compaction of Single-Chain DNA by Histone-Inspired Nanoparticles. Physical Review Letters, 95(22); 228101-1 to 228101-4 (Nov. 25, 2005).
Schutze, T. et al. A calibrated diversity assay for nucleic acid libraries using DiStRO—a Diversity Standard of Random Oligonucleotides. Nucleic Acids Research, 38(4):e23 (pp. 1-5) Mar. 2010; epub Dec. 3, 2009.
Bansal et al., Hapcut: an efficient and accurate algorithm for the haplotype assembly problem, Bioinformatics, 24(16): i153-i159 (Aug. 9, 2008).
Ferraiuolo, M.A. et al. From cells to chromatin: capturing snapshots of genome organization with 5C technology. Methods. Nov. 2012;58(3):255-67. Epub Nov. 5. 2012.
Putnam, Nicholas H. et al. Chromosome-scale shotgun assembly using an in vitro method for long-range linkage. Genome Research, 26(3):342-350 (Mar. 2016).
Splinter, E. et al. Determining long-range chromatin interactions for selected genomic sites using 4C-seq technology: from fixation to computation. Methods. Nov. 2012;58(3):221-30. (Epub May 17, 2012).
Xie et al. De Novo Plant Genome Assembly Based on Chromatin Interactions: A Case Study of *Arabidopsis thaliana*. Mol Plant 8(3):489-92 (2015).

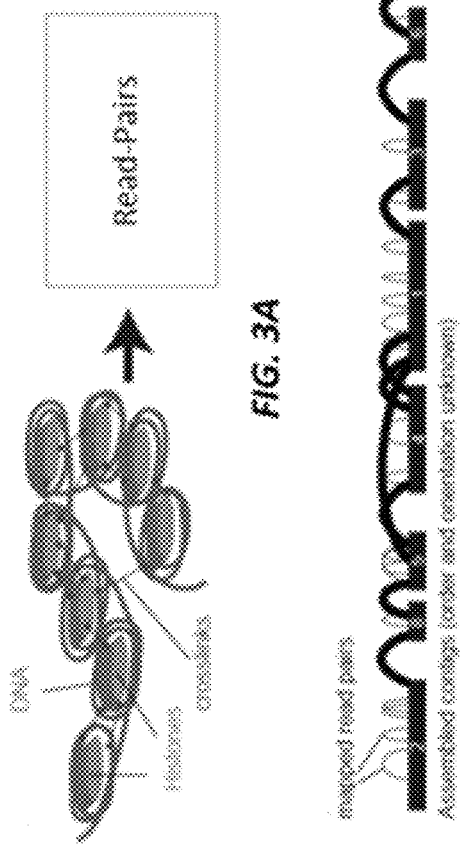
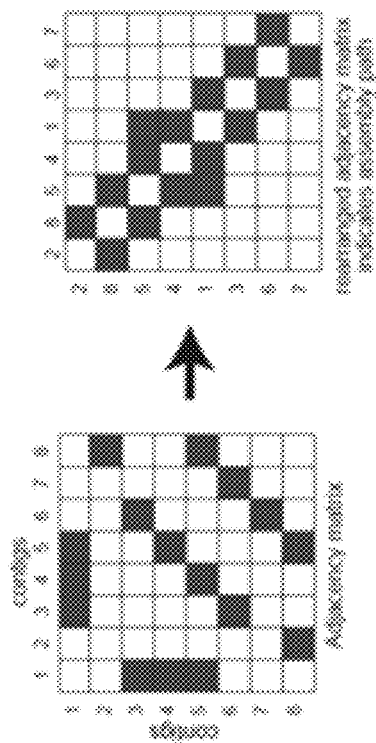
FIG. 3A
FIG. 3B
FIG. 3C

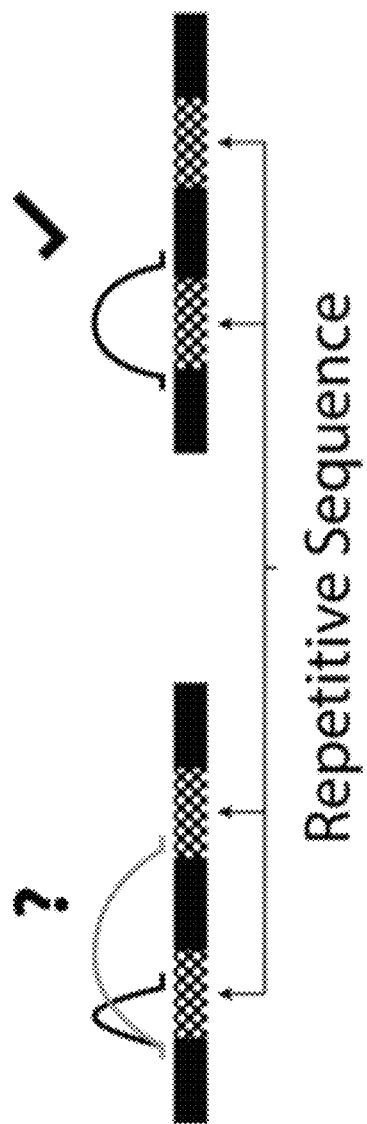
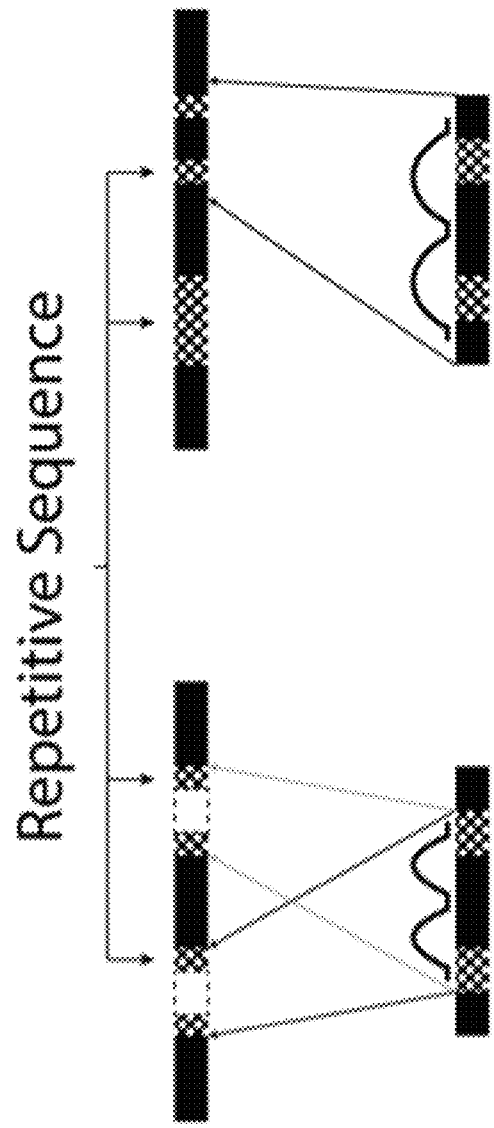

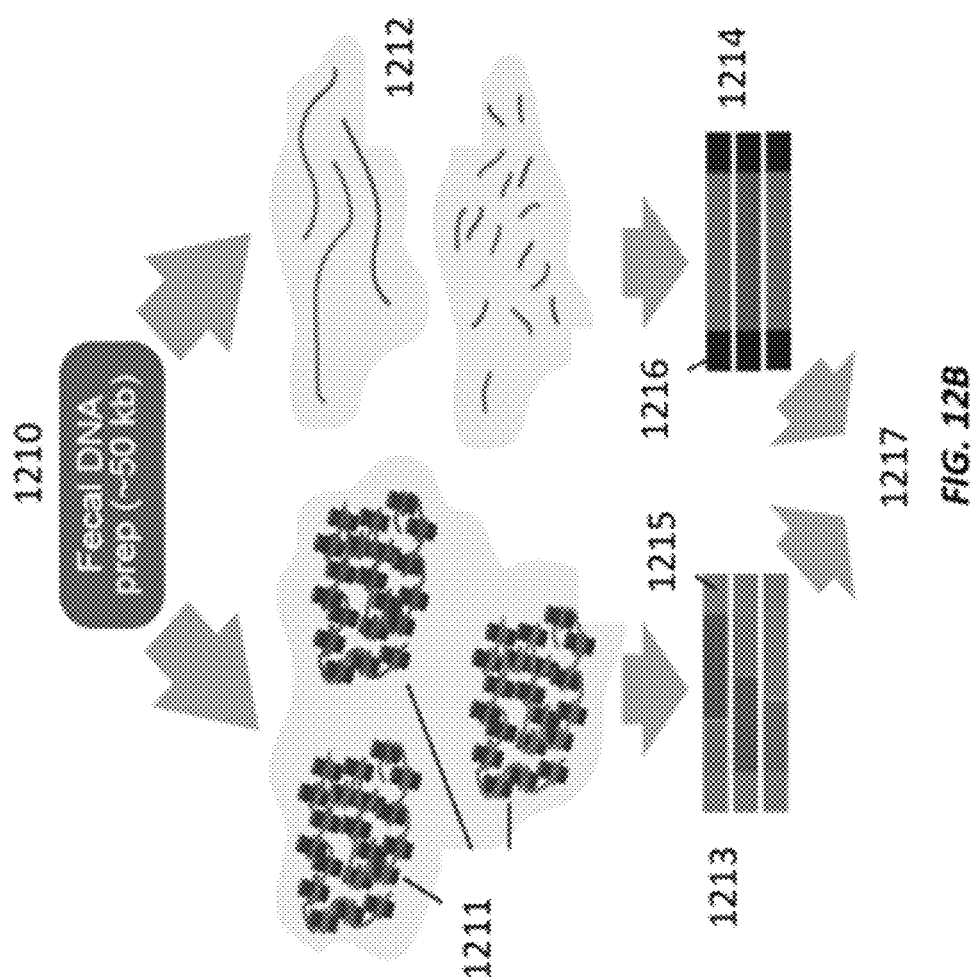

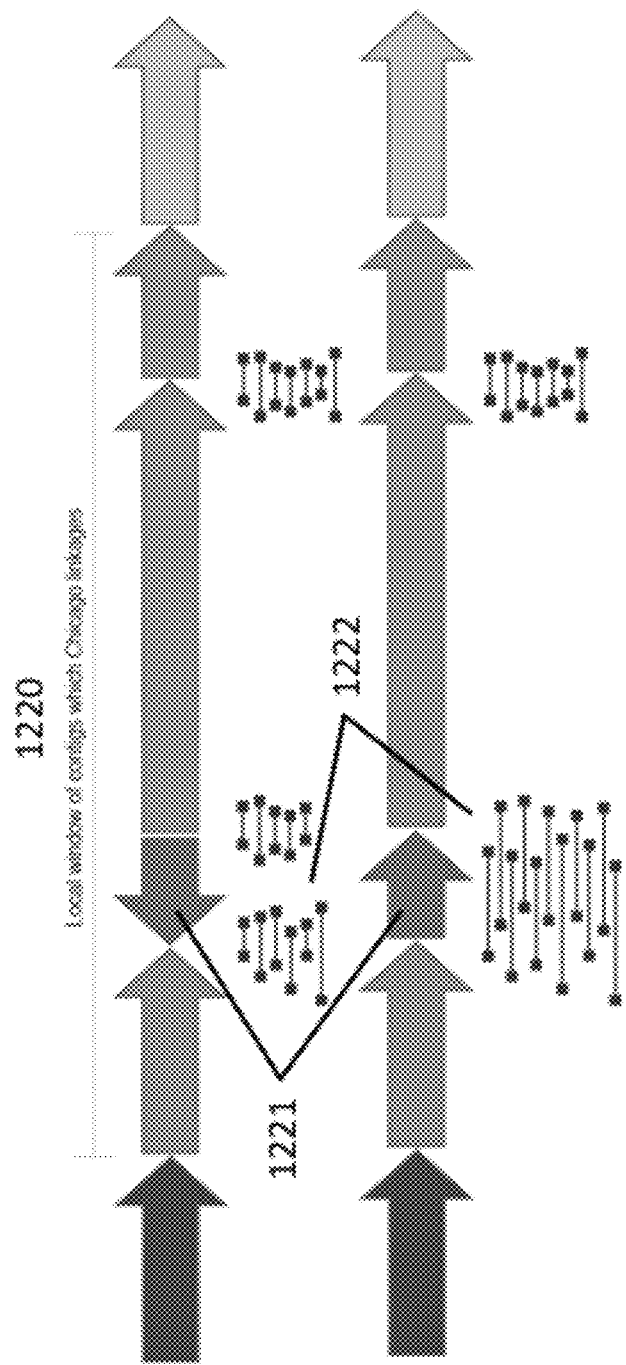

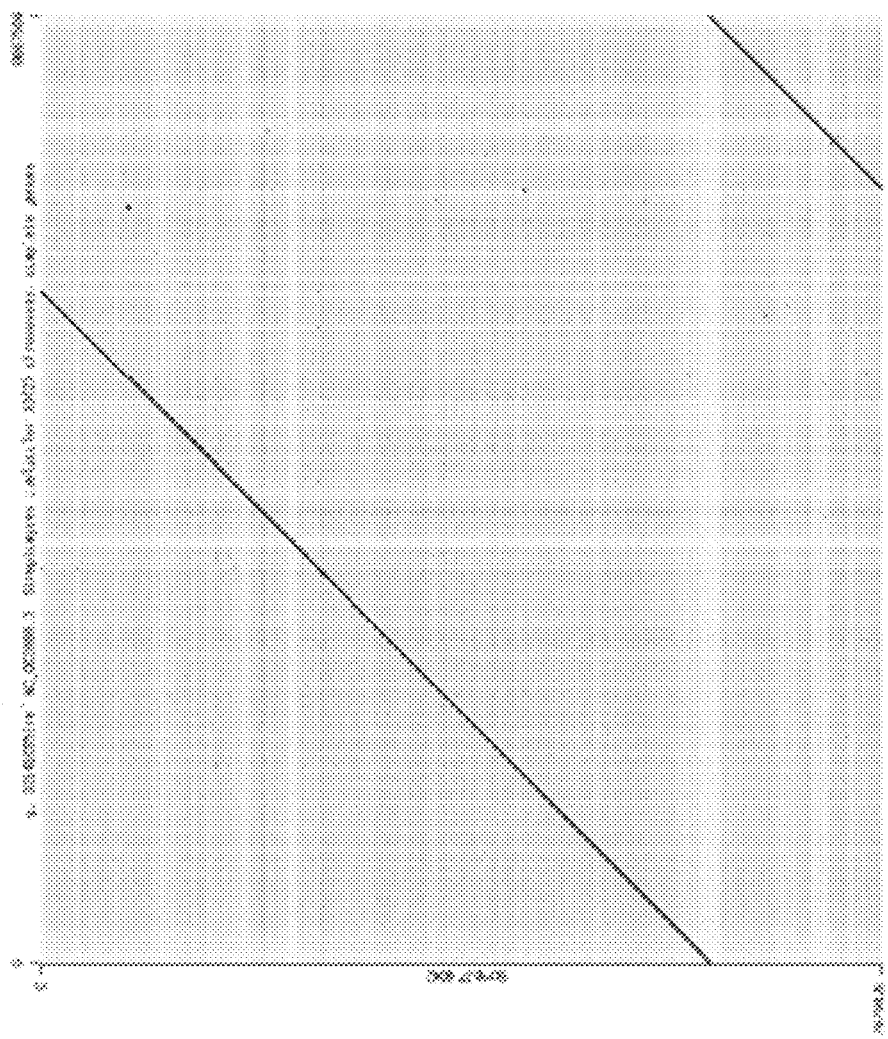

METHODS FOR GENOME ASSEMBLY, HAPLOTYPE PHASING, AND TARGET INDEPENDENT NUCLEIC ACID DETECTION

CROSS-REFERENCE

This application is a continuation of PCT/US2016/57557, filed Oct. 18, 2016, which claims the benefit of U.S. Provisional Patent Application No. 62/243,576, filed Oct. 19, 2015, which is hereby incorporated by reference in its entirety, U.S. Provisional Application No. 62/243,591, filed Oct. 19, 2015, which is hereby incorporated by reference in its entirety, U.S. Provisional Application No. 62/255,953, filed Nov. 16, 2015, which is hereby incorporated by reference in its entirety, and U.S. Provisional Patent Application No. 62/294,198, filed Feb. 11, 2016, which is hereby incorporated by reference in its entirety.

SEQUENCE LISTING

The instant application contains a Sequence Listing which has been submitted electronically in ASCII format and is hereby incorporated by reference in its entirety. Said ASCII copy, created on Jul. 13, 2017, is named 45269-713-302-SL.txt and is 4,873 bytes in size. No new matter is introduced through incorporation of the sequence listing.

STATEMENT AS TO FEDERALLY SPONSORED RESEARCH

This invention was made with the support of the United States government under Contract number 5R44HG008719-02 by the National Human Genome Research Institute.

BACKGROUND

It remains difficult in theory and in practice to produce high-quality, highly contiguous genome sequences. High-throughput sequencing allows genetic analysis of the organisms that inhabit a wide variety of environments of biomedical, ecological, or biochemical interest. Shotgun sequencing of environmental samples, which often contain microbes that are refractory to culture, can reveal the genes and biochemical pathways present within the organisms in a given environment. Careful filtering and analysis of these data can also reveal signals of phylogenetic relatedness between reads in the data. However, high-quality de novo assembly of these highly complex datasets is generally considered to be intractable.

SUMMARY

A persistent shortcoming of next generation sequencing (NGS) data is the inability to span large repetitive regions of genomes due to short read lengths and relatively small insert sizes. This deficiency significantly affects de novo assembly. Contigs separated by long repetitive regions cannot be linked or re-sequenced, since the nature and placement of genomic rearrangements are uncertain. Further, since variants cannot be confidently associated with haplotypes over long-distances, phasing information is indeterminable. The disclosure can address all of these problems simultaneously by generating extremely long-range read pairs (XLRPs) that span genomic distances on the order of hundreds of kilo-bases, and up to megabases with the appropriate input DNA. Such data can be invaluable for overcoming the substantial barriers presented by large repetitive regions in genomes, including centromeres; enable cost-effective de novo assembly; and produce re-sequencing data of sufficient integrity and accuracy for personalized medicine.

Of significant importance is the use of reconstituted chromatin in forming associations among very distant, but molecularly-linked, segments of DNA. The disclosure enables distant segments to be brought together and covalently linked by chromatin conformation, thereby physically connecting previously distant portions of the DNA molecule. Subsequent processing can allow for the sequence of the associated segments to be ascertained, yielding read pairs whose separation on the genome extends up to the full length of the input DNA molecules. Since the read pairs are derived from the same molecule, these pairs also contain phase information.

Many aspects of health and fitness are impacted by the rich microbial communities in gastro-intestinal tracts, on skin, and in other locations. Herein are described simple and powerful approaches to revealing the full genomic complexity of such microbial communities. These techniques can allow quick, accurate, and quantitative assaying of the full genetic repertoire present in locations such the human body (e.g., gut) and other sites where microbial communities are found.

Such techniques include in vitro proximity-ligation methods, e.g. for fecal metagenomics applications. These techniques can provide a powerful and efficient approach to de novo metagenomics assembly that will allow research and biomedical analysis to move beyond methods such as single locus molecule counting or statistical inference.

The techniques of the present disclosure can provide a single, integrated workflow for accurate assembly of all major constituents of complex metagenomics communities. These techniques can enable a comprehensive understanding of the ways the microbiome (e.g., the gut microbiome) influences health and disease in humans, other animals, plants, other life forms, and environments.

Techniques disclosed herein can provide for efficient capture and representation of the diversity of microbes present in a sample, such as a human fecal sample. Also disclosed are computational approaches to metagenomics assembly that exploits the rich datatype these techniques generate. Such computational approaches can achieve highly contiguous scaffolding and strain deconvolution. Techniques of the present disclosure can provide for robust, fool-proof laboratory protocols and software products that can allow generation of a comprehensive view of a dynamic microbial environment (e.g., human gut) from a small sample (e.g., fecal sample) in a manner of days.

In some embodiments, the disclosure provides methods that can produce high quality assemblies with far less data than previously required. For example, the methods disclosed herein provide for genomic assembly from only two lanes of Illumina HiSeq data.

In other embodiments, the disclosure provides methods that can generate chromosome-level phasing using a long-distance read pair approach. For example, the methods disclosed herein can phase 90% or more of the heterozygous single nucleotide polymorphisms (SNPs) for that individual to an accuracy of at least 99% or greater. This accuracy is on par with phasing produced by substantially more costly and laborious methods.

In some examples, methods that can produce fragments of genomic DNA up to megabase scale can be used with the methods disclosed herein. Long DNA fragments can be generated to confirm the ability of the present methods to generate read pairs spanning the longest fragments offered by those extractions. In some cases, DNA fragments beyond 150 kbp in length can be extracted and used to generate XLRP libraries.

The disclosure provides methods for greatly accelerating and improving de novo genome assembly. The methods disclosed herein utilize methods for data analysis that allow for rapid and inexpensive de novo assembly of genomes from one or more subjects. The disclosure provides that the methods disclosed herein can be used in a variety of applications, including haplotype phasing, and metagenomics analysis.

In certain embodiments, the disclosure provides for a method for genome assembly comprising the steps of: generating a plurality of contigs; generating a plurality of read pairs from data produced by probing the physical layout of chromosomes, chromatin, or reconstituted chromatin; mapping or assembling the plurality of read pairs to the plurality of contigs; constructing an adjacency matrix of contigs using the read-mapping or assembly data; and analyzing the adjacency matrix to determine a path through the contigs that represent their order and/or orientation to the genome. In some embodiments, the disclosure provides that at least about 90% of the read pairs are weighted by taking a function of each read's distance to the edge of the contig so as to incorporate information about which read pairs indicate short-range contacts and which read pairs indicate longer-range contacts. In other embodiments, the adjacency matrix can be re-scaled to down-weight the high number of contacts on some contigs that represent promiscuous regions of the genome, such as conserved binding sites for one or more agents that regulate the scaffolding interactions of chromatin, like transcriptional repressor CTCF. In other embodiments, the disclosure provides for a method for the genome assembly of a human subject, whereby the plurality of contigs is generated from the human subject's DNA, and whereby the plurality of read pairs is generated from analyzing the human subject's chromosomes, chromatin, or reconstituted chromatin made from the subject's naked DNA.

In some embodiments herein, a benefit is a reduction on the number of steps required to isolate complexes tagged so as to provide phase information. In many techniques in the prior art, complexes comprise tagged nucleic acids or tagged association moieties such as proteins or nanoparticles, for example biotin-tagged, so as to facilitate binding of complexes to a solid surface labeled with, for example, avidin or streptavidin. In some methods and compositions of the present disclosure, solid surfaces are coated with a moiety that binds complexes either directly or mediated through a solvent, such that the complex does not need to be modified with a ligand to facilitate binding to the solid surface. A number of moieties are contemplated herein, such as hydrophilic moieties, hydrophobic moieties, positively charged moieties, negatively charged moieties, PEG, polyamines, amino-moieties, poly-carboxylic acid moieties, or other moieties or combinations of moieties. In some cases the surface is a SPRI surface, such as a SPRI surface that binds the association moiety-nucleic acid complex directly or through a solvent.

The disclosure provides that a plurality of contigs can be generated by using a shotgun sequencing method comprising: fragmenting long stretches of a subject's DNA into random fragments of indeterminate size; sequencing the fragments using high throughput sequencing methods to generate a plurality of sequencing reads; and assembling the sequencing reads so as to form a plurality of contigs.

In certain embodiments, the disclosure provides that a plurality of read pairs can be generated by probing the physical layout of chromosomes, chromatin, or reconstituted chromatin using a chromatin capture based technique. In some embodiments, the chromatin capture based technique comprises, crosslinking chromosomes, chromatin, or reconstituted chromatin with a fixative agent, such as formaldehyde, to form DNA-protein cross links; cutting the crosslinked DNA-Protein with one or more nuclease enzymes (e.g., restriction enzymes) so as to generate a plurality of DNA-protein complexes comprising sticky ends; filling in the sticky ends with nucleotides containing one or more markers, such as biotin, to create blunt ends that are then ligated together; fragmenting the plurality of DNA-protein complexes into fragments; pulling down junction containing fragments by using the one or more of the markers; and sequencing the junction containing fragments using high throughput sequencing methods to generate a plurality of read pairs. In some embodiments, the plurality of read pairs for the methods disclosed herein is generated from data produced by probing the physical layout of reconstituted chromatin.

In some embodiments, the present disclosure provides methods for generating a tagged sequence, comprising: binding the DNA molecule to an association molecule; cutting the bound DNA-Protein so as to generate a plurality of DNA-protein complexes comprising segment ends; ligating the segment ends to tags; and sequencing the junction containing fragments using high throughput sequencing methods to generate a plurality of read pairs. A number of association molecules that bind DNA are contemplated, including chromatin constituents sensu strictu such as histones, but also chromatin constituents more generally defined, such as DNA binding proteins, transcription factors, nuclear proteins, transposons, or non-polypeptide DNA binding association molecules such as nanoparticles having surfaces comprising DNA-affinity molecules. In some cases, the tags are ligated to segment ends, for example using ligases or using transposases loaded using tag molecules. In some cases, the segment ends comprising a common tag are assigned to a common molecule of origin, which is often indicative of phase. In some embodiments, the plurality of read pairs for the methods disclosed herein is generated from data produced by probing the physical layout of reconstituted chromatin.

In various embodiments, the disclosure provides that a plurality of read pairs can be determined by probing the physical layout of chromosomes or chromatin isolated from cultured cells or primary tissue. In other embodiments, the plurality of read pairs can be determined by probing the physical layout of reconstituted chromatin formed by complexing naked DNA obtained from a sample of one or more subjects with isolated histones.

The disclosure provides methods to determine haplotype phasing comprising a step of identifying one or more sites of heterozygosity in the plurality of read pairs, wherein phasing data for allelic variants can be determined by identifying read pairs that comprise a pair of heterozygous sites.

In various embodiments, the disclosure provides methods for high-throughput bacterial genome assembly, comprising a step of generating a plurality of read pairs by probing the physical layout of a plurality of microbial chromosomes using a modified chromatin capture based method, comprising the modified steps of: collecting microbes from an environment; adding a fixative agent, such as formaldehyde, so as to form cross-links within each microbial cell, and wherein read pairs mapping to different contigs indicate which contigs are from the same species.

In some embodiments, the disclosure provides methods for genome assembly comprising: (a) generating a plurality of contigs; (b) determining a plurality of read pairs from data generated by probing the physical layout of chromosomes, chromatin, or reconstituted chromatin; (c) mapping the plurality of read pairs to the plurality of contigs; (d) constructing an adjacency matrix of contigs using the read-mapping data; and (e) analyzing the adjacency matrix to determine a path through the contigs that represent their order and/or orientation to the genome.

The disclosure provides methods to generate a plurality of read pairs by probing the physical layout of chromosomes, chromatin, or reconstituted chromatin using a chromatin capture based technique. In some embodiments, the chromatin capture based technique comprises (a) crosslinking chromosomes, chromatin, or reconstituted chromatin with a fixative agent to form DNA-protein cross links; (b) cutting the crosslinked DNA-Protein with one or more nuclease (e.g., restriction) enzymes so as to generate a plurality of DNA-protein complexes comprising sticky ends; (c) filling in the sticky ends with nucleotides containing one or more markers to create blunt ends that are then ligated together; (d) shearing the plurality of DNA-protein complexes into fragments; (e) pulling down junction containing fragments by using one or more of the markers; and (f) sequencing the junction containing fragments using high throughput sequencing methods to generate a plurality of read pairs.

In certain embodiments, the plurality of read pairs is determined by probing the physical layout of chromosomes or chromatin isolated from cultured cells or primary tissue. In other embodiments, the plurality of read pairs is determined by probing the physical layout of reconstituted chromatin formed by complexing naked DNA obtained from a sample of one or more subjects with isolated histones.

In some embodiments, at least about 60%, about 70%, about 80%, about 90%, about 95% or about 99% or more of the plurality of read pairs are weighted by taking a function of the read's distance to the edge of the contig so as to incorporate a higher probability of shorter contacts than longer contacts. In some embodiments, the adjacency matrix is re-scaled to down-weight the high number of contacts on some contigs that represent promiscuous regions of the genome.

In certain embodiments, the promiscuous regions of the genome include one or more conserved binding sites for one or more agents that regulate the scaffolding interactions of chromatin. In some examples, the agent is transcriptional repressor CTCF.

In some embodiments, the methods disclosed herein provide for the genome assembly of a human subject, whereby the plurality of contigs is generated from the human subject's DNA, and whereby the plurality of read pairs is generated from analyzing the human subject's chromosomes, chromatin, or reconstituted chromatin made from the subject's naked DNA.

In other embodiments, the disclosure provides methods for determining haplotype phasing, comprising identifying one or more sites of heterozygosity in the plurality of read pairs, wherein phasing data for allelic variants can be determined by identifying read pairs that comprise a pair of heterozygous sites.

In yet other embodiments, the disclosure provides methods for meta-genomics assemblies, wherein the plurality of read pairs is generated by probing the physical layout of a plurality of microbial chromosomes using a modified chromatin capture based method, comprising: collecting microbes from an environment; and adding a fixative agent so as to form cross-links within each microbial cell, and wherein read pairs mapping to different contigs indicate which contigs are from the same species. In some examples, the fixative agent is formaldehyde.

In some embodiments, the disclosure provides methods of assembling a plurality of contigs originating from a DNA molecule, comprising generating a plurality of read-pairs from the DNA molecule and assembling the contigs using the read-pairs, wherein at least 1% of the read-pairs span greater than 50 kB on the DNA molecule and the read-pairs are generated within 14 days. In some embodiments, at least 10% of the read-pairs span a distance greater than 50 kB on the DNA molecule. In some embodiments, at least 1% of the read-pairs span a distance greater than 100 kB on the DNA molecule. In some cases, the read-pairs are generated within 7 days.

In other embodiments, the disclosure provides methods of assembling a plurality of contigs originating from a single DNA molecule, comprising generating a plurality of read-pairs from the single DNA molecule in vitro and assembling the contigs using the read-pairs, wherein at least 1% of the read-pairs span a distance greater than 30 kB on the single DNA molecule. In some embodiments, at least 10% of the read-pairs span a distance greater than 30 kB on the single DNA molecule. In other embodiments, at least 1% of the read-pairs span a distance greater than 50 kB on the single DNA molecule.

In yet other embodiments, the disclosure provides methods of haplotype phasing, comprising generating a plurality of read-pairs from a single DNA molecule and assembling a plurality of contigs of the DNA molecule using the read-pairs, wherein at least 1% of the read-pairs spans a distance greater than 50 kB on the single DNA molecule and the haplotype phasing is performed at greater than 70% accuracy. In some embodiments, at least 10% of the read-pairs span a distance greater than 50 kB on the single DNA molecule. In other embodiments, wherein at least 1% of the read-pairs span a distance greater than 100 kB on the single DNA molecule. In some embodiments, the haplotype phasing is performed at greater than 90% accuracy.

The disclosure provides methods of haplotype phasing, comprising generating a plurality of read-pairs from a single DNA molecule in vitro and assembling a plurality of contigs of the DNA molecule using the read-pairs, wherein at least 1% of the read-pairs spans a distance greater than 30 kB on the single DNA molecule and the haplotype phasing is performed at greater than 70% accuracy. In some embodiments, at least 10% of the read-pairs span a distance greater than 30 kB on the single DNA molecule. In other embodiments, at least 1% of the read-pairs span a distance greater than 50 kB on the single DNA molecule. In yet other embodiments, the haplotype phasing is performed at greater than 90% accuracy. In some embodiments, the haplotype phasing is performed at greater than 70% accuracy.

In some embodiments, the disclosure provides methods of generating a first read-pair from a first DNA molecule, comprising: (a) binding the first DNA molecule to a plurality of association molecules in vitro, wherein the first DNA molecule comprises a first DNA segment and a second DNA segment; (b) tagging the first DNA segment and the second DNA segment and thereby forming at least one tagged DNA segment; and (c) sequencing the tagged DNA segment, or at least a recognizable portion of the tagged DNA segment, such as a portion adjacent to the tag or a portion at an opposite end from the tagged end, and thereby obtaining the tagged sequence, wherein the plurality of association molecules are not covalently modified with an affinity label prior to and during steps (a), and (b).

In certain embodiments, the present disclosure provides methods of generating a tagged sequence from a first DNA molecule, comprising: (a) crosslinking binding said first DNA molecule to a plurality of association molecules in vitro; (b) immobilizing said first DNA molecule on a solid support; (c) severing said first DNA molecule to generate a first DNA segment and a second DNA segment; (d) tagging said first DNA segment and said second DNA segment and thereby forming at least one tagged DNA segment; and sequencing said tagged DNA segment, or at least a recognizable portion of the tagged DNA segment, such as a portion adjacent to the tag or a portion at an opposite end from the tagged end, or sequencing a recognizable portion of each end of the tagged DNA segment, and thereby obtaining said tagged sequence, wherein said first DNA molecule is directly bound to said solid support. In some examples, the solid support comprises a polymer bead (e.g. SPRI bead) that binds to DNA without further modifications with any affinity label (e.g. biotin, streptavidin, avidin, polyhistidine, digoxigenin, EDTA, or derivatives thereof).

In some embodiments, a plurality of association molecules, such as from reconstituted chromatin, are cross-linked to the first DNA molecule. In some examples, the association molecules comprise amino acids. In some cases, the association molecules are peptides or proteins. In certain examples, the association molecules are histone proteins. In some cases, the histone proteins are from a different source than the first DNA molecule. In various examples, the association molecules are transposases. In some cases, the first DNA molecule is non-covalently bound to the association molecules. In other cases, the first DNA molecule is covalently bound to the association molecules. In certain examples, the first DNA molecule is crosslinked to the association molecules. In certain embodiments, the first DNA molecule is cross-linked with a fixative agent. In some examples, the fixative agent is formaldehyde. In various embodiments, the method comprises immobilizing the plurality of association molecules on a solid support. In some cases, the solid support is a bead. In some examples, the bead comprises a polymer. In some examples, the polymer is polystyrene. In certain examples, the polymer is polyethylene glycol (PEG). In certain examples, the bead is a magnetic bead. In some examples, the bead is a solid-phase reversible immobilization (SPRI) bead. In certain cases, the solid support comprises a surface, wherein the surface comprises a plurality of carboxyl groups. In various cases, the solid support is not covalently linked to any polypeptide (e.g. streptavidin). In some cases, the association molecule is not covalently linked to an affinity label (e.g. biotin) prior to immobilization to the solid support.

In some embodiments, the first DNA segment and the second DNA segment are generated by severing the first DNA molecule. In some cases, the first DNA molecule is severed after the first DNA molecule is bound to the plurality of association molecules. In certain cases, the first DNA molecule is severed using a restriction enzyme (e.g. MboI). In some cases, the first DNA molecule is severed using a transposase (e.g. Tn5). In other cases, the first DNA molecule is severed using a physical method (e.g. sonication, mechanical shearing). In certain embodiments, the first DNA and the second DNA segment are modified with an affinity label. In some examples, the affinity label can comprise biotin, which can be captured with a streptavidin bead, an avidin bead, or derivatives thereof. In certain examples, the affinity label is a biotin-modified nucleoside triphosphate (dNTP). In some examples, the affinity label is a biotin-modified deoxyribocytosine triphosphate (dCTP). In some examples, the affinity label is a biotin-modified deoxyribocytosine triphosphate (dGTP). In some examples, the affinity label is a biotin-modified deoxyribocytosine triphosphate (dATP). In some examples, the affinity label is a biotin-modified deoxyribocytosine triphosphate (dUTP). In certain cases, the first DNA segment is tagged at at least a first end with a first tag and the second DNA segment is tagged at at least a second end with a second tag. In certain examples, the first tag and the second tag are identical. In various examples, the first DNA segment and the second DNA segment are tagged using a transposase (e.g. Tn5). In some cases, the first DNA segment is tagged with the second DNA segment and the second DNA segment is tagged with the first DNA segment. For example, the first DNA segment can be linked to the second DNA segment. In some examples, the first DNA segment is linked to the second DNA segment using a ligase. In some cases, the linked DNA segment is severed prior to the sequencing in step (c). In certain examples, the linked DNA segment is severed using a restriction enzyme (e.g. ExoIII). In other cases, the linked DNA segment is severed using a physical method (e.g. sonication, mechanical shearing).

In some embodiments, the first DNA segment is washed for less than about 10 times before the first DNA segment is linked to the second DNA segment. In some embodiments, the first DNA segment is washed for less than about 6 times before the first DNA segment is linked to the second DNA segment. In some embodiments, the method comprises connecting the linked DNA segment to sequencing adaptors.

In certain embodiments, the method comprises assembling a plurality of contigs using the tagged sequence. In some embodiments, each of the first and the second DNA segment are connected to at least one affinity label and the linked DNA segment is captured using the affinity label. In various embodiments, the method comprises phasing the first DNA segment and the second DNA segment using the tagged sequence. In some cases, 'tagging' is effectuated by ligating a first DNA segment to a second DNA segment, thereby generating a read pair segment.

In some embodiments, the method comprises: (a) providing a plurality of association molecules, such as from reconstituted chromatin, to at least a second DNA molecule; (b) crosslinking the association molecules to the second DNA molecule and thereby forming a second complex in vitro; (c) severing the second complex thereby generating a third DNA segment and a fourth segment; (d) linking the third DNA segment with the fourth DNA segment and thereby forming a second linked DNA segment; and (e) sequencing the second linked DNA segment and thereby obtaining a second read-pair. In some examples, less than 40% of the DNA segments from the DNA molecules are linked with DNA segments from any other DNA molecule. In some examples, less than 20% of the DNA segments from the DNA molecules are linked with DNA segments from any other DNA molecule.

In some embodiments, the disclosure provides methods of generating a first read-pair from a first DNA molecule comprising a predetermined sequence, comprising: (a) providing one or more DNA-binding molecules to the first DNA molecule, wherein the one or more DNA-binding molecules bind to the predetermined sequence; (b) cross-linking the first DNA molecule in vitro, wherein the first DNA molecule comprises a first DNA segment and a second DNA segment; (c) linking the first DNA segment with the second DNA segment and thereby forming a first linked DNA segment; and (d) sequencing the first linked DNA segment and thereby obtaining the first read-pair; wherein the probability that the predetermined sequence appears in the read-pair is affected by the binding of the DNA-binding molecule to the predetermined sequence.

In some embodiments, the DNA-binding molecule is a nucleic acid that can hybridize to the predetermined sequence. In some examples the nucleic acid is RNA. In other examples, the nucleic acid is DNA. In other embodiments, the DNA-binding molecule is a small molecule. In some examples, the small molecule binds to the predetermined sequence with a binding affinity less than 100 µM. In some examples, the small molecule binds to the predetermined sequence with a binding affinity less than 1 µM. In some embodiments, the DNA-binding molecule is immobilized on a surface or a solid support.

In some embodiments, the probability that the predetermined sequence appears in the read-pair is decreased. In other embodiments, the probability that the predetermined sequence appears in the read-pair is increased.

The present disclosure provides methods for generating a plurality of tagged sequences from a plurality of DNA molecules, comprising: (a) binding the plurality of DNA molecules to a plurality of association molecules in vitro; (b) severing each of the DNA molecules to generate at least a plurality of DNA segments; (c) tagging at least a portion of the DNA segments to form a plurality of tagged DNA segments; and (d) sequencing the tagged DNA segments, or at least a recognizable portion of the tagged DNA segments, such as a portion adjacent to the tag or a portion at an opposite end from the tagged end, to obtain a plurality of tagged sequences; wherein the plurality of association molecules are not covalently modified with an affinity label prior to and during steps (a) and (b). In some cases, less than 40% of DNA segments from the DNA molecules are linked with DNA segments from any other DNA molecule. In some cases, less than 20% of DNA segments from the DNA molecules are linked with DNA segments from any other DNA molecule.

In some embodiments, the association molecules comprise amino acids joined by peptide bonds. In certain embodiments, the association molecules are polypeptides or proteins. In some examples, the association molecules are histone proteins. In some examples, the histone proteins are from a different source than the DNA molecules. For example, the histone proteins can be isolated from a non-human organism and the DNA molecules can be isolated from humans. In various examples, the association molecules are transposases (e.g. Tn5). In some cases, the first DNA molecule is non-covalently bound to the association molecules. In other cases, the first DNA molecule is covalently bound to the association molecules. In certain examples, the first DNA molecule is crosslinked to the association molecules. In some examples, the DNA molecules are cross-linked with a fixative agent. For example, the fixative agent can be formaldehyde. In some cases, the method comprises immobilizing the plurality of association molecules on a plurality of solid supports. In certain cases, the solid supports are beads. In some examples, the beads comprise a polymer. In some examples, the polymer is polystyrene. In certain examples, the polymer is polyethylene glycol (PEG). In certain examples, the beads are magnetic beads. In some examples, the beads are SPRI beads. In various examples, the solid support comprises a surface, wherein the surface comprises a plurality of carboxyl groups. In various cases, the solid support is not covalently linked to any polypeptide (e.g. streptavidin). In some cases, the association molecule is not covalently linked to an affinity label (e.g. biotin) prior to immobilization to the solid support.

In some embodiments, the first DNA molecule is severed after the first DNA molecule is bound to the plurality of association molecules. In some cases, the first DNA molecule is severed using a restriction enzyme (e.g. MboII). In certain cases, the first DNA molecule is severed using a transposase (e.g. Tn5). In certain embodiments, the portion of the DNA segments are modified with an affinity label. In some cases, the affinity label comprises biotin. In some examples, the affinity label is a biotin-modified nucleoside triphosphate (dNTP). In some examples, the biotin-modified nucleoside triphosphate (dNTP) is a biotin-modified deoxyribocytosine triphosphate (dCTP). In some cases, a portion of the DNA segments are tagged at tat least a first end with a first tag. In some examples, the DNA segments are tagged using a transposase. In various cases, a portion of the DNA segments are tagged by linking each of said DNA segments to at least one other DNA segment. In some examples, the portion of DNA segments are linked to the other DNA segments using a ligase. In certain cases, the linked DNA segment is severed prior to step (c). In various cases, the linked DNA segment is severed using a physical method (e.g. sonication, mechanical shearing). In some embodiments, the method comprises connecting the linked DNA segments to sequencing adaptors.

In some cases, the DNA segments are washed for less than about 10 times before the DNA segments are linked to form the linked DNA segments. In certain cases, the DNA segments are washed for less than about 6 times before the DNA segments are linked to form the linked DNA segments. In various cases, the method comprises assembling a plurality of contigs of the DNA molecules using the tagged segments. In some cases, the method comprises phasing the DNA segments using the tagged segments.

The disclosure provides an in vitro library comprising a plurality of read-pairs each comprising at least a first sequence element and a second sequence element, wherein the first and the second sequence elements originate from a single DNA molecule and wherein at least 1% of the read-pairs comprise first and second sequence elements that are at least 50 kB apart on the single DNA molecule. In some embodiments, at least 10% of the read-pairs comprise first and second sequence elements that are at least 50 kB apart on the single DNA molecule. In other embodiments, at least 1% of the read-pairs comprise first and second sequence elements that are at least 100 kB apart on the single DNA molecule. In some embodiments, less than 20% of the read-pairs comprise one or more predetermined sequences. In some embodiments, less than 10% of the read-pairs comprise one or more predetermined sequences. In some embodiments, less than 5% of the read-pairs comprise one or more predetermined sequences.

In some embodiments, the predetermined sequences are determined by one or more nucleic acids that can hybridize to the predetermined sequences. In some examples, the one or more nucleic acids is RNA. In other examples, the one or more nucleic acids is DNA. In some examples, the one or more nucleic acids is immobilized to a surface or a solid support.

In some embodiments, the predetermined sequences are determined by one or more small molecule. In some examples, the one or more small molecule binds to the predetermined sequences with a binding affinity less than 100 μM. In some examples, the one or more small molecule binds to the predetermined sequences with a binding affinity less than 1 μM.

The disclosure provides a composition comprising a DNA fragment and a plurality of association molecules, such as from reconstituted chromatin, wherein: (a) the association molecules are cross-linked to the DNA fragment in an in vitro complex; and (b) the in vitro complex is immobilized on a solid support.

The disclosure provides a composition comprising a DNA fragment, a plurality of association molecules, and a DNA-binding molecule, wherein: (a) the DNA-binding molecule is bound to a predetermined sequence of the DNA fragment; and (b) the association molecules are cross-linked to the DNA fragment. The DNA-binding molecule is a nucleic acid that can hybridize to the predetermined sequence in some cases. In some examples, the nucleic acid is RNA. In other examples, the nucleic acid is DNA. In some examples, the nucleic acid is immobilized to a surface or a solid support. In other embodiments, the DNA-binding molecule is a small molecule. In some examples, the small molecule binds to the predetermined sequence with a binding affinity less than 100 μM. In other examples, the small molecule binds to the predetermined sequence with a binding affinity less than 1 μM.

The present disclosure provides a composition comprising a plurality of association molecules bound to a DNA fragment in an in vitro complex, wherein said in vitro complex is immobilized on a solid support, and wherein said solid support is not covalently linked to any polypeptides. In some cases, the solid support is not covalently linked to streptavidin. In some cases, the solid support is a bead. In some examples, the bead comprises a polymer. In some examples, the polymer is polystyrene. In certain examples, the polymer is polyethylene glycol (PEG). In certain examples, the bead is a magnetic bead. In some examples, the bead is a solid-phase reversible immobilization (SPRI) bead. In certain cases, the solid support comprises a surface, wherein the surface comprises a plurality of carboxyl groups. In various cases, the solid support is not covalently linked to any polypeptide (e.g. streptavidin).

In some examples, the association molecules comprise amino acids bound by peptide bonds. In some examples, the association molecules are peptides or proteins. In certain examples, the association molecules are histone proteins. In some cases, the histone proteins are from a different source than the first DNA molecule. In certain examples, the association molecules are transposases. In some cases, the first DNA molecule is non-covalently bound to the association molecules. In other cases, the first DNA molecule is non-covalently bound to the association molecules. In some examples, the first DNA molecule is crosslinked to the association molecules. In certain embodiments, the first DNA molecule is cross-linked with a fixative agent. In some examples, the fixative agent is formaldehyde.

In certain embodiments, the DNA fragment is modified with an affinity label. In some examples, the affinity label can comprise biotin, which can be captured with a streptavidin bead, an avidin bead, or derivatives thereof. In certain examples, the affinity label is a biotin-modified nucleoside triphosphate (dNTP). In some examples, the affinity label is a biotin-modified deoxyribocytosine triphosphate (dCTP). In some cases, the linked DNA segment is further severed prior to the sequencing in step (c). In certain examples, the linked DNA segment is severed using a restriction enzyme (e.g. ExoIII). In other cases, the linked DNA segment is severed using a physical method (e.g. sonication, mechanical shearing).

Methods and compositions disclosed herein are useful for the assembly of genome information into scaffolds up to and including phased whole chromosomes. In some cases the information generated herein guides assembly of previously generated sequence information into scaffolds up to and including phased whole chromosomes. In some cases the methods and compositions herein are used to assemble de novo generated nucleic acid information into phased scaffolds up to and including whole chromosomes.

Tag information does not in all cases strictly correspond to phase, but is informative as to phase information. Generally referring to the disclosure herein, the presence of a common tag pattern on a pair of sequence reads indicates that the reads either 1) originated from a common molecule, or 2) are shared in common by chance.

In most cases, common tagging will not arise by chance, and thus most commonly tagged sequences, particularly commonly tagged sequences that are independently mapped to a common contig, are safely inferred to map to a common phase of that contig, that is, to the same haploid molecule of a diploid organism. Groups of reads that map together to a single or a few contigs suspected of being adjacent and that share a tag sequence are likely to be in phase on a single molecule. Groups of reads that share a common tag sequence but that map to contigs suspected to be on separate chromosomes, for example, are more likely to have obtained their common tag sequences by chance. Multiple instances of sequence clusters sharing the exact tag sequence but mapping to two separate contigs or suspected chromosomes, however, may indicate that a translocation has occurred by which a fragment of one chromosome has become attached to a second, such that the reads are in fact in phase on the chromosome that is the result of the translocation.

The presence of a non-identical tag pattern among a pair of sequence reads indicates that the sequences did not arise from a common molecule immediately prior to tagging. However, if multiple identical or overlapping copies of a nucleic acid molecule exist in a single sample, then two sets of sequence reads can arise that differ in their tag patterns, indicating that they arose from different molecules in the sample, but that nonetheless map to the same in phase chromosome in a diploid cell. That is, tag pattern information is indicative as to whether sequences arose from a common molecule, and in general, tag pattern information correlates to phase information. However, as discussed above, in discrepancies, tag pattern information is more properly indicative of a common molecule of origin. In cases where molecule of origin and nucleic acid phase determinations show some discrepancy, one of skill in the art is able to resolve these discrepancies such that some phase information is nonetheless determinable from the tag pattern information generated through the methods herein.

Disclosed herein are methods of generating a tagged sequence from a first DNA molecule, comprising: (a) binding said first DNA molecule to a plurality of association molecules, to form a first complex, wherein said first DNA molecule comprises a first DNA segment and a second DNA segment; (b) tagging said first DNA segment and said second DNA segment and thereby forming at least one tagged DNA segment; (c) binding the complex to a solid support having a surface that directly binds a constituent of the complex; and (d) sequencing a recognizable portion of the tagged DNA segment, such as a portion adjacent to the tag or a portion at an opposite end from the tagged end and thereby obtaining said tagged sequence; wherein said plurality of association molecules are not covalently modified with an affinity label prior to or during steps (a) and (b).

Disclosed herein are methods of generating a tagged sequence from a first DNA molecule, comprising: (a) binding said first DNA molecule to a plurality of association molecules; (b) immobilizing said first DNA molecule on a solid support; (c) severing said first DNA molecule to generate a first DNA segment and a second DNA segment; (d) tagging said first DNA segment and said second DNA segment and thereby forming at least one tagged DNA segment; and (e) sequencing said tagged DNA segment and thereby obtaining said tagged sequence; wherein said first DNA molecule is directly bound to said solid support.

Disclosed herein are methods for generating a plurality of tagged sequences from a plurality of DNA molecules, comprising: (a) binding said plurality of DNA molecules to a plurality of association molecules; (b) severing said plurality of DNA molecules to generate a plurality of DNA segments; (c) tagging at least a portion of said DNA segments to form a plurality of tagged DNA segments; and (d) sequencing said tagged DNA segments to obtain a plurality of tagged sequences; wherein said plurality of association molecules are not covalently modified with an affinity label prior to or during steps (a) and (b).

Disclosed herein are compositions comprising a plurality of association molecules bound to a DNA fragment in an in vitro complex, wherein said in vitro complex is immobilized on a solid support, and wherein said solid support is not covalently linked to any polypeptides.

Disclosed herein are methods for generating a plurality of tagged sequences from a plurality of DNA molecules, comprising: (a) obtaining a plurality of DNA molecules bound to a plurality of association molecules; (b) severing said DNA molecules to generate at least a plurality of DNA segments; (c) tagging at least a portion of said DNA segments to form a plurality of tagged DNA segments; and (d) sequencing said tagged DNA segments to obtain a plurality of tagged sequences; wherein a total amount of said plurality of DNA molecules is less than about 5 micrograms (μg).

Disclosed herein are methods of identifying a microbial host of an antibiotic resistance gene comprising: a) obtaining a stabilized sample from an individual having a condition that demonstrates microbial antibiotic resistance; b) treating the stabilized sample to cleave double-stranded DNA in the stabilized sample; c) labeling exposed DNA ends; d) ligating labeled exposed DNA ends to form labeled paired ends; and e) sequencing across labeled paired ends to generate a paired sequence; wherein sequence adjacent to an antibiotic resistance gene sequence is indicative of a microbial host of an antibiotic resistance gene.

Disclosed herein are methods of determining genomic linkage information for a heterogeneous nucleic acid sample comprising: (a) obtaining a stabilized heterogeneous nucleic acid sample; (b) treating the stabilized sample to cleave double-stranded DNA in the stabilized sample; (c) labeling exposed DNA ends; (d) ligating labeled exposed DNA ends to form labeled paired ends; (e) sequencing across labeled paired ends to generate a plurality of paired sequence reads; (f) assigning each half of a paired sequence read of the plurality of sequence reads to a common nucleic acid molecule of origin.

Disclosed herein are methods for meta-genomics assemblies, comprising: (a) collecting microbes from an environment; (b) obtaining a plurality of contigs from the microbes; (c) generating a plurality of read pairs from data produced by probing the physical layout of reconstituted chromatin; and (d) mapping the plurality of read pairs to the plurality of contigs thereby producing read-mapping data, wherein read pairs mapping to different contigs indicate that the different contigs are from a common species.

Disclosed herein are methods of detecting a pathogen in a host population, comprising: a) obtaining a stabilized sample from each of a plurality of individuals suspected of harboring a common pathogen; b) treating the stabilized sample to cleave double-stranded DNA in the stabilized sample; c) tagging exposed DNA ends of a first portion of the stabilized sample using a first barcode tag and tagging exposed ends of a second portion of the stabilized sample using a second barcode tag; d) sequencing across barcode tagged ends to generate a plurality of barcode tagged sequence reads; and e) assigning commonly barcode tagged sequence read of the plurality of sequence reads to a common organism of origin; wherein an organism of origin common to individuals suspected of harboring a common pathogen is the pathogen.

Disclosed herein are methods of identifying a microbial host of an antibiotic resistance gene comprising: a) obtaining a stabilized sample from an individual having a condition that demonstrates microbial antibiotic resistance; b) treating the stabilized sample to cleave double-stranded DNA in the stabilized sample; c) tagging exposed DNA ends of a first portion of the stabilized sample using a first barcode tag and tagging exposed ends of a second portion of the stabilized sample using a second barcode tag; d) sequencing across barcode tagged ends to generate a plurality of barcode tagged sequence reads; wherein sequence having a barcode tag identical to a barcode tag of an antibiotic resistance gene sequence is indicative of a microbial host of an antibiotic resistance gene.

Disclosed herein are methods of determining genomic linkage information for a heterogeneous nucleic acid sample comprising: (a) obtaining a stabilized heterogeneous nucleic acid sample; (b) treating the stabilized sample to cleave double-stranded DNA in the stabilized sample; (c) tagging exposed DNA ends of a first portion of the stabilized sample using a first barcode tag and tagging exposed ends of a second portion of the stabilized sample using a second barcode tag; (d) sequencing across barcode tagged ends to generate a plurality of barcode tagged sequence reads; (e) assigning commonly tagged sequence reads to a common nucleic acid molecule of origin.

Disclosed herein are methods of detecting a pathogen in a host population, comprising: a) obtaining a stabilized sample from each of a plurality of subjects; b) treating the stabilized sample to cleave double-stranded DNA in the stabilized sample, thereby generating exposed DNA ends; c) labeling at least a portion of the exposed DNA ends; d) ligating the exposed DNA ends to form labeled paired ends; e) sequencing at least a recognizable portion of the labeled paired ends to generate a plurality of read-pairs; and f) assigning each half of a read-pair to a common organism of origin; wherein an organism of origin common to the subjects is detected as the pathogen.

Disclosed herein are methods of identifying a microbial host of an antibiotic resistance gene comprising: a) obtaining a stabilized sample from a subject having a condition that demonstrates microbial antibiotic resistance; b) treating the stabilized sample to cleave double-stranded DNA in the stabilized sample, thereby generating exposed DNA ends; c) labeling at least a portion of the exposed DNA ends; d) ligating the labeled exposed DNA ends to form labeled paired ends; and e) sequencing at least a recognizable portion of the ligated paired ends to generate a paired sequence; wherein the paired sequence adjacent to an antibiotic resistance gene sequence is indicative of a microbial host of an antibiotic resistance gene.

Disclosed herein are methods of determining genomic linkage information for a heterogeneous nucleic acid sample comprising: (a) stabilizing the heterogeneous nucleic acid sample; (b) treating the stabilized sample to cleave double-stranded DNA in the stabilized sample, thereby generating exposed DNA ends; (c) labeling at least a portion of the exposed DNA ends; (d) ligating the labeled exposed DNA ends to form labeled paired ends; (e) sequencing at least a recognizable portion of the labeled paired ends to generate a plurality of read-pairs; (f) assigning each half of a read-pair to a common nucleic acid molecule of origin.

Disclosed herein are methods for meta-genomics assemblies, comprising: (a) collecting microbes from an environment; (b) obtaining a plurality of contigs from the microbes; (c) generating a plurality of read pairs from data produced by probing the physical layout of reconstituted chromatin; and (d) mapping the plurality of read pairs to the plurality of contigs thereby producing read-mapping data, wherein read pairs mapping to different contigs indicate that the different contigs originate from a common individual.

Disclosed herein are methods for detecting a bacterial infectious agent, comprising: (a) obtaining a plurality of contigs from the bacterial infectious agent; (b) generating a plurality of read pairs from data produced by probing the physical layout of reconstituted chromatin; (c) mapping the plurality of read pairs to the plurality of contigs thereby producing read-mapping data; (d) arranging the contigs using the read-mapping data to assemble the contigs into a genome assembly; and (e) using the genome assembly to determine presence of the bacterial infectious agent.

Disclosed herein are methods of obtaining genomic sequence information from an organism comprising: (a) obtaining a stabilized sample from said organism; (b) treating the stabilized sample to cleave double-stranded DNA in the stabilized sample, thereby generating exposed DNA ends; (c) tagging at least a portion of the exposed DNA ends to generate tagged DNA segments; (d) sequencing at least a recognizable portion of the tagged DNA segment and thereby obtaining tagged sequences; and (e) mapping said tagged sequences to generate genomic sequence information of said organism, wherein said genomic sequence information covers at least 75% of the genome of said organism.

Disclosed herein are methods of analyzing a sample, comprising: (a) obtaining a stabilized sample comprising nucleic acids from a plurality of organisms; (b) treating the stabilized sample to cleave double-stranded DNA in the stabilized sample, thereby producing exposed DNA ends; (c) ligating said exposed DNA ends to form paired ends; (d) sequencing across said paired ends to generate a plurality of paired sequence reads; and (e) assigning each half of a paired sequence read of said plurality of sequence reads to a common organism of origin.

Disclosed herein are methods of assaying for nucleic acid molecular diversity in a heterogeneous sample, comprising a) obtaining a stabilized nucleic acid sample comprising a diverse plurality of nucleic acids stabilized such that, for at least one member of the plurality, a first nucleic acid segment and a second nucleic acid segment are held together independent of their common phosphodiester backbone, wherein said phosphodiester backbone is cleaved between said first nucleic acid segment and said second nucleic acid segment; b) tagging said first nucleic acid segment and said second nucleic acid segment such that said first nucleic acid segment and said second nucleic acid segment are identifiable as arising from a common nucleic acid of the diverse plurality of nucleic acids; c) sequencing at least an identifiable portion of said first nucleic acid segment and its tag, and an identifiable portion of said second nucleic acid segment and its tag; d) assigning said first nucleic acid segment and said second nucleic acid segment to a scaffold corresponding to said tag; e) such that a plurality of segments of said diverse plurality of nucleic acids are assigned to at least one scaffold; and f) determining a number corresponding to how many scaffolds are generated; wherein the number of scaffolds generated corresponds to the nucleic acid molecular diversity of the heterogeneous sample. In some aspects, tagging said first nucleic acid segment and said second nucleic acid segment comprises adding a first oligo to the first nucleic acid segment and adding a second oligo to the second segment, said first oligo and said second oligo sharing a common sequence. In some aspects, nucleic acid segments having said common oligo sequence are assigned to a common scaffold. In some aspects, the method further comprises mapping said identifiable portion of said first nucleic acid segment to a contig dataset, and including any matching contig of said contig data set into said common scaffold. In some aspects, the contig data set is concurrently generated. In some aspects, the contig dataset is obtained from a database. In some aspects, tagging said first nucleic acid segment and said second nucleic acid segment comprises ligating said first nucleic acid segment to said second nucleic acid segment, and wherein said first nucleic acid segment and said second nucleic acid segment are assigned to a common scaffold. In some aspects, the method further comprises mapping said identifiable portion of said first nucleic acid segment to a contig dataset, and including any matching contig of said contig data set into said common scaffold. In some aspects, the contig data set is concurrently generated. In some aspects, the contig dataset is obtained from a database. In some aspects, the heterogeneous sample comprises a plurality of allelic variants. In some aspects, the number of allelic variants is greater than the number of scaffolds. In some aspects, the number of allelic variants is equal to the number of number of scaffolds generated. In some aspects, said phosphodiester backbone is cleaved subsequent to said obtaining a stabilized sample. In some aspects, said stabilized sample is contacted to a crosslinking agent. In some aspects, said stabilized sample is an FFPE sample. In some aspects, the method further comprises contacting said heterogeneous sample to a reverse transcriptase. In some aspects, the method further comprises searching at least one of said scaffold against a nucleic acid sequence database. In some aspects, the method further comprises categorizing said scaffold as novel if nucleic acid sequence uniquely mapping to said scaffold is absent from said database. In some aspects, the method further comprises categorizing said scaffold as corresponding to a sample condition when a plurality of samples correlating to said condition have said scaffold and if a plurality of samples lacking said condition lack said sample In some aspects, the heterogeneous sample comprises nucleic acids mapping to at least two individuals of a common species. In some aspects, the heterogeneous sample comprises nucleic acids mapping to at least three individuals of a common species. In some aspects, the heterogeneous sample comprises nucleic acids mapping to at least two species In some aspects, the heterogeneous sample comprises nucleic acids mapping to at least three species. In some aspects, the heterogeneous sample comprises nucleic acids mapping to at least four species. In some aspects, the sequence reads assemble into at least two nucleic acid scaffolds without reference to exogenous sequence information. In some aspects, the sequence reads assemble into at least three nucleic acid scaffolds without reference to exogenous sequence information. In some aspects, the sequence reads assemble into at least two nucleic acid scaffolds, such that at least 50% of a first genome and at least 50% of a second genome are represented in said at least two nucleic acid scaffolds. In some aspects, the sequence reads assemble into at least two nucleic acid scaffolds, such that at least 60% of a first genome and at least 60% of a second genome are represented in said at least two nucleic acid scaffolds. In some aspects, the sequence reads assemble into at least two nucleic acid scaffolds, such that at least 70% of a first genome and at least 70% of a second genome are represented in said at least two nucleic acid scaffolds. In some aspects, the sequence reads assemble into at least two nucleic acid scaffolds, such that at least 80% of a first genome and at least 80% of a second genome are represented in said at least two nucleic acid scaffolds. In some aspects, the method comprises using SPRI beads. In some aspects, the stabilized sample comprises no greater than about 5 micrograms of DNA.

INCORPORATION BY REFERENCE

All publications, patents, and patent applications mentioned in this specification are herein incorporated by reference to the same extent as if each individual publication, patent, or patent application was specifically and individually indicated to be incorporated by reference. All publications, patents, and patent applications mentioned in this specification are herein incorporated by reference in its entirety as well as any references cited therein.

BRIEF DESCRIPTION OF THE DRAWINGS

The novel features of the disclosure are set forth with particularity in the appended claims. A better understanding of the features and advantages of the disclosure will be obtained by reference to the following detailed description that sets forth illustrative embodiments, in which the principles of the disclosure are utilized, and the accompanying drawings of which:

(FIG. 2A) demonstrates where DNA is cross-linked and processed to created biotinylated junction fragments for sequencing; and (FIG. 2B-2D) provide contact map data on human chr14 for a variety of restriction enzymes. As shown, most contacts are local along the chromosome.

FIGS. 3A-C provides methods of the disclosure using chromatin capture sequence data to assist genome assembly: (FIG. 3A) illustrates where DNA is cross-linked and processed using a chromatin capture based protocol; (FIG. 3B) demonstrates where read-pair data is mapped to assembled contigs, generated from random shotgun sequencing and assembly; and (FIG. 3C) illustrates that after filtering and weighting, an adjacency matrix summarizing all inter-contig read pair data can be constructed. This matrix can be re-ordered to indicate the correct assembly path. As shown, most of the read pairs will map within a contig. From which, it is possible to learn the distribution of contact distances (e.g., see FIG. 6). Read pairs that map to different contigs provide data about which contigs are adjacent in a correct genome assembly.

FIGS. 5A-B provides an illustration of the ambiguities that arise in genomic assembly and alignment from repetitive regions in the genome. (FIG. 5A) Uncertainty in linkage results from read pairs that cannot bridge repetitive regions. (FIG. 5B) Uncertainty in placement of segment because read pairs cannot span bordering repeats.

FIG. 12B shows an exemplary schematic of two pipelines for sample preparation for metagenomic analysis.

FIG. 12C shows an exemplary schematic of scaffolding techniques.

FIG. 24 depicts a single scaffold comprising 89% of the 8.67 Mb *S. coelicolor* genome.

DETAILED DESCRIPTION

Figure 1:
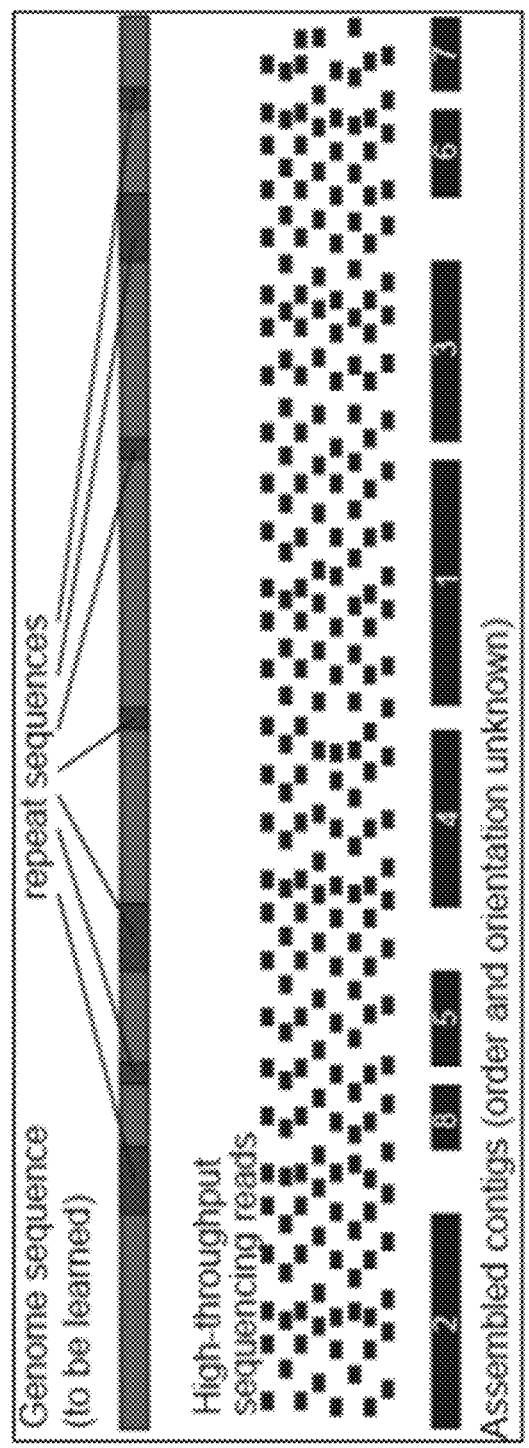
FIG. 1 presents an illustration of genome assembly using high-throughput sequencing reads. The genome to be assembled is shown (top). Typically, genomes have many repeat sequences that are difficult to assemble. Random, high-throughput sequence data from genomes (middle) are collected and assembled into "contigs" in regions that are unique in the genome (bottom). Contig assembly generally stops at the many repeat sequences. The final output is a set of thousands of contigs whose order and orientation relative to one another are not known. In the figure, they are arbitrarily numbered from longest to shortest.
Figure 2A:
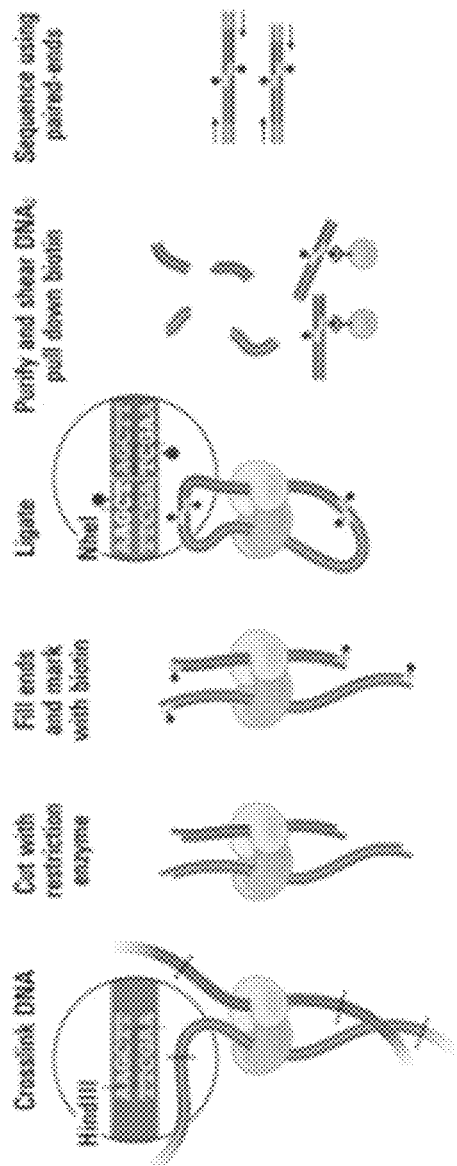
FIGS. 2A-D illustrates a chromatin capture based protocol of the disclosure.
Figure 2B:
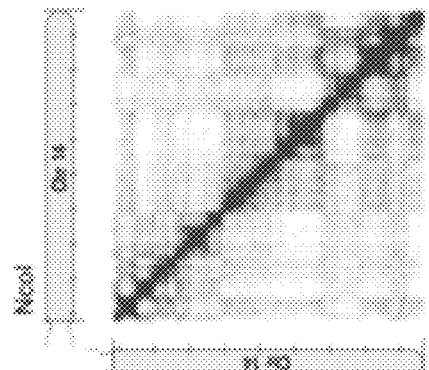
Figure 2C:
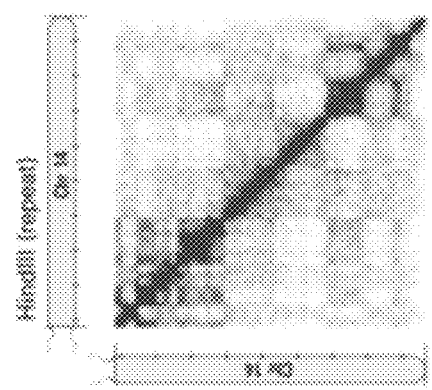
Figure 2D:
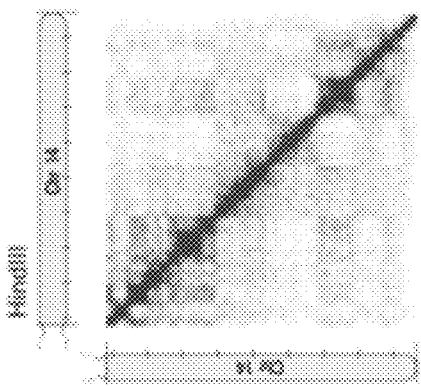

As used herein and in the appended claims, the singular forms "a," "and," and "the" include plural referents unless the context clearly dictates otherwise. Thus, for example, reference to "contig" includes a plurality of such contigs and reference to "probing the physical layout of chromosomes" includes reference to one or more methods for probing the physical layout of chromosomes and equivalents thereof known to those skilled in the art, and so forth.

Also, the use of "and" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

The term "about" as used herein to describe a number, unless otherwise specified, refers to a range of values including that number plus or minus 10% of that number.

The term "read," "sequence read," or "sequencing read" as used herein, refers to the sequence of a fragment or segment of DNA or RNA nucleic acid that is determined in a single reaction or run of a sequencing reaction.

The term "contigs" as used herein, refers to contiguous regions of DNA sequence. "Contigs" can be determined by any number methods known in the art, such as, by comparing sequencing reads for overlapping sequences, and/or by comparing sequencing reads against a databases of known sequences in order to identify which sequencing reads have a high probability of being contiguous.

The terms "polynucleotide," "nucleotide," "nucleic acid" and "oligonucleotide" are often used interchangeably. They generally refer to a polymeric form of nucleotides of any length, either deoxyribonucleotides or ribonucleotides, or analogs thereof. Polynucleotides comprise base monomers that are joined at their ribose backbones by phosphodiester bonds. Polynucleotides may have any three-dimensional structure, and may perform any function, known or unknown. The following are non-limiting examples of polynucleotides: coding or non-coding regions of a gene or gene fragment, intergenic DNA, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), small nucleolar RNA, ribozymes, complementary DNA (cDNA), which is a DNA representation of mRNA, usually obtained by reverse transcription of messenger RNA (mRNA) or by amplification; DNA molecules produced synthetically or by amplification, genomic DNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. Generally, an oligonucleotide comprises only a few bases, while a polynucleotide can comprise any number but is generally longer, while a nucleic acid can refer to a polymer of any length, up to and including the length of a chromosome or an entire genome. Also, the term nucleic acid is often used collectively, such that a nucleic acid sample does not necessarily refer to a single nucleic acid molecule; rather it may refer to a sample comprising a plurality of nucleic acid molecules. The term nucleic acid can encompass double- or triple-stranded nucleic acids, as well as single-stranded molecules. In double- or triple-stranded nucleic acids, the nucleic acid strands need not be coextensive, e.g., a double-stranded nucleic acid need not be double-stranded along the entire length of both strands. The term nucleic acid can encompass any chemical modification thereof, such as by methylation and/or by capping. Nucleic acid modifications can include addition of chemical groups that incorporate additional charge, polarizability, hydrogen bonding, electrostatic interaction, and functionality to the individual nucleic acid bases or to the nucleic acid as a whole. Such modifications may include base modifications such as 2'-position sugar modifications, 5-position pyrimidine modifications, 8-position purine modifications, modifications at cytosine exocyclic amines, substitutions of 5-bromo-uracil, backbone modifications, unusual base pairing combinations such as the isobases isocytidine and isoguanidine, and the like.

The term "subject" as used herein can refer to any eukaryotic or prokaryotic organism.

The term "naked DNA" as used herein can refer to DNA that is substantially free of complexed DNA binding proteins. For example, it can refer to DNA complexed with less than about 10%, about 5%, or about 1% of the endogenous proteins found in the cell nucleus, or less than about 10%, about 5%, or about 1% of the endogenous DNA-binding proteins regularly bound to the nucleic acid in vivo, or less than about 10%, about 5%, or about 1% of an exogenously added nucleic acid binding protein or other nucleic acid binding moiety, such as a nanoparticle. In some cases, naked DNA refers to DNA that is not complexed to DNA binding proteins.

The terms "polypeptide" and "protein" are often used interchangeably and generally refer to a polymeric form of amino acids, or analogs thereof bound by polypeptide bonds. Polypeptides and proteins can be polymers of any length. Polypeptides and proteins can have any three-dimensional structure, and may perform any function, known or unknown. Polypeptides and proteins can comprise modifications, including phosphorylation, lipidation, prenylation, sulfation, hydroxylation, acetylation, formation of disulfide bonds, and the like. In some cases, "protein" refers to a polypeptide having a known function or known to occur naturally in a biological system, but this distinction is not always adhered to in the art.

As used herein, nucleic acids are "stabilized" if they are bound by a binding moiety or binding moieties such that separate segments of a nucleic acid are held in a single complex independent of their common phosphodiester backbone. Stabilized nucleic acids in complexes remain bound independent of their phosphodiester backbones, such that treatment with a restriction endonuclease does not result in disintegration of the complex, and internal double-stranded DNA breaks are accessible without the complex losing its integrity.

Alternately or in combination, nucleic acid complexes comprising nucleic acids and nucleic acid binding moieties are "stabilized" by treatment that increases their binding or renders them otherwise resistant to degradation or dissolution. An example of stabilizing a complex comprises treating the complex with a fixative such as formaldehyde or psorlen, or treating with UV light so as to induce cross-linking between nucleic acids and binding moieties, or among binding moieties, such that the complex or complexes are resistant to degradation or dissolution, for example following restriction endonuclease treatment or treatment to induce nucleic acid shearing.

The term "scaffold" as used herein generally refers to contigs separated by gaps of known length but unknown sequence or separated by unknown length but known to reside on a single molecule, or ordered and oriented sets of contigs that are linked to one another by mate pairs of sequencing reads. In cases where contigs are separated by gaps of known length, the sequence of the gaps may be determined by various methods, including PCR amplification followed by sequencing (for smaller gaps) and bacterial artificial chromosome (BAC) cloning methods followed by sequencing (for larger gaps).

The term "stabilized sample" as used herein refers to a nucleic acid that is stabilized in relation to an association molecule via intermolecular interactions such that the nucleic acid and association molecule are bound in a manner that is resistant to molecular manipulations such as restriction endonuclease treatment, DNA shearing, labeling of nucleic acid breaks, or ligation. Nucleic acids known in the art include but are not limited to DNA and RNA, and derivatives thereof. The intermolecular interactions can be covalent or non-covalent. Exemplary methods of covalent binding include but are not limited to crosslinking techniques, coupling reactions, or other methods that are known to one of ordinary skill in the art. Exemplary methods of noncovalent interactions involve binding via ionic interactions, hydrogen bonding, halogen bonding, Van der Waals forces (e.g. dipole interactions), π-effects (e.g. π-π interactions, cation-π and anion-π interactions, polar π interactions, etc.), hydrophobic effects, and other noncovalent interactions that are known to one of ordinary skill in the art. Examples of association molecules include, but are not limited to, chromosomal proteins (e.g. histones), transposases, and any nanoparticle that is known to covalently or non-covalently interact with nucleic acids.

The term "heterogeneous sample" as used herein refers a biological sample comprising a diverse population of nucleic acids (e.g. DNA, RNA), cells, organisms, or other biological molecules. In many cases the nucleic acids originate from one than one organism. For example, a heterogeneous nucleic acid sample can comprise at least about 1000, 2000, 3000, 4000, 5000, 6000, 7000, 8000, 9000, 10,000, 20,000, 50,000, 100,000, 200,000, 500,000, 1,000,000, 2,000,000, 5,000,000, 10,000,000, or more DNA molecules. Further, each of the DNA molecules can comprise the full or partial genome of at least one or at least two or more than two organisms, such that the heterogeneous nucleic sample can comprise the full or partial genome of at least about 1000, 2000, 3000, 4000, 5000, 6000, 7000, 8000, 9000, 10,000, 20,000, 50,000, 100,000, 200,000, 500,000, 1,000, 000, 2,000,000, 5,000,000, 10,000,000, or more different organisms. Examples of heterogeneous samples are those obtained from a variety of sources, including but not limited to a subject's blood, sweat, urine, stool, or skin; or an environmental source (e.g. soil, seawater); a food source; a waste site such as a garbage dump, sewer or public toilet; or a trash can.

A "partial genome" of an organism can comprise at least about 10%, 20%, 30%, 40%, 50%, 60%, 70%, 80%, 90%, 95%, 99% or more the entire genome of an organism, or can comprise a sequence data set comprising at least about 10%, 20%, 30%, 40%, 50%, 60%, 70%, 80%, 90%, 95%, 99% or more of the sequence information of the entire genome.

The term "reconstituted chromatin" as used herein can refer to forming chromatin formed by complexing isolated nuclear proteins to naked DNA.

The term "tagged sequence" as used herein can refer to a DNA sequence that comprises an added sequence that can be used to identify or associate the sequence for analytical purposes. For example, a group of tagged sequences that share the same tag can be binned together. In some examples, the tagged sequences that are in the same bin are further assigned a common phase or are assigned to a common molecule of origin. Exemplary methods of "tagging" include but are not limited to introducing a tag using an enzyme (e.g. transposase, ligase), and/or covalently linking DNA segments to each other to obtain read-pairs. A tagged sequence is 'sequenced' by, for example, obtaining end reads wherein one end read comprises tag sequence and the other end read comprises sequence of the segment to which the tag has been added. In some cases the entire tag, the tag-segment junction, and the entire segment are sequenced. However, this is not always necessary for tagging and sequencing to be effective. On the contrary, in many cases, sequencing of an identifiable portion of the tag end and an identifiable portion of the segment end is sufficient to effect 'sequencing of the tagged segment,' particularly but not exclusively when contig information is available, such as previously generated or concurrently generated contig information. Similarly, a paired-end tag sequence is 'sequenced' in some cases by obtaining end reads where each end read comprises recognizable sequence of a ligated segment. Paired end fragments may be completely sequenced such that the junction sequence is obtained, but this is not always necessary for paired end tagging and sequencing to be effective. Accordingly, as used herein, 'sequencing a tagged segment' or 'sequencing a paired-end read' need not comprise obtaining a complete end-to-end sequence of the ligated molecule. So long as identifiable sequences of either end of the molecule be obtained such that the identity of the nucleic acids joined to form the ligated molecule are obtained, the joined fragment may be referred to as having been 'sequenced'. In some cases, the sequencing comprises end-to-end sequencing that spans the ligation junction. In some cases the sequencing comprises generating reads from either end of the joined molecule.

The term "read pair" or "read-pair" as used herein can refer to two or more elements that are linked to provide sequence information. In some cases, the number of read-pairs can refer to the number of mappable read-pairs. In other cases, the number of read-pairs can refer to the total number of generated read-pairs.

The terms "bind", "binding", "associate", "association", or "associating", or derivatives thereof, as used herein refers to stabilizing a molecule to another molecule via intermolecular interactions. The intermolecular interactions can be covalent or non-covalent in nature. Exemplary methods of covalent binding include but are not limited to crosslinking techniques, coupling reactions, or other methods that are known to one of ordinary skill in the art. Exemplary methods of noncovalent interactions include ionic interactions, hydrogen bonding, halogen bonding, Van der Waals forces (e.g. dipole interactions), π-effects (e.g. π-π interactions, cation-π and anion-π interactions, polar π interactions, etc.), hydrophobic effects, and other noncovalent interactions that are known to one of ordinary skill in the art.

The term "immobilizing" or "immobilization" as used herein refers to stabilizing a molecule or complex in relation to an object. For example, a DNA complex is immobilized to a solid support when the DNA complex is stabilized in relation to the solid support. In some cases, the immobilized DNA complex will remain stabilized in relation to the solid support even when subjected to various wash steps.

Unless defined otherwise, all technical and scientific terms used herein have the same meaning as commonly understood to one of ordinary skill in the art to which this disclosure belongs. Although any methods and reagents similar or equivalent to those described herein can be used in the practice of the disclosed methods and compositions, the exemplary methods and materials are now described.

The disclosure provides methods for generating extremely long-range read pairs and to utilize that data for the advancement of all of the aforementioned pursuits. In some embodiments, the disclosure provides methods that produce a highly contiguous and accurate human genomic assembly with only ~300 million read pairs. In other embodiments, the disclosure provides methods that phase 90% or more of heterozygous variants in a human genome with 99% or greater accuracy. Further, the range of the read pairs generated by the disclosure can be extended to span much larger genomic distances. The assembly is produced from a standard shotgun library in addition to an extremely long-range read pair library. In yet other embodiments, the disclosure provides software that is capable of utilizing both of these sets of sequencing data. Phased variants are produced with a single long-range read pair library, the reads from which are mapped to a reference genome and then used to assign variants to one of the individual's two parental chromosomes. Finally, the disclosure provides for the extraction of even larger DNA fragments using known techniques, so as to generate exceptionally long reads.

The mechanism by which these repeats obstruct assembly and alignment processes is fairly straightforward and is ultimately a consequence of ambiguity (FIG. 5). In the case of large repetitive regions, the difficulty is one of span. If a read or read pair is not long enough to span a repetitive region, one cannot confidently connect regions bordering the repetitive element. In the case of smaller repetitive elements, the problem is primarily placement. When a region is flanked by two repetitive elements that are common in the genome, determining its exact placement becomes difficult if not impossible due to the similarity of the flanking elements to all others of their class. In both cases it is the lack of distinguishing information in the repeat that makes the identification, and thus placement of a particular repeat challenging. What is needed is the ability to experimentally establish connection between unique segments hemmed or separated by repetitive regions.

The methods of the disclosure greatly advance the field of genomics by overcoming the substantial barriers posed by these repetitive regions, and can thereby enable important advances in many domains of genomic analysis. To perform a de novo assembly with previous technologies, one must either settle for an assembly fragmented into many small scaffolds or commit substantial time and resources to producing a large-insert library or using other approaches to generate a more contiguous assembly. Such approaches may include acquiring very deep sequencing coverage, constructing BAC or fosmid libraries, optical mapping, or, most likely, some combination of these and other techniques. The intense resource and time requirements put such approaches out of reach for most small labs and prevents studying non-model organisms. Since the methods described herein can produce very long-range read pairs, de novo assembly can be achieved with a single sequencing run. This would cut assembly costs by orders of magnitude and shorten the time required from months or years to weeks. In some cases, the methods disclosed herein allow for generating a plurality of read-pairs in less than 14 days, less than 13 days, less than 12 days, less than 11 days, less than 10 days, less than 9 days, less than 8 days, less than 7 days, less than 6 days, less than 5 days, less than 4 days, or in a range between any two of foregoing specified time periods. For example, the methods can allow for generating a plurality of read-pairs in about 10 days to 14 days. Building genomes for even the most niche of organisms would become routine, phylogenetic analyses would suffer no lack of comparisons, and projects such as Genome 10 k could be realized.

Similarly, structural and phasing analyses for medical purposes also remain challenging. There is astounding heterogeneity among cancers, individuals with the same type of cancer, or even within the same tumor. Teasing out the causative from consequential effects requires very high precision and throughput at a low per-sample cost. In the domain of personalized medicine, one of the gold standards of genomic care is a sequenced genome with all variants thoroughly characterized and phased, including large and small structural rearrangements and novel mutations. To achieve this with previous technologies demands effort akin to that required for a de novo assembly, which is currently too expensive and laborious to be a routine medical procedure. The disclosed methods can rapidly produce complete, accurate genomes at low cost and can thereby yield many highly sought capabilities in the study and treatment of human disease.

Finally, applying the methods disclosed herein to phasing can combine the convenience of statistical approaches with the accuracy of familial analysis, providing savings—money, labor, and samples—than using either method alone. De novo variant phasing, a highly desirable phasing analysis that is prohibitive with previous technologies, can be performed readily using the methods disclosed herein. This is particularly important as the vast majority of human variation is rare (less than 5% minor allele frequency). Phasing information is valuable for population genetic studies that gain significant advantages from networks of highly connected haplotypes (collections of variants assigned to a single chromosome), relative to unlinked genotypes. Haplotype information can enable higher resolution studies of historical changes in population size, migrations, and exchange between subpopulations, and allows us to trace specific variants back to particular parents and grandparents. This in turn clarifies the genetic transmission of variants associated with disease, and the interplay between variants when brought together in a single individual. The methods of the disclosure can eventually enable the preparation, sequencing, and analysis of extremely long range read pair (XLRP) libraries.

In some embodiments of the disclosure, a tissue or a DNA sample from a subject can be provided and the method can return an assembled genome, alignments with called variants (including large structural variants), phased variant calls, or any additional analyses. In other embodiments, the methods disclosed herein can provide XLRP libraries directly for the individual.

In various embodiments of the disclosure, the methods disclosed herein can generate extremely long-range read pairs separated by large distances. The upper limit of this distance may be improved by the ability to collect DNA samples of large size. In some cases, the read pairs can span up to 50, 60, 70, 80, 90, 100, 125, 150, 175, 200, 225, 250, 300, 400, 500, 600, 700, 800, 900, 1000, 1500, 2000, 2500, 3000, 4000, 5000 kbp or more in genomic distance. In some examples, the read pairs can span up to 500 kbp in genomic distance. In other examples, the read pairs can span up to 2000 kbp in genomic distance. The methods disclosed herein can integrate and build upon standard techniques in molecular biology, and are further well-suited for increases in efficiency, specificity, and genomic coverage. In some cases, the read pairs can be generated in less than about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 60, or 90 days. In some examples, the read pairs can be generated in less than about 14 days. In some examples, the read pairs can be generated in less about 10 days. In some cases, the methods of the present disclosure can provide greater than about 5%, about 10%, about 15%, about 20%, about 30%, about 40%, about 50%, about 60%, about 70%, about 80%, about 90%, about 95%, about 99%, or about 100% of the read pairs with at least about 50%, about 60%, about 70%, about 80%, about 90%, about 95%, about 99%, or about 100% accuracy in correctly ordering and/or orientating the plurality of contigs. For example, the methods can provide about 90 to 100% accuracy in correctly ordering and/or orientating the plurality of contigs.

In other embodiments, the methods disclosed herein can be used with currently employed sequencing technology. For example, the methods can be used in combination with well-tested and/or widely deployed sequencing instruments. In some embodiments, the methods disclosed herein can be used with technologies and approaches derived from currently employed sequencing technology.

The methods of the disclosure dramatically simplify de novo genomic assembly for a wide range of organisms. Using previous technologies, such assemblies are currently limited by the short inserts of economical mate-pair libraries. While it may be possible to generate read pairs at genomic distances up to the 40-50 kbp accessible with fosmids, these are expensive, cumbersome, and too short to span the longest repetitive stretches, including those within centromeres, which, in humans, range in size from 300 kbp to 5 Mbp. The methods disclosed herein can provide read pairs capable of spanning large distances (e.g., megabases or longer) and thereby overcome these scaffold integrity challenges. Accordingly, producing chromosome-level assemblies can be routine by utilizing the methods of the disclosure. More laborious avenues for assembly—currently costing research labs incredible amounts of time and money, and prohibiting expansive genomic catalogs—may become unnecessary, freeing up resources for more meaningful analyses. Similarly, the acquisition of long-range phasing information can provide tremendous additional power to population genomic, phylogenetic, and disease studies. The methods disclosed herein enable accurate phasing for large numbers of individuals, thus extending the breadth and depth of our ability to probe genomes at the population and deep-time levels.

In the realm of personalized medicine, the XLRP read pairs generated from the methods disclosed herein represents a meaningful advance toward accurate, low-cost, phased, and rapidly produced personal genomes. Current methods are insufficient in their ability to phase variants at long distances, thereby preventing the characterization of the phenotypic impact of compound heterozygous genotypes. Additionally, structural variants of substantial interest for genomic diseases are difficult to accurately identify and characterize with current techniques due to their large size in comparison to reads and read pair inserts used to study them. Read pairs spanning tens of kilobases to megabases or longer can help alleviate this difficulty, thereby allowing for highly parallel and personalized analyses of structural variation.

Basic evolutionary and biomedical research is being driven by technological advances in high-throughput sequencing. Whereas whole genome sequencing and assembly used to be the provenance of large genome sequencing centers, commercially available sequencers are now inexpensive enough that most research universities have one or several of these machines. It is now relatively inexpensive to generate massive quantities of DNA sequence data. However, it remains difficult in theory and in practice to produce high-quality, highly contiguous genome sequences with current technology. Furthermore, because most organisms that one would care to analyze, including humans, are diploid, each individual has two haploid copies of the genome. At sites of heterozygosity (e.g., where the allele given by the mother differs from the allele given by the father), it is difficult to know which sets of alleles came from which parent (known as haplotype phasing). This information can be used for performing a number of evolutionary and biomedical studies such as disease and trait association studies.

In various embodiments, the disclosure provides methods for genome assembly that combine technologies for DNA preparation with paired-end sequencing for high-throughput discovery of short, intermediate and long term connections within a given genome. The disclosure further provides methods using these connections to assist in genome assembly, for haplotype phasing, and/or for metagenomic studies.

While the methods presented herein can be used to determine the assembly of a subject's genome, it should also be understood that the methods presented herein can also be used to determine the assembly of portions of the subject's genome such as chromosomes, or the assembly of the subject's chromatin of varying lengths.

In some embodiments, the disclosure provides for one or more methods disclosed herein that comprise the step of generating a plurality of contigs from sequencing fragments of target DNA obtained from a subject. Long stretches of target DNA can be fragmented by cutting the DNA with one or more nuclease enzymes (e.g., restriction enzymes), shearing the DNA, or a combination thereof. The resulting fragments can be sequenced using high throughput sequencing methods to obtain a plurality of sequencing reads. Examples of high throughput sequencing methods which can be used with the methods of the disclosure include, but are not limited to, 454 pyrosequencing methods developed Roche Diagnostics, "clusters" sequencing methods developed by Illumina, SOLiD and Ion semiconductor sequencing methods developed by Life Technologies, and DNA nanoball sequencing methods developed by Complete Genomics. Overlapping ends of different sequencing reads can then be assembled to form a contig. Alternatively, fragmented target DNA can be cloned into vectors. Cells or organisms are then transfected with the DNA vectors to form a library. After replicating the transfected cells or organisms, the vectors are isolated and sequenced to generate a plurality of sequencing reads. The overlapping ends of different sequencing reads can then be assembled to form a contig.

As shown in FIG. 1, genome assembly, especially with high-throughput sequencing technology can be problematic. Often, the assembly consists of thousands or tens of thousands of short contigs. The order and orientation of these contigs is generally unknown, limiting the usefulness of the genome assembly. Technologies exist to order and orient these scaffolds, but they are generally expensive, labor intensive, and often fail in discovering very long range interactions.

Samples comprising target DNA used to generate contigs can be obtained from a subject by any number of means, including by taking bodily fluids (e.g., blood, urine, serum, lymph, saliva, anal and vaginal secretions, perspiration and semen), taking tissue, or by collecting cells/organisms. The sample obtained may be comprised of a single type of cell/organism, or may be comprised multiple types of cells/organisms. The DNA can be extracted and prepared from the subject's sample. For example, the sample may be treated to lyse a cell comprising the polynucleotide, using known lysis buffers, sonication techniques, electroporation, and the like. The target DNA may be further purified to remove contaminants, such as proteins, by using alcohol extractions, cesium gradients, and/or column chromatography.

In other embodiments of the disclosure, a method to extract very high molecular weight DNA is provided. In some cases, the data from an XLRP library can be improved by increasing the fragment size of the input DNA. In some examples, extracting megabase-sized fragments of DNA from a cell can produce read pairs separated by megabases in the genome. In some cases, the produced read-pairs can provide sequence information over a span of greater than about 10 kB, about 50 kB, about 100 kB, about 200 kB, about 500 kB, about 1 Mb, about 2 Mb, about 5 Mb, about 10 Mb, or about 100 Mb. In some examples, the read-pairs can provide sequence information over a span of greater than about 500 kB. In some examples, the read-pairs can provide sequence information over a span of greater than about 2 Mb. In some cases, the very high molecular weight DNA can be extracted by very gentle cell lysis (Teague, B. et al. (2010) *Proc. Nat. Acad. Sci. USA* 107(24), 10848-53) and agarose plugs (Schwartz, D. C., & Cantor, C. R. (1984) *Cell*, 37(1), 67-75). In other cases, commercially available machines that can purify DNA molecules up to megabases in length can be used to extract very high molecular weight DNA.

In various embodiments, the disclosure provides for one or more methods disclosed herein that comprise the step of probing the physical layout of chromosomes within living cells. Examples of techniques to probe the physical layout of chromosomes through sequencing include the "C" family of techniques, such as chromosome conformation capture ("3C"), circularized chromosome conformation capture ("4C"), carbon-copy chromosome capture ("5C"), and other chromatin capture based methods; and ChIP based methods, such as ChIP-loop, ChIP-PET. These techniques utilize the fixation of chromatin in live cells to cement spatial relationships in the nucleus. Subsequent processing and sequencing of the products allows a researcher to recover a matrix of proximate associations among genomic regions. With further analysis these associations can be used to produce a three-dimensional geometric map of the chromosomes as they are physically arranged in live nuclei. Such techniques describe the discrete spatial organization of chromosomes in live cells, and provide an accurate view of the functional interactions among chromosomal loci. One issue that plagued these functional studies was the presence of non-specific interactions, associations present in the data that are attributable to nothing more than chromosomal proximity. In the disclosure, these nonspecific intrachromosomal interactions are captured by the methods presented herein so as to provide valuable information for assembly.

In some embodiments, the intrachromosomal interactions correlate with chromosomal connectivity. In some cases, the intrachromosomal data can aid genomic assembly. In some cases, the chromatin is reconstructed in vitro. This can be advantageous because chromatin—particularly histones, the major protein component of chromatin—is important for fixation under the most common "C" family of techniques for detecting chromatin conformation and structure through sequencing: 3C, 4C, 5C, and chromatin capture. Chromatin is highly non-specific in terms of sequence and will generally assemble uniformly across the genome. In some cases, the genomes of species that do not use chromatin can be assembled on a reconstructed chromatin and thereby extend the horizon for the disclosure to all domains of life.

A chromatin conformation capture technique is summarized in FIG. 2. In brief, cross-links are created between genome regions that are in close physical proximity. Cross-linking of proteins (such as histones) to the DNA molecule, e.g. genomic DNA, within chromatin can be accomplished according to a suitable method described in further detail elsewhere herein or otherwise known in the art. In some cases, two or more nucleotide sequences or, more strictly speaking, two or more nucleic acid segments, can be cross-linked via proteins bound to one or more nucleotide sequences. One approach is to expose the chromatin to ultraviolet irradiation (Gilmour et al., Proc. Nat'l. Acad. Sci. USA 81:4275-4279, 1984). Crosslinking of polynucleotide segments may also be performed utilizing other approaches, such as chemical or physical (e.g. optical) crosslinking. Suitable chemical crosslinking agents include, but are not limited to, formaldehyde and psoralen (Solomon et al., Proc. NatL. Acad. Sci. USA 82:6470-6474, 1985; Solomon et al., Cell 53:937-947, 1988). For example, cross-linking can be performed by adding 2% formaldehyde to a mixture comprising the DNA molecule and chromatin proteins. Other examples of agents that can be used to cross-link DNA include, but are not limited to, UV light, mitomycin C, nitrogen mustard, melphalan, 1,3-butadiene diepoxide, cis diaminedichloroplatinum(II) and cyclophosphamide. Suitably, the cross-linking agent will form cross-links that bridge relatively short distances—such as about 2 Å—thereby selecting intimate interactions that can be reversed.

In some embodiments, the DNA molecule may be immunoprecipitated prior to or after crosslinking. In some cases, the DNA molecule can be fragmented. Fragments may be contacted with a binding partner, such as an antibody that specifically recognizes and binds to acetylated histones, e.g., H3. Examples of such antibodies include, but are not limited to, Anti Acetyl ated Histone H3, available from Upstate Biotechnology, Lake Placid, N.Y. The polynucleotides from the immunoprecipitate can subsequently be collected from the immunoprecipitate. Prior to fragmenting the chromatin, the acetylated histones can be crosslinked to adjacent polynucleotide sequences.

In certain embodiments, the DNA molecule is bound to a plurality of association molecules, wherein the association molecules are not covalently modified with an affinity label (e.g. biotin, streptavidin, avidin, polyhistidine, EDTA, etc.). In some cases, association molecules are isolated directly from an organism. In some examples, the association molecules comprise amino acids. In certain examples, the association molecules comprise polypeptides or proteins. In some examples, the association molecules comprise histone proteins. In various examples, the association molecules are from a different source than the DNA molecule. For example, the DNA molecule can be crosslinked to a plurality of histones, wherein said histones are not covalently modified with an affinity label. In yet further cases, the association molecules are transposases. In some examples, the first DNA molecule is non-covalently bound to the association molecules. In other examples, the first DNA molecule is non-covalently bound to the association molecules. In some cases, the first DNA molecule is crosslinked to the association molecules. In some examples, the first DNA molecule is crosslinked to the association molecule using a fixative agent (e.g. formaldehyde). However, in certain cases, the DNA molecule comprises DNA segments, which can be modified with an affinity label. In some examples, the affinity label comprises biotin. In certain examples, the affinity label is a biotin-modified nucleoside triphosphate (dNTP). In some examples, the affinity label is affinity label is a biotin-modified deoxyribocytosine triphosphate (dCTP). In various cases, the affinity label is used to isolate or purify the DNA segments.

Using association molecules without covalent modification reduces the number of steps and/or enhance the efficiency of the methods provided in the present disclosure. In some cases, the DNA segments are washed for less than about 20, 18, 16, 15, 14, 13, 12, 11, 10, 9, 8, 7, 6, 5, 4, 3, 2, or 1 time(s) before the DNA segments are linked to form the linked DNA segments. In certain cases, the DNA segments are washed for less than about 15, 14, 13, 12, 11, 10, 9, 8, 7, 6, or 5 times before the DNA segments are linked to form the linked DNA segments. In some cases, the DNA segments are washed for less than about 12, 11, 10, 9, 8, 7, or 6 times before the DNA segments are linked to form the linked DNA segments. In some examples, the DNA segments are washed for less than about 10 times before the DNA segments are linked to form the linked DNA segments. In certain examples, the DNA segments are washed for less than about 8 times before the DNA segments are linked to form the linked DNA segments. In some examples, the DNA segments are washed for less than about 6 times before the DNA segments are linked to form the linked DNA segments.

In some embodiments, the bound DNA molecule is immobilized on a solid support. In some cases, the solid support is a bead. In some examples, the bead comprises a polymer. In some examples, the polymer is polystyrene. In other examples, the polymer is polyethylene glycol (PEG). In various examples, the bead is a magnetic bead. In some examples, the bead is a solid phase reversible immobilization (SPRI) bead. In other cases, the solid support is an array. In certain examples, the solid support is not covalently linked to an affinity label (e.g. biotin, streptavidin, avidin, polyhistidine, EDTA, or derivatives thereof). In various examples, the solid support is not linked to any polypeptide (e.g. streptavidin, avidin, polyhistidine tag, or derivatives thereof).

Rather than covalently modifying an association molecule to facilitate its isolation by binding to a surface of a solid support (such as a surface coated with streptavidin to bind biotin covalently attached to an association molecule, for example), in some cases solid supports are modified to bind association molecule in the absence of covalent modification. In some cases, this is direct binding of the association molecule to the surface of the association molecule. Alternately, in some cases binding is mediated by at least one constituent in a solvent. In some cases, a solid support is coated using a moiety that binds the association molecule directly. In some cases, the solid surface is coated using a moiety that binds the nucleic acid directly. Suitable coatings in various embodiments include polyamines, positively charged moieties, carboxy-groups, and negatively charged moieties.

In some cases, the crosslinked DNA molecule is treated to fractionate or sever polynucleotides in the mixture. Fractionation techniques are known in the art and include, for example, shearing techniques to generate smaller genomic fragments. Fragmentation can be accomplished using established methods for fragmenting chromatin, including, for example, sonication, shearing and/or the use of nucleases (e.g., restriction enzymes) or fragmentation enzymes (e.g., dsDNA fragmentase). The restriction enzyme can have a restriction site of 1, 2, 3, 4, 5, or 6 bases long. A nuclease can be an endonuclease, an exonuclease, or an endo-exonuclease. Examples of nucleases include but are not limited to DNase I and MNase. Examples of restriction enzymes include but are not limited to AatII, Acc65I, AccI, AciI, AclI, AcuI, AfeI, AflII, AflIII, AgeI, AhdI, AleI, AluI, AlwI, AlwNI, ApaI, ApaLI, ApeKI, ApoI, AscI, AseI, AsiSI, AvaI, AvaII, AvrII, BaeGI, BaeI, BamHI, BanI, BanII, BbsI, BbvCI, BbvI, BccI, BceAI, BcgI, BciVI, BclII, BfaI, BfuAI, BfuCI, BglI, BglII, BlpI, BmgBI, BmrI, BmtI, BpmI, BpuI0I, BpuEI, BsaAI, BsaBI, BsaHI, BsaI, BsaJI, BsaWI, BsaXI, BscRI, BscYI, BsgI, BsiEI, BsiHKAI, BsiWI, BsII, BsmAI, BsmBI, BsmFI, BsmI, BsoBI, Bsp1286I, BspCNI, BspDI, BspEI, BspHI, BspMI, BspQI, BsrBI, BsrDI, BsrFI, BsrGI, BsrI, BssHII, BssKI, BssSI, BstAPI, BstBI, BstEII, BstNI, BstUI, BstXI, BstYI, BstZ17I Bsu36I, BtgI, BtgZI, BtsCI, BtsI, Cac8I, ClaI, CspCI, CviAII, CviKI-I, CviQI, DdeI, DpnI, DpnII, DraI, DraIII, DrdI, EacI, EagI, EarI, EciI, Eco53kI, EcoNI, EcoO109I, EcoP15I, EcoRI, EcoRV, FatI, FauI, Fnu4HI, FokI, FseI, FspI, HaeII, HaeIII, HgaI, HhaI, HincII, HindIII, HinfI, HinPII, HpaI, HpaII, HphI, Hpy166II, Hpy188I, Hpy188III, Hpy99I, HpyAV, HpyCH4III, HpyCH4IV, HpyCH4V, KasI, KpnI, MboI, MboII, MfeI, MluI, MlyI, MmeI, MnII, MscI, MseI, MsII, MspAII, MspI, MwoI, NaeI, NarI, Nb.BbvCI, Nb.BsmI, Nb.BsrDI, Nb.BtsI, NciI, NcoI, NdeI, NgoMIV, NheI, NlaIII, NlaIV, NmeAIII, NotI, NruI, NsiI, NspI, Nt.AlwI, Nt.BbvCI, Nt.BsmAI, Nt.BspQI, Nt.BstNBI, Nt.CviPII, PacI, PaeR7I, PciI, PflFI, PflMI, PhoI, PleI, PmeI, PmlI, PpuMI, PshAI, PsiI, PspGI, PspOMI, PspXI, PstI, PvuI, PvuII, RsaI, RsrII, SacI, SacII, SalI, SapI, Sau3AI, Sau96I, SbfI, ScaI, ScrFI, ScxAI, SfaNI, SfcI, SfiI, SfoI, SgrAI, SmaI, SmlI, SnaBI, SpeI, SphI, SspI, StuI, StyD4I, StyI, SwaI, T, Taqα1, TfiI, TliI, TseI, Tsp45I, Tsp509I, TspMI, TspRI, Tth111I, XbaI, XcmI, XhoI, XmaI, XmnI, and ZraI. The resulting fragments can vary in size. The resulting fragments may also comprise a single-stranded overhand at the 5' or 3' end. The nuclease can be a nucleic-acid guided nuclease. The nucleic acid guided nuclease can be an RNA guided nuclease, such as from the Cas family of nucleases (e.g., Cas9), including CAS Class I Type I, CAS Class I Type III, CAS Class I Type IV, CAS Class II Type II, and CAS Class II Type V, such as Cas9, Cpf1, Cas3, Cas8a-c, Cas10, Cse1, Csy1, Csn2, Cas4, Csm2, Cm5, and Csf1.

In some embodiments, using sonication techniques, fragments of about 100 to 5000 nucleotides can be obtained. Alternatively, fragments of about 100 to 1000, about 150 to 1000, about 150 to 500, about 200 to 500, or about 200 to 400 nucleotides can be obtained. The sample can be prepared for sequencing of coupled sequence segments that are cross-linked. In some cases, a single, short stretch of polynucleotide can be created, for example, by ligating two sequence segments that were intramolecularly crosslinked. Sequence information may be obtained from the sample using any suitable sequencing technique described in further detail elsewhere herein or otherwise known in the art, such as a high throughput sequencing method. For example, ligation products can be subjected to paired-end sequencing obtaining sequence information from each end of a fragment. Pairs of sequence segments can be represented in the obtained sequence information, associating haplotyping information over a linear distance separating the two sequence segments along the polynucleotide.

One feature of the data generated by chromatin capture is that most reads pairs, when mapped back to the genome, are found to be in close linear proximity That is, most read pairs are found to be close to one another in the genome. In the resulting data sets, the probability of intrachromosomal contacts is on average much higher than that of interchromosomal contacts, as expected if chromosomes occupy distinct territories. Moreover, although the probability of interaction decays rapidly with linear distance, even loci separated by >200 Mb on the same chromosome are more likely to interact than loci on different chromosomes. In detecting long-range intra-chromosomal and especially inter-chromosomal contacts, this "background" of short and intermediate range intra-chromosomal contacts are background noise to be factored out using chromatin capture analysis.

Notably, chromatin capture experiments in eukaryotes have shown, in addition to species-specific and cell type-specific chromatin interactions, two canonical interaction patterns. One pattern, distance-dependent decay (DDD), is a general trend of decay in interaction frequency as a function of genomic distance. The second pattern, cis-trans ratio (CTR), is a significantly higher interaction frequency between loci located on the same chromosome, even when separated by tens of megabases of sequence, versus loci on different chromosomes. These patterns may reflect general polymer dynamics, where proximal loci have a higher probability of randomly interacting, as well as specific nuclear organization features such as the formation of chromosome territories, the phenomenon of interphase chromosomes tending to occupy distinct volumes in the nucleus with little mixing. Although the exact details of these two patterns may vary between species, cell types and cellular conditions, they are ubiquitous and prominent. These patterns are so strong and consistent that they are used to assess experiment quality and are usually normalized out of the data in order to reveal detailed interactions. However, in the methods disclosed herein, genome assembly can take advantage of the three-dimensional structure of genomes. Features which make the canonical chromatin capture interaction patterns a hindrance for the analysis of specific looping interactions, namely their ubiquity, strength and consistency, can be used as powerful tool for estimating the genomic position of contigs.

In a particular implementation, examination of the physical distance between intra-chromosomal read pairs indicates several useful features of the data with respect to genome assembly. First, shorter range interactions are more common than longer-range interactions (e.g., see FIG. 6). That is, each read of a read-pair is more likely to be mated with a region close by in the actual genome than it is to be with a region that is far away. Second, there is a long tail of intermediate and long-range interactions. That is, read-pairs carry information about intra-chromosomal arrangement at kilobase (kB) or even megabase (Mb) distances. For example, read-pairs can provide sequence information over a span of greater than about 10 kB, about 50 kB, about 100 kB, about 200 kB, about 500 kB, about 1 Mb, about 2 Mb, about 5 Mb, about 10 Mb, or about 100 Mb. These features of the data simply indicate that regions of the genome that are nearby on the same chromosome are more likely to be in close physical proximity—an expected result because they are chemically linked to one another through the DNA backbone. It was speculated that genome-wide chromatin interaction data sets, such as those generated by chromatin capture, would provide long-range information about the grouping and linear organization of sequences along entire chromosomes.

Although the experimental methods for chromatin capture are straightforward and relatively low cost, current protocols for genome assembly and haplotyping require $10^6$-$10^8$ cells, a fairly large amount of material that may not be feasible to obtain, particularly from certain human patient samples. By contrast, the methods disclosed herein include methods that allow for accurate and predictive results for genotype assembly, haplotype phasing, and metagenomics with significantly less material from cells. For example, less than about 0.1 μg, about 0.2 μg, about 0.3 μg, about 0.4 μg, about 0.5 μg, about 0.6 μg, about 0.7 μg, about 0.8 μg, about 0.9 μg, about 1.0 μg, about 1.2 μg, about 1.4 μg, about 1.6 μg, about 1.8 μg, about 2.0 μg, about 2.5 μg, about 3.0 μg, about 3.5 μg, about 4.0 μg, about 4.5 μg, about 5.0 μg, about 6.0 μg, about 7.0 μg, about 8.0 μg, about 9.0 μg, about 10 μg, about 15 μg, about 20 μg, about 30 μg, about 40 μg, about 50 μg, about 60 μg, about 70 μg, about 80 μg, about 90 μg, about 100 μg, about 150 μg, about 200 μg, about 300 μg, about 400 μg, about 500 μg, about 600 μg, about 700 μg, about 800 μg, about 900 μg, or about 1000 μg of DNA can be used with the methods disclosed herein. In some examples, the DNA used in the methods disclosed herein can be extracted from less than about 1,000,000, about 500,000, about 100,000, about 50,000, about 10,000, about 5,000, about 1,000, about 5,000, or about 1,000, about 500, or about 100 cells.

In some cases, less than about 80%, 60%, 50%, 40%, 30%, 20%, 15%, 10%, 9%, 8%, 7%, 6%, 5%, 4%, 3%, 2%, 1%, 0.5%, or 0.1% of DNA segments from the DNA molecules are linked with DNA segments from any other DNA molecule. In certain cases, less than 50%, 40%, 30%, 20%, 15%, 10%, 9%, 8%, 7%, 6%, or 5% of DNA segments from the DNA molecules are linked with DNA segments from any other DNA molecule. In some cases, less than 40%, 30%, 20%, 15%, or 10% of DNA segments from the DNA molecules are linked with DNA segments from any other DNA molecule. In some examples, less than 40% of DNA segments from the DNA molecules are linked with DNA segments from any other DNA molecule. In certain examples, less than 20% of DNA segments from the DNA molecules are linked with DNA segments from any other DNA molecule. In some examples, less than 10% of DNA segments from the DNA molecules are linked with DNA segments from any other DNA molecule.

Universally, procedures for probing the physical layout of chromosomes, such as chromatin capture based techniques, utilize chromatin that is formed within a cell/organism, such as chromatin isolated from cultured cells or primary tissue. The disclosure provides not only for the use of such techniques with chromatin isolated from a cell/organism but also with reconstituted chromatin. Reconstituted chromatin is differentiated from chromatin formed within a cell/organism over various features. First, for many samples, the collection of naked DNA samples can be achieved by using a variety of noninvasive to invasive methods, such as by collecting bodily fluids, swabbing buccal or rectal areas, taking epithelial samples, etc. Second, reconstituting chromatin substantially prevents the formation of inter-chromosomal and other long-range interactions that generate artifacts for genome assembly and haplotype phasing. In some cases, a sample may have less than about 20, 15, 12, 11, 10, 9, 8, 7, 6, 5, 4, 3, 2, 1, 0.5, 0.4, 0.3, 0.2, 0.1% or less inter-chromosomal or intermolecular crosslinking according to the methods and compositions of the disclosure. In some examples, the sample may have less than about 5% inter-chromosomal or intermolecular crosslinking. In some examples, the sample may have less than about 3% inter-chromosomal or intermolecular crosslinking. In some examples, may have less than about 1% inter-chromosomal or intermolecular crosslinking. Third, the frequency of sites that are capable of crosslinking and thus the frequency of intramolecular crosslinks within the polynucleotide can be adjusted. For example, the ratio of DNA to histones can be varied, such that the nucleosome density can be adjusted to a desired value. In some cases, the nucleosome density is reduced below the physiological level. Accordingly, the distribution of crosslinks can be altered to favor longer-range interactions. In some embodiments, sub-samples with varying cross-linking density may be prepared to cover both short- and long-range associations. For example, the cross-linking conditions can be adjusted such that at least about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 25%, about 30%, about 40%, about 45%, about 50%, about 60%, about 70%, about 80%, about 90%, about 95%, or about 100% of the crosslinks occur between DNA segments that are at least about 50 kb, about 60 kb, about 70 kb, about 80 kb, about 90 kb, about 100 kb, about 110 kb, about 120 kb, about 130 kb, about 140 kb, about 150 kb, about 160 kb, about 180 kb, about 200 kb, about 250 kb, about 300 kb, about 350 kb, about 400 kb, about 450 kb, or about 500 kb apart on the sample DNA molecule.

In various embodiments, the disclosure provides a variety of methods that enable the mapping of the plurality of read pairs to the plurality of contigs. There are several publicly available computer programs for mapping reads to contig sequences. These read-mapping programs data also provide data describing how unique a particular read-mapping is within the genome. From the population of reads that map uniquely, with high confidence within a contig, we can infer the distribution of distances between reads in each read pair. These are the data shown in FIG. 6. For read pairs whose reads map confidently to different contigs, this mapping data implies a connection between the two contigs in question. It also implies a distance between the two contigs that is proportional to the distribution of distances learned from the analysis described above. Thus, each read pair whose reads map to different contigs implies a connection between those two contigs in a correct assembly. The connections inferred from all such mapped read pairs can be summarized in an adjacency matrix wherein each contig is represented by both a row and column. Read pairs that connect contigs are marked as a non-zero value in the corresponding row and column denoting the contigs to which the reads in the read pair were mapped. Most of the read pairs will map within in a contig, and from which the distribution of distances between read pairs can be learned, and from which an adjacency matrix of contigs can be constructed using read pairs that map to different contigs.

In various embodiments, the disclosure provides methods comprising constructing an adjacency matrix of contigs using the read-mapping data from the read-pair data. In some embodiments, the adjacency matrix uses a weighting scheme for read pairs that incorporate the tendency for short-range interactions over long-range interactions (e.g., see FIG. 3). Read pairs spanning shorter distances are generally more common than read pairs that span longer distances. A function describing the probability of a particular distance can be fit using the read pair data that map to a single contig to learn this distribution. Therefore, one important feature of read pairs that map to different contigs is the position on the contig where they map. For read pairs that both map near one end of a contig, the inferred distance between these contigs can be short and therefore the distance between the joined reads small. Since shorter distances between read pairs are more common than longer distances, this configuration provides stronger evidence that these two contigs are adjacent than would reads mapping far from the edges of the contig. Therefore, the connections in the adjacency matrix are further weighted by the distance of the reads to the edge of the contigs. In some embodiments, the adjacency matrix is re-scaled to down-weight the high number of contacts on some contigs that represent promiscuous regions of the genome. These regions of the genome, identifiable by having a high proportion of reads mapping to them, are a priori more likely to contain spurious read mappings that might misinform assembly. In yet further embodiments, this scaling can be directed by searching for one or more conserved binding sites for one or more agents that regulate the scaffolding interactions of chromatin, such as transcriptional repressor CTCF, endocrine receptors, cohesins, or covalently modified histones.

In some embodiments, the disclosure provides for one or more methods disclosed herein that comprise a step of analyzing the adjacency matrix to determine a path through the contigs that represent their order and/or orientation to the genome. In other embodiments, the path through the contigs can be chosen so that each contig is visited exactly once. In some embodiments, the path through the contigs is chosen so that the path through the adjacency matrix maximizes the sum of edge-weights visited. In this way, the most probably contig connections are proposed for the correct assembly. In yet further embodiments, the path through the contigs can be chosen so that each contig is visited exactly once and that edge-weighting of adjacency matrix is maximized.

In diploid genomes, it often important to know which allelic variants are linked on the same chromosome. This is known as the haplotype phasing. Short reads from high-throughput sequence data rarely allow one to directly observe which allelic variants are linked. Computational inference of haplotype phasing can be unreliable at long distances. The disclosure provides one or methods that allow for determining which allelic variants are linked using allelic variants on read pairs.

In various embodiments, the methods and compositions of the disclosure enable the haplotype phasing of diploid or polyploid genomes with regard to a plurality of allelic variants. The methods described herein can thus provide for the determination of linked allelic variants are linked based on variant information from read pairs and/or assembled contigs using the same. Examples of allelic variants include, but are not limited to those that are known from the 1000 genomes, U10K, HapMap and other projects for discovering genetic variation among humans. Disease association to a specific gene can be revealed more easily by having haplotype phasing data as demonstrated, for example, by the finding of unlinked, inactivating mutations in both copies *SH3TC2* leading to Charcot-Marie-Tooth neuropathy (Lupski J R, Reid J G, Gonzaga-Jauregui C, et al. *N. Engl. J. Med.* 362:1181-91, 2010) and unlinked, inactivating mutations in both copies of *ABCG5* leading to hypercholesterolemia 9 (Rios J, Stein E, Shendure J, et al. *Hum. Mol. Genet.* 19:4313-18, 2010).

Humans are heterozygous at an average of 1 site in 1,000. In some cases, a single lane of data using high throughput sequencing methods can generate at least about 150,000,000 read pairs. Read pairs can be about 100 base pairs long. From these parameters, one-tenth of all reads from a human sample is estimated to cover a heterozygous site. Thus, on average one-hundredth of all read pairs from a human sample is estimated to cover a pair of heterozygous sites. Accordingly, about 1,500,000 read pairs (one-hundredth of 150,000,000) provide phasing data using a single lane. With approximately 3 billion bases in the human genome, and one in one-thousand being heterozygous, there are approximately 3 million heterozygous sites in an average human genome. With about 1,500,000 read pairs that represent a pair of heterozygous sites, the average coverage of each heterozygous site to be phased using a single lane of a high throughput sequence method is about (1×), using a typical high throughput sequencing machine. A diploid human genome can therefore be reliably and completely phased with one lane of a high-throughput sequence data relating sequence variants from a sample that is prepared using the methods disclosed herein. In some examples, a lane of data can be a set of DNA sequence read data. In some examples, a lane of data can be a set of DNA sequence read data from a single run of a high throughput sequencing instrument.

As the human genome consists of two homologous sets of chromosomes, understanding the true genetic makeup of an individual requires delineation of the maternal and paternal copies or haplotypes of the genetic material. Obtaining a haplotype in an individual is useful in several ways. First, haplotypes are useful clinically in predicting outcomes for donor-host matching in organ transplantation and are increasingly used as a means to detect disease associations.

Second, in genes that show compound heterozygosity, haplotypes provide information as to whether two deleterious variants are located on the same allele, greatly affecting the prediction of whether inheritance of these variants is harmful. Third, haplotypes from groups of individuals have provided information on population structure and the evolutionary history of the human race. Lastly, recently described widespread allelic imbalances in gene expression suggest that genetic or epigenetic differences between alleles may contribute to quantitative differences in expression. An understanding of haplotype structure will delineate the mechanisms of variants that contribute to allelic imbalances.

In certain embodiments, the methods disclosed herein comprise a technique (e.g., in vitro or in vivo) to fix and capture associations among distant regions of a genome as needed for long-range linkage and phasing. In some cases, the method comprises constructing and sequencing an XLRP library to deliver very genomically distant read pairs. In some cases, the interactions primarily arise from the random associations within a single DNA fragment. In some examples, the genomic distance between segments can be inferred because segments that are near to each other in a DNA molecule interact more often and with higher probability, while interactions between distant portions of the molecule will be less frequent. Consequently, there is a systematic relationship between the number of pairs connecting two loci and their proximity on the input DNA. The disclosure can produce read pairs capable of spanning the largest DNA fragments in an extraction, as demonstrated in FIG. 2. The input DNA for this library had a maximum length of 150 kbp, which is the longest meaningful read pair we observe from the sequencing data. This suggests that the present method can link still more genomically distant loci if provided larger input DNA fragments. By applying improved assembly software tools that are specifically adapted to handle the type of data produced by the present method, a complete genomic assembly may be possible.

Extremely high phasing accuracy can be achieved by the data produced using the methods and compositions of the disclosure. In comparison to previous methods, the methods described herein can phase a higher proportion of the variants. Phasing can be achieved while maintaining high levels of accuracy. This phase information can be extended to longer ranges, for example greater than about 200 kbp, about 300 kbp, about 400 kbp, about 500 kbp, about 600 kbp, about 700 kbp, about 800 kbp, about 900 kbp, about 1 Mbp, about 2 Mbp, about 3 Mbp, about 4 Mbp, about 5 Mbp, or about 10 Mbp. In some embodiments, more than 90% of the heterozygous SNPs for a human sample can be phased at an accuracy greater than 99% using less than about 250 million reads or read pairs, e.g. by using only 1 lane of Illumina HiSeq data. In other cases, more than about 40%, 50%, 60%, 70%, 80%, 90%, 95% or 99% of the heterozygous SNPs for a human sample can be phased at an accuracy greater than about 70%, 80%, 90%, 95%, or 99% using less than about 250 million or about 500 million reads or read pairs, e.g. by using only 1 or 2 lanes of Illumina HiSeq data. For example, more than 95% or 99% of the heterozygous SNPs for a human sample can be phase at an accuracy greater than about 95% or 99% using less about 250 million or about 500 million reads. In some cases, additional variants can be captured by increasing the read length to about 200 bp, 250 bp, 300 bp, 350 bp, 400 bp, 450 bp, 500 bp, 600 bp, 800 bp, 1000 bp, 1500 bp, 2 kbp, 3 kbp, 4 kbp, 5 kbp, 10 kbp, 20 kbp, 50 kbp, or 100 kbp.

Figure 6:
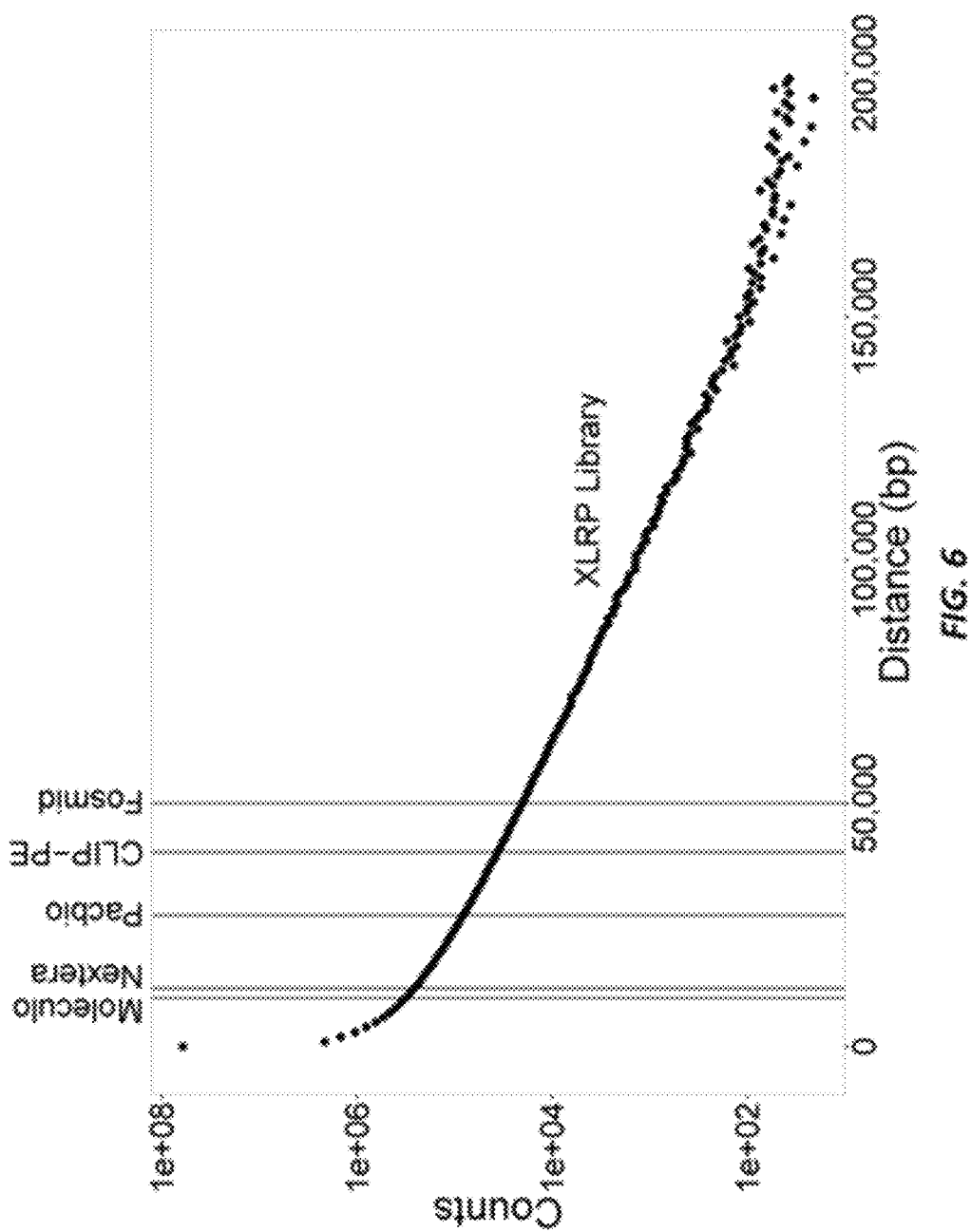
FIG. 6 illustrates the distribution of genomic distances between read pairs from a human XLRP library. Maximum distances achievable with other technologies are indicated for comparison.

In other embodiments of the disclosure, the data from an XLRP library can be used to confirm the phasing capabilities of the long-range read pairs. As shown in FIG. 6, the accuracy of those results is on par with the best technologies previously available, but further extending to significantly longer distances. The current sample preparation protocol for a particular sequencing method recognizes variants located within a read-length, e.g. 150 bp, of a targeted restriction site for phasing. In one example, from an XLRP library built for NA12878, a benchmark sample for assembly, 44% of the 1,703,909 heterozygous SNPs present were phased with an accuracy greater than 99%. In some cases, this proportion can be expanded to nearly all variable sites with the judicious choice of restriction enzyme or with combinations of different enzymes.

In some embodiments, the compositions and methods described herein allow for the investigation of meta-genomes, for example those found in the human gut. Accordingly, the partial or whole genomic sequences of some or all organisms that inhabit a given ecological environment can be investigated. Examples include random sequencing of all gut microbes, the microbes found on certain areas of skin, and the microbes that live in toxic waste sites. The composition of the microbe population in these environments can be determined using the compositions and methods described herein and as well as the aspects of interrelated biochemistries encoded by their respective genomes. The methods described herein can enable metagenomic studies from complex biological environments, for example, those that comprise more than 2, 3, 4, 5, 6, 7, 8, 9, 10, 12, 15, 20, 25, 30, 40, 50, 60, 70, 80, 90, 100, 125, 150, 175, 200, 250, 300, 400, 500, 600, 700, 800, 900, 1000, 5000, 10000 or more organisms and/or variants of organisms.

High degrees of accuracy required by cancer genome sequencing can be achieved using the methods and systems described herein. Inaccurate reference genomes can make base-calling challenges when sequencing cancer genomes. Heterogeneous samples and small starting materials, for example a sample obtained by biopsy introduce additional challenges. Further, detection of large scale structural variants and/or losses of heterozygosity is often crucial for cancer genome sequencing, as well as the ability to differentiate between somatic variants and errors in base-calling.

Systems and methods described herein may generate accurate long sequences from complex samples containing 2, 3, 4, 5, 6, 7, 8, 9, 10, 12, 15, 20 or more varying genomes. Mixed samples of normal, benign, and/or tumor origin may be analyzed, optionally without the need for a normal control. In some embodiments, starting samples as little as 100 ng or even as little as hundreds of genome equivalents are utilized to generate accurate long sequences. Systems and methods described herein may allow for detection of large scale structural variants and rearrangements, phased variant calls may be obtained over long sequences spanning about 1 kbp, about 2 kbp, about 5 kbp, about 10 kbp, 20 kbp, about 50 kbp, about 100 kbp, about 200 kbp, about 500 kbp, about 1 Mbp, about 2 Mbp, about 5 Mbp, about 10 Mbp, about 20 Mbp, about 50 Mbp, or about 100 Mbp or more nucleotides. For example, phase variant call may be obtained over long sequences spanning about 1 Mbp or about 2 Mbp.

Haplotypes determined using the methods and systems described herein may be assigned to computational resources, for example computational resources over a network, such as a cloud system. Short variant calls can be corrected, if necessary, using relevant information that is stored in the computational resources. Structural variants can be detected based on the combined information from short variant calls and the information stored in the computational resources. Problematic parts of the genome, such as segmental duplications, regions prone to structural variation, the highly variable and medically relevant MHC region, centromeric and telomeric regions, and other heterochromatic regions including but limited to those with repeat regions, low sequence accuracy, high variant rates, ALU repeats, segmental duplications, or any other relevant problematic parts known in the art, can be reassembled for increased accuracy.

A sample type can be assigned to the sequence information either locally or in a networked computational resource, such as a cloud. In cases where the source of the information is known, for example when the source of the information is from a cancer or normal tissue, the source can be assigned to the sample as part of a sample type. Other sample type examples generally include, but are not limited to, tissue type, sample collection method, presence of infection, type of infection, processing method, size of the sample, etc. In cases where a complete or partial comparison genome sequence is available, such as a normal genome in comparison to a cancer genome, the differences between the sample data and the comparison genome sequence can be determined and optionally output.

The methods of the can be used in the analysis of genetic information of selective genomic regions of interest as well as genomic regions which may interact with the selective region of interest. Amplification methods as disclosed herein can be used in the devices, kits, and methods known to the art for genetic analysis, such as, but not limited to those found in U.S. Pat. Nos. 6,449,562, 6,287,766, 7,361,468, 7,414,117, 6,225,109, and 6,110,709. In some cases, amplification methods of the present disclosure can be used to amplify target nucleic acid for DNA hybridization studies to determine the presence or absence of polymorphisms. The polymorphisms, or alleles, can be associated with diseases or conditions such as genetic disease. In other cases, the polymorphisms can be associated with susceptibility to diseases or conditions, for example, polymorphisms associated with addiction, degenerative and age related conditions, cancer, and the like. In other cases, the polymorphisms can be associated with beneficial traits such as increased coronary health, or resistance to diseases such as HIV or malaria, or resistance to degenerative diseases such as osteoporosis, Alzheimer's or dementia.

The compositions and methods of the disclosure can be used for diagnostic, prognostic, therapeutic, patient stratification, drug development, treatment selection, and screening purposes. The present disclosure provides the advantage that many different target molecules can be analyzed at one time from a single biomolecular sample using the methods of the disclosure. This allows, for example, for several diagnostic tests to be performed on one sample.

The composition and methods of the disclosure can be used in genomics. The methods described herein can provide an answer rapidly which is very desirable for this application. The methods and composition described herein can be used in the process of finding biomarkers that may be used for diagnostics or prognostics and as indicators of health and disease. The methods and composition described herein can be used to screen for drugs, e.g., drug development, selection of treatment, determination of treatment efficacy and/or identify targets for pharmaceutical development. The ability to test gene expression on screening assays involving drugs is very important because proteins are the final gene product in the body. In some embodiments, the methods and compositions described herein will measure both protein and gene expression simultaneously which will provide the most information regarding the particular screening being performed.

The composition and methods of the disclosure can be used in gene expression analysis. The methods described herein discriminate between nucleotide sequences. The difference between the target nucleotide sequences can be, for example, a single nucleic acid base difference, a nucleic acid deletion, a nucleic acid insertion, or rearrangement. Such sequence differences involving more than one base can also be detected. The process of the present disclosure is able to detect infectious diseases, genetic diseases, and cancer. It is also useful in environmental monitoring, forensics, and food science. Examples of genetic analyses that can be performed on nucleic acids include e.g., SNP detection, STR detection, RNA expression analysis, promoter methylation, gene expression, virus detection, viral subtyping and drug resistance.

The present methods can be applied to the analysis of biomolecular samples obtained or derived from a patient so as to determine whether a diseased cell type is present in the sample, the stage of the disease, the prognosis for the patient, the ability to the patient to respond to a particular treatment, or the best treatment for the patient. The present methods can also be applied to identify biomarkers for a particular disease.

In some embodiments, the methods described herein are used in the diagnosis of a condition. As used herein the term "diagnose" or "diagnosis" of a condition may include predicting or diagnosing the condition, determining predisposition to the condition, monitoring treatment of the condition, diagnosing a therapeutic response of the disease, or prognosis of the condition, condition progression, or response to particular treatment of the condition. For example, a blood sample can be assayed according to any of the methods described herein to determine the presence and/or quantity of markers of a disease or malignant cell type in the sample, thereby diagnosing or staging a disease or a cancer.

In some embodiments, the methods and composition described herein are used for the diagnosis and prognosis of a condition.

Numerous immunologic, proliferative and malignant diseases and disorders are especially amenable to the methods described herein. Immunologic diseases and disorders include allergic diseases and disorders, disorders of immune function, and autoimmune diseases and conditions. Allergic diseases and disorders include but are not limited to allergic rhinitis, allergic conjunctivitis, allergic asthma, atopic eczema, atopic dermatitis, and food allergy. Immunodeficiencies include but are not limited to severe combined immunodeficiency (SCID), hypereosinophilic syndrome, chronic granulomatous disease, leukocyte adhesion deficiency I and II, hyper IgE syndrome, Chediak Higashi, neutrophilias, neutropenias, aplasias, Agammaglobulinemia, hyper-IgM syndromes, DiGeorge/Velocardial-facial syndromes and Interferon gamma-TH1 pathway defects. Autoimmune and immune dysregulation disorders include but are not limited to rheumatoid arthritis, diabetes, systemic lupus erythematosus, Graves' disease, Graves ophthalmopathy, Crohn's disease, multiple sclerosis, psoriasis, systemic sclerosis, goiter and struma lymphomatosa (Hashimoto's thyroiditis, lymphadenoid goiter), alopecia aerata, autoimmune myocarditis, lichen sclerosis, autoimmune uveitis, Addison's disease, atrophic gastritis, myasthenia gravis, idiopathic thrombocytopenic purpura, hemolytic anemia, primary biliary cirrhosis, Wegener's granulomatosis, polyarteritis nodosa, and inflammatory bowel disease, allograft rejection and tissue destructive from allergic reactions to infectious microorganisms or to environmental antigens.

Proliferative diseases and disorders that may be evaluated by the methods of the disclosure include, but are not limited to, hemangiomatosis in newborns; secondary progressive multiple sclerosis; chronic progressive myelodegenerative disease; neurofibromatosis; ganglioneuromatosis; keloid formation; Paget's Disease of the bone; fibrocystic disease (e.g., of the breast or uterus); sarcoidosis; Peronies and Duputren's fibrosis, cirrhosis, atherosclerosis and vascular restenosis.

Malignant diseases and disorders that may be evaluated by the methods of the disclosure include both hematologic malignancies and solid tumors.

Hematologic malignancies are especially amenable to the methods of the disclosure when the sample is a blood sample, because such malignancies involve changes in blood-borne cells. Such malignancies include non-Hodgkin's lymphoma, Hodgkin's lymphoma, non-B cell lymphomas, and other lymphomas, acute or chronic leukemias, polycythemias, thrombocythemias, multiple myeloma, myelodysplastic disorders, myeloproliferative disorders, myelofibroses, atypical immune lymphoproliferations and plasma cell disorders.

Plasma cell disorders that may be evaluated by the methods of the disclosure include multiple myeloma, amyloidosis and Waldenstrom's macroglobulinemia.

Example of solid tumors include, but are not limited to, colon cancer, breast cancer, lung cancer, prostate cancer, brain tumors, central nervous system tumors, bladder tumors, melanomas, liver cancer, osteosarcoma and other bone cancers, testicular and ovarian carcinomas, head and neck tumors, and cervical neoplasms.

Genetic diseases can also be detected by the process of the present disclosure. This can be carried out by prenatal or post-natal screening for chromosomal and genetic aberrations or for genetic diseases. Examples of detectable genetic diseases include: 21 hydroxylase deficiency, cystic fibrosis, Fragile X Syndrome, Turner Syndrome, Duchenne Muscular Dystrophy, Down Syndrome or other trisomies, heart disease, single gene diseases, HLA typing, phenylketonuria, sickle cell anemia, Tay-Sachs Disease, thalassemia, Klinefelter Syndrome, Huntington Disease, autoimmune diseases, lipidosis, obesity defects, hemophilia, inborn errors of metabolism, and diabetes.

The methods described herein can be used to diagnose pathogen infections, for example infections by intracellular bacteria and viruses, by determining the presence and/or quantity of markers of bacterium or virus, respectively, in the sample.

A wide variety of infectious diseases can be detected by the process of the present disclosure. The infectious diseases can be caused by bacterial, viral, parasite, and fungal infectious agents. The resistance of various infectious agents to drugs can also be determined using the present disclosure.

Bacterial infectious agents which can be detected by the present disclosure include *Escherichia coli, Salmonella, Shigella, KlESBiella, Pseudomonas, Listeria monocytogenes, Mycobacterium tuberculosis, Mycobacterium avium-intracellulare, Yersinia, Francisella, Pasteurella, Brucella, Clostridia, Bordetella pertussis, Bacteroides, Staphylococcus aureus, Streptococcus pneumonia, B-Hemolytic strep., Corynebacteria, Legionella, Mycoplasma, Ureaplasma, Chlamydia, Neisseria gonorrhea, Neisseria meningitides, Hemophilus influenza, Enterococcus faecalis, Proteus vul-*

*garis, Proteus mirabilis, Helicobacter pylori, Treponema palladium, Borrelia burgdorferi, Borrelia recurrentis, Rickettsial pathogens, Nocardia,* and *Acitnomycetes.*

Fungal infectious agents which can be detected by the present disclosure include *Cryptococcus neoformans, Blastomyces dermatitidis, Histoplasma capsulatum, Coccidioides immitis, Paracoccidioides brasiliensis, Candida albicans, Aspergillus fumigautus, Phycomycetes (Rhizopus), Sporothrix schenckii, Chromomycosis,* and *Maduromycosis.*

Viral infectious agents which can be detected by the present disclosure include human immunodeficiency virus, human T-cell lymphocytotrophic virus, hepatitis viruses (e.g., Hepatitis B Virus and Hepatitis C Virus), Epstein-Barr virus, cytomegalovirus, human papillomaviruses, orthomyxo viruses, paramyxo viruses, adenoviruses, corona viruses, rhabdo viruses, polio viruses, toga viruses, bunya viruses, arena viruses, rubella viruses, and reo viruses.

Parasitic agents which can be detected by the present disclosure include *Plasmodium falciparum, Plasmodium malaria, Plasmodium vivax, Plasmodium ovale, Onchoverva volvulus, Leishmania, Trypanosoma* spp., *Schistosoma* spp., *Entamoeba histolytica, Cryptosporidum, Giardia* spp., *Trichimonas* spp., *Balatidium coli, Wuchereria bancrofti, Toxoplasma* spp., *Enterobius vermicularis, Ascaris lumbricoides, Trichuris trichiura, Dracunculus medinesis, trematodes, Diphyllobothrium latum, Taenia* spp., *Pneumocystis carinii,* and *Necator americanis.*

The present disclosure is also useful for detection of drug resistance by infectious agents. For example, vancomycin-resistant *Enterococcus faecium,* methicillin-resistant *Staphylococcus aureus,* penicillin-resistant *Streptococcus pneumoniae,* multi-drug resistant *Mycobacterium tuberculosis,* and AZT-resistant human immunodeficiency virus can all be identified with the present disclosure.

Thus, the target molecules detected using the compositions and methods of the disclosure can be either patient markers (such as a cancer marker) or markers of infection with a foreign agent, such as bacterial or viral markers.

The compositions and methods of the disclosure can be used to identify and/or quantify a target molecule whose abundance is indicative of a biological state or disease condition, for example, blood markers that are upregulated or downregulated as a result of a disease state.

In some embodiments, the methods and compositions of the present disclosure can be used for cytokine expression. The low sensitivity of the methods described herein would be helpful for early detection of cytokines, e.g., as biomarkers of a condition, diagnosis or prognosis of a disease such as cancer, and the identification of subclinical conditions.

The different samples from which the target polynucleotides are derived can comprise multiple samples from the same individual, samples from different individuals, or combinations thereof. In some embodiments, a sample comprises a plurality of polynucleotides from a single individual. In some embodiments, a sample comprises a plurality of polynucleotides from two or more individuals. An individual is any organism or portion thereof from which target polynucleotides can be derived, non-limiting examples of which include plants, animals, fungi, protists, monerans, viruses, mitochondria, and chloroplasts. Sample polynucleotides can be isolated from a subject, such as a cell sample, tissue sample, or organ sample derived therefrom, including, for example, cultured cell lines, biopsy, blood sample, or fluid sample containing a cell. The subject may be an animal, including but not limited to, an animal such as a cow, a pig, a mouse, a rat, a chicken, a cat, a dog, etc., and is usually a mammal, such as a human. Samples can also be artificially derived, such as by chemical synthesis. In some embodiments, the samples comprise DNA. In some embodiments, the samples comprise genomic DNA. In some embodiments, the samples comprise mitochondrial DNA, chloroplast DNA, plasmid DNA, bacterial artificial chromosomes, yeast artificial chromosomes, oligonucleotide tags, or combinations thereof. In some embodiments, the samples comprise DNA generated by primer extension reactions using any suitable combination of primers and a DNA polymerase, including but not limited to polymerase chain reaction (PCR), reverse transcription, and combinations thereof. Where the template for the primer extension reaction is RNA, the product of reverse transcription is referred to as complementary DNA (cDNA). Primers useful in primer extension reactions can comprise sequences specific to one or more targets, random sequences, partially random sequences, and combinations thereof. Reaction conditions suitable for primer extension reactions are known in the art. In general, sample polynucleotides comprise any polynucleotide present in a sample, which may or may not include target polynucleotides.

In some embodiments, nucleic acid template molecules (e.g., DNA or RNA) are isolated from a biological sample containing a variety of other components, such as proteins, lipids and non-template nucleic acids. Nucleic acid template molecules can be obtained from any cellular material, obtained from an animal, plant, bacterium, fungus, or any other cellular organism. Biological samples for use in the present disclosure include viral particles or preparations. Nucleic acid template molecules can be obtained directly from an organism or from a biological sample obtained from an organism, e.g., from blood, urine, cerebrospinal fluid, seminal fluid, saliva, sputum, stool and tissue. Any tissue or body fluid specimen may be used as a source for nucleic acid for use in the disclosure. Nucleic acid template molecules can also be isolated from cultured cells, such as a primary cell culture or a cell line. The cells or tissues from which template nucleic acids are obtained can be infected with a virus or other intracellular pathogen. A sample can also be total RNA extracted from a biological specimen, a cDNA library, viral, or genomic DNA. A sample may also be isolated DNA from a non-cellular origin, e.g. amplified/isolated DNA from the freezer.

Methods for the extraction and purification of nucleic acids are well known in the art. For example, nucleic acids can be purified by organic extraction with phenol, phenol/chloroform/isoamyl alcohol, or similar formulations, including TRIzol and TriReagent. Other non-limiting examples of extraction techniques include: (1) organic extraction followed by ethanol precipitation, e.g., using a phenol/chloroform organic reagent (Ausubel et al., 1993), with or without the use of an automated nucleic acid extractor, e.g., the Model 341 DNA Extractor available from Applied Biosystems (Foster City, Calif.); (2) stationary phase adsorption methods (U.S. Pat. No. 5,234,809; Walsh et al., 1991); and (3) salt-induced nucleic acid precipitation methods (Miller et al., (1988), such precipitation methods being typically referred to as "salting-out" methods. Another example of nucleic acid isolation and/or purification includes the use of magnetic particles to which nucleic acids can specifically or non-specifically bind, followed by isolation of the beads using a magnet, and washing and eluting the nucleic acids from the beads (see e.g. U.S. Pat. No. 5,705,628). In some embodiments, the above isolation methods may be preceded by an enzyme digestion step to help eliminate unwanted protein from the sample, e.g., digestion with proteinase K, or other like proteases. See, e.g., U.S. Pat. No. 7,001,724. If desired, RNase inhibitors may be added to the lysis buffer. For certain cell or sample types, it may be desirable to add a protein denaturation/digestion step to the protocol. Purification methods may be directed to isolate DNA, RNA, or both. When both DNA and RNA are isolated together during or subsequent to an extraction procedure, further steps may be employed to purify one or both separately from the other. Sub-fractions of extracted nucleic acids can also be generated, for example, purification by size, sequence, or other physical or chemical characteristic. In addition to an initial nucleic isolation step, purification of nucleic acids can be performed after any step in the methods of the disclosure, such as to remove excess or unwanted reagents, reactants, or products.

Nucleic acid template molecules can be obtained as described in U.S. Patent Application Publication Number US2002/0190663 A1, published Oct. 9, 2003. Generally, nucleic acid can be extracted from a biological sample by a variety of techniques such as those described by Maniatis, et al., Molecular Cloning: A Laboratory Manual, Cold Spring Harbor, N.Y., pp. 280-281 (1982). In some cases, the nucleic acids can be first extracted from the biological samples and then cross-linked in vitro. In some cases, native association proteins (e.g. histones) can be further removed from the nucleic acids.

In other embodiments, the disclosure can be easily applied to any high molecular weight double stranded DNA including, for example, DNA isolated from tissues, cell culture, bodily fluids, animal tissue, plant, bacteria, fungi, viruses, etc.

In some embodiments, each of the plurality of independent samples can independently comprise at least about 1 ng, 2 ng, 5 ng, 10 ng, 20 ng, 30 ng, 40 ng, 50 ng, 75 ng, 100 ng, 150 ng, 200 ng, 250 ng, 300 ng, 400 ng, 500 ng, 1 µg, 1.5 µg, 2 µg, 5 µg, 10 µg, 20 µg, 50 µg, 100 µg, 200 µg, 500 µg, or 1000 µg, or more of nucleic acid material. In some embodiments, each of the plurality of independent samples can independently comprise less than about 1 ng, 2 ng, 5 ng, 10 ng, 20 ng, 30 ng, 40 ng, 50 ng, 75 ng, 100 ng, 150 ng, 200 ng, 250 ng, 300 ng, 400 ng, 500 ng, 1 µg, 1.5 µg, 2 µg, 5 µg, 10 µg, 20 µg, 50 µg, 100 µg, 200 µg, 500 µg, or 1000 µg, or more of nucleic acid.

In some embodiments, end repair is performed to generate blunt end 5' phosphorylated nucleic acid ends using commercial kits, such as those available from Epicentre Biotechnologies (Madison, Wis.).

An adapter oligonucleotide includes any oligonucleotide having a sequence, at least a portion of which is known, that can be joined to a target polynucleotide. Adapter oligonucleotides can comprise DNA, RNA, nucleotide analogues, non-canonical nucleotides, labeled nucleotides, modified nucleotides, or combinations thereof. Adapter oligonucleotides can be single-stranded, double-stranded, or partial duplex. In general, a partial-duplex adapter comprises one or more single-stranded regions and one or more double-stranded regions. Double-stranded adapters can comprise two separate oligonucleotides hybridized to one another (also referred to as an "oligonucleotide duplex"), and hybridization may leave one or more blunt ends, one or more 3' overhangs, one or more 5' overhangs, one or more bulges resulting from mismatched and/or unpaired nucleotides, or any combination of these. In some embodiments, a single-stranded adapter comprises two or more sequences that are able to hybridize with one another. When two such hybridizable sequences are contained in a single-stranded adapter, hybridization yields a hairpin structure (hairpin adapter). When two hybridized regions of an adapter are separated from one another by a non-hybridized region, a "bubble" structure results. Adapters comprising a bubble structure can consist of a single adapter oligonucleotide comprising internal hybridizations, or may comprise two or more adapter oligonucleotides hybridized to one another. Internal sequence hybridization, such as between two hybridizable sequences in an adapter, can produce a double-stranded structure in a single-stranded adapter oligonucleotide. Adapters of different kinds can be used in combination, such as a hairpin adapter and a double-stranded adapter, or adapters of different sequences. Hybridizable sequences in a hairpin adapter may or may not include one or both ends of the oligonucleotide. When neither of the ends are included in the hybridizable sequences, both ends are "free" or "overhanging." When only one end is hybridizable to another sequence in the adapter, the other end forms an overhang, such as a 3' overhang or a 5' overhang. When both the 5'-terminal nucleotide and the 3'-terminal nucleotide are included in the hybridizable sequences, such that the 5'-terminal nucleotide and the 3'-terminal nucleotide are complementary and hybridize with one another, the end is referred to as "blunt." Different adapters can be joined to target polynucleotides in sequential reactions or simultaneously. For example, the first and second adapters can be added to the same reaction. Adapters can be manipulated prior to combining with target polynucleotides. For example, terminal phosphates can be added or removed.

Adapters can contain one or more of a variety of sequence elements, including but not limited to, one or more amplification primer annealing sequences or complements thereof, one or more sequencing primer annealing sequences or complements thereof, one or more barcode sequences, one or more common sequences shared among multiple different adapters or subsets of different adapters, one or more restriction enzyme recognition sites, one or more overhangs complementary to one or more target polynucleotide overhangs, one or more probe binding sites (e.g. for attachment to a sequencing platform, such as a flow cell for massive parallel sequencing, such as developed by Illumina, Inc.), one or more random or near-random sequences (e.g. one or more nucleotides selected at random from a set of two or more different nucleotides at one or more positions, with each of the different nucleotides selected at one or more positions represented in a pool of adapters comprising the random sequence), and combinations thereof. Two or more sequence elements can be non-adjacent to one another (e.g. separated by one or more nucleotides), adjacent to one another, partially overlapping, or completely overlapping. For example, an amplification primer annealing sequence can also serve as a sequencing primer annealing sequence. Sequence elements can be located at or near the 3' end, at or near the 5' end, or in the interior of the adapter oligonucleotide. When an adapter oligonucleotide is capable of forming secondary structure, such as a hairpin, sequence elements can be located partially or completely outside the secondary structure, partially or completely inside the secondary structure, or in between sequences participating in the secondary structure. For example, when an adapter oligonucleotide comprises a hairpin structure, sequence elements can be located partially or completely inside or outside the hybridizable sequences (the "stem"), including in the sequence between the hybridizable sequences (the "loop"). In some embodiments, the first adapter oligonucleotides in a plurality of first adapter oligonucleotides having different barcode sequences comprise a sequence element common among all first adapter oligonucleotides in the plurality. In some embodiments, all second adapter oligonucleotides comprise a sequence element common among all second adapter oligonucleotides that is different from the common sequence element shared by the first adapter oligonucleotides. A difference in sequence elements can be any such that at least a portion of different adapters do not completely align, for example, due to changes in sequence length, deletion or insertion of one or more nucleotides, or a change in the nucleotide composition at one or more nucleotide positions (such as a base change or base modification). In some embodiments, an adapter oligonucleotide comprises a 5' overhang, a 3' overhang, or both that is complementary to one or more target polynucleotides. Complementary overhangs can be one or more nucleotides in length, including but not limited to 1, 2, 3, 4, 5, 6, 7, 8, 9, 10, 11, 12, 13, 14, 15, or more nucleotides in length. For example, the complementary overhangs can be about 1, 2, 3, 4, 5 or 6 nucleotides in length. Complementary overhangs may comprise a fixed sequence. Complementary overhangs may comprise a random sequence of one or more nucleotides, such that one or more nucleotides are selected at random from a set of two or more different nucleotides at one or more positions, with each of the different nucleotides selected at one or more positions represented in a pool of adapters with complementary overhangs comprising the random sequence. In some embodiments, an adapter overhang is complementary to a target polynucleotide overhang produced by restriction endonuclease digestion. In some embodiments, an adapter overhang consists of an adenine or a thymine.

Adapter oligonucleotides can have any suitable length, at least sufficient to accommodate the one or more sequence elements of which they are comprised. In some embodiments, adapters are about, less than about, or more than about 10, 15, 20, 25, 30, 35, 40, 45, 50, 55, 60, 65, 70, 75, 80, 90, 100, 200, or more nucleotides in length. In some examples, the adaptors can be about 10 to about 50 nucleotides in length. In some examples, the adaptors can be about 20 to about 40 nucleotides in length.

As used herein, the term "barcode" refers to a known nucleic acid sequence that allows some feature of a polynucleotide with which the barcode is associated to be identified. In some embodiments, the feature of the polynucleotide to be identified is the sample from which the polynucleotide is derived. In some embodiments, barcodes can be at least 3, 4, 5, 6, 7, 8, 9, 10, 11, 12, 13, 14, 15, or more nucleotides in length. For example, barcodes can be at least 10, 11, 12, 13, 14, or 15 nucleotides in length. In some embodiments, barcodes can be shorter than 10, 9, 8, 7, 6, 5, or 4 nucleotides in length. For example, barcodes can be shorter than 10 nucleotides in length. In some embodiments, barcodes associated with some polynucleotides are of different length than barcodes associated with other polynucleotides. In general, barcodes are of sufficient length and comprise sequences that are sufficiently different to allow the identification of samples based on barcodes with which they are associated. In some embodiments, a barcode, and the sample source with which it is associated, can be identified accurately after the mutation, insertion, or deletion of one or more nucleotides in the barcode sequence, such as the mutation, insertion, or deletion of 1, 2, 3, 4, 5, 6, 7, 8, 9, 10, or more nucleotides. In some examples, 1, 2 or 3 nucleotides can be mutated, inserted and/or deleted. In some embodiments, each barcode in a plurality of barcodes differ from every other barcode in the plurality at least two nucleotide positions, such as at least 2, 3, 4, 5, 6, 7, 8, 9, 10, or more positions. In some examples, each barcode can differ from every other barcode by in at least 2, 3, 4 or 5 positions. In some embodiments, both a first site and a second site comprise at least one of a plurality of barcode sequences. In some embodiments, barcodes for second sites are selected independently from barcodes for first adapter oligonucleotides. In some embodiments, first sites and second sites having barcodes are paired, such that sequences of the pair comprise the same or different one or more barcodes. In some embodiments, the methods of the disclosure further comprise identifying the sample from which a target polynucleotide is derived based on a barcode sequence to which the target polynucleotide is joined. In general, a barcode may comprise a nucleic acid sequence that when joined to a target polynucleotide serves as an identifier of the sample from which the target polynucleotide was derived.

In eukaryotes, genomic DNA is packed into chromatin to consist as chromosomes within the nucleus. The basic structural unit of chromatin is the nucleosome, which consists of 146 base pairs (bp) of DNA wrapped around a histone octamer. The histone octamer consists of two copies each of the core histone H2A-H2B dimers and H3-H4 dimers. Nucleosomes are regularly spaced along the DNA in what is commonly referred to as "beads on a string".

The assembly of core histones and DNA into nucleosomes is mediated by chaperone proteins and associated assembly factors. Nearly all of these factors are core histone-binding proteins. Some of the histone chaperones, such as nucleosome assembly protein-1 (NAP-1), exhibit a preference for binding to histones H3 and H4. It has also been observed that newly synthesized histones are acetylated and then subsequently deacetylated after assembly into chromatin. The factors that mediate histone acetylation or deacetylation therefore play an important role in the chromatin assembly process.

In general, two in vitro methods have been developed for reconstituting or assembling chromatin. One method is ATP-independent, while the second is ATP-dependent. The ATP-independent method for reconstituting chromatin involves the DNA and core histones plus either a protein like NAP-1 or salt to act as a histone chaperone. This method results in a random arrangement of histones on the DNA that does not accurately mimic the native core nucleosome particle in the cell. These particles are often referred to as mononucleosomes because they are not regularly ordered, extended nucleosome arrays and the DNA sequence used is usually not longer than 250 bp (Kundu, T. K. et al., Mol. Cell 6: 551-561, 2000). To generate an extended array of ordered nucleosomes on a greater length of DNA sequence, the chromatin must be assembled through an ATP-dependent process.

The ATP-dependent assembly of periodic nucleosome arrays, which are similar to those seen in native chromatin, requires the DNA sequence, core histone particles, a chaperone protein and ATP-utilizing chromatin assembly factors. ACF (ATP-utilizing chromatin assembly and remodeling factor) or RSF (remodeling and spacing factor) are two widely researched assembly factors that are used to generate extended ordered arrays of nucleosomes into chromatin in vitro (Fyodorov, D. V., and Kadonaga, J. T. Method Enzymol. 371: 499-515, 2003; Kundu, T. K. et al. Mol. Cell 6: 551-561, 2000).

In particular embodiments, the methods of the disclosure can be easily applied to any type of fragmented double stranded DNA including but not limited to, for example, free DNA isolated from plasma, serum, and/or urine; apoptotic DNA from cells and/or tissues; DNA fragmented enzymatically in vitro (for example, by DNase I and/or restriction endonuclease); and/or DNA fragmented by mechanical forces (hydro-shear, sonication, nebulization, etc.).

Nucleic acid obtained from biological samples can be fragmented to produce suitable fragments for analysis. Template nucleic acids may be fragmented or sheared to desired length, using a variety of mechanical, chemical and/or enzymatic methods. DNA may be randomly sheared via sonication, e.g. Covaris method, brief exposure to a DNase, or using a mixture of one or more restriction enzymes, or a transposase or nicking enzyme. RNA may be fragmented by brief exposure to an RNase, heat plus magnesium, or by shearing. The RNA may be converted to cDNA. If fragmentation is employed, the RNA may be converted to cDNA before or after fragmentation. In some embodiments, nucleic acid from a biological sample is fragmented by sonication. In other embodiments, nucleic acid is fragmented by a hydroshear instrument. Generally, individual nucleic acid template molecules can be from about 2 kb bases to about 40 kb. In various embodiments, nucleic acids can be about 6 kb-10 kb fragments. Nucleic acid molecules may be single-stranded, double-stranded, or double-stranded with single-stranded regions (for example, stem- and loop-structures).

In some embodiments, cross-linked DNA molecules may be subjected to a size selection step. Size selection of the nucleic acids may be performed to cross-linked DNA molecules below or above a certain size. Size selection may further be affected by the frequency of cross-links and/or by the fragmentation method, for example by choosing a frequent or rare cutter restriction enzyme. In some embodiments, a composition may be prepared comprising cross-linking a DNA molecule in the range of about 1 kb to 5 Mb, about 5 kb to 5 Mb, about 5 kB to 2 Mb, about 10 kb to 2 Mb, about 10 kb to 1 Mb, about 20 kb to 1 Mb about 20 kb to 500 kb, about 50 kb to 500 kb, about 50 kb to 200 kb, about 60 kb to 200 kb, about 60 kb to 150 kb, about 80 kb to 150 kb, about 80 kb to 120 kb, or about 100 kb to 120 kb, or any range bounded by any of these values (e.g. about 150 kb to 1 Mb).

In some embodiments, sample polynucleotides are fragmented into a population of fragmented DNA molecules of one or more specific size range(s). In some embodiments, fragments can be generated from at least about 1, about 2, about 5, about 10, about 20, about 50, about 100, about 200, about 500, about 1000, about 2000, about 5000, about 10,000, about 20,000, about 50,000, about 100,000, about 200,000, about 500,000, about 1,000,000, about 2,000,000, about 5,000,000, about 10,000,000, or more genome-equivalents of starting DNA. Fragmentation may be accomplished by methods known in the art, including chemical, enzymatic, and mechanical fragmentation. In some embodiments, the fragments have an average length from about 10 to about 10,000, about 20,000, about 30,000, about 40,000, about 50,000, about 60,000, about 70,000, about 80,000, about 90,000, about 100,000, about 150,000, about 200,000, about 300,000, about 400,000, about 500,000, about 600,000, about 700,000, about 800,000, about 900,000, about 1,000,000, about 2,000,000, about 5,000,000, about 10,000,000, or more nucleotides. In some embodiments, the fragments have an average length from about 1 kb to about 10 Mb. In some embodiments, the fragments have an average length from about 1 kb to 5 Mb, about 5 kb to 5 Mb, about 5 kB to 2 Mb, about 10 kb to 2 Mb, about 10 kb to 1 Mb, about 20 kb to 1 Mb about 20 kb to 500 kb, about 50 kb to 500 kb, about 50 kb to 200 kb, about 60 kb to 200 kb, about 60 kb to 150 kb, about 80 kb to 150 kb, about 80 kb to 120 kb, or about 100 kb to 120 kb, or any range bounded by any of these values (e.g. about 60 to 120 kb). In some embodiments, the fragments have an average length less than about 10 Mb, less than about 5 Mb, less than about 1 Mb, less than about 500 kb, less than about 200 kb, less than about 100 kb, or less than about 50 kb. In other embodiments, the fragments have an average length more than about 5 kb, more than about 10 kb, more than about 50 kb, more than about 100 kb, more than about 200 kb, more than about 500 kb, more than about 1 Mb, more than about 5 Mb, or more than about 10 Mb. In some embodiments, the fragmentation is accomplished mechanically comprising subjection sample DNA molecules to acoustic sonication. In some embodiments, the fragmentation comprises treating the sample DNA molecules with one or more enzymes under conditions suitable for the one or more enzymes to generate double-stranded nucleic acid breaks. Examples of enzymes useful in the generation of DNA fragments include sequence specific and non-sequence specific nucleases. Non-limiting examples of nucleases include DNase I, Fragmentase, restriction endonucleases, variants thereof, and combinations thereof. For example, digestion with DNase I can induce random double-stranded breaks in DNA in the absence of $Mg^{++}$ and in the presence of $Mn^{++}$. In some embodiments, fragmentation comprises treating the sample DNA molecules with one or more restriction endonucleases. Fragmentation can produce fragments having 5' overhangs, 3' overhangs, blunt ends, or a combination thereof. In some embodiments, such as when fragmentation comprises the use of one or more restriction endonucleases, cleavage of sample DNA molecules leaves overhangs having a predictable sequence. In some embodiments, the method includes the step of size selecting the fragments via standard methods such as column purification or isolation from an agarose gel.

In some embodiments, the 5' and/or 3' end nucleotide sequences of fragmented DNA are not modified prior to ligation. For example, fragmentation by a restriction endonuclease can be used to leave a predictable overhang, followed by ligation with a nucleic acid end comprising an overhang complementary to the predictable overhang on a DNA fragment. In another example, cleavage by an enzyme that leaves a predictable blunt end can be followed by ligation of blunt-ended DNA fragments to nucleic acids, such as adapters, oligonucleotides, or polynucleotides, comprising a blunt end. In some embodiments, the fragmented DNA molecules are blunt-end polished (or "end repaired") to produce DNA fragments having blunt ends, prior to being joined to adapters. The blunt-end polishing step may be accomplished by incubation with a suitable enzyme, such as a DNA polymerase that has both 3' to 5' exonuclease activity and 5' to 3' polymerase activity, for example T4 polymerase. In some embodiments, end repair can be followed by an addition of 1, 2, 3, 4, 5, 6, 7, 8, 9, 10, 11, 12, 13, 14, 15, 16, 17, 18, 19, 20 or more nucleotides, such as one or more adenine, one or more thymine, one or more guanine, or one or more cytosine, to produce an overhang. For example, the end pair can be followed by an addition of 1, 2, 3, 4, 5, or 6 nucleotides. DNA fragments having an overhang can be joined to one or more nucleic acids, such as oligonucleotides, adapter oligonucleotides, or polynucleotides, having a complementary overhang, such as in a ligation reaction. For example, a single adenine can be added to the 3' ends of end repaired DNA fragments using a template independent polymerase, followed by ligation to one or more adapters each having a thymine at a 3' end. In some embodiments, nucleic acids, such as oligonucleotides or polynucleotides can be joined to blunt end double-stranded DNA molecules which have been modified by extension of the 3' end with one or more nucleotides followed by 5' phosphorylation. In some cases, extension of the 3' end may be performed with a polymerase such as, Klenow polymerase or any of the suitable polymerases provided herein, or by use of a terminal deoxynucleotide transferase, in the presence of one or more dNTPs in a suitable buffer that can contain magnesium. In some embodiments, target polynucleotides having blunt ends are joined to one or more adapters comprising a blunt end. Phosphorylation of 5' ends of DNA fragment molecules may be performed for example with T4 polynucleotide kinase in a suitable buffer containing ATE and magnesium. The fragmented DNA molecules may optionally be treated to dephosphorylate 5' ends or 3' ends, for example, by using enzymes known in the art, such as phosphatases.

The terms "connecting", "joining" and "ligation" as used herein, with respect to two Polynucleotides, such as an adapter oligonucleotide and a target polynucleotide, refers to the covalent attachment of two separate DNA segments to produce a single larger polynucleotide with a contiguous backbone. Methods for joining two DNA segments are known in the art, and include without limitation, enzymatic and non-enzymatic (e.g. chemical) methods. Examples of ligation reactions that are non-enzymatic include the non-enzymatic ligation techniques described in U.S. Pat. Nos. 5,780,613 and 5,476,930, which are herein incorporated by reference. In some embodiments, an adapter oligonucleotide is joined to a target polynucleotide by a ligase, for example a DNA ligase or RNA ligase. Multiple ligases, each having characterized reaction conditions, are known in the art, and include, without limitation NAD$^+$-dependent ligases including tRNA ligase, Taq DNA ligase, *Thermus fillformis* DNA ligase, *Escherichia coli* DNA ligase, Tth DNA ligase, *Thermus scotoductus* DNA ligase (I and II), thermostable ligase, *Ampligase thermostable* DNA ligase, VanC-type ligase, 9° N DNA Ligase, Tsp DNA ligase, and novel ligases discovered by bioprospecting; ATP-dependent ligases including T4 RNA ligase, T4 DNA ligase, T3 DNA ligase, T7 DNA ligase, Pfu DNA ligase, DNA ligase 1, DNA ligase III, DNA ligase IV, and novel ligases discovered by bioprospecting: and wild-type, mutant isoforms, and genetically engineered variants thereof.

Ligation can be between DNA segments having hybridizable sequences, such as complementary overhangs. Ligation can also be between two blunt ends. Generally, a 5' phosphate is utilized in a ligation reaction. The 5' phosphate can be provided by the target polynucleotide, the adapter oligonucleotide, or both. 5' phosphates can be added to or removed from DNA segments to be joined, as needed. Methods for the addition or removal of 5' phosphates are known in the art, and include without limitation enzymatic and chemical processes. Enzymes useful in the addition and/or removal of 5' phosphates include kinases, phosphatases, and polymerases. In some embodiments, both of the two ends joined in a ligation reaction (e.g. an adapter end and a target polynucleotide end) provide a 5' phosphate, such that two covalent linkages are made in joining the two ends. In some embodiments, only one of the two ends joined in a ligation reaction (e.g. only one of an adapter end and a target polynucleotide end) provides a 5' phosphate, such that only one covalent linkage is made in joining the two ends.

In some embodiments, only one strand at one or both ends of a target polynucleotide is joined to an adapter oligonucleotide. In some embodiments, both strands at one or both ends of a target polynucleotide are joined to an adapter oh gonucleotide. In some embodiments, 3' phosphates are removed prior to ligation. In some embodiments, an adapter oligonucleotide is added to both ends of a target polynucleotide, wherein one or both strands at each end are joined to one or more adapter oligonucleotides. When both strands at both ends are joined to an adapter oligonucleotide, joining can be followed by a cleavage reaction that leaves a 5' overhang that can serve as a template for the extension of the corresponding 3' end, which 3' end may or may not include one or more nucleotides derived from the adapter oligonucleotide. In some embodiments, a target polynucleotide is joined to a first adapter oligonucleotide on one end and a second adapter oligonucleotide on the other end. In some embodiments, two ends of a target polynucleotide are joined to the opposite ends of a single adapter oligonucleotide. In some embodiments, the target polynucleotide and the adapter oligonucleotide to which it is joined comprise blunt ends. In some embodiments, separate ligation reactions can be carried out for each sample, using a different first adapter oligonucleotide comprising at least one barcode sequence for each sample, such that no barcode sequence is joined to the target polynucleotides of more than one sample. A DNA segment or a target polynucleotide that has an adapter oligonucleotide joined to it is considered "tagged" by the joined adapter.

In some cases, the ligation reaction can be performed at a DNA segment or target polynucleotide concentration of about 0.1 ng/μL, about 0.2 ng/μL, about 0.3 ng/μL, about 0.4 ng/μL, about 0.5 ng/μL, about 0.6 ng/μL, about 0.7 ng/μL, about 0.8 ng/μL, about 0.9 ng/μL, about 1.0 ng/μL, about 1.2 ng/μL, about 1.4 ng/μL, about 1.6 ng/μL, about 1.8 ng/μL, about 2.0 ng/μL, about 2.5 ng/μL, about 3.0 ng/μL, about 3.5 ng/μL, about 4.0 ng/μL, about 4.5 ng/μL, about 5.0 ng/μL, about 6.0 ng/μL, about 7.0 ng/μL, about 8.0 ng/μL, about 9.0 ng/μL, about 10 ng/μL, about 15 ng/μL, about 20 ng/μL, about 30 ng/μL, about 40 ng/μL, about 50 ng/μL, about 60 ng/μL, about 70 ng/μL, about 80 ng/μL, about 90 ng/μL, about 100 ng/μL, about 150 ng/μL, about 200 ng/μL, about 300 ng/μL, about 400 ng/μL, about 500 ng/μL, about 600 ng/μL, about 800 ng/μL, or about 1000 ng/μL. For example, the ligation can be performed at a DNA segment or target polynucleotide concentration of about 100 ng/μL, about 150 ng/μL, about 200 ng/μL, about 300 ng/μL, about 400 ng/μL, or about 500 ng/μL.

In some cases, the ligation reaction can be performed at a DNA segment or target polynucleotide concentration of about 0.1 to 1000 ng/μL, about 1 to 1000 ng/μL, about 1 to 800 ng/μL, about 10 to 800 ng/μL, about 10 to 600 ng/μL, about 100 to 600 ng/μL, or about 100 to 500 ng/μL.

In some cases, the ligation reaction can be performed for more than about 5 minutes, about 10 minutes, about 20 minutes, about 30 minutes, about 40 minutes, about 50 minutes, about 60 minutes, about 90 minutes, about 2 hours, about 3 hours, about 4 hours, about 5 hours, about 6 hours, about 8 hours, about 10 hours, about 12 hours, about 18 hours, about 24 hours, about 36 hours, about 48 hours, or about 96 hours. In other cases, the ligation reaction can be performed for less than about 5 minutes, about 10 minutes, about 20 minutes, about 30 minutes, about 40 minutes, about 50 minutes, about 60 minutes, about 90 minutes, about 2 hours, about 3 hours, about 4 hours, about 5 hours, about 6 hours, about 8 hours, about 10 hours, about 12 hours, about 18 hours, about 24 hours, about 36 hours, about 48 hours, or about 96 hours. For example, the ligation reaction can be performed for about 30 minutes to about 90 minutes. In some embodiments, joining of an adapter to a target polynucleotide produces a joined product polynucleotide having a 3' overhang comprising a nucleotide sequence derived from the adapter.

In some embodiments, after joining at least one adapter oligonucleotide to a target polynucleotide, the 3' end of one or more target polynucleotides is extended using the one or more joined adapter oligonucleotides as template. For example, an adapter comprising two hybridized oligonucleotides that is joined to only the 5' end of a target polynucleotide allows for the extension of the unjoined 3' end of the target using the joined strand of the adapter as template, concurrently with or following displacement of the unjoined strand. Both strands of an adapter comprising two hybridized oligonucleotides may be joined to a target polynucleotide such that the joined product has a 5' overhang, and the complementary 3' end can be extended using the 5' overhang as template. As a further example, a hairpin adapter oligonucleotide can be joined to the 5' end of a target polynucleotide. In some embodiments, the 3' end of the target polynucleotide that is extended comprises one or more nucleotides from an adapter oligonucleotide. For target polynucleotides to which adapters are joined on both ends, extension can be carried out for both 3' ends of a double-stranded target polynucleotide having 5' overhangs. This 3' end extension, or "fill-in" reaction, generates a complementary sequence, or "complement," to the adapter oligonucleotide template that is hybridized to the template, thus filling in the 5' overhang to produce a double-stranded sequence region. Where both ends of a double-stranded target polynucleotide have 5' overhangs that are filled in by extension of the complementary strands 3' ends, the product is completely double-stranded. Extension can be carried out by any suitable polymerase known in the art, such as a DNA polymerase, many of which are commercially available. DNA polymerases can comprise DNA-dependent DNA polymerase activity, RNA-dependent DNA polymerase activity, or DNA-dependent and RNA-dependent DNA polymerase activity. DNA polymerases can be thermostable or non-thermostable. Examples of DNA polymerases include, but are not limited to, Taq polymerase, Tth polymerase, Tli polymerase, Pfu polymerase, Pfutuho polymerase, Pyrobest polymerase, Pwo polymerase, KOD polymerase. Bst polymerase, Sac polymerase, Sso polymerase, Poc polymerase, Pab polymexase, Mth polymerase, Pho polymerase, ES4 polymerase, VENT polymerase, DEEPVENT polymerase, EX-Taq polymerase, LA-Taq polymerase, Expand polymerases, Platinum Taq pckymerases, polymerase, Thr polymerase, polymerase, Tru polymerase, Tac polymerase, Tne polymerase, Tma polymerase, Tih polymerase, Tfi polymerase, Klenow fragment, and variants, modified products and derivatives thereof 3' end extension can be performed before or after pooling of target polynucleotides from independent samples.

In certain embodiments, the disclosure provides methods for the enrichment of a target nucleic acids and analysis of the target nucleic acids. In some cases, the methods for enrichment is in a solution based format. In some cases, the target nucleic acid can be labeled with a labeling agent. In other cases, the target nucleic acid can be crosslinked to one or more association molecules that are labeled with a labeling agent. Examples of labeling agents include but are not limited to biotin, polyhistidine labels, and chemical labels (e.g. alkyne and azide derivatives used in Click Chemistry methods). Further, the labeled target nucleic acid can be captured and thereby enriched by using a capturing agent. The capturing agent can be streptavidin and/or avidin, an antibody, a chemical moiety (e.g. alkyne, azide), and any biological, chemical, physical, or enzymatic agents used for affinity purification known in the art.

In some cases, immobilized or non-immobilized nucleic acid probes can be used to capture the target nucleic acids. For example, the target nucleic acids can be enriched from a sample by hybridization to the probes on a solid support or in solution. In some examples, the sample can be a genomic sample. In some examples, the probes can be an amplicon. The amplicon can comprise a predetermined sequence. Further, the hybridized target nucleic acids can be washed and/or eluted off of the probes. The target nucleic acid can be a DNA, RNA, cDNA, or mRNA molecule.

In some cases, the enrichment method can comprise contacting the sample comprising the target nucleic acid to the probes and binding the target nucleic acid to a solid support. In some cases, the sample can be fragmented using chemical, physical or enzymatic methods to yield the target nucleic acids. In some cases, the probes can be specifically hybridized to the target nucleic acids. In some cases, the target nucleic acids can have an average size of about 50 to 5000, about 50 to 2000, about 100 to 2000, about 100 to 1000, about 200 to 1000, about 200 to 800, or about 300 to 800, about 300 to 600, or about 400 to 600 nucleotide residues. The target nucleic acids can be further separated from the unbound nucleic acids in the sample. The solid support can be washed and/or eluted to provide the enriched target nucleic acids. In some examples, the enrichment steps can be repeated for about 1, 2, 3, 4, 5, 6, 7, 8, 9, or 10 times. For example, the enrichment steps can be repeated for about 1, 2, or 3 times.

Figure 4:
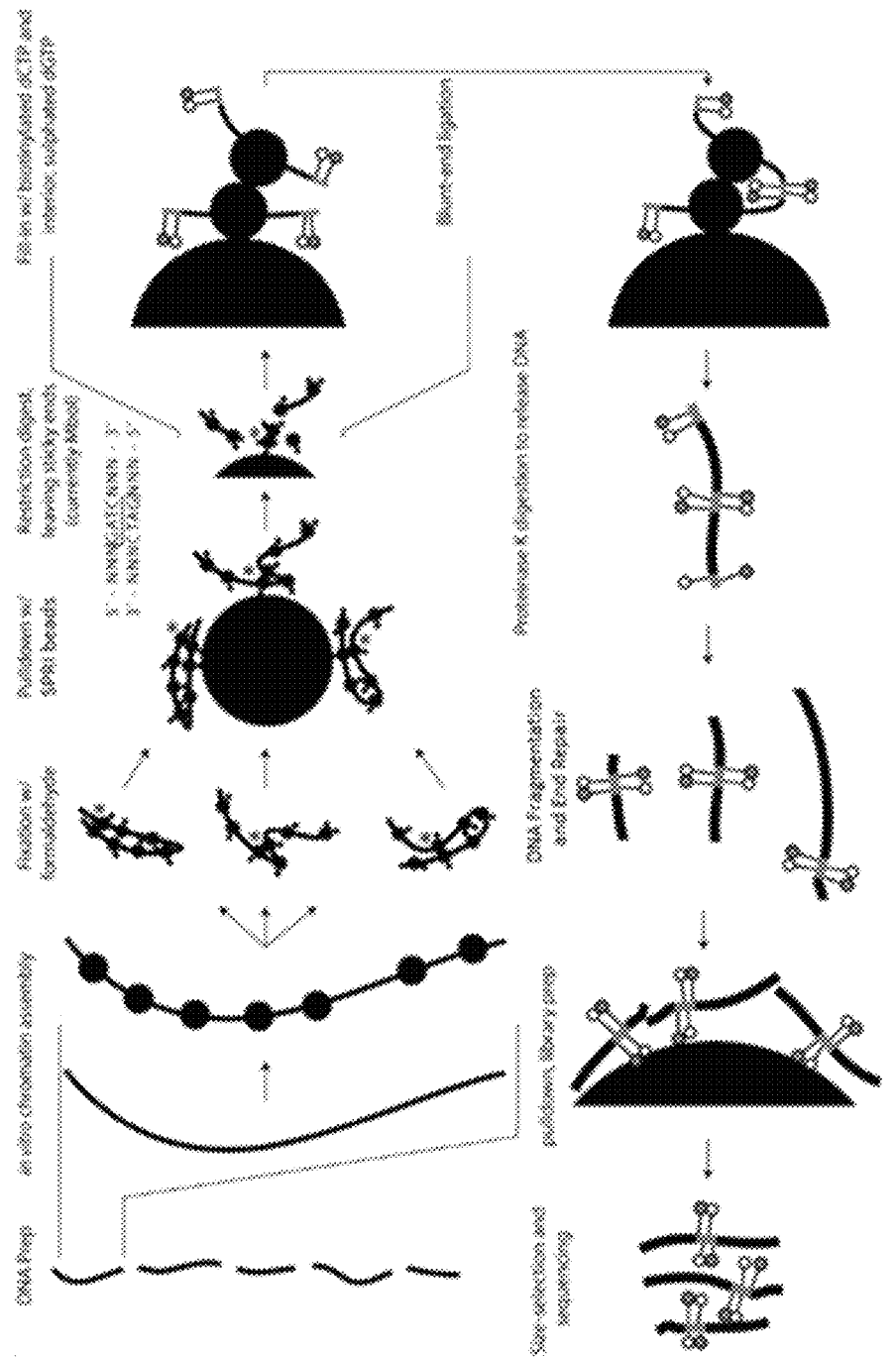
FIG. 4 illustrates an exemplary protocol of the disclosure: DNA fragments are first generated and prepared; followed by in vitro chromatin assembly; the chromatin/DNA complex is then fixed with formaldehyde and pulled down with SPRI beads; the complexes are then restriction digested to generate sticky ends that are then filled with biotinylated dCTP and interior, sulfated GTP; following blunt-end ligation, the chromatin/DNA complex undergoes proteinase digestion and shearing; after which the DNA fragments are pulled down with SPRI beads and ligated with a sequencing adaptor; and finally, the DNA fragments are selected by size and sequenced.

In some cases, the enrichment method can comprise providing probe derived amplicons wherein the probes for amplification are attached to a solid support. The solid support can comprise support-immobilized nucleic acid probes to capture specific target nucleic acid from a sample. The probe derived amplicons can hybridize to the target nucleic acids. Following hybridization to the probe amplicons, the target nucleic acids in the sample can be enriched by capturing (e.g., via capturing agents as biotin, antibodies, etc.) and washing and/or eluting the hybridized target nucleic acids from the captured probes (FIG. 4). The target nucleic acid sequence(s) may be further amplified using, for example, PCR methods to produce an amplified pool of enriched PCR products.

In some cases, the solid support can be a microarray, a slide, a chip, a microwell, a column, a tube, a particle or a bead. In some examples, the solid support can be coated with streptavidin and/or avidin. In other examples, the solid support can be coated with an antibody. Further, the solid support can comprise a glass, metal, ceramic or polymeric material. In some embodiments, the solid support can be a nucleic acid microarray (e.g. a DNA microarray). In other embodiments, the solid support can be a paramagnetic bead.

In some cases, the enrichment method can comprise digestion with a secondary restriction enzyme, self-ligation (e.g. self-circularization), and re-digestion with the original restriction enzyme. In particular examples, only the ligation products will be linearized and available for adapter-ligation and sequencing. In other cases, the ligation junction sequence itself can be used for hybridization based enrichment using a bait-probe complimentary to the junction sequence.

In particular embodiments, the disclosure provides methods for amplifying the enriched DNA. In some cases, the enriched DNA is a read-pair. The read-pair can be obtained by the methods of the present disclosure.

In some embodiments, the one or more amplification and/or replication steps are used for the preparation of a library to be sequenced. Any amplification method known in the art may be used. Examples of amplification techniques that can be used include, but are not limited to, quantitative PCR, quantitative fluorescent PCR (QF-PCR), multiplex fluorescent PCR (MF-PCR), real time PCR (RTPCR), single cell PCR, restriction fragment length polymorphism PCR (PCR-RFLP), PCK-RFLPIRT-PCR-IRFLP, hot start PCR, nested PCR, in situ polony PCR, in situ rolling circle amplification (RCA), bridge PCR, ligation mediated PCR, Qb replicase amplification, inverse PCR, picotiter PCR and emulsion PCR. Other suitable amplification methods include the ligase chain reaction (LCR), transcription amplification, self-sustained sequence replication, selective amplification of target polynucleotide sequences, consensus sequence primed polymerase chain reaction (CP-PCR), arbitrarily primed polymerase chain reaction (AP-PCR), degenerate oligonucleotide-primed PCR (DOP-PCR) and nucleic acid based sequence amplification (NABSA). Other amplification methods that can be used herein include those described in U.S. Pat. Nos. 5,242,794; 5,494,810; 4,988,617; and 6,582,938.

In particular embodiments, PCR is used to amplify DNA molecules after they are dispensed into individual partitions. In some cases, one or more specific priming sequences within amplification adapters are utilized for PCR amplification. The amplification adapters may be ligated to fragmented DNA molecules before or after dispensing into individual partitions. Polynucleotides comprising amplification adapters with suitable priming sequences on both ends can be PCR amplified exponentially. Polynucleotides with only one suitable priming sequence due to, for example, imperfect ligation efficiency of amplification adapters comprising priming sequences, may only undergo linear amplification. Further, polynucleotides can be eliminated from amplification, for example PCR amplification, all together, if no adapters comprising suitable priming sequences are ligated. In some embodiments, the number of PCR cycles vary between 10-30, but can be as low as 9, 8, 7, 6, 5, 4, 3, 2 or less or as high as 40, 45, 50, 55, 60 or more. As a result, exponentially amplifiable fragments carrying amplification adapters with a suitable priming sequence can be present in much higher (1000 fold or more) concentration compared to linearly amplifiable or un-amplifiable fragments, after a PCR amplification. Benefits of PCR, as compared to whole genome amplification techniques (such as amplification with randomized primers or Multiple Displacement Amplification using phi29 polymerase) include, but are not limited to a more uniform relative sequence coverage—as each fragment can be copied at most once per cycle and as the amplification is controlled by thermocycling program, a substantially lower rate of forming chimeric molecules than for example MDA (Lasken et al., 2007, BMC Biotechnology)—as chimeric molecules pose significant challenges for accurate sequence assembly by presenting nonbiological sequences in the assembly graph, which may result in higher rate of misassemblies or highly ambiguous and fragmented assembly, reduced sequence specific biases that may result from binding of randomized primers commonly used in MDA versus using specific priming sites with a specific sequence, a higher reproducibility in the amount of final amplified DNA product, which can be controlled by selection of the number of PCR cycles, and a higher fidelity in replication with the polymerases that are commonly used in PCR as compared to common whole genome amplification techniques known in the art.

In some embodiments, the fill-in reaction is followed by or performed as part of amplification of one or more target polynucleotides using a first primer and a second primer, wherein the first primer comprises a sequence that is hybridizable to at least a portion of the complement of one or more of the first adapter oligonucleotides, and further wherein the second primer comprises a sequence that is hybridizable to at least a portion of the complement of one or more of the second adapter oligonucleotides. Each of the first and second primers may be of any suitable length, such as about, less than about, or more than about 10, 15, 20, 25, 30, 35, 40, 45, 50, 55, 60, 65, 70, 75, 80, 90, 100, or more nucleotides, any portion or all of which may be complementary to the corresponding target sequence (e.g. about, less than about, or more than about 5, 10, 15, 20, 25, 30, 35, 40, 45, 50, or more nucleotides). For example, about 10 to 50 nucleotides can be complementary to the corresponding target sequence.

In some cases amplification adapters are used in the library generation process. Amplification adapters are oligomer pairs that share partial reverse complementarity, such that they can be annealed to form a molecule having both a double-stranded portion and a single-stranded portion. Through use of amplification adapters, one is able to ligate separate annealing targets to each end of a library molecule. Because the single stranded portion of the amplification adapter comprises sequence that is not reverse-complementary, primers are available that anneal only to one or the other, or the reverse complement of the other, of the single strand arms of the amplification adapter. Accordingly, amplification adapters allow one to add a first distinct primer binding site to a first end of a library molecule, and a second distinct primer binding site to a second end of a library molecule.

Oligo that are suitable for generation of amplification adapters are indicated below (* is phosphorothioate bond). Oligos are listed as P5/P7 pairs, with each P7 oligo synthesized to work with the P5 oligo immediately preceding it. For each pair, the last ten nucleotide bases prior to the phosphothioate bond of the P5 oligo are reverse complementary to the first ten bases after the /5Phos/ of the second oligo.

| SEQ ID NO | Position | Sequence (5' to 3') |
|---|---|---|
| 1 | P5_full | ACACTCTTTCCCTACACGACGCTCTTCCGATG*T |
| 2 | P7_rev | /5Phos/CATCGGAAGAGCACACGTCTGAACTCCAGTCA*/3ddC/ |
| 3 | P5_full | ACACTCTTTCCCTACACGACGCTCTTCCGACC*T |
| 4 | P7_rev | /5Phos/GGTCGGAAGAGCACACGTCTGAACTCCAGTCA*/3ddC/ |
| 5 | P5_full | ACACTCTTTCCCTACACGACGCTCTACCGATC*T |
| 6 | P7_rev | /5Phos/GATCGGTAGAGCACACGTCTGAACTCCAGTCA*/3ddC/ |
| 7 | P5_full | ACACTCTTTCCCTACACGACGCTATTCCGATC*T |

-continued

| SEQ ID NO | Position | Sequence (5' to 3') |
|---|---|---|
| 8 | P7_rev | /5Phos/GATCGGAATAGCACACGTCTGAACTCCAGTCA*/3ddC/ |
| 9 | P5_full | ACACTCTTTCCCTACACGACGCTCTTCCGGATC*T |
| 10 | P7_rev | /5Phos/GATCCGAAGAGCACACGTCTGAACTCCAGTCA*/3ddC/ |
| 11 | P5_full | ACACTCTTTCCCTACACGACCCTCTTCCGATC*T |
| 12 | P7_rev | /5Phos/GATCGGAAGAGGACACGTCTGAACTCCAGTCA*/3ddC/ |
| 13 | P5_full | ACACTCTTTCCCTACACGACGCACTTCCGATC*T |
| 14 | P7_rev | /5Phos/GATCGGAAGTGCACACGTCTGAACTCCAGTCA*/3ddC/ |
| 15 | P5_full | ACACTCTTTCCCTACACGACGCTCTTCCGATC*T |
| 16 | P7_rev | /5Phos/GATCGGAAGAGCACACGTCTGAACTCCAGTCA*/3ddC/ |

"Amplification" refers to any process by which the copy number of a target sequence is increased. In some cases, a replication reaction may produce only a single complimentary copy/replica of a polynucleotide. Methods for primer-directed amplification of target polynucleotides are known in the art, and include without limitation, methods based on the polymerase chain reaction (PCR). Conditions favorable to the amplification of target sequences by PCR are known in the art, can be optimized at a variety of steps in the process, and depend on characteristics of elements in the reaction, such as target type, target concentration, sequence length to be amplified, sequence of the target and/or one or more primers, primer length, primer concentration, polymerase used, reaction volume, ratio of one or more elements to one or more other elements, and others, some or all of which can be altered. In general, PCR involves the steps of denaturation of the target to be amplified (if double stranded), hybridization of one or more primers to the target, and extension of the primers by a DNA polymerase, with the steps repeated (or "cycled") in order to amplify the target sequence. Steps in this process can be optimized for various outcomes, such as to enhance yield, decrease the formation of spurious products, and/or increase or decrease specificity of primer annealing. Methods of optimization are well known in the art and include adjustments to the type or amount of elements in the amplification reaction and/or to the conditions of a given step in the process, such as temperature at a particular step, duration of a particular step, and/or number of cycles.

In some embodiments, an amplification reaction can comprise at least about 5, 10, 15, 20, 25, 30, 35, 40, 50, 60, 70, 80, 90, 100, 150, 200 or more cycles. In some examples, an amplification reaction can comprise at least about 20, 25, 30, 35 or 40 cycles. In some embodiments, an amplification reaction comprises no more than about 5, 10, 15, 20, 25, 35, 40, 50, 60, 70, 80, 90, 100, 150, 200 or more cycles. Cycles can contain any number of steps, such as 1, 2, 3, 4, 5, 6, 7, 8, 9, 10 or more steps. Steps can comprise any temperature or gradient of temperatures, suitable for achieving the purpose of the given step, including but not limited to, 3' end extension (e.g. adapter fill-in), primer annealing, primer extension, and strand denaturation. Steps can be of any duration, including but not limited to about, less than about, or more than about 1, 5, 10, 15, 20, 25, 30, 35, 40, 45, 50, 55, 60, 70, 80, 90, 100, 120, 180, 240, 300, 360, 420, 480, 540, 600, 1200, 1800, or more seconds, including indefinitely until manually interrupted. Cycles of any number comprising different steps can be combined in any order. In some embodiments, different cycles comprising different steps are combined such that the total number of cycles in the combination is about, less that about, or more than about 5, 10, 15, 20, 25, 30, 35, 40, 50, 60, 70, 80, 90, 100, 150, 200 or more cycles. In some embodiments, amplification is performed following the fill-in reaction.

In some embodiments, the amplification reaction can be carried out on at least about 1, 2, 3, 4, 5, 6, 7, 8, 9, 10, 12, 14, 16, 18, 20, 25, 30, 40, 50, 100, 200, 300, 400, 500, 600, 800, 1000 ng of the target DNA molecule. In other embodiments, the amplification reaction can be carried out on less than about 1, 2, 3, 4, 5, 6, 7, 8, 9, 10, 12, 14, 16, 18, 20, 25, 30, 40, 50, 100, 200, 300, 400, 500, 600, 800, 1000 ng of the target DNA molecule.

Amplification can be performed before or after pooling of target polynucleotides from independent samples.

Methods of the disclosure involve determining an amount of amplifiable nucleic acid present in a sample. Any known method may be used to quantify amplifiable nucleic acid, and an exemplary method is the polymerase chain reaction (PCR), specifically quantitative polymerase chain reaction (qPCR). qPCR is a technique based on the polymerase chain reaction, and is used to amplify and simultaneously quantify a targeted nucleic acid molecule. qPCR allows for both detection and quantification (as absolute number of copies or relative amount when normalized to DNA input or additional normalizing genes) of a specific sequence in a DNA sample. The procedure follows the general principle of polymerase chain reaction, with the additional feature that the amplified DNA is quantified as it accumulates in the reaction in real time after each amplification cycle. QPCR is described, for example, in Kurnit et al. (U.S. Pat. No. 6,033,854), Wang et al. (U.S. Pat. Nos. 5,567,583 and 5,348,853), Ma et al. (The Journal of American Science, 2(3), 2006), Heid et al. (Genome Research 986-994, 1996), Sambrook and Russell (Quantitative PCR, Cold Spring Harbor Protocols, 2006), and Higuchi (U.S. Pat. Nos. 6,171, 785 and 5,994,056). The contents of these are incorporated by reference herein in their entirety.

Other methods of quantification include use of fluorescent dyes that intercalate with double-stranded DNA, and modified DNA oligonucleotide probes that fluoresce when hybridized with a complementary DNA. These methods can be broadly used but are also specifically adapted to real-time PCR as described in further detail as an example. In the first method, a DNA-binding dye binds to all double-stranded (ds)DNA in PCR, resulting in fluorescence of the dye. An increase in DNA product during PCR therefore leads to an increase in fluorescence intensity and is measured at each cycle, thus allowing DNA concentrations to be quantified. The reaction is prepared similarly to a standard PCR reaction, with the addition of fluorescent (ds)DNA dye. The reaction is run in a thermocycler, and after each cycle, the levels of fluorescence are measured with a detector; the dye only fluoresces when bound to the (ds)DNA (i.e., the PCR product). With reference to a standard dilution, the (ds)DNA concentration in the PCR can be determined. Like other real-time PCR methods, the values obtained do not have absolute units associated with it. A comparison of a measured DNA/RNA sample to a standard dilution gives a fraction or ratio of the sample relative to the standard, allowing relative comparisons between different tissues or experimental conditions. To ensure accuracy in the quantification and/or expression of a target gene can be normalized with respect to a stably expressed gene. Copy numbers of unknown genes can similarly be normalized relative to genes of known copy number.

The second method uses a sequence-specific RNA or DNA-based probe to quantify only the DNA containing a probe sequence; therefore, use of the reporter probe significantly increases specificity, and allows quantification even in the presence of some non-specific DNA amplification. This allows for multiplexing, i.e., assaying for several genes in the same reaction by using specific probes with differently colored labels, provided that all genes are amplified with similar efficiency.

This method is commonly carried out with a DNA-based probe with a fluorescent reporter (e.g. 6-carboxyfluorescein) at one end and a quencher (e.g., 6-carboxy-tetramethylrhodamine) of fluorescence at the opposite end of the probe. The close proximity of the reporter to the quencher prevents detection of its fluorescence. Breakdown of the probe by the 5' to 3' exonuclease activity of a polymerase (e.g., Taq polymerase) breaks the reporter-quencher proximity and thus allows unquenched emission of fluorescence, which can be detected. An increase in the product targeted by the reporter probe at each PCR cycle results in a proportional increase in fluorescence due to breakdown of the probe and release of the reporter. The reaction is prepared similarly to a standard PCR reaction, and the reporter probe is added. As the reaction commences, during the annealing stage of the PCR both probe and primers anneal to the DNA target. Polymerization of a new DNA strand is initiated from the primers, and once the polymerase reaches the probe, its 5'-3'-exonuclease degrades the probe, physically separating the fluorescent reporter from the quencher, resulting in an increase in fluorescence. Fluorescence is detected and measured in a real-time PCR thermocycler, and geometric increase of fluorescence corresponding to exponential increase of the product is used to determine the threshold cycle in each reaction.

Relative concentrations of DNA present during the exponential phase of the reaction are determined by plotting fluorescence against cycle number on a logarithmic scale (so an exponentially increasing quantity will give a straight line). A threshold for detection of fluorescence above background is determined. The cycle at which the fluorescence from a sample crosses the threshold is called the cycle threshold, $C_t$. Since the quantity of DNA doubles every cycle during the exponential phase, relative amounts of DNA can be calculated, e.g. a sample with a $C_t$ of 3 cycles earlier than another has $2^3=8$ times more template. Amounts of nucleic acid (e.g., RNA or DNA) are then determined by comparing the results to a standard curve produced by a real-time PCR of serial dilutions (e.g. undiluted, 1:4, 1:16, 1:64) of a known amount of nucleic acid.

In certain embodiments, the qPCR reaction involves a dual fluorophore approach that takes advantage of fluorescence resonance energy transfer (FRET), e.g., LIGHTCYCLER hybridization probes, where two oligonucleotide probes anneal to the amplicon (e.g. see U.S. Pat. No. 6,174,670). The oligonucleotides are designed to hybridize in a head-to-tail orientation with the fluorophores separated at a distance that is compatible with efficient energy transfer. Other examples of labeled oligonucleotides that are structured to emit a signal when bound to a nucleic acid or incorporated into an extension product include: SCORPIONS probes (e.g., Whitcombe et al., Nature Biotechnology 17:804-807, 1999, and U.S. Pat. No. 6,326,145), Sunrise (or AMPLIFLOUR) primers (e.g., Nazarenko et al., Nuc. Acids Res. 25:2516-2521, 1997, and U.S. Pat. No. 6,117,635), and LUX primers and MOLECULAR BEACONS probes (e.g., Tyagi et al., Nature Biotechnology 14:303-308, 1996 and U.S. Pat. No. 5,989,823).

In other embodiments, a qPCR reaction uses fluorescent Taqman methodology and an instrument capable of measuring fluorescence in real time (e.g., ABI Prism 7700 Sequence Detector). The Taqman reaction uses a hybridization probe labeled with two different fluorescent dyes. One dye is a reporter dye (6-carboxyfluorescein), the other is a quenching dye (6-carboxy-tetramethylrhodamine). When the probe is intact, fluorescent energy transfer occurs and the reporter dye fluorescent emission is absorbed by the quenching dye. During the extension phase of the PCR cycle, the fluorescent hybridization probe is cleaved by the 5'-3' nucleolytic activity of the DNA polymerase. On cleavage of the probe, the reporter dye emission is no longer transferred efficiently to the quenching dye, resulting in an increase of the reporter dye fluorescent emission spectra. Any nucleic acid quantification method, including real-time methods or single-point detection methods may be used to quantify the amount of nucleic acid in the sample. The detection can be performed several different methodologies (e.g., staining, hybridization with a labeled probe; incorporation of biotinylated primers followed by avidin-enzyme conjugate detection; incorporation of 32P-labeled deoxynucleotide triphosphates, such as dCTP or dATP, into the amplified segment), as well as any other suitable detection method known in the art for nucleic acid quantification. The quantification may or may not include an amplification step.

In some embodiments, the disclosure provides labels for identifying or quantifying the linked DNA segments. In some cases, the linked DNA segments can be labeled in order to assist in downstream applications, such as array hybridization. For example, the linked DNA segments can be labeled using random priming or nick translation.

A wide variety of labels (e.g. reporters) may be used to label the nucleotide sequences described herein, including but not limited to during the amplification step. Suitable labels include radionuclides, enzymes, fluorescent, chemiluminescent, or chromogenic agents as well as ligands, cofactors, inhibitors, magnetic particles and the like. Examples of such labels are included in U.S. Pat. Nos. 3,817,837; 3,850,752; 3,939,350; 3,996,345; 4,277,437; 4,275,149 and 4,366,241, which are incorporated by reference in its entirety.

Additional labels include but are not limited to β-galactosidase, invertase, green fluorescent protein, luciferase, chloramphenicol, acetyltransferase, β-glucuronidase, exoglucanase and glucoamylase. Fluorescent labels may also be used, as well as fluorescent reagents specifically synthesized with particular chemical properties. A wide variety of ways to measure fluorescence are available. For example, some fluorescent labels exhibit a change in excitation or emission spectra, some exhibit resonance energy transfer where one fluorescent reporter loses fluorescence, while a second gains in fluorescence, some exhibit a loss (quenching) or appearance of fluorescence, while some report rotational movements.

Further, in order to obtain sufficient material for labeling, multiple amplifications may be pooled, instead of increasing the number of amplification cycles per reaction. Alternatively, labeled nucleotides can be incorporated in to the last cycles of the amplification reaction, e.g. 30 cycles of PCR (no label) +10 cycles of PCR (plus label).

In particular embodiments, the disclosure provides probes that can attach to the linked DNA segments. As used herein, the term "probe" refers to a molecule (e.g., an oligonucleotide, whether occurring naturally as in a purified restriction digest or produced synthetically, recombinantly or by PCR amplification), that is capable of hybridizing to another molecule of interest (e.g., another oligonucleotide). When probes are oligonucleotides they may be single-stranded or double-stranded. Probes are useful in the detection, identification and isolation of particular targets (e.g., gene sequences). In some cases, the probes may be associated with a label so that is detectable in any detection system, including, but not limited to enzyme (e.g., ELISA, as well as enzyme-based histochemical assays), fluorescent, radioactive, and luminescent systems With respect to arrays and microarrays, the term "probe" is used to refer to any hybridizable material that is affixed to the array for the purpose of detecting a nucleotide sequence that has hybridized to the probe. In some cases, the probes can about 10 bp to 500 bp, about 10 bp to 250 bp, about 20 bp to 250 bp, about 20 bp to 200 bp, about 25 bp to 200 bp, about 25 bp to 100 bp, about 30 bp to 100 bp, or about 30 bp to 80 bp. In some cases, the probes can be greater than about 10 bp, about 20 bp, about 30 bp, about 40 bp, about 50 bp, about 60 bp, about 70 bp, about 80 bp, about 90 bp, about 100 bp, about 150 bp, about 200 bp, about 250 bp, about 300 bp, about 400 bp, or about 500 bp in length. For example, the probes can be about 20 to about 50 bp in length. Examples and rationale for probe design can be found in WO95/11995, EP 717,113 and WO97/29212

In some cases, one or more probes can be designed such that they can hybridize close to the sites that are digested by a restriction enzyme. For example, the probe(s) can be within about 10 bp, about 20 bp, about 30 bp, about 40 bp, about 50 bp, about 60 bp, about 70 bp, about 80 bp, about 90 bp, about 100 bp, about 150 bp, about 200 bp, about 250 bp, about 300 bp, about 400 bp, or about 500 bp of the restriction enzyme recognition site.

In other cases, a single, unique, probe can designed within about 10 bp, about 20 bp, about 30 bp, about 40 bp, about 50 bp, about 60 bp, about 70 bp, about 80 bp, about 90 bp, about 100 bp, about 150 bp, about 200 bp, about 250 bp, about 300 bp, about 400 bp, or about 500 bp at each side of the sites that are digested by the restriction enzyme. The probes can be designed such that they can hybridize at either side of the sites that are digested by the restriction enzyme. For example, a single probe at each side of the primary restriction enzyme recognition site can be used In some cases, 2, 3, 4, 5, 6, 7, 8, or more probes can be designed at each side of the restriction enzyme recognition site, which can then be used to investigate the same ligation event. For example, 2 or 3 probes can be designed at each side of the restriction enzyme recognition site. In some examples, the use of multiple (e.g. 2, 3, 4, 5, 6, 7 or 8 or more) probes per primary restriction enzyme recognition site can be useful to minimize the problem of obtaining false negative results from individual probes.

As used herein, the term "set of probes" refers to a suite or a collection of probes that can hybridize to one or more of the primary restriction enzyme recognition sites for a primary restriction enzyme in a genome.

In some cases, a set of probes can be complementary in sequence to the nucleic acid sequence adjacent to one or more of the primary restriction enzyme recognition sites for a restriction enzyme in genomic DNA. For example, the set of probes can be complementary in sequence to the about 10 bp to 500 bp, about 10 bp to 250 bp, about 20 bp to 250 bp, about 20 bp to 200 bp, about 25 bp to 200 bp, about 25 bp to 100 bp, about 30 bp to 100 bp, or about 30 bp to 80 bp nucleotides that are adjacent to one or more of the restriction enzyme recognition sites in genomic DNA. The set of probes may be complementary in sequence to one (e.g. either) side or both sides of the restriction enzyme recognition site. Accordingly, the probes may be complementary in sequence to the nucleic acid sequence adjacent to each side of one or more of the primary restriction enzyme recognition sites in the genomic DNA. Further, the set of probes can be complementary in sequence to the nucleic acid sequence that is less than about 10 bp, about 20 bp, about 30 bp, about 40 bp, about 50 bp, about 60 bp, about 70 bp, about 80 bp, about 90 bp, about 100 bp, about 150 bp, about 200 bp, about 250 bp, about 300 bp, about 400 bp, or about 500 bp from one or more of the primary restriction enzyme recognition sites in genomic DNA In some cases, two or more probes can be designed to be capable of hybridizing to the sequence adjacent to one or more of the restriction enzyme recognition sites in genomic DNA. The probes may overlap or partially overlap.

The probes, array of probes or set of probes can be immobilized on a support. Supports (e.g. solid supports) can be made of a variety of materials—such as glass, silica, plastic, nylon or nitrocellulose. Supports are preferably rigid and have a planar surface. Supports can have from about 1 to 10,000,000 resolved loci. For example, a support can have about 10 to 10,000,000, about 10 to 5,000,000, about 100 to 5,000,000, about 100 to 4,000,000, about 1000 to 4,000,000, about 1000 to 3,000,000, about 10,000 to 3,000,000, about 10,000 to 2,000,000, about 100,000 to 2,000,000, or about 100,000 to 1,000,000 resolved loci. The density of resolved loci can be at least about 10, about 100, about 1000, about 10,000, about 100,000 or about 1,000,000 resolved loci within a square centimeter. In some cases, each resolves loci can be occupied by >95% of a single type of oligonucleotide. In other cases, each resolved locus can be occupied by pooled mixtures of probes or a set of probes. In some cases, some resolved loci are occupied by pooled mixtures of probes or a set of probes, and other resolved loci are occupied by >95% of a single type of oligonucleotide.

In some cases, the number of probes for a given nucleotide sequence on the array can be in large excess to the DNA sample to be hybridized to such array. For example, the array can have about 10, about 100, about 1000, about 10,000, about 100,000, about 1,000,000, about 10,000,000, or about 100,000,000 times the number of probes relative to the amount of DNA in the input sample.

In some cases, an array can have about 10, about 100, about 1000, about 10,000, about 100,000, about 1,000,000, about 10,000,000, about 100,000,000, or about 1,000,000,000 probes.

Arrays of probes or sets of probes may be synthesized in a step-by-step manner on a support or can be attached in presynthesized form. One method of synthesis is VLSIPS™ (as described in U.S. Pat. No. 5,143,854 and EP 476,014), which entails the use of light to direct the synthesis of oligonucleotide probes in high-density, miniaturized arrays. Algorithms for design of masks to reduce the number of synthesis cycles are described in U.S. Pat. Nos. 5,571,639 and 5,593,839, Arrays can also be synthesized in a combinatorial fashion by delivering monomers to cells of a support by mechanically constrained flowpaths, as described in EP 624,059. Arrays can also be synthesized by spotting reagents on to a support using an ink jet printer (see, for example, EP 728,520).

In some embodiments, the present disclosure provides methods for hybridizing the linked DNA segments onto an array. A "substrate" or an "array" is an intentionally created collection of nucleic acids which can be prepared either synthetically or biosynthetically and screened for biological activity in a variety of different formats (e.g., libraries of soluble molecules; and libraries of oligonucleotides tethered to resin beads, silica chips, or other solid supports). Additionally, the term "array" includes those libraries of nucleic acids which can be prepared by spotting nucleic acids of essentially any length (e.g., from 1 to about 1000 nucleotide monomers in length) onto a substrate.

Array technology and the various associated techniques and applications are described generally in numerous textbooks and documents. For example, these include Lemieux et al., 1998, *Molecular Breeding* 4, 277-289; Schena and Davis, *Parallel Analysis with Biological Chips*. in *PCR Methods Manual* (eds. M. Innis, D. Gelfand, J. Sninsky); Schena and Davis, 1999. *Genes, Genomes and Chips*. In *DNA Microarrays: A Practical Approach* (ed. M. Schena), Oxford University Press, Oxford, UK, 1999); *The Chipping Forecast* (Nature Genetics special issue; January 1999 Supplement); Mark Schena (Ed.), *Microarray Biochip Technology*, (Eaton Publishing Company); Cortes, 2000, *The Scientist* 14[17]:25; Gwynn and Page, *Microarray analysis: the next revolution in molecular biology, Science,* 1999 Aug. 6; and Eakins and Chu, 1999, *Trends in Biotechnology,* 17, 217-218.

In general, any library may be arranged in an orderly manner into an array, by spatially separating the members of the library. Examples of suitable libraries for arraying include nucleic acid libraries (including DNA, cDNA, oligonucleotide, etc. libraries), peptide, polypeptide and protein libraries, as well as libraries comprising any molecules, such as ligand libraries, among others.

The library can be fixed or immobilized onto a solid phase (e.g. a solid substrate), to limit diffusion and admixing of the members, in some cases, libraries of DNA binding ligands may be prepared. In particular, the libraries may be immobilized to a substantially planar solid phase, including membranes and non-porous substrates such as plastic and glass. Furthermore, the library can be arranged in such a way that indexing (i.e., reference or access to a particular member) is facilitated. In some examples, the members of the library can be applied as spots in a grid formation. Common assay systems may be adapted for this purpose. For example, an array may be immobilized on the surface of a microplate, either with multiple members in a well, or with a single member in each well. Furthermore, the solid substrate may be a membrane, such as a nitrocellulose or nylon membrane (for example, membranes used in blotting experiments). Alternative substrates include glass, or silica based substrates. Thus, the library can be immobilized by any suitable method known in the art, for example, by charge interactions, or by chemical coupling to the walls or bottom of the wells, or the surface of the membrane. Other means of arranging and fixing may be used, for example, pipetting, drop-touch, piezoelectric means, ink-jet and bubblejet technology, electrostatic application, etc. In the case of silicon-based chips, photolithography may be utilized to arrange and fix the libraries on the chip.

The library may be arranged by being "spotted" onto the solid substrate; this may be done by hand or by making use of robotics to deposit the members. In general, arrays may be described as macroarrays or microarrays, the difference being the size of the spots. Macroarrays can contain spot sizes of about 300 microns or larger and may be easily imaged by existing gel and blot scanners. The spot sizes microarrays can be less than 200 microns in diameter and these arrays usually contain thousands of spots. Thus, microarrays may require specialized robotics and imaging equipment, which may need to be custom made Instrumentation is described generally in a review by Cortese, 2000, *The Scientist* 14[11]:26.

Techniques for producing immobilized libraries of DNA molecules have been described in the art. Generally, most prior art methods described how to synthesize single-stranded nucleic acid molecule libraries, using for example masking techniques to build up various permutations of sequences at the various discrete positions on the solid substrate. U.S. Pat. No. 5,837,832 describes an improved method for producing DNA arrays immobilized to silicon substrates based on very large scale integration technology. In particular, U.S. Pat. No. 5,837,832 describes a strategy called "thing" to synthesize specific sets of probes at spatially-defined locations on a substrate which may be used to produce the immobilized DNA libraries of the present disclosure. U.S. Pat. No. 5,837,832 also provides references for earlier techniques that may also be used. In other cases, arrays may also be built using photo deposition chemistry.

Arrays of peptides (or peptidomimetics) may also be synthesized on a surface in a manner that places each distinct library member (e.g., unique peptide sequence) at a discrete, predefined location in the array. The identity of each library member is determined by its spatial location in the array. The locations in the array where binding interactions between a predetermined molecule (e.g., a target or probe) and reactive library members occur is determined, thereby identifying the sequences of the reactive library members on the basis of spatial location. These methods are described in U.S. Pat. No. 5,143,854; WO90/15070 and WO92/10092; Fodor et al. (1991) *Science.* 251: 767; Dower and Fodor (1991) *Ann. Rep. Med. Chem.,* 26: 271

To aid detection, labels can be used (as discussed above) such as any readily detectable reporter, for example, a fluorescent, bioluminescent, phosphorescent, radioactive, etc. reporter. Such reporters, their detection, coupling to targets/probes, etc. are discussed elsewhere in this document. Labelling of probes and targets is also disclosed in Shalon et al., 1996, *Genome Res* 6(7):639-45.

Examples of some commercially available microarray formats are set out in Table 1 below (see also Marshall and Hodgson, 1998, *Nature Biotechnology,* 16(1), 27-31).

TABLE 1

Examples of currently available hybridization microarray formats

| Company | Product name | Arraying method | Hybridizaton step | Readout |
|---|---|---|---|---|
| Affymetrix, Inc., Santa Clara, California | GeneChip ® | In situ (on-chip) photolithographic synthesis of ~20-25-mer oligos onto silicon wafers, which are diced into 1.25 $cm^2$ or 5.25 $cm^2$ chips | 10,000-260,000 oligo features probed with labeled 30-40 nucleotide fragments of sample cDNA or antisense RNA | Fluorescence |
| Brax, Cambridge, UK | | Short synthetic oligo, synthesized off-chip | 1000 oligos on a "universal chip" probed with tagged nucleic acid | Mass spectrometry |
| Gene Logic. Inc., Columbia, Maryland | READS ™ | | | |
| Genometrix Inc., The Woodlands, Texas | Universal Arrays ™ | | | |
| GENSET, Paris, France | | | | |
| Hyseq Inc., Sunnyvale, California | HyChip ™ | 500-2000 nt DNA samples printed onto 0.6 $cm^2$ (HyGnostics) or ~18 $cm^2$ (Gene Discovery) membranes | 64 sample cDNA spots probed with 8,000 7-mer oligos (HyGnostics) or <=55,000 sample cDNA spots probed with 300 7-mer oligo (Gene Discovery) | Radioisotope |
| | | Fabricated 5-mer oligos printed as 1.15 $cm^2$ arrays onto glass (HyChip) | Universal 1024 oligo spots probed 10 kb sample cDNAs, labeled 5-mer oligo, and ligase | Fluorescence |
| Incyte Pharmaceuticals, Inc., Palo Alto, California | GEM | Piezoelectric printing for spotting PCR fragments and on-chip synthesis of oligos | <=1000 (eventually 10,000) oligo/PCR fragment spots probed with labeled RNA | Fluorescence and radioisotope |
| Molecular Dynamics, Inc., Sunnyvale, California | Storm ® FluorImager ® | 500-5000 nt cDNAs printed by pen onto ~10 $cm^2$ on glass slide | ~10,000 cDNA spots probed with 200-400 at labeled sample cDNAs | Fluorscence |
| Nanogen, San Diego, California | Semiconductor Microchip | Prefabricated ~20-mer oligos, captured onto electroactive spots on silicon wafers, which are diced into <=1 $cm^2$ chips | 25, 64, 400 (and eventually 10,000) oligo spots polarized to enhance hybridization to 200-400 nt labeled sample cDNAs | Fluorescence |
| Protogene Laboratories, Palo Alto, California | | On-chip synthesis of 40-50-mer oligos onto 9 $cm^2$ glass chip via printing to a surface-tensions array | <=8,000 oligo spots probed with 200-400 at labeled sample nucleic acids | Fluorescence |
| Sequenom, Hamburg, Germany, and San Diego, California | Mass Array SpectoChip | Off-set printing of array; around 20-25-mer oligos | 250 locations per SpectroChip interrogated by laser desorbtion and mass spectrometry | Mass spectrometry |
| Synteni, Inc., Fremont, California | UniGEM ™ | 500-5,000 nt cDNAs printed by tip onto ~4 $cm^2$ glass chip | <=10,000 cDNA spots probed with 200-400 nt labeled sample cDNAs | Fluorescence |
| Nimblegen Systems Inc., Madison | *Homo sapiens* Whole-Genome 60mer Microarray | 38,000 transcripts with 5 probes per gene 17.4 mm × 13 mm | | 5-micron scanning platform |
| The German Cancer Institute, Heidelberg, Germany | | Prototypic PNA macrochip with on-chip synthesis of probes using f-moc or t-moc chemistry | Around 1,000 spots on a 8 × 12 cm chip | Fluorescence/mass spectrometry |

In order to generate data from array-based assays a signal can detected to signify the presence of or absence of hybridization between a probe and a nucleotide sequence. Further, direct and indirect labeling techniques can also be utilized. For example, direct labeling incorporates fluorescent dyes directly into the nucleotide sequences that hybridize to the array associated probes (e.g., dyes are incorporated into nucleotide sequence by enzymatic synthesis in the presence of labeled nucleotides or PCR primers). Direct labeling schemes can yield strong hybridization signals, for example by using families of fluorescent dyes with similar chemical structures and characteristics, and can be simple to implement. In cases comprising direct labeling of nucleic acids, cyanine or alexa analogs can be utilized in multiple-fluor comparative array analyses. In other embodiments, indirect labeling schemes can be utilized to incorporate epitopes into the nucleic acids either prior to or after hybridization to the microarray probes. One or more staining procedures and reagents can be used to label the hybridized complex (e.g., a fluorescent molecule that binds to the epitopes, thereby providing a fluorescent signal by virtue of the conjugation of dye molecule to the epitope of the hybridized species).

In various embodiments, suitable sequencing methods described herein or otherwise known in the art will be used to obtain sequence information from nucleic acid molecules within a sample. Sequencing can be accomplished through classic Sanger sequencing methods which are well known in the art. Sequence can also be accomplished using high-throughput systems some of which allow detection of a sequenced nucleotide immediately after or upon its incorporation into a growing strand, i.e., detection of sequence in real time or substantially real time. In some cases, high throughput sequencing generates at least 1,000, at least 5,000, at least 10,000, at least 20,000, at least 30,000, at least 40,000, at least 50,000, at least 100,000 or at least 500,000 sequence reads per hour; where the sequencing reads can be at least about 50, about 60, about 70, about 80, about 90, about 100, about 120, about 150, about 180, about 210, about 240, about 270, about 300, about 350, about 400, about 450, about 500, about 600, about 700, about 800, about 900, or about 1000 bases per read.

In some embodiments, high-throughput sequencing involves the use of technology available by Illumina's Genome Analyzer IIX, MiSeq personal sequencer, or HiSeq systems, such as those using HiSeq 2500, HiSeq 1500, HiSeq 2000, or HiSeq 1000 machines. These machines use reversible terminator-based sequencing by synthesis chemistry. These machine can do 200 billion DNA reads or more in eight days. Smaller systems may be utilized for runs within 3, 2, 1 days or less time.

In some embodiments, high-throughput sequencing involves the use of technology available by ABI Solid System. This genetic analysis platform that enables massively parallel sequencing of clonally-amplified DNA fragments linked to beads. The sequencing methodology is based on sequential ligation with dye-labeled oligonucleotides.

The next generation sequencing can comprise ion semiconductor sequencing (e.g., using technology from Life Technologies (Ion Torrent)). Ion semiconductor sequencing can take advantage of the fact that when a nucleotide is incorporated into a strand of DNA, an ion can be released. To perform ion semiconductor sequencing, a high density array of micromachined wells can be formed. Each well can hold a single DNA template. Beneath the well can be an ion sensitive layer, and beneath the ion sensitive layer can be an ion sensor. When a nucleotide is added to a DNA, H+ can be released, which can be measured as a change in pH. The H+ ion can be converted to voltage and recorded by the semiconductor sensor. An array chip can be sequentially flooded with one nucleotide after another. No scanning, light, or cameras can be required. In some cases, an IONPROTON™ Sequencer is used to sequence nucleic acid. In some cases, an IONPGM™ Sequencer is used. The Ion Torrent Personal Genome Machine (PGM). The PGM can do 10 million reads in two hours.

In some embodiments, high-throughput sequencing involves the use of technology available by Helicos BioSciences Corporation (Cambridge, Mass.) such as the Single Molecule Sequencing by Synthesis (SMSS) method. SMSS is unique because it allows for sequencing the entire human genome in up to 24 hours. Finally, SMSS is described in part in US Publication Application Nos. 20060024711; 20060024678; 20060012793; 20060012784; and 20050100932.

In some embodiments, high-throughput sequencing involves the use of technology available by 454 Lifesciences, Inc. (Branford, Conn.) such as the PicoTiterPlate device which includes a fiber optic plate that transmits chemiluminescent signal generated by the sequencing reaction to be recorded by a CCD camera in the instrument. This use of fiber optics allows for the detection of a minimum of 20 million base pairs in 4.5 hours.

Methods for using bead amplification followed by fiber optics detection are described in Marguiles, M., et al. "Genome sequencing in microfabricated high-density picoliter reactors", Nature, doi:10.1038/nature03959; and well as in US Publication Application Nos. 20020012930; 20030068629; 20030100102; 20030148344; 20040248161; 20050079510, 20050124022; and 20060078909.

In some embodiments, high-throughput sequencing is performed using Clonal Single Molecule Array (Solexa, Inc.) or sequencing-by-synthesis (SBS) utilizing reversible terminator chemistry. These technologies are described in part in U.S. Pat. Nos. 6,969,488; 6,897,023; 6,833,246; 6,787,308; and US Publication Application Nos. 20040106110; 20030064398; 20030022207; and Constans, A., The Scientist 2003, 17(13):36.

The next generation sequencing technique can comprise real-time (SMRT™) technology by Pacific Biosciences. In SMRT, each of four DNA bases can be attached to one of four different fluorescent dyes. These dyes can be phospho linked A single DNA polymerase can be immobilized with a single molecule of template single stranded DNA at the bottom of a zero-mode waveguide (ZMW). A ZMW can be a confinement structure which enables observation of incorporation of a single nucleotide by DNA polymerase against the background of fluorescent nucleotides that can rapidly diffuse in an out of the ZMW (in microseconds). It can take several milliseconds to incorporate a nucleotide into a growing strand. During this time, the fluorescent label can be excited and produce a fluorescent signal, and the fluorescent label can be cleaved off. The ZMW can be illuminated from below. Attenuated light from an excitation beam can penetrate the lower 20-30 nm of each ZMW. A microscope with a detection limit of 20 zepto liters (10" liters) can be created. The tiny detection volume can provide 1000-fold improvement in the reduction of background noise. Detection of the corresponding fluorescence of the dye can indicate which base was incorporated. The process can be repeated.

In some cases, the next generation sequencing is nanopore sequencing (See, e.g., Soni G V and Meller A. (2007) Clin Chem 53: 1996-2001). A nanopore can be a small hole, of the order of about one nanometer in diameter. Immersion of a nanopore in a conducting fluid and application of a potential across it can result in a slight electrical current due to conduction of ions through the nanopore. The amount of current which flows can be sensitive to the size of the nanopore. As a DNA molecule passes through a nanopore, each nucleotide on the DNA molecule can obstruct the nanopore to a different degree. Thus, the change in the current passing through the nanopore as the DNA molecule passes through the nanopore can represent a reading of the DNA sequence. The nanopore sequencing technology can be from Oxford Nanopore Technologies; e.g., a GridION system. A single nanopore can be inserted in a polymer membrane across the top of a microwell. Each microwell can have an electrode for individual sensing. The microwells can be fabricated into an array chip, with 100,000 or more microwells (e.g., more than 200,000, 300,000, 400,000, 500,000, 600,000, 700,000, 800,000, 900,000, or 1,000,000) per chip. An instrument (or node) can be used to analyze the chip. Data can be analyzed in real-time. One or more instruments can be operated at a time. The nanopore can be a protein nanopore, e.g., the protein alpha-hemolysin, a heptameric protein pore. The nanopore can be a solid-state nanopore made, e.g., a nanometer sized hole formed in a synthetic membrane (e.g., $SiN_x$, or $SiO_2$). The nanopore can be a hybrid pore (e.g., an integration of a protein pore into a solid-state membrane). The nanopore can be a nanopore with an integrated sensor (e.g., tunneling electrode detectors, capacitive detectors, or graphene based nano-gap or edge state detectors (see e.g., Garaj et al. (2010) Nature vol. 67, doi: 10.1038/nature09379)). A nanopore can be functionalized for analyzing a specific type of molecule (e.g., DNA, RNA, or protein). Nanopore sequencing can comprise "strand sequencing" in which intact DNA polymers can be passed through a protein nanopore with sequencing in real time as the DNA translocates the pore. An enzyme can separate strands of a double stranded DNA and feed a strand through a nanopore. The DNA can have a hairpin at one end, and the system can read both strands. In some cases, nanopore sequencing is "exonuclease sequencing" in which individual nucleotides can be cleaved from a DNA strand by a processive exonuclease, and the nucleotides can be passed through a protein nanopore. The nucleotides can transiently bind to a molecule in the pore (e.g., cyclodextran). A characteristic disruption in current can be used to identify bases.

Nanopore sequencing technology from GENIA can be used. An engineered protein pore can be embedded in a lipid bilayer membrane. "Active Control" technology can be used to enable efficient nanopore-membrane assembly and control of DNA movement through the channel. In some cases, the nanopore sequencing technology is from NABsys. Genomic DNA can be fragmented into strands of average length of about 100 kb. The 100 kb fragments can be made single stranded and subsequently hybridized with a 6-mer probe. The genomic fragments with probes can be driven through a nanopore, which can create a current-versus-time tracing. The current tracing can provide the positions of the probes on each genomic fragment. The genomic fragments can be lined up to create a probe map for the genome. The process can be done in parallel for a library of probes. A genome-length probe map for each probe can be generated. Errors can be fixed with a process termed "moving window Sequencing By Hybridization (mwSBH)." In some cases, the nanopore sequencing technology is from IBM/Roche. An electron beam can be used to make a nanopore sized opening in a microchip. An electrical field can be used to pull or thread DNA through the nanopore. A DNA transistor device in the nanopore can comprise alternating nanometer sized layers of metal and dielectric. Discrete charges in the DNA backbone can get trapped by electrical fields inside the DNA nanopore. Turning off and on gate voltages can allow the DNA sequence to be read.

The next generation sequencing can comprise DNA nanoball sequencing (as performed, e.g., by Complete Genomics; see e.g., Drmanac et al. (2010) Science 327: 78-81). DNA can be isolated, fragmented, and size selected. For example, DNA can be fragmented (e.g., by sonication) to a mean length of about 500 bp. Adaptors (Ad1) can be attached to the ends of the fragments. The adaptors can be used to hybridize to anchors for sequencing reactions. DNA with adaptors bound to each end can be PCR amplified. The adaptor sequences can be modified so that complementary single strand ends bind to each other forming circular DNA. The DNA can be methylated to protect it from cleavage by a type IIS restriction enzyme used in a subsequent step. An adaptor (e.g., the right adaptor) can have a restriction recognition site, and the restriction recognition site can remain non-methylated. The non-methylated restriction recognition site in the adaptor can be recognized by a restriction enzyme (e.g., AcuI), and the DNA can be cleaved by AcuI 13 bp to the right of the right adaptor to form linear double stranded DNA. A second round of right and left adaptors (Ad2) can be ligated onto either end of the linear DNA, and all DNA with both adapters bound can be PCR amplified (e.g., by PCR). Ad2 sequences can be modified to allow them to bind each other and form circular DNA. The DNA can be methylated, but a restriction enzyme recognition site can remain non-methylated on the left Ad1 adapter. A restriction enzyme (e.g., AcuI) can be applied, and the DNA can be cleaved 13 bp to the left of the Ad1 to form a linear DNA fragment. A third round of right and left adaptor (Ad3) can be ligated to the right and left flank of the linear DNA, and the resulting fragment can be PCR amplified. The adaptors can be modified so that they can bind to each other and form circular DNA. A type III restriction enzyme (e.g., EcoP15) can be added; EcoP15 can cleave the DNA 26 bp to the left of Ad3 and 26 bp to the right of Ad2. This cleavage can remove a large segment of DNA and linearize the DNA once again. A fourth round of right and left adaptors (Ad4) can be ligated to the DNA, the DNA can be amplified (e.g., by PCR), and modified so that they bind each other and form the completed circular DNA template.

Rolling circle replication (e.g., using Phi 29 DNA polymerase) can be used to amplify small fragments of DNA. The four adaptor sequences can contain palindromic sequences that can hybridize and a single strand can fold onto itself to form a DNA nanoball (DNB™) which can be approximately 200-300 nanometers in diameter on average. A DNA nanoball can be attached (e.g., by adsorption) to a microarray (sequencing flowcell). The flow cell can be a silicon wafer coated with silicon dioxide, titanium and hexamehtyldisilazane (HMDS) and a photoresist material. Sequencing can be performed by unchained sequencing by ligating fluorescent probes to the DNA. The color of the fluorescence of an interrogated position can be visualized by a high resolution camera. The identity of nucleotide sequences between adaptor sequences can be determined.

In some embodiments, high-throughput sequencing can take place using AnyDot.chips (Genovoxx, Germany). In particular, the AnyDot.chips allow for 10×-50× enhancement of nucleotide fluorescence signal detection. AnyDot.chips and methods for using them are described in part in International Publication Application Nos. WO 02088382, WO 03020968, WO 03031947, WO 2005044836, PCT/EP 05/05657, PCT/EP 05/05655; and German Patent Application Nos. DE 101 49 786, DE 102 14

395, DE 103 56 837, DE 10 2004 009 704, DE 10 2004 025 696, DE 10 2004 025 746, DE 10 2004 025 694, DE 10 2004 025 695, DE 10 2004 025 744, DE 10 2004 025 745, and DE 10 2005 012 301.

Other high-throughput sequencing systems include those disclosed in Venter, J., et al. Science 16 Feb. 2001; Adams, M. et al. Science 24 Mar. 2000; and M. J. Levene, et al. Science 299:682-686, January 2003; as well as US Publication Application No. 20030044781 and 2006/0078937. Overall such system involve sequencing a target nucleic acid molecule having a plurality of bases by the temporal addition of bases via a polymerization reaction that is measured on a molecule of nucleic acid, i.e. the activity of a nucleic acid polymerizing enzyme on the template nucleic acid molecule to be sequenced is followed in real time. Sequence can then be deduced by identifying which base is being incorporated into the growing complementary strand of the target nucleic acid by the catalytic activity of the nucleic acid polymerizing enzyme at each step in the sequence of base additions. A polymerase on the target nucleic acid molecule complex is provided in a position suitable to move along the target nucleic acid molecule and extend the oligonucleotide primer at an active site. A plurality of labeled types of nucleotide analogs are provided proximate to the active site, with each distinguishable type of nucleotide analog being complementary to a different nucleotide in the target nucleic acid sequence. The growing nucleic acid strand is extended by using the polymerase to add a nucleotide analog to the nucleic acid strand at the active site, where the nucleotide analog being added is complementary to the nucleotide of the target nucleic acid at the active site. The nucleotide analog added to the oligonucleotide primer as a result of the polymerizing step is identified. The steps of providing labeled nucleotide analogs, polymerizing the growing nucleic acid strand, and identifying the added nucleotide analog are repeated so that the nucleic acid strand is further extended and the sequence of the target nucleic acid is determined.

The present disclosure provides methods of haplotype phasing, comprising generating a plurality of read-pairs from a single DNA molecule and assembling a plurality of contigs of the DNA molecule using the read-pairs, wherein at least 1% of the read-pairs spans a distance greater than 50 kB on the single DNA molecule and the haplotype phasing is performed at greater than 70% accuracy. In some embodiments, at least 10% of the read-pairs span a distance greater than 50 kB on the single DNA molecule. In other embodiments, wherein at least 1% of the read-pairs span a distance greater than 100 kB on the single DNA molecule. In some embodiments, the haplotype phasing is performed at greater than 90% accuracy.

In a further aspect, the present disclosure provides methods of haplotype phasing, comprising generating a plurality of read-pairs from a single DNA molecule (e.g., in vitro) and assembling a plurality of contigs of the DNA molecule using the read-pairs, wherein at least 1% of the read-pairs spans a distance greater than 30 LE on the single DNA molecule and the haplotype phasing is performed at greater than 70% accuracy. In some embodiments, at least 10% of the read-pairs span a distance greater than 30 kB on the single DNA molecule. In other embodiments, at least 1% of the read-pairs span a distance greater than 50 kB on the single DNA molecule. In yet other embodiments, the haplotype phasing is performed at greater than 90% accuracy. In some embodiments, the haplotype phasing is performed at greater than 70% accuracy.

In particular embodiments, the present disclosure further provides kits comprising one or more components of the disclosure. The kits can be used for any application apparent to those of skill in the art, including those described above. The kits can comprise, for example, a plurality of association molecules, a fixative agent, an endonuclease (e.g., a restriction endonuclease), a ligase, and/or a combination thereof. In some cases, the association molecules can be proteins including, for example, histones, in some cases, the fixative agent can be formaldehyde or any other DNA crosslinking agent.

In some cases, the kit comprises a plurality of beads. The beads can be paramagnetic and/or are coated with a capturing agent. For example, the beads can be coated with streptavidin and/or an antibody.

In some cases, the kit can comprise adaptor oligonucleotides and/or sequencing primers. Further, the kit can comprise a device capable of amplifying the read-pairs using the adaptor oligonucleotides and/or sequencing primers.

In some cases, the kit can also comprise other reagents including but not limited to lysis buffers, ligation reagents (e.g. dNTPs, polymerase, polynucleotide kinase, and/or ligase buffer, etc.), and PCR reagents (e.g. polymerase, and/or PCR buffer, etc.).

The kit can also include instructions for using the components of the kit and/or for generating the read-pairs.

Techniques of the present disclosure can provide a number of advantages compared to other techniques, such as other chromatin assembly procedures. Advantages include but are not limited to reduced input DNA amount requirements, shortened total time to complete the protocol, shortened hands-on time to complete the protocol, improved DNA recovery, removal of costly and/or time-consuming steps, easier automation, easier scale-up, and higher throughput.

The techniques disclosed herein can require small amounts of input DNA. For example, the input DNA required can be less than about 5 micrograms (µg), less than about 4.5 µg, less than about 4 µg, less than about 3.5 µg, less than about 3 µg, less than about 2.5 µg, less than about 2 µg, less than about 1.5 µg, less than about 1 µg, less than about 900 nanograms (ng), less than about 800 ng, less than about 700 ng, less than about 600 ng, less than about 500 ng, less than about 400 ng, less than about 300 ng, less than about 200 ng, or less than about 100 ng. In some cases, the input DNA required is less than about 500 ng.

The total elapsed time (i.e., "wall clock time") to prepare a sequencing library from a sample can be short. For example, the total time to prepare a sequencing library (e.g., a chromatin assembly library) from a sample can be less than about 5.5 days, less than about 5 days, less than about 4.5 days, less than about 4 days, less than about 3.5 days, less than about 3 days, less than about 2.5 days, less than about 2 days, less than about 1.5 days, less than about 1 day, or less than about 0.5 days. In some cases, the total time to prepare a sequencing library is less than about 2 days.

The amount of active time required (i.e., "hands-on time") from a user (e.g., a scientist or a technician) to prepare a sequencing library can be short. For example, the amount of hands-on time can be less than about 8 hours, less than about 7 hours, less than about 6 hours, less than about 5 hours, less than about 4 hours, less than about 3 hours, less than about 2 hours, or less than about 1 hour. In some cases, the amount of hands-on time to prepare a sequencing library is less than about 4 hours.

The amount of recovered DNA, for example after a cross-link reversal step, can be improved using the techniques disclosed herein. For example, DNA recovery after a cross-link reversal step can be at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%. In some cases, DNA recovery after a cross-link reversal step is from at least 30% to at least 50%.

Certain steps, including costly or time-consuming steps, can be avoided using techniques of the present disclosure. For example, sequencing libraries can be prepared without the need for dialysis. Sequencing libraries can be prepared without the need for chromatin biotinylation. Sequencing libraries can be prepared without the need for chromatin pulldown. Sequencing libraries can be prepared without the need for a biotin bead occupy step. Sequencing libraries can be prepared without the need for particular digests, such as an ExoIII digest. The amount of chromatin required can also be reduced. For example, compared to previous chromatin assembly library preparations, the amount of chromatin required can be reduced by at least 2-fold, at least 3-fold, at least 4-fold, at least 5-fold, at least 6-fold, at least 7-fold, at least 8-fold, at least 9-fold, or at least 10-fold. The amount of chromatin required can be less than about 5 units, less than about 4.5 units, less than about 4 units, less than about 3.5 units, less than about 3 units, less than about 2.5 units, less than about 2 units, less than about 1.5 units, less than about 1 unit, less than about 0.9 units, less than about 0.8 units, less than about 0.7 units, less than about 0.6 units, less than about 0.5 units, less than about 0.4 units, less than about 0.3 units, less than about 0.2 units, or less than about 0.1 units. 1 unit of chromatin is the equivalent of 1 microgram (µg) of DNA assembled into chromatin.

Figure 8:
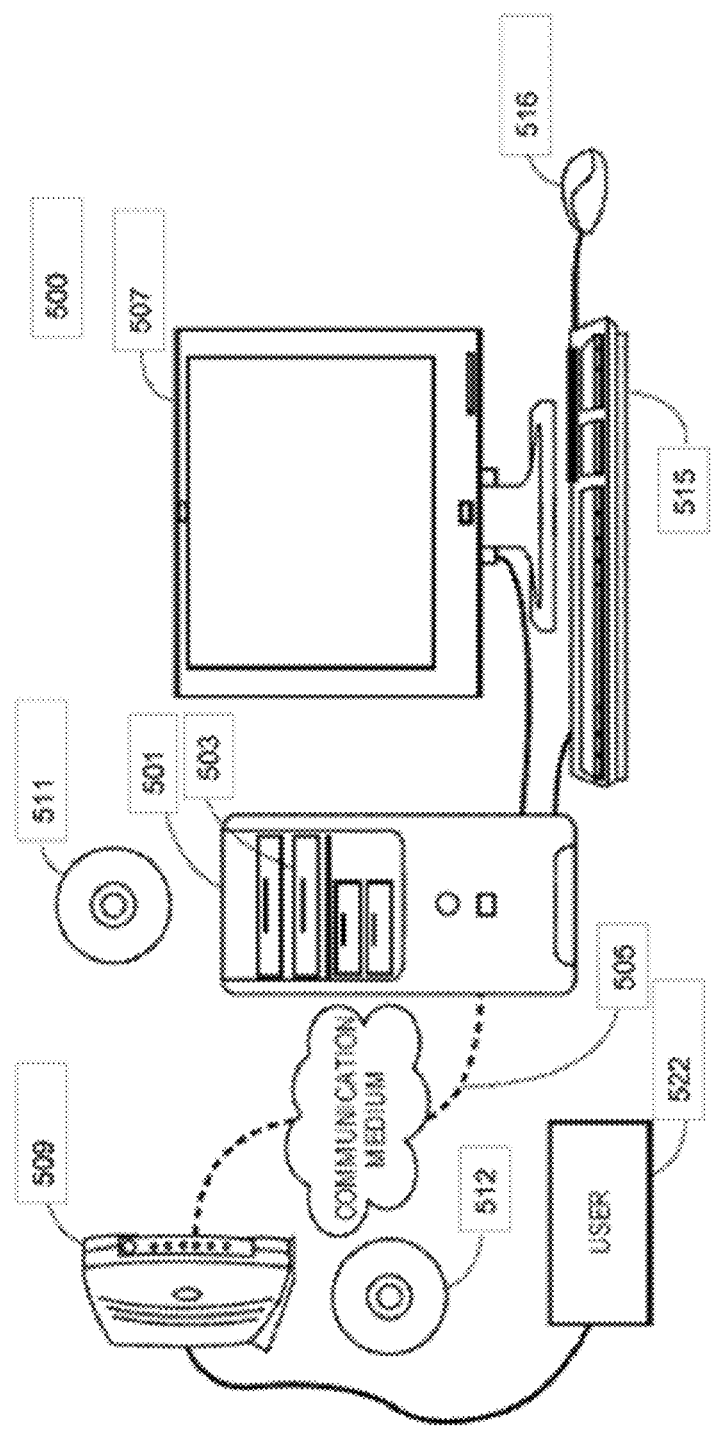
FIG. 8 illustrates various components of an exemplary computer system according to various embodiments of the present disclosure.

The computer system 500 illustrated in FIG. 8 may be understood as a logical apparatus that can read instructions from media 511 and/or a network port 505, which can optionally be connected to server 509 having fixed media 512. The system, such as shown in FIG. 8 can include a CPU 501, disk drives 503, optional input devices such as keyboard 515 and/or mouse 516 and optional monitor 507. Data communication can be achieved through the indicated communication medium to a server at a local or a remote location. The communication medium can include any means of transmitting and/or receiving data. For example, the communication medium can be a network connection, a wireless connection or an internet connection. Such a connection can provide for communication over the World Wide Web. It is envisioned that data relating to the present disclosure can be transmitted over such networks or connections for reception and/or review by a party 522 as illustrated in FIG. 8.

Figure 9:
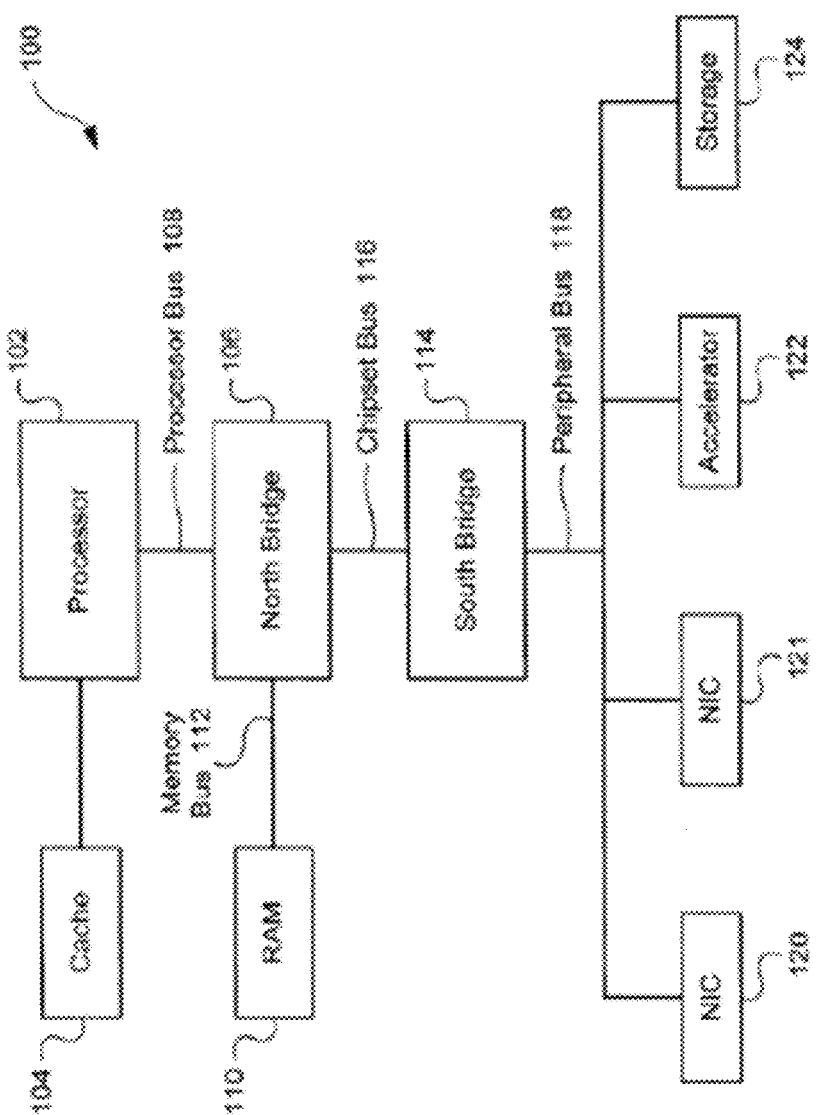
FIG. 9 is a block diagram illustrating the architecture of an exemplary computer system that can be used in connection with various embodiments of the present disclosure.

FIG. 9 is a block diagram illustrating a first example architecture of a computer system 100 that can be used in connection with example embodiments of the present disclosure. As depicted in FIG. 9, the example computer system can include a processor 102 for processing instructions. Non-limiting examples of processors include: Intel Xeon™ processor, AMD Opteron™ processor, Samsung 32-bit RISC ARM 1176JZ(F)-S v1.0™ processor, ARM Cortex-A8 Samsung S5PC100™ processor, ARM Cortex-A8 Apple A4™ processor, Marvell PXA 930™ processor, or a functionally-equivalent processor. Multiple threads of execution can be used for parallel processing. In some embodiments, multiple processors or processors with multiple cores can also be used, whether in a single computer system, in a cluster, or distributed across systems over a network comprising a plurality of computers, cell phones, and/or personal data assistant devices.

As illustrated in FIG. 9, a high speed cache 104 can be connected to, or incorporated in, the processor 102 to provide a high speed memory for instructions or data that have been recently, or are frequently, used by processor 102. The processor 102 is connected to a north bridge 106 by a processor bus 108. The north bridge 106 is connected to random access memory (RAM) 110 by a memory bus 112 and manages access to the RAM 110 by the processor 102. The north bridge 106 is also connected to a south bridge 114 by a chipset bus 116. The south bridge 114 is, in turn, connected to a peripheral bus 118. The peripheral bus can be, for example, PCI, PCI-X, PCI Express, or other peripheral bus. The north bridge and south bridge are often referred to as a processor chipset and manage data transfer between the processor, RAM, and peripheral components on the peripheral bus 118. In some alternative architectures, the functionality of the north bridge can be incorporated into the processor instead of using a separate north bridge chip.

In some embodiments, system 100 can include an accelerator card 122 attached to the peripheral bus 118. The accelerator can include field programmable gate arrays (FPGAs) or other hardware for accelerating certain processing. For example, an accelerator can be used for adaptive data restructuring or to evaluate algebraic expressions used in extended set processing.

Software and data are stored in external storage 124 and can be loaded into RAM 110 and/or cache 104 for use by the processor. The system 100 includes an operating system for managing system resources; non-limiting examples of operating systems include: Linux, Windows™, MACOS™ BlackBerry OS™, iOS™, and other functionally-equivalent operating systems, as well as application software running on top of the operating system for managing data storage and optimization in accordance with example embodiments of the present disclosure.

In this example, system 100 also includes network interface cards (NICs) 120 and 121 connected to the peripheral bus for providing network interfaces to external storage, such as Network Attached Storage (NAS) and other computer systems that can be used for distributed parallel processing.

Figure 10:
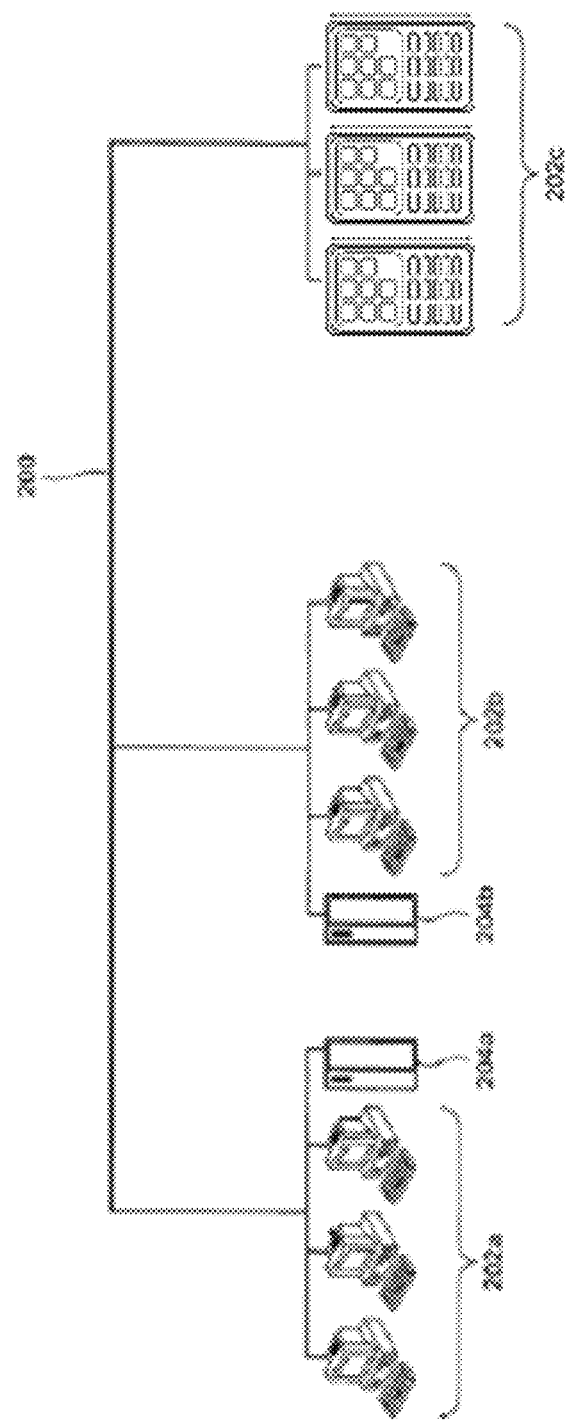
FIG. 10 is a diagram illustrating an exemplary computer network that can be used in connection with various embodiments of the present disclosure.

FIG. 10 is a diagram showing a network 200 with a plurality of computer systems 202a, and 202b, a plurality of cell phones and personal data assistants 202c, and Network Attached Storage (NAS) 204a, and 204b. In example embodiments, systems 202a, 202b, and 202c can manage data storage and optimize data access for data stored in Network Attached Storage (NAS) 204a and 204b. A mathematical model can be used for the data and be evaluated using distributed parallel processing across computer systems 202a, and 202b, and cell phone and personal data assistant systems 202c. Computer systems 202a, and 202b, and cell phone and personal data assistant systems 202c can also provide parallel processing for adaptive data restructuring of the data stored in Network Attached Storage (NAS) 204a and 204b. FIG. 10 illustrates an example only, and a wide variety of other computer architectures and systems can be used in conjunction with the various embodiments of the present disclosure. For example, a blade server can be used to provide parallel processing. Processor blades can be connected through a back plane to provide parallel processing. Storage can also be connected to the back plane or as Network Attached Storage (NAS) through a separate network interface.

In some example embodiments, processors can maintain separate memory spaces and transmit data through network interfaces, back plane or other connectors for parallel processing by other processors. In other embodiments, some or all of the processors can use a shared virtual address memory space.

Figure 11:
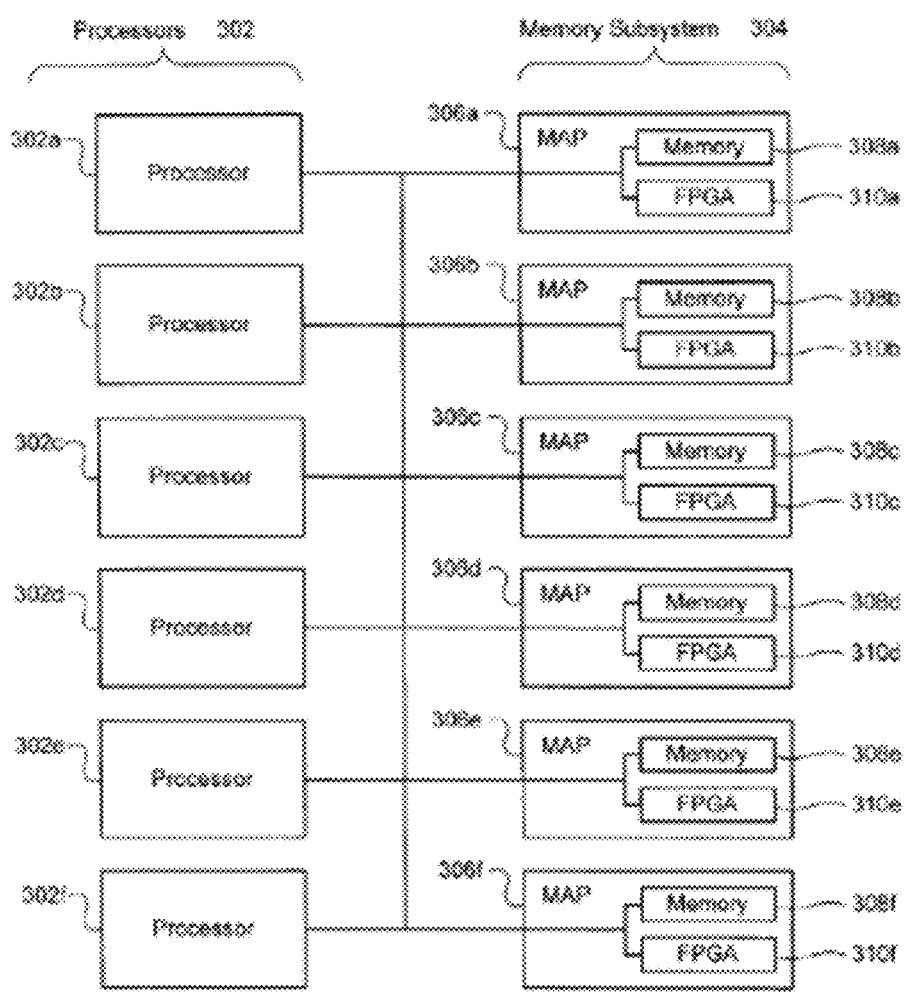
FIG. 11 is a block diagram illustrating the architecture of another exemplary computer system that can be used in connection with various embodiments of the present disclosure.

FIG. 11 is a block diagram of a multiprocessor computer system 300 using a shared virtual address memory space in accordance with an example embodiment. The system includes a plurality of processors 302a-f that can access a shared memory subsystem 304. The system incorporates a plurality of programmable hardware memory algorithm processors (MAPs) 306a-f in the memory subsystem 304. Each MAP 306a-f can comprise a memory 308a-f and one or more field programmable gate arrays (FPGAs) 310a-f. The MAP provides a configurable functional unit and particular algorithms or portions of algorithms can be provided to the FPGAs 310a-f for processing in close coordination with a respective processor. For example, the MAPs can be used to evaluate algebraic expressions regarding the data model and to perform adaptive data restructuring in example embodiments. In this example, each MAP is globally accessible by all of the processors for these purposes. In one configuration, each MAP can use Direct Memory Access (DMA) to access an associated memory 308a-f, allowing it to execute tasks independently of, and asynchronously from, the respective microprocessor 302a-f. In this configuration, a MAP can feed results directly to another MAP for pipelining and parallel execution of algorithms.

The above computer architectures and systems are examples only, and a wide variety of other computer, cell phone, and personal data assistant architectures and systems can be used in connection with example embodiments, including systems using any combination of general processors, co-processors, FPGAs and other programmable logic devices, system on chips (SOCs), application specific integrated circuits (ASICs), and other processing and logic elements. In some embodiments, all or part of the computer system can be implemented in software or hardware. Any variety of data storage media can be used in connection with example embodiments, including random access memory, hard drives, flash memory, tape drives, disk arrays, Network Attached Storage (NAS) and other local or distributed data storage devices and systems.

In example embodiments, the computer system can be implemented using software modules executing on any of the above or other computer architectures and systems. In other embodiments, the functions of the system can be implemented partially or completely in firmware, programmable logic devices such as field programmable gate arrays (FPGAs) as referenced in FIG. 11, system on chips (SOCs), application specific integrated circuits (ASICs), or other processing and logic elements. For example, the Set Processor and Optimizer can be implemented with hardware acceleration through the use of a hardware accelerator card, such as accelerator card 122 illustrated in FIG. 9.

Metagenomics and Complex Samples

Microbial contents of biological or biomedical samples, ecological or environmental samples, and food samples are frequently either identified or quantified through culture dependent methods. A significant amount of microbial biodiversity can be overlooked by cultivation-based methods as many microbes are unculturable, or not amenable to culture in the lab. Shotgun metagenomic sequencing approaches, in which thousands of organisms are sequenced in parallel, can allow researchers to comprehensively sample a majority of genes in a majority of organisms present in a given complex sample. This approach can enable the evaluation of bacterial diversity and the study of unculturable microorganisms that can otherwise be difficult to analyze. However, unsupported shotgun sequencing methods generate a significant number of reads comprising short read sequences that can be difficult to assemble without a reference sequence or without some source of long-range linkage information as needed to assemble sequences de novo. Bioinformatics analysis of short-read shotgun data (e.g., ConStrains) can require only shotgun data; however, the output consists of contigs binned by sequence features but not assembled, and recent horizontal transfer segments can be incorrectly binned. Single molecule long-read sequencing (e.g., Pacific Biosciences & Oxford Nanopore Technologies MinION) provides potential for long-range assembly; however, they can provide poor coverage of low abundance genomes, and cost per assembled base is relatively high. 16S RNA amplification can be used to deeply sample community 16S RNA; however, this technique provides only coarse taxonomic information, without resolving strain differences, pathogenic types, etc. Synthetic long reads (e.g., Moleculo, 10x) can provide true scaffolding of contigs; however, sample prep can be complicated and not standardized, costs per sample can be higher, and high levels of contamination were reported in Moleculo studies. In vivo proximity ligation can provide long-range scaffolding and can place extra-genomic elements (e.g., plasmids) with host; however, it requires intact cells, and can result in uneven representation of community components in proximity data due to uneven compaction of genomes or association with DNA-binding proteins.

Microbial communities are often comprised of tens, hundreds, or thousands of recognizable operational taxonomic units (OTUs), at very uneven abundance, each with varying amounts of strain variation. Further compounding the problem, microbes frequently exchange genetic materials through various means of conjugal exchange, and these segments of genetic material can be incorporated into the chromosomes of their hosts, resulting in rampant horizontal gene transfer within bacterial communities. Thus, microbial genomes are often described in terms of a core genome of genes that are widely present and others that may or may not be present in a particular strain. Describing the constituent genomes from and dynamics of a complex microbial community, such as the human gut microbiome, is an important and difficult challenge.

As a result of the difficulty of de novo metagenomic assembly, several simpler approaches have been developed and widely adopted to interrogate and describe their components. For example, 16S RNA amplification and sequencing is a common way to assess the community composition. While this approach can be used in a comparative framework to describe the dynamics of microbial communities before and after various stimuli or treatments, it provides a very narrow view of actual community composition since nothing is learned about the actual genomes outside their 16S regions. Binning approaches have also proved useful for classifying shotgun reads or contigs assembled from them. These approaches are useful for getting a provisional assignment of isolated genomic fragments to OTUs. However, they are essentially hypothesis generators and are powerless to order and orient these fragments or to assign fragments to strains within an OTU. Importantly, they are ill-suited to identify horizontally transferred sequences, since they detect OTU-of-origin rather than current linkages. From this perspective, these binning approaches based on k-mer occurrence, sequencing depth, and other features are a stop-gap method to understand isolated metagenomics components because highly contiguous assembly has heretofore not been possible in a reliable, fast, and economically reasonable way.

The techniques disclosed herein provide several key advantages over existing technologies. First, our "Chicago" libraries can provide extensive genome linkage information and can be made quickly and reliably. As described herein, the protocol can address the special features of DNA derived from metagenomic communities. Sequencing libraries can be generated ready for sequencing in less than two days. Additionally, because these libraries can be generated in a completely in vitro protocol, it can be unnecessary to culture anything. In principle, then, these techniques can assemble any microbiome community member whose DNA can be recovered. Third, this approach is simpler, faster, and more complete than other methods for de novo assembly and scaffolding.

Disclosed herein are methods and tools for genetic analysis of organisms in metagenomic samples, such as microbes that cannot be cultured in a laboratory environment and that inhabit a wide variety of environments. The present disclosure provides methods of de novo genome assembly of read data from complex metagenomics datasets comprising connectivity data. Methods and compositions disclosed herein generate scaffolding data that uniformly and completely represents the composite species in a metagenomics sample.

Figure 12A:
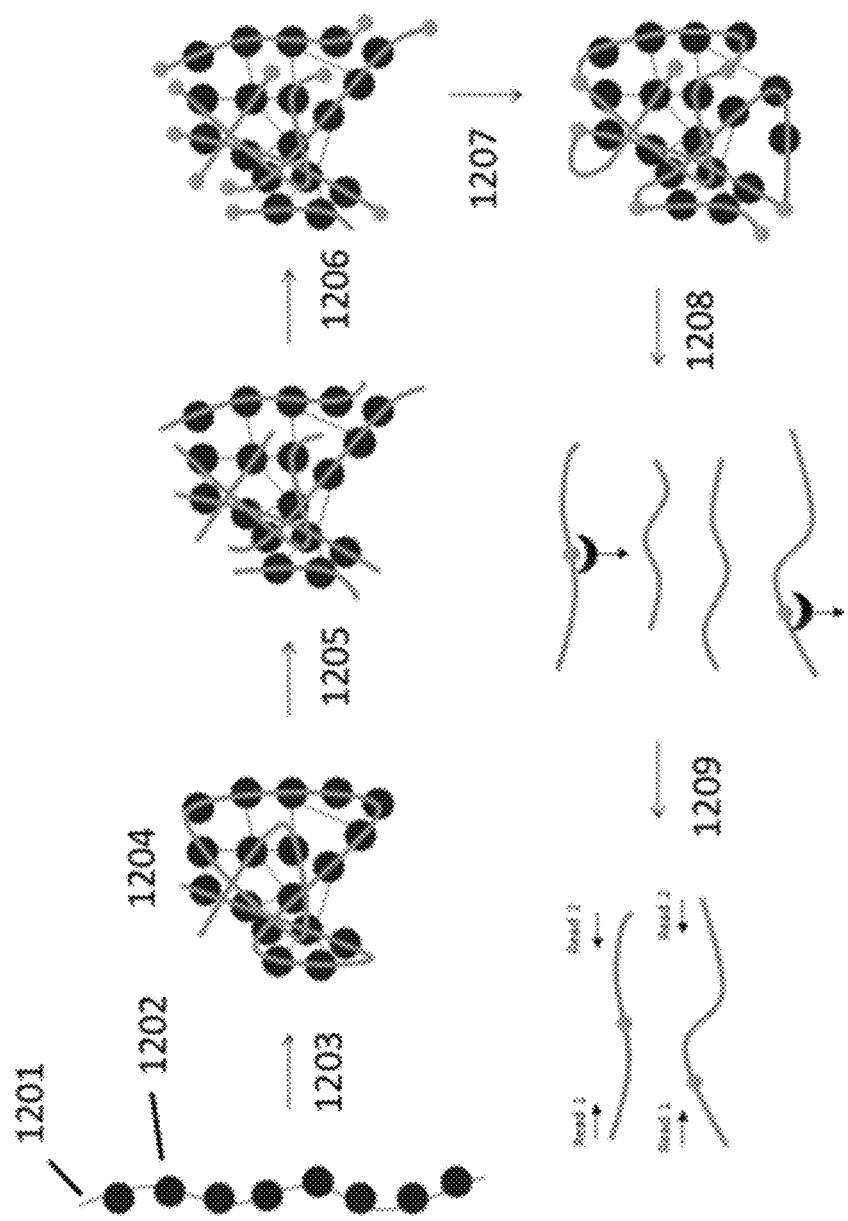
FIG. 12A shows an exemplary schematic of a procedure for proximity ligation.

FIG. 12A shows a schematic of a procedure for proximity ligation. DNA 1201, such as high molecular weight DNA, is incubated with histones 1202, and then crosslinked 1203 (e.g., with formaldehyde) to form a chromatin aggregate 1204. This locks the DNA molecules into a scaffold for further manipulation and analysis. The DNA is then digested 1205, and digested ends are filled in 1206 with a marker such as biotin. Marked ends are then randomly ligated to each other 1207, and the ligated aggregate is then liberated 1208, for example by protein digestion. The markers can then be used to select for DNA molecules containing ligation junctions 1209, such as through streptavidin-biotin binding. These molecules can then be sequenced, and the reads in each read pair derive from two different regions of the source molecule, separated by some insert distance up to the size of the input DNA.

FIG. 12B shows two pipelines for sample preparation for metagenomic analysis, which can be employed separately or together. A single DNA preparation 1210 (e.g., from fecal samples) is input into the process. In the case of fecal samples, collected DNA can be in approximately 50 kilobase fragments, such as from a preparation using the Qiagen fecal DNA kit. From this DNA, in vitro chromatin assemblies 1211 (e.g., "Chicago") and shotgun 1212 libraries preparations can be made. The chromatin assembly library 1213 and the shotgun library 1214 can use different barcodes 1215 and 1216 from each other. These two libraries can then be pooled for sequencing 1217. Using such a protocol, a single DNA prep can serve as input for two sequencing libraries: shotgun and in vitro chromatin assembly. Less than 1 μg of input DNA is required to generate both libraries, and these libraries can be individually barcoded for pooling during sequencing. These data can then be assembled first into contigs and then scaffolded using the long-range linkage information from the in vitro chromatin assembly libraries. These data alone can generate many scaffolds of greater than one megabase, enabling a much more comprehensive view of microbial genome structure and dynamics than is currently achievable. Processing time to go from sample to highly contiguous assemblies can be under one week.

FIG. 12C shows an exemplary schematic of scaffolding techniques that can be employed with the procedures of the present disclosure. In vitro chromatin assembly read pairs can be used to generate a spanning tree of contigs (not shown) to determine which contigs (colored arrows) are in proximity to one another in the correct assembly. Then, within local windows (e.g., 1220), all possible ordering and orientation can be tested against the in vitro chromatin assembly data. As shown in FIG. 1C, in two possible orientations of the green contig 1221, the in vitro chromatin assembly pairs 1222 would span short distances (top) or farther distances (bottom). The likelihood of each can be compared against a model of in vitro chromatin assembly distances trained for each library. During proximity ligation, the probability of ligating two segments can be described by a slowly decreasing function of how far apart they are along the linear polymer of DNA. Thus, pairs are recovered that span short, medium, and long-distances all from the same single library. The probability of a particular distance can be well-modeled by a decreasing power law function. That is, it is increasingly less likely to observe read pairs spanning greater and greater distances. Assembly techniques disclosed herein (e.g., "HiRise") can exploit this facet of the data to accurately order and orient contigs into scaffolds Some embodiments of the subject methods comprise proximity ligation and sequencing of in vitro assembled chromatin aggregates comprising metagenomic DNA samples, or DNA samples from uncultured microorganisms obtained directly from a sample, such as, for example, a biomedical or biological sample, an ecological or environmental sample, or a food sample. In compatible embodiments, nucleic acids are assembled into complexes, bound, cleaved to expose internal double-strand breaks, labeled to facilitate isolation of break junctions, and re-ligated so as to generate paired end sequences that are sequenced. In some such paired end sequences, both ends of the paired end read are inferred to map to a common nucleic acid molecule, even if the sequences of the paired read map to distinct contigs.

In similarly preferred embodiments, exposed ends of bound complexes are tagged using identifiers such as nucleic acid barcodes, such that a complex is tagged or barcoded such that tag-adjacent sequence is inferred to likely arise from a single nucleic acid. Again, commonly barcoded sequences may map to multiple contigs, but the contigs are then inferred to map to a common nucleic acid molecule.

In similarly preferred embodiments, complexes are assembled through the addition of nucleic acid binding proteins other than histones, such as nuclear proteins, transposases, transcription factors, topoisomerases, specific or nonspecific double-stranded DNA binding proteins, or other suitable proteins. Alternately or in combination, complexes are assembled using nanoparticles rather than histones or other nucleic acid binding proteins.

In similarly preferred embodiments, natively occurring complexes are relied upon to preserve linkage information for nucleic acid complexes. In some such cases, nucleic acids are isolated so as to preserve complexes natively assembled, or are treated with a stabilizing agent such as a fixative prior to treatment or isolation.

In any assembled or isolated complex, cross-linking can be relied upon in some cases to stabilize nucleic acid complex formation, while in alternate cases the nucleic acid-binding moiety interactions are sufficient to maintain complex integrity in the absence of cross-linking.

The methods and compositions herein, alone or in combination with independently obtained or generated sequence data such as shotgun sequencing data, can generate assemblies of genomic information for genomes, chromosomes or independent nucleic acid molecules in heterogeneous nucleic acid samples. Genomes can be assembled representing organisms, culturable or unculturable, such as abundant or rare organisms in a wide range of metagenomics communities, such as the human oral or gut microbiomes, and including organisms that are not amenable to growth in culture. Organisms can also be individuals in a sample with genetic material from a mixed group or population of other individuals, such as a sample containing cells or nucleic acids from multiple different human individuals. Methods of the present disclosure offer fast and simple approaches to high-throughput, culture-free assembly of genomes, in some cases using widely available high-throughput sequencing technology.

Applications of Target-Independent Microbe Detection

Microbial contents of biological or biomedical samples, ecological or environmental samples, industrial microbial samples, and food samples are frequently either identified or quantified through culture dependent methods. Culturing a microorganism can depend on various factors including, but not limited to, pH, temperature, humidity, and nutrients. It is often a time-consuming and difficult process to determine the culturing conditions for an unknown or previously uncultured organism.

Many microorganisms currently cannot be cultured in the laboratory. A significant amount of microbial biodiversity is overlooked by cultivation-based methods. Methods and compositions of the present disclosure can be applied to genetic analysis of organisms in metagenomic samples, such as microbes or viruses that cannot be cultured in a laboratory environment and that inhabit a wide variety of environments. Non-limiting examples of metagenomic samples include biological samples including tissues, urine, sweat, saliva, sputum, and feces; the air and atmosphere; water samples from bodies of water such as ponds, lakes, seas, oceans, etc; ecological samples such as soil and dirt; and foodstuffs. Analysis of microbial content in various metagenomic samples is useful in applications including, but not limited to, medicine, forensics, environmental monitoring, and food science.

Individual microbes or a "microbial signature" or "microbial fingerprint" comprising a panel of microbes is identified in a biological or biomedical sample obtained from a subject, for example mammalian subjects such as a human or other animal. In some aspects, such information is used for medical applications or purposes. In some aspects, identification comprises determining the presence or the absence of a microbial genus or species, or microbial genera or species with previously unidentified or uncommon genetic mutations, such as mutations that can confer antibiotic resistance to bacterial strains. In some aspects, identification comprises determining the levels of microbial DNA from one or more microbial species or one or more microbial genera. In some cases, a microbial signature or fingerprint indicates a level of microbial DNA of a particular genus or species that is increased or significantly higher compared to the level of microbial DNA from a different genera or species in a sample. In some aspects, the microbial signature or fingerprint of a sample indicates a level of microbial DNA from a particular genus or species that is decreased or significantly lower compared to the level of microbial DNA from other genera or species in the sample. In some aspects, a microbial signature or fingerprint of a sample is determined by quantifying the levels of microbial DNA of various types of microbes (e.g., different genera or species) that are present in the sample. In some aspects, the levels of microbial DNA of various genera or species of microbes that are present in a sample is determined and compared to that of a control sample or standard.

In some aspects, the presence of a microbial genera or species in a subject suspected of having a medical condition is confidently diagnosed as having a medical condition being caused by the microbial genera or species. In some cases, this information is used to quarantine an individual from other individuals if the microbial genera or species is suspected of being transmittable to other individuals, for example by contact or proximity. In some cases, information regarding the microbe or microbial species present in a sample is used to determine a particular medical treatment to eliminate the microbe in the subject and treat, for example, a bacterial infection.

In some aspects, if the level of microbial DNA of a particular genus or species in a sample is decreased or significantly lower than a control sample or standard, the subject from which the sample was obtained is diagnosed as suffering from a disease, such as for example cancer (e.g., breast cancer). In some aspects, the levels of microbial DNA of various genera or species of microbes that are present in a sample is determined and compared between the other various genera or species present in the sample. In some aspects, if the level of microbial DNA of a particular genus or species in a sample is decreased or significantly lower than the microbial DNA of other microbial genera or species detected in the sample, the subject from which the sample was obtained is likely suffering from a disease, such as for example cancer.

Individual microbes or a "microbial signature" or "microbial fingerprint" comprising a panel of microbes are identified in environmental or ecological samples, for example air samples, water samples, and soil or dirt samples. In some aspects, identification of microbes and analysis of microbial diversity in environmental or ecological samples is used to improve strategies for monitoring the impact of pollutants on ecosystems and for cleaning up contaminated environments. Increased understanding of how microbial communities cope with pollutants improves assessments of the potential of contaminated sites to recover from pollution and increases the chances of bioaugmentation or biostimulation. Such information provides valuable insights into the functional ecology of environmental communities. Microbial analysis is also used more broadly in some cases to identify species present the air, specific bodies of water, and samples of soil and dirt. This can, for example, be used to establish the range of invasive species and endangered species, and track seasonal populations.

Identification and analysis of microbial communities in environmental or ecological samples are also useful for agricultural applications. Microbial consortia perform a wide variety of ecosystem services necessary for plant growth, including fixing atmospheric nitrogen, nutrient cycling, suppressing disease, and sequestering iron and other metals. Such information is useful, for example to improve disease detection in crops and livestock and the adaptation of enhanced farming practices which improve crop health by harnessing the relationship between microbes and plants.

In some embodiments, individual microbes or a "microbial signature" or "microbial fingerprint" comprising a panel of microbes are identified in industrial samples of microbes, for example microbial communities used to produce various biologically active chemicals, such as fine chemicals, agrochemicals, and pharmaceuticals. Microbial communities produce a vast array of biologically active chemicals.

Microbial detection and identification based on sequence analysis are also useful for food safety, food authenticity, and fraud detection. For example, microbial detection and identification in metagenomic samples allow for detection and identification of nonculturable and previously unknown pathogens, including bacteria, viruses and parasites, in foods suspected of spoilage or contamination. With estimates that around 80 percent of foodborne disease cases in the U.S. are caused by unspecified agents, including known agents not yet recognized as causing foodborne illness, substances known to be in food but of unproven pathogenicity, and unknown agents, microbial analysis of entire populations can provide opportunities to reduce foodborne illnesses. With increasing awareness of the global supply of food and increasing awareness of sustainable practices in procuring foods such as seafood and shellfish, microbial detection cis useful to assess the authenticity of foods, for example determining if fish claiming to be from a particular region of the world is truly from that region of the world.

Applications of Linkage Determination in a Heterologous Sample

Applications of the methods herein also relate to linkage determination for known or unknown molecules in a heterogeneous sample. Also contemplated herein are applications related to determination of linkage information in heterogeneous samples aside from novel organism detection. In some embodiments, linkage information is determined for nucleic acids such as chromosomes in a heterogeneous nucleic acid sample. A sample comprising DNA from a plurality of individuals is obtained, such as a sample from a crime scene, a urinal or toilet, a battlefield, a sink or garbage waste. Nucleic acid sequence information is obtained, for example via shotgun sequencing, and linkage information is determined. Often, an individual's unique genomic information is not identified by a single locus but by a combination of loci such as single nucleotide polymorphisms (SNPs), insertions or deletions (in/dels) or point mutations or alleles that collectively represent a unique or substantially unique genetic combination of traits. In many cases, no individual trait is sufficient to identify a specific individual. However, using linkage information such as that made available through practice of the methods herein, one identifies not only the aggregate alleles present in a heterogeneous sample, as with shotgun or alternate high-throughput sequencing approaches available in the art, bit one also determines specific combinations of alleles present in specific molecules in the sample. Thus, one determines not simply specific alleles in the sample, but the combinations of these alleles on chromosomes as necessary to map the allele combinations to specific individuals for which genome information is available through a previously obtained genomic sequence or through sequence information available from relatives. Linkage information is also valuable in cases where a gene is known to exist in a heterogeneous sample, but its genomic context is unknown. For example, in some cases an individual is known to harbor a harmful infection that is resistant to an antibiotic treatment. Shotgun sequencing is likely to identify the antibiotic resistance gene. However, through practice of the methods herein, valuable information is gained regarding the genomic context of the antibiotic resistance gene. Thus, by identifying not only the antibiotic resistance gene but the genome of the organism in which it resides, one is able to identify alternate treatments to target the antibiotic resistance gene host in light of the remainder of its genomic information. For example, a metabolic pathway absent from the resistant microbe or vulnerable to a second antibiotic is targeted such that the resistant microbe is cleared despite being resistant to the antibiotic if first choice. Alternately, using more complete genomic information regarding the host of an antibiotic resistance gene in a patient, one determines whether the resistance gene arises from a 'wild' microbial organism, or whether it is likely to have arisen from a laboratory strain of a microbe that 'escaped' from the laboratory or was intentionally released.

Samples

A sample in which microbes are detected can be any sample comprising a microbial population or heterogeneous nucleic acid population. Examples include biological or biomedical samples from a human subject or animal subject; an environmental and ecological sample including but not limited to soil and water samples such as a water sample from a pond, lake, sea, ocean, etc; or foodstuffs suspected of being spoiled or contaminated.

Biological samples can be obtained from a biological subject. A subject can refer to any animal (e.g., a mammal), including but not limited to humans, non-human primates, rodents, dogs, cats, pigs, fish, and the like. Samples can be obtained from any subject, individual, or biological source including, for example, human or non-human animals, including mammals and non-mammals, vertebrates and invertebrates. A sample can comprise an infected or contaminated tissue sample, such as for example a tissue sample comprising skin, heart, lung, kidney, breast, pancreas, liver, muscle, smooth muscle, bladder, gall bladder, colon, intestine, brain, prostate, esophagus, and thyroid. A sample can comprise an infected or contaminated biological sample, such as for example blood, urine, cerebrospinal fluid, seminal fluid, saliva, sputum, and stool.

Heterogeneous samples in some cases comprise nucleic acids derived from at least two individuals, such as a sample obtained from a urinal or toilet used by two or more individuals, or a site where blood or tissue from at least two individuals is comingled such as a battlefield or a crime scene. Through the practice of methods disclosed herein, linkage information for the sample Methods for obtaining a sample can be selected for the appropriate sample type and desired application. For example, a tissue sample may be obtained by biopsy or resection during a surgical procedure; blood may be obtained by venipuncture; and saliva, sputum, and stool can be self-provided by an individual in a receptacle.

In some aspects, a stool sample is derived from an animal such as a mammal (e.g., non-human primate, equine, bovine, canine, feline, porcine and human). A stool sample can be of any suitable weight. A stool sample can be at least 50 g, 60 g, 70 g, 80 g, 90 g, 100 g, 110 g, 120 g, 130 g, 140 g, 150 g or more. A stool sample can contain water. In some aspects, a stool sample contains at least 60%, 65%, 70%, 75%, 80%, 85%, or 90% or more of water. In some aspects, a stool sample is stored. Stool samples can be stored for several days (e.g. between 3-5 days) at 2-8° C., or for longer periods of time (e.g. more than 5 days) at temperatures at −20° C. or lower. In some aspects, a stool sample can be provided by an individual or subject. In some aspects, a stool sample can be collected from a place where stool is deposited. In some aspects, a stool sample can comprise multiple samples collected from a single individual over a predetermined period of time. Stool samples collected over a period of time at multiple time-points can be used to monitor the biodiversity in the stool of an individual, for example during the course of treatment for an infection. In some aspects, a stool sample comprises samples from several individuals, for example several individuals suspected of being infected with the same pathogen or to have contracted the same disease.

In some cases, samples comprise environmental or ecological samples comprising a microbial population or community. Non-limiting examples of environmental samples include atmosphere or air samples, soil or dirt samples, and water samples. Air samples can be analyzed to determine the microbial composition of air, for example air in areas that are suspected of harboring microbes considered health threats, for example, viruses causing illnesses. In some aspects, understanding the microbial make-up of an air sample can be used to monitor changes in the environment.

Water samples can be analyzed for purposes including but not limited to public safety and environmental monitoring. Water samples, for example, from a drinking water supply reservoir, can be analyzed to determine the microbial diversity in the drinking water supply and potential impact on human health. Water samples can be analyzed to determine the impact on microbial environments resulting from changes in local temperatures and compositions of gases in the atmosphere. Water samples, for example water sample from a pond, lake, sea, ocean, or other water body, can be sampled at various times of the year. In some aspects, multiple samples are acquired at various times of the year. Water samples can be collected at various depths from the surface of the body of water. For example, a water sample can be collected at the surface or at least 1 meter (e.g. at least 2, 3, 4, 5, 6, 7, 8, 9 meters or farther) from the surface of the body of water. In some aspects, the water sample can be collected from the floor of the body of water.

Soil and dirt samples can be sampled to study microbial diversity. Soil samples can provide information regarding movement of viruses and bacteria in soils and waters and may be useful in bioremediation, in which genetic engineering can be applied to develop soil microbes capable of degrading hazardous pollutants. Soil microbial communities can harbor thousands of different organisms that contain a substantial number of genetic information, for example ranging from 2,000 to 18,000 different genomes estimated in one gram of soil. A soil sample can be collected at various depths from the surface. In some aspects, soil is collected at the surface. In some aspects, soil is collected at least 1 in (e.g. at least 2, 3, 4, 5, 6, 7, 8, 9 or 10 in or farther) below the surface. In some aspects, soil is collected at depths between 1-10 in (e.g. between 2-9 in, 3-8 in, 4-7 in, or 5-6 in) below the surface. A soil sample can be collected at various times during the year. In some aspects, a soil sample is collected in a specific season, such as winter, spring, summer or fall. In some aspects, a soil sample is collected in a particular month. In some aspects, a soil sample is collected after an environmental phenomenon, including but not limited to a tornado, hurricane, or thunderstorm. In some cases, multiple soil samples are collected over a period of time to allow for monitoring of microbial diversity over a time course. A soil sample can be collected from various ecosystems, such as agroecosystems, forest ecosystems, and ecosystems from various geographical regions.

A food sample can be any foodstuff suspected of contamination, spoilage, a cause of human illness or otherwise suspected of harboring a microbe or nucleic acid of interest. A food sample can be produced on a small scale, such as in a single shop. A food sample can be produced on an industrial scale, such as in a large food manufacturing or food processing plant. Examples of food samples without limitation include animal products including raw or cooked seafood, shellfish, raw or cooked eggs, undercooked meats including beef, pork, and poultry, unpasteurized milk, unpasteurized soft cheeses, raw hot dogs, and deli meats; plant products including fresh produce and salads; fruit products such as fresh produce and fruit juice; and processed and/or prepared foods such as home-made canned goods, mass-manufactured canned goods, and sandwiches. In some aspects, a food sample for analysis, for example a food sample suspected of being contaminated or spoiled, may have been stored at room temperature, for example between 20° C. and 25° C. In some aspects, a food sample was stored at a temperature less than room temperature, such as a temperature less than 20° C., 18° C., 16° C., 14° C., 12° C., 10° C., 8° C., 6° C., 4° C., 2° C., 0° C., −10° C., −20° C., −40° C., −60° C., or −80° C. or lower. In some aspects, a food sample was stored at a temperature greater than room temperature, such as a temperature greater than 26° C., 28° C., 30° C., 32° C., 34° C., 36° C., 38° C., 40° C., or 50° C. or higher. In some aspects, a food sample was stored at an unknown temperature. A food sample may have been stored for a certain period of time, such as for example 1 day, 1 week, 1 month or 1 year. In some cases, a food sample was stored for at least 1 day, 1 week, 1 month, 6 months, 1 year, 2 years or longer. A food sample can be perishable and have a limited shelf life. A food sample produced in a manufacturing plant can be obtained from a particular production lot or production period. Food samples may be obtained from different stores in different communities and from different manufacturing plants.

Nucleic Acid Molecules

Nucleic acid molecules (e.g., DNA or RNA) can be isolated from a metagenomic sample containing a variety of other components, such as proteins, lipids and non-template nucleic acids. Nucleic acid molecules can be obtained from any cellular material, obtained from an animal, plant, bacterium, fungus, or any other cellular organism. Biological samples for use in the present disclosure also include viral particles or preparations. Nucleic acid molecules may be obtained directly from an organism or from a biological sample obtained from an organism, e.g., from blood, urine, cerebrospinal fluid, seminal fluid, saliva, sputum, stool and tissue. Nucleic acid molecules may be obtained directly from an ecological or environmental sample obtained from an organism, e.g., from an air sample, a water sample, and soil sample. Nucleic acid template may be obtained directly from food sample suspected of being spoiled or contaminated, e.g., a meat sample, a produce sample, a fruit sample, a raw food sample, a processed food sample, a frozen sample, etc.

Nucleic acids are extracted and purified using various methods. In some cases, nucleic acids are purified by organic extraction with phenol, phenol/chloroform/isoamyl alcohol, or similar formulations, including TRIzol and TriReagent. Other non-limiting examples of extraction techniques include: (1) organic extraction followed by ethanol precipitation, e.g., using a phenol/chloroform organic reagent (Ausubel et al., 1993), with or without the use of an automated nucleic acid extractor, e.g., the Model 341 DNA Extractor available from Applied Biosystems (Foster City, Calif.); (2) stationary phase adsorption methods (U.S. Pat. No. 5,234,809; Walsh et al., 1991); and (3) salt-induced nucleic acid precipitation methods (Miller et al., 1988), such precipitation methods being typically referred to as "salting-out" methods. Nucleic acid isolation and/or purification may comprise the use of magnetic particles to which nucleic acids can specifically or non-specifically bind, followed by isolation of the beads using a magnet, and washing and eluting the nucleic acids from the beads (see e.g. U.S. Pat.

No. 5,705,628). The above isolation methods can be preceded by an enzyme digestion step to help eliminate unwanted protein from the sample, e.g., digestion with proteinase K, or other like proteases. See, e.g., U.S. Pat. No. 7,001,724. If desired, RNase inhibitors may be added to the lysis buffer. For certain cell or sample types, a protein denaturation/digestion step can be added to the protocol. Purification methods may be directed to isolate DNA, RNA, or both. When both DNA and RNA are isolated together during or subsequent to an extraction procedure, further steps may be employed to purify one or both separately from the other. Sub-fractions of extracted nucleic acids can be generated, for example, by purification based on size, sequence, or other physical or chemical characteristic. In addition to an initial nucleic isolation step, purification of nucleic acids can be performed after any step in the methods of the disclosure, such as to remove excess or unwanted reagents, reactants, or products. In some cases, such as when the detection of RNA-encoded genomes is contemplated, nucleic acid samples are treated with reverse transcriptase so that RNA molecules in a nucleic acid sample serve as templates for the synthesis of complementary DNA molecules. In some cases, such a treatment facilitates downstream analysis of the nucleic acid sample.

Nucleic acid template molecules are in some cases obtained as described in U.S. Patent Application Publication Number US2002/0190663 A1, published Oct. 9, 2003. Nucleic acid molecules are in some cases extracted from a biological sample by a variety of techniques such as those described by Maniatis, et al., Molecular Cloning: A Laboratory Manual, Cold Spring Harbor, N.Y., pp. 280-281 (1982) and in more recent updates to the well-known laboratory resource. The nucleic acids may first be extracted from the biological samples and then cross-linked in vitro. Native association proteins (e.g., histones) can further be removed from the nucleic acids.

The methods disclosed herein can be applied to any high molecular weight double stranded DNA including, for example, DNA isolated from tissues, cell culture, bodily fluids, animal tissue, plant, bacteria, fungi, viruses, etc.

Each of the plurality of independent samples independently may comprise at least 1 ng, 2 ng, 5 ng, 10 ng, 20 ng, 30 ng, 40 ng, 50 ng, 75 ng, 100 ng, 150 ng, 200 ng, 250 ng, 300 ng, 400 ng, 500 ng, 1 µg, 1.5 µg, 2 µg, 5 µg, 10 µg, 20 µg, 50 µg, 100 µg, 200 µg, 500 µg, or 1000 µg, or more of nucleic acid material. In some cases, each of the plurality of independent samples independently may comprise less than about 1 ng, 2 ng, 5 ng, 10 ng, 20 ng, 30 ng, 40 ng, 50 ng, 75 ng, 100 ng, 150 ng, 200 ng, 250 ng, 300 ng, 400 ng, 500 ng, 1 µg, 1.5 µg, 2 µg, 5 µg, 10 µg, 20 µg, 50 µg, 100 µg, 200 µg, 500 µg, 1000 µg or more of nucleic acid.

Various methods for quantifying nucleic acids are available. Non-limiting examples of methods for quantifying nucleic acids include spectrophotometric analysis and measuring fluorescence intensity of dyes that bind to nucleic acids and selectively fluoresce when bound, such as for example Ethidium Bromide.

Nucleic Acid Complexes

Nucleic acids comprising DNA from a metagenomic or otherwise heterogeneous sample or samples is in some cases bound to association molecules or nucleic acid binding moieties to form nucleic acid complexes. In some cases, nucleic acid complexes comprise nucleic acids bound to a plurality of association molecules or moieties, such as polypeptides; non-protein organic molecules; and nanoparticles. Binding agents bind to individual nucleic acids at multiple points of contact in some cases, such that the segments at these points of contact are held together independent of their common phosphodiester backbone.

In some cases, binding a nucleic acid comprises forming linkages, for example covalent linkages, between segments of a nucleic acid molecule. Linkages can be formed between distant segments of a nucleic acid molecule. In some cases, binding a nucleic acid to form a nucleic acid complex comprises cross-linking a nucleic acid to an association molecule or moiety (herein also referred to as a nucleic acid binding molecule or moiety). In some cases, association molecules comprise amino acids, including but not limited to peptides and proteins such as DNA binding proteins. Exemplary DNA binding proteins include native chromatin constituents such as histone, for example Histones 2A, 2B, 3A, 3B, 4A, and 4B. In some cases, the plurality of nucleic acid binding moieties comprises reconstituted chromatin or in vitro assembled chromatin. Chromatin can be reconstituted from DNA molecules that are about 150 kbp in length. In some cases, chromatin is reconstituted from DNA molecules that are at least 50, 100, 125, 150, 200, 250 kbp or more in length. In some cases, binding proteins comprise transcription factors or transposases. Non-protein organic molecules are also compatible with the disclosure herein, such as protamine, spermine, spermidine or other positively charged molecules. In some cases, the association molecules comprise nanoparticles, such as nanoparticles having a positively charged surface. A number of nanoparticle compositions are compatible with the disclosure herein. In some aspects, the nanoparticles comprise silicon, such as silicon coated with a positive coating so as to bind negatively charged nucleic acids. In some cases, the nanoparticle is a platinum-based nanoparticle. The nanoparticles can be magnetic, which may facilitate the isolation of the cross-linked sequence segments.

A nucleic acid is bound to an association molecule by various methods consistent with the disclosure herein. In some cases, a nucleic acid is cross-linked to an association molecule. Methods of crosslinking include ultraviolet irradiation, chemical and physical (e.g., optical) crosslinking. Non-limiting examples of chemical crosslinking agents include formaldehyde and psoralen (Solomon et al., Proc. Natl. Acad. Sci. USA 82:6470-6474, 1985; Solomon et al., Cell 53:937-947, 1988). In some cases, cross-linking is performed by adding a solution comprising about 2% formaldehyde to a mixture comprising the nucleic acid molecule and chromatin proteins. Other non-limiting examples of agents that can be used for cross-linking DNA include, but are not limited to, mitomycin C, nitrogen mustard, melphalan, 1,3-butadiene diepoxide, cis diaminedichloroplatinum(II) and cyclophosphamide. In some cases, the cross-linking agent forms cross-links that bridge relatively short distances—such as about 2 Å, 3 Å, 4 Å, or 5 Å.

In some cases, nucleic acid complexes, for example nucleic acids bound to in vitro assembled chromatin (herein referred to as chromatin aggregates) are attached to a solid support, including but not limited to beads, for example magnetic beads.

In some embodiments nucleic acid complexes are existent in a sample rather than being assembled subsequent to or concurrent with extraction. Often, nucleic acid complexes in such situations comprise native nucleosomes or other native nucleic acid binding molecules complexed to nucleic acids of the sample.

Nucleic acid complexes, either native or subsequently generated, are in some cases independently stable. In some cases, nucleic acid complexes, either native or subsequently generated, are stabilized by treatment with a cross-linking agent.

Chromatin Reconstitution

Reconstituted chromatin as a binding moiety is accomplished by a number of approaches. Reconstituted chromatin as contemplated herein is used broadly to encompass binding of a broad number of binding moieties to a naked nucleic acid. Binding moieties include histones and nucleosomes, but in some interpretations of reconstituted chromatin also other nuclear proteins such as transcription factors, transposons, or other DNA or other nucleic acid binding proteins, spermine or spermidine or other non-polypeptide nucleic acid binding moieties, nanoparticles such as organic or inorganic nanoparticle nucleic acid binding agents.

In some cases, reconstituted chromatin is used in reference to the reassembly of native chromatin constituents or homologues of native chromatin constituents onto a naked nucleic acid, such as reassembly of histones or nucleosomes onto a native nucleic acid.

Two approaches to reconstitute chromatin include (1) ATP-independent random deposition of histones onto DNA, and (2) ATP-dependent assembly of periodic nucleosomes. This disclosure contemplates the use of either approach with one or more methods disclosed herein. Examples of both approaches to generate chromatin can be found in Lusser et al. ("Strategies for the reconstitution of chromatin," Nature Methods (2004), 1(1):19-26), which is incorporated herein by reference in its entirety.

Other approaches to reconstituting chromatin, either strictly defined as nucleosome or histone addition to naked nucleic acids, or more broadly defined as the addition of any moiety to a naked nucleic acid, are contemplated herein, and neither the composition of chromatin nor the approach to its reconstitution should be considered limiting in some embodiments. In some cases, 'chromatin reconstitution' refers to the generation not of native chromatin but of generation of novel nucleic acid complexes, such as complexes comprising nucleic acids stabilized by binding to nanoparticles, such as nanoparticles having a surface comprising a moiety that facilitates nucleic acid binding or nucleic acid binding and cross-linking.

Alternately, in some cases no reconstitution is performed, and native nucleic acid complexes are relied upon to stabilize nucleic acids for downstream analysis. Often, such nucleic acid complexes comprise native histones, but complexes comprising other nuclear proteins, DNA binding proteins, transposases, topoisomerases, or other DNA binding proteins are contemplated.

Cleaving Nucleic Acid Molecules

Nucleic acid molecules, such as bound nucleic acid molecules from a metagenomic sample in nucleic acid complexes, can be cleaved to expose internal nucleic acid ends and create double-stranded breaks. In some cases, a nucleic acid molecule, such as a nucleic acid molecule in a nucleic acid complex, is cleaved to expose nucleic acid ends and form at least two fragments or segments that are not physically linked at their phosphodiester backbone. Various methods can be used to cleave internal nucleic acid ends and/or generate fragments derived from a nucleic acid, including but not limited to mechanical, chemical, and enzymatic methods such as shearing, sonication, nonspecific endonuclease treatment, or specific endonuclease treatment. Alternate approaches involve enzymatic cleavage, such as with a topoisomerase, a base-repair enzyme, a transpose such as Tn5, or a phosphodiester backbone nicking enzyme.

In some cases, a nucleic acid is cleaved by digesting. Digestion can comprise contacting with a restriction endonuclease. Restriction endonucleases can be selected in light of known genomic sequence information to tailor an average number of free nucleic acid ends that result from digesting. Restriction endonucleases can cleave at or near specific recognition nucleotide sequences known as restriction sites. Restriction endonucleases having restriction sites with higher relative abundance throughout the genome can be used during digestion to produce a greater number of exposed nucleic acid ends compared to restriction endonucleases having restriction sites with lower relative abundance, as more restrictions sites can result in more cleaved sites. In some cases, restriction endonucleases with non-specific restriction sites, or more than one restriction site, are used. A non-limiting example of a non-specific restriction site is CCTNN. The bases A, C, G, and T refer to the four nucleotide bases of a DNA strand—adenine, cytosine, guanine, and thymine. The base N represents any of the four DNA bases—A, C, G, and T. Rather than recognizing a specific sequence for cleavage, an enzyme with the corresponding restriction site can recognize more than one sequence for cleavage. For example, the first five bases that are recognized can be CCTAA, CCTAT, CCTAG, CCTAC, CCTTA, CCTTT, CCTTG, CCTTC, CCTCA, CCTCT, CCTCG, CCTCC, CCTGA, CCTGT, CCTGG, or CCTGC (16 possibilities). In some cases, use of an enzyme with a non-specific restriction site results in a larger number of cleavage sites compared to an enzyme with a specific restriction site. Restriction endonucleases can have restriction recognition sequences of at least 4, 5, 6, 7, 8 base pairs or longer. Restriction enzymes for digesting nucleic acid complexes can cleave single-stranded and/or double-stranded nucleic acids. Restriction endonucleases can produce single-stranded breaks or double-stranded breaks. Restriction endonuclease cleavage can produce blunt ends, 3' overhangs, or 5' overhangs. A 3' overhang can be at least 1, 2, 3, 4, 5, 6, 7, 8, or 9 bases in length or longer. A 5' overhang can be at least 1, 2, 3, 4, 5, 6, 7, 8, or 9 bases in length or longer. Examples of restriction enzymes include, but are not limited to, AatII, Acc65I, AcCI, AciI, AclI, AcuI, AfeI, AflII, AflIII, AgeI, AhdI, AleI, AluI, AlwI, AlwNI, ApaI, ApaLI, ApeKI, ApoI, AscI, AseI, AsiSI, AvaI, AvaII, AvrII, BaeGI, BaeI, BamHI, BanI, BanII, BbsI, BbvCI, BbvI, BccI, BceAI, BcgI, BciVI, BclI, BfaI, BfuAI, BfuCI, BglI, BglII, BlpI, BmgBI, BmrI, BmtI, BpmI, Bpu10I, BpuEI, BsaAI, BsaBI, BsaHI, BsaI, BsaJI, BsaWI, BsaXI, BscRI, BscYI, BsgI, BsiEI, BsiHKAI, BsiWI, BslI, BsmAI, BsmBI, BsmFI, BsmI, BsoBI, Bsp1286I, BspCNI, BspDI, BspEI, BspHI, BspMI, BspQI, BsrBI, BsrDI, BsrFI, BsrGI, BsrI, BssHII, BssKI, BssSI, BstAPI, BstBI, BstEII, BstNI, BstUI, BstXI, BstYI, BstZ17I, Bsu36I, BtgI, BtgZI, BtsCI, BtsI, Cac8I, ClaI, CspCI, CviAII, CviKI-1, CviQI, DdeI, DpnI, DpnII, DraI, DraIII, DrdI, EacI, EagI, EarI, EciI, Eco53kI, EcoNI, EcoO109I, EcoP15I, EcoRI, EcoRV, FatI, FauI, Fnu4HI, FokI, FseI, FspI, HaeII, HaeIII, HgaI, HhaI, HincII, HindIII, HinfI, HinP1I, HpaI, HpaII, HphI, Hpy166II, Hpy188I, Hpy188III, Hpy99I, HpyAV, HpyCH4III, HpyCH4IV, HpyCH4V, KasI, KpnI, MboI, MboII, MfeI, MluI, MlyI, MmeI, MnlI, MscI, MseI, MslI, MspA1I, MspI, MwoI, NaeI, NanI, Nb.BbvCI, Nb.BsmI, Nb.BsrDI, Nb.BtsI, NciI, NcoI, NdeI, NgoMIV, NheI, NlaIII, NlaIV, NmeAIII, NotI, NruI, NsiI, NspI, Nt.AlwI, Nt.BbvCI, Nt.BsmAI, Nt.BspQI, Nt.BstNBI, Nt.CviPII, PacI, PaeR7I, PciI, PflFI, PflMI, PhoI, PleI, PmeI, PmlI, PpuMI, PshAI, PsiI, PspGI, PspOMI, PspXI, PstI, PvuI, PvuII, RsaI, RsrII, SacI, SacII, SalI, SapI, Sau3AI, Sau96I, SbfI, ScaI, ScrFI, SexAI, SfaNI, SfcI, SfiI, SfoI, SgrAI, SmaI, SmlI, SnaBI, SpeI, SphI, SspI, StuI, StyD4I, StyI, SwaI, T, Taqαl, TfiI, TliI, TseI, Tsp45I, Tsp509I, TspMI, TspRI, Tth111I, XbaI, XcmI, XhoI, XmaI, XmnI, and ZraI.

Ligation

Cleaved nucleic acid molecules can be ligated by proximity ligation using various methods. Ligation of cleaved nucleic acid molecules can be accomplished by enzymatic and non-enzymatic protocols. Examples of ligation reactions that are non-enzymatic can include the non-enzymatic ligation techniques described in U.S. Pat. Nos. 5,780,613 and 5,476,930, each of which is herein incorporated by reference in its entirety. Enzymatic ligation reactions can comprise use of a ligase enzyme. Non-limiting examples of ligase enzymes are ATP-dependent double-stranded polynucleotide ligases, NAD+ dependent DNA or RNA ligases, and single-strand polynucleotide ligases. Non-limiting examples of ligases are *Escherichia coli* DNA ligase, Thermus filiformis DNA ligase, Tth DNA ligase, *Thermus scotoductus* DNA ligase (I and II), T3 DNA ligase, T4 DNA ligase, T4 RNA ligase, T7 DNA ligase, Taq ligase, Ampligase (Epicentre®Technologies Corp.), VanC-type ligase, 9° N DNA Ligase, Tsp DNA ligase, DNA ligase I, DNA ligase III, DNA ligase IV, Sso7-T3 DNA ligase, Sso7-T4 DNA ligase, Sso7-T7 DNA ligase, Sso7-Taq DNA ligase, Sso7-*E. coli* DNA ligase, Sso7-Ampligase DNA ligase, and thermostable ligases. Ligase enzymes may be wild-type, mutant isoforms, and genetically engineered variants. Ligation reactions can contain a buffer component, small molecule ligation enhancers, and other reaction components.

Sequencing

Suitable sequencing methods described herein or otherwise known in the art can be used to obtain sequence information from nucleic acid molecules. Sequencing can be accomplished through classic Sanger sequencing methods. Sequencing can also be accomplished using high-throughput next-generation sequencing systems. Non-limiting examples of next-generation sequencing methods include single-molecule real-time sequencing, ion semiconductor sequencing, pyrosequencing, sequencing by synthesis, sequencing by ligation, and chain termination.

Microbes

The microbes detected herein may be bacteria, viruses, fungi, mold, or any other microscopic organism or a combination thereof.

In some aspects, a microbe detected in a biomedical sample, such as for example a biological fluid or a solid sample including but not limited to saliva, blood, and stool, is at least one bacterial species associated with a medical condition. Non-limiting examples of clinically relevant bacteria include *Acetobacter aurantius, Acinetobacter baumannii, Actinomyces israelii, Agrobacterium radiobacter, Agrobacterium tumefaciens, Anaplasma phagocytophilum, Azorhizobium caulinodans, Azotobacter vinelandii, Bacillus anthracis, Bacillus brevis, Bacillus cereus, Bacillus fusifomiis, Bacillus licheniformis, Bacillus megaterium, Bacillus mycoides, Bacillus stearothermophilus, Bacillus subtilis, Bacteroides fragilis, Bacteroides gingivalis, Bacteroides melaninogenicus* (now known as *Prevotella melaninogenica*), *Bartonella henselae, Bartonella quintana, Bordetella bronchiseptica, Bordetella pertussis, Borrelia burgdorferi, Brucella abortus, Brucella melitensis, Brucella suis, Burkholderia mallei, Burkholderia pseudomallei, Burkholderia cepacia, Calymmatobacterium granulomatis, Campylobacter coli, Campylobacter fetus, Campylobacter jejuni, Campylobacter pylori, Chlamydia trachomatis, Chlamydophila pneumoniae* (previously called *Chlamydia pneumoniae*), *Chlamydophila psittaci* (previously called *Chlamydia psittaci*), *Clostridium botulinum, Clostridium difficile, Clostridium perfringens* (previously called *Clostridium welchii*), *Clostridium tetani, Corynebacterium diphtheriae, Corynebacterium fusiforme, Coxiella burnetii, Ehrlichia chaffeensis, Enterobacter cloacae, Enterococcus avium, Enterococcus durans, Enterococcus faecalis, Enterococcus faecium, Enterococcus galllinarum, Enterococcus maloratus, Escherichia coli, Francisella tularensis, Fusobacterium nucleatum, Gardnerella vaginalis, Haemophilus ducreyi, Haemophilus influenzae, Haemophilus parainfluenzae, Haemophilus pertussis, Haemophilus vaginalis, Helicobacter pylori, Klebsiella pneumoniae, Lactobacillus acidophilus, Lactobacillus bulgaricus, Lactobacillus casei, Lactococcus lactis, Legionella pneumophila, Listeria monocytogenes, Methanobacterium extroquens, Microbacterium multiforme, Micrococcus luteus, Moraxella catarrhalis, Mycobacterium avium, Mycobacterium bovis, Mycobacterium diphtheriae, Mycobacterium intracellulare, Mycobacterium leprae, Mycobacterium lepraemurium, Mycobacterium phlei, Mycobacterium smegmatis, Mycobacterium tuberculosis, Mycoplasma fermentans, Mycoplasma genitalium, Mycoplasma hominis, Mycoplasma penetrans, Mycoplasma pneumoniae, Neisseria gonorrhoeae, Neisseria meningitidis, Pasteurella multocida, Pasteurella tularensis, Peptostreptococcus, Porphyromonas gingivalis, Prevotella melaninogenica* (previously called *Bacteroides melaninogenicus*), *Pseudomonas aeruginosa, Rhizobium radiobacter, Rickettsia prowazekii, Rickettsia psittaci, Rickettsia quintana, Rickettsia rickettsii, Rickettsia trachomae, Rochalimaea henselae, Rochalimaea quintana, Rothia dentocariosa, Salmonella enteritidis, Salmonella typhi, Salmonella typhimurium, Serratia marcescens, Shigella dysenteriae, Staphylococcus aureus, Staphylococcus epidermidis, Stenotrophomonas maltophilia, Streptococcus agalactiae, Streptococcus avium, Streptococcus bovis, Streptococcus cricetus, Streptococcus faceium, Streptococcus faecalis, Streptococcus ferus, Streptococcus gallinarum, Streptococcus lactis, Streptococcus mitior, Streptococcus mitis, Streptococcus mutans, Streptococcus oralis, Streptococcus pneumoniae, Streptococcus pyogenes, Streptococcus rattus, Streptococcus salivarius, Streptococcus sanguis, Streptococcus sobrinus, Treponema pallidum, Treponema denticola, Vibrio cholerae, Vibrio comma, Vibrio parahaemolyticus, Vibrio vulnificus, Wolbachia, Yersinia enterocolitica, Yersinia pestis,* and *Yersinia pseudotuberculosis.*

In some aspects, a microbe detected in a biomedical sample, such as for example a biological fluid or a solid sample including but not limited to saliva, blood, and stool, is at least virus associated with a medical condition. In some aspects, viruses are DNA viruses. In some aspects, viruses are RNA viruses. Human viral infections can have a zoonotic, or wild or domestic animal, origin. Several zoonotic viruses are transmitted to humans directly via contact with an animal or indirectly via exposure to the urine or feces of infected animals or the bite of a bloodsucking arthropod. If a virus is able to adapt and replicate in its new human host, human-to-human transmissions may occur. In some aspects, a microbe detected in a biomedical sample is a virus having a zoonotic origin.

In some aspects, a microbe detected in a biomedical sample, such as for example a biological fluid or a solid sample including but not limited to saliva, blood, and stool, is at least fungus associated with a medical condition. Non-limiting examples of clinically relevant fungal genuses include *Aspergillus, Basidiobolus, Blastomyces, Candida, Chrysosporium, Coccidioides, Conidiobolus, Cryptococcus,*

*Epidermophyton, Histoplasma, Microsporum, Pneumocystis, Sporothrix,* and *Trichophyton.*

In some aspects, a microbe detected in a food sample, such a food sample suspected of causing illness, can be a pathogenic bacterium, virus, or parasite. Non-limiting examples of pathogenic bacteria, viruses, or parasites that can cause illness include *Salmonella* species such as *S. enterica* and *S. bongori; Campylobacter* species such as *C. jejuni, C. coli,* and *C. fetus; Yersinia* species such as *Y. enterocolitica* and *Y. pseudotuberculosis; Shigella* species such as *S. sonnei, S. boydii, S. flexneri,* and *S. dysenteriae; Vibrio* species such as *V. parahaemolyticus, Vibrio cholerae* Serogroups O1 and O139, *Vibrio cholerae* Serogroups non-O1 and non-O139, *Vibrio vulnificus; Coxiella* species such as *C. burnetii; Mycobacterium* species such as *M. bovis* which is the causative agent of tuberculosis in cattle but can also infect humans; *Brucella* species such as *B. melitensis, B. abortus, B. suis, B. neotomae, B. canis,* and *B. ovis; Cronobacter* species (formery *Enterobacter sakazakii*); *Aeromonas* species such as *A. hydrophila; Plesiomonas* species such as *P. shigelloides; Francisella* species such as *F. tularensis; Clostridium* species such as *C. perfringens* and *C. botulinum; Staphylococcus* species such as *S. aureus; Bacillus* species such as *B. cereus; Listeria* species such as *L. monocytogenes; Streptococcus* species such as *S. pyo* genes of Group A; Noroviruses (NoV, groups GI, GII, GIII, GIV, and GV); Hepatitis A virus (HAV, genotypes I-VI); Hepatitis E virus (HEV); *Reoviridae* viruses such as Rotavirus; *Astroviridae* viruses such as Astroviruses; *Calciviridae* viruses such as Sapoviruses; *Adenoviridae* viruses such as Enteric adenoviruses; *Parvoviridae* viruses such as Parvoviruses; and *Picornarviridae* viruses such as Aichi virus.

A benefit of the methods disclosed herein is that they facilitate the detection of a microbe or pathogen of unknown identity in a sample, and the assembly of the sequence information for that unknown microbe or pathogen into a partially or fully assembled genome, alone or in combination with additional sequence information such as concurrently generated sequence information generated by shotgun sequencing or other means. Accordingly, approaches disclosed herein are not limited to the detection of one or more of the organisms listed immediately above; on the contrary, through the methods disclosed herein, one is able to identify and determine substantial partial or total genome information for an unknown pathogen in the list above, or an organism not on the list above, or an organism for which no sequence information is available, or an organism that is not known to science.

The methods disclosed herein are applicable to a number of heterogeneous nucleic acid samples, such as exploratory surveys of gut microfluora; pathogen detection in a sick individual or population, such as a population suffering from an epidemic of unknown cause; the assay of a heterogeneous nucleic acid sample for the presence of nucleic acids having linkage information characteristic of a known individual; or the detection of the microbe or microbes responsible for antibiotic resistance in an individual exhibiting an antibiotic resistant infection. A common aspect of many of these embodiments is that they benefit from the generation of long-range linkage information such as that suitable for the assembly of shotgun sequence information into contigs, scaffolds or partial or complete genome sequences. Shotgun or other high-throughput sequence information is relevant to at least some of the issues listed above, but substantial benefit is gained from the result of the practice of the methods disclosed herein, to assemble shotgun sequence into larger phased nucleic acid assemblies, up to and including partial, substantially complete or complete genomes. Accordingly, use of the methods disclosed herein provides substantially more than the practice of shotgun sequencing alone on the heterogeneous samples as known in the art.

In addition to illness caused by direct bacterial infection after ingesting contaminated and/or spoiled food, microbes can produce toxins, such as an enterotoxin, that cause illness. In some aspects, a microbe detected in a food sample can produce a toxin such as an enterotoxin, which is a protein exotoxin that targets the intestines, and mycotoxin, which is a toxic secondary metabolite produced by organisms of the fungi kingdom, commonly known as molds.

A benefit of the present disclosure is that it enables one to obtain long-range genome contiguity information for a heterogeneous sample without relying upon previously or even concurrently generated sequence information for the genome or genomes to be assembled. Scaffolds, representing genomes or chromosomes of organisms in the sample, are assembled using commonly tagged reads, such as reads sharing a common oligo tag or paired-end reads that are ligated or otherwise fused to one another, thereby indicating that commonly tagged sequence information arises from a common genomic or chromosomal molecule.

Accordingly, scaffold information is generated without reliance upon previously generated contig or other sequence read information. There are a number of benefits of de novo scaffold information. For example, sequence reads can be assigned to common scaffolds even if no previous sequence information is available, such that entirely new genomes are scaffolded without reliance upon previous sequencing efforts. This benefit is particularly useful when a heterogeneous sample comprises an unknown, uncultured or unculturable organism. Whereas a sequencing project relying upon untargeted sequence read generation may generate a collection of sequence reads that are not assigned to any known contig sequence, there would be little or no information relating to the number or identity of the unknown organisms from which the sequence reads were obtained. They could, for example, represent a single individual, a population of individuals of a common species having a high degree of heterogeneity or heterozygosity in genomic sequence, a complex of closely related species, or a complex of different species. Relying solely on sequence read information, one would not easily distinguish among the aforementioned scenarios.

However, using the methods or compositions as disclosed herein, one is able to distinguish among, for example, a sample comprising clonal duplicates of a common genotype or genome, from a sample comprising a heterogeneous population of representatives of a single species, from a sample comprising loosely related organisms of different species, or combinations of these scenarios. Relying upon sequence similarity to assemble contigs rather than independently generating scaffold information, one is challenged to distinguish heterozygosity from sequencing error. Even assuming that no substantial sequencing error occurs, one is challenged to even estimate the number of genotypes from which closely-related genome information is obtained. One cannot, for example, distinguish a sample comprising two widely divergent representatives of a single species, heterozygous relative to one another at a number of distinct loci, from a sample comprising a broad diversity of closely related genotypes, each differing from the others at one or only a few loci. Using sequence read information alone, both of these scenarios appear as a single contig assembly having substantial allelic diversity. However, using the methods and compositions disclosed herein, one is able to determine with confidence which alleles map to a common scaffold, even if the alleles are separated by considerable regions of uniform or unknown sequence.

This benefit of the data generated herein is particularly useful in some cases when a heterogeneous sample comprises a viral population, such as a DNA-genome based viral population or a retrovirus or other RNA-based viral population is studied (via reverse transcription of the RNA genomes or, alternately or in combination, assembling complexes on RNA in the sample). As viral populations are often considerably heterogeneous, understanding the distribution of the heterogeneity within the population (either among a few highly divergent populations or among a large number of closely related populations) is of particular benefit in selecting a treatment target and in tracing the origin of the virus in the heterogeneous sample being studied.

This is not to say that the compositions and methods disclosed herein are incompatible with contig information or concurrently generated sequence reads. On the contrary, the scaffolding information generated through use of the methods and compositions herein are particularly suited for improved contig assembly or contig arrangement into scaffolds. Indeed, concurrently generated sequence read information is assembled into contigs in some embodiments of the disclosure herein. Sequence read information is generated in parallel, using traditional sequencing approaches such as next-generation sequencing approaches. Alternately or in combination, paired read or oligo-tagged read information is used as sequence information itself to generate contigs 'traditionally' using aligned overlapping sequence. This information is further used to position contigs relative to one another in light of the scaffolding information generated through the compositions and methods disclosed herein.

Embodiments of the present disclosure are also illustrated through the following numbered embodiments.

Numbered embodiment 1 comprises a method of generating a tagged sequence from a first DNA molecule, comprising: (a) binding said first DNA molecule to a plurality of association molecules, to form a first complex, wherein said first DNA molecule comprises a first DNA segment and a second DNA segment; (b) tagging said first DNA segment and said second DNA segment and thereby forming at least one tagged DNA segment; (c) binding the complex to a solid support having a surface that directly binds a constituent of the complex; and (d) sequencing a recognizable portion of the tagged DNA segment, such as a portion adjacent to the tag or a portion at an opposite end from the tagged end and thereby obtaining said tagged sequence; wherein said plurality of association molecules are not covalently modified with an affinity label prior to or during steps (a) and (b). Numbered embodiment 2 comprises the method of numbered embodiments 1, wherein said association molecules comprise amino acids bound by peptide bonds. Numbered embodiment 3 comprises the method of any one of numbered embodiments 1-2, wherein said association molecules comprise polypeptides or proteins. Numbered embodiment 4 comprises the method of any one of numbered embodiments 1-3, wherein said association molecules comprise histone proteins. Numbered embodiment 5 comprises the method of any one of numbered embodiments 1-3, wherein said histone proteins are from a different source than said first DNA molecule. Numbered embodiment 6 comprises the method of any one of numbered embodiments 1-3, wherein said association molecules comprise transposases. Numbered embodiment 7 comprises the method of any one of numbered embodiments 1-6, wherein said first DNA molecule is non-covalently bound to at least one of said association molecules. Numbered embodiment 8 comprises the method of any one of numbered embodiments 1-7, wherein said first DNA molecule is covalently bound to at least one of said association molecules. Numbered embodiment 9 comprises the method of any one of numbered embodiments 1-8, wherein said first DNA molecule is crosslinked to at least one of said association molecules. Numbered embodiment 10 comprises the method of any one of numbered embodiments 1-9, wherein said first DNA molecule is crosslinked using a fixative agent. Numbered embodiment 11 comprises the method of any one of numbered embodiments 1-10, wherein said fixative agent comprise formaldehyde. Numbered embodiment 12 comprises the method of any one of numbered embodiments 1-11, comprising immobilizing said plurality of association molecules on a solid support. Numbered embodiment 13 comprises the method of any one of numbered embodiments 1-12, wherein said solid support comprise a bead. Numbered embodiment 14 comprises the method of any one of numbered embodiments 1-13, wherein said bead comprises a polymer. Numbered embodiment 15 comprises the method of any one of numbered embodiments 1-14, wherein said polymer is polystyrene or polyethylene glycol (PEG). Numbered embodiment 16 comprises the method of any one of numbered embodiments 1-13, wherein said bead is a magnetic bead. Numbered embodiment 17 comprises the method of any one of numbered embodiments 1-13, wherein said bead is a solid phase reversible immobilization (SPRI) bead. Numbered embodiment 18 comprises the method of any one of numbered embodiments 1-13, wherein said solid support comprises a surface, and wherein said surface comprises a plurality of carboxyl groups. Numbered embodiment 19 comprises the method of any one of numbered embodiments 1-12, wherein said solid support is not covalently linked to any polypeptide. Numbered embodiment 20 comprises the method of any one of numbered embodiments 1-12, wherein said association molecule is not covalently linked to biotin prior to immobilization to said solid support. Numbered embodiment 21 comprises the method of any one of numbered embodiments 1-20, wherein said first DNA segment and said second DNA segment are generated by severing said first DNA molecule. Numbered embodiment 22 comprises the method of any one of numbered embodiments 1-21, wherein said first DNA molecule is severed after said first DNA molecule is bound to said plurality of association molecules. Numbered embodiment 23 comprises the method of any one of numbered embodiments 1-21, wherein said first DNA molecule is severed using a nuclease enzyme. Numbered embodiment 24 comprises the method of any one of numbered embodiments 1-23, wherein said first DNA segment and said second DNA segment are modified using an affinity label. Numbered embodiment 25 comprises the method of any one of numbered embodiments 1-24, wherein said affinity label comprises biotin. Numbered embodiment 26 comprises the method of any one of numbered embodiments 1-25, wherein said affinity label is a biotin-modified nucleoside triphosphate (dNTP). Numbered embodiment 27 comprises the method of any one of numbered embodiments 1-26, wherein said affinity label is a biotin-modified deoxyribocytosine triphosphate (dCTP). Numbered embodiment 28 comprises the method of any one of numbered embodiments 1-27, wherein said first DNA segment is tagged at at least a first end with a first tag and the second DNA segment is tagged at at least a second end with a second tag. Numbered embodiment 29 comprises the method of any one of numbered embodiments 1-28, wherein said first tag and said second tag are identical. Numbered embodiment 30 comprises the method of any one of numbered embodiments 1-28, wherein said first DNA segment and said second DNA segment are tagged using a transposase. Numbered embodiment 31 comprises the method of any one of numbered embodiments 1-30, wherein said first DNA segment is tagged with said second DNA segment and said second DNA segment is tagged with said first DNA segment by linking said first DNA segment to said second DNA segment. Numbered embodiment 32 comprises the method of any one of numbered embodiments 1-31, wherein said first DNA segment is linked to said second DNA segment using a ligase. Numbered embodiment 33 comprises the method of any one of numbered embodiments 1-32, wherein said linked DNA segment is severed prior to step (c). Numbered embodiment 34 comprises the method of any one of numbered embodiments 1-24, wherein said linked DNA segment is severed using a physical method. Numbered embodiment 35 comprises the method of any one of numbered embodiments 1-34, comprising connecting said linked DNA segment to sequencing adaptors. Numbered embodiment 36 comprises the method of any one of numbered embodiments—351, wherein said first DNA segment is washed for less than 10 times before said first DNA segment is linked to said second DNA segment. Numbered embodiment 37 comprises the method of any one of numbered embodiments 1-36, wherein said first DNA segment is washed for less than 6 times before said first DNA segment is linked to said second DNA segment. Numbered embodiment 38 comprises the method of any one of any one of numbered embodiments 1 to 37, comprising assembling a plurality of contigs of said first DNA molecule using said tagged sequence. Numbered embodiment 39 comprises the method of any one of any one of numbered embodiments 1 to 37, comprising phasing said first DNA segment and said second DNA segment using said tagged sequence. Numbered embodiment 40 comprises the method of any one of any one of numbered embodiments 1 to 39, wherein the method is completed in no more than two days. Numbered embodiment 41 comprises the method of any one of numbered embodiments 1-40, wherein said binding said first DNA molecule is conducted in vitro. Numbered embodiment 42 comprises the method of any one of numbered embodiments 1-41, wherein said binding said first DNA molecule is conducted in vivo. Numbered embodiment 43 comprises the method of any one of numbered embodiments 1-42, where the method is completed in no more than 2 days. Numbered embodiment 44 comprises the method of any one of numbered embodiments 1-43, where the amount of hands-on time required for steps (a)-(d) is no greater than 6 hours. Numbered embodiment 45 comprises the method of any one of numbered embodiments 1-44, wherein said first DNA molecule is directly bound to said solid support. Numbered embodiment 46 comprises the method of any one of numbered embodiments 1-45, wherein no dialysis is performed between steps (a)-(d).

Number embodiment 47 comprises a method of generating a tagged sequence from a first DNA molecule, comprising: (a) binding said first DNA molecule to a plurality of association molecules; (b) immobilizing said first DNA molecule on a solid support; (c) severing said first DNA molecule to generate a first DNA segment and a second DNA segment; (d) tagging said first DNA segment and said second DNA segment and thereby forming at least one tagged DNA segment; and (e) sequencing said tagged DNA segment and thereby obtaining said tagged sequence; wherein said first DNA molecule is directly bound to said solid support. Numbered embodiment 48 comprises the method of numbered embodiments 47, wherein said association molecules comprise amino acids. Numbered embodiment 49 comprises the method of any one of numbered embodiments 47-48, wherein said association molecules comprise polypeptides or proteins. Numbered embodiment 50 comprises the method of any one of numbered embodiments 47-49, wherein said association molecules comprise histone proteins. Numbered embodiment 51 comprises the method of any one of numbered embodiments 47-49, wherein said histone proteins are from a different source than said first DNA molecule Numbered embodiment 52 comprises the method of any one of numbered embodiments 47-51, wherein said association molecules comprise transposases. Numbered embodiment 53 comprises the method of any one of numbered embodiments 47-52, wherein said first DNA molecule is non-covalently bound to said association molecules. Numbered embodiment 54 comprises the method of any one of numbered embodiments 47-53, wherein said first DNA molecule is covalently bound to said association molecules. Numbered embodiment 55 comprises the method of any one of numbered embodiments 47-54, wherein said first DNA molecule is crosslinked to said association molecules. Numbered embodiment 56 comprises the method of any one of numbered embodiments 47-55, wherein said first DNA molecule is cross-linked using a fixative agent. Numbered embodiment 57 comprises the method of any one of numbered embodiments 47-56, wherein said fixative agent is formaldehyde. Numbered embodiment 58 comprises the method of any one of numbered embodiments 47-57, wherein said solid support comprise a bead. Numbered embodiment 59 comprises the method of any one of numbered embodiments 47-58, wherein said bead comprises a polymer. Numbered embodiment 60 comprises the method of any one of numbered embodiments 47-59, wherein said polymer comprise polystyrene or polyethylene glycol (PEG). Numbered embodiment 61 comprises the method of any one of numbered embodiments 47-58, wherein said bead is a magnetic bead. Numbered embodiment 62 comprises the method of any one of numbered embodiments 47-58, wherein said bead is a SPRI bead. Numbered embodiment 63 comprises the method of any one of numbered embodiments 47-62, wherein said solid support comprises a surface, and wherein said surface comprises a plurality of carboxyl groups. Numbered embodiment 64 comprises the method of any one of numbered embodiments 47-63, wherein said solid support is not covalently linked to any polypeptide. Numbered embodiment 65 comprises the method of any one of numbered embodiments 47-64, wherein said association molecule is not covalently linked to biotin prior to immobilization to said solid support. Numbered embodiment 66 comprises the method of any one of numbered embodiments 47-65, wherein said first DNA molecule is severed after said first DNA molecule is bound to at least one of said plurality of association molecules. Numbered embodiment 67 comprises the method of any one of numbered embodiments 47-66, wherein said first DNA molecule is severed using a nuclease enzyme. Numbered embodiment 68 comprises the method of any one of numbered embodiments 47-67, wherein said first DNA segment and said second DNA segment are modified using an affinity label. Numbered embodiment 69 comprises the method of any one of numbered embodiments 47-68, wherein said affinity label comprises biotin. Numbered embodiment 70 comprises the method of any one of numbered embodiments 47-69, wherein said affinity label is a biotin-modified nucleoside triphosphate (dNTP). Numbered embodiment 71 comprises the method of any one of numbered embodiments 47-70, wherein said affinity label is a biotin-modified deoxyribocytosine triphosphate (dCTP). Numbered embodiment 72 comprises the method of any one of numbered embodiments 47-71, wherein said first DNA segment is tagged at at least a first end with a first tag and the second DNA segment is tagged at at least a second end with a second tag. Numbered embodiment 73 comprises the method of any one of numbered embodiments 47-72, wherein said first tag and said second tag are identical. Numbered embodiment 74 comprises the method of any one of numbered embodiments 47-72, wherein said first DNA segment and said second DNA segment are tagged using a transposase. Numbered embodiment 75 comprises the method of any one of numbered embodiments 47-74, wherein said first DNA segment is tagged with said second DNA segment and said second DNA segment is tagged with said first DNA segment by linking said first DNA segment to said second DNA segment. Numbered embodiment 76 comprises the method of any one of numbered embodiments 47-75, wherein said first DNA segment is linked to said second DNA segment using a ligase. Numbered embodiment 77 comprises the method of any one of numbered embodiments 47-76, wherein said linked DNA segment is severed using a physical method. Numbered embodiment 78 comprises the method of any one of numbered embodiments 47-77, comprising connecting said linked DNA segment to sequencing adaptors. Numbered embodiment 79 comprises the method of any one of numbered embodiments 47-78, wherein said first DNA segment is washed for less than 10 times before said first DNA segment is linked to said second DNA segment. Numbered embodiment 80 comprises the method of any one of numbered embodiments 47-79, wherein said first DNA segment is washed for less than 6 times before said first DNA segment is linked to said second DNA segment. Numbered embodiment 81 comprises the method of any one of any one of numbered embodiments 47 to 80, comprising assembling a plurality of contigs of said first DNA molecule using said tagged sequence. Numbered embodiment 82 comprises the method of any one of any one of numbered embodiments 47 to 80, comprising phasing said first DNA segment and said second DNA segment using said tagged sequence. Numbered embodiment 83 comprises the method of any one of numbered embodiments 47-82, wherein the tagged sequence comprises a read pair. Numbered embodiment 84 comprises the method of any one of any one of numbered embodiments 47 to 83, wherein the method is completed in no more than 2 days. Numbered embodiment 85 comprises the method of any one of numbered embodiments 47-84, wherein said binding said first DNA molecule is conducted in vitro. Numbered embodiment 86 comprises the method of any one of numbered embodiments 47-85, wherein said binding said first DNA molecule is conducted in vivo. Numbered embodiment 87 comprises the method of any one of numbered embodiments 47-86, where the amount of hands-on time required for steps (a)-(d) is no greater than 6 hours. Numbered embodiment 88 comprises the method of any one of numbered embodiments 47-87, wherein no dialysis is performed between steps (a)-(d).

Numbered embodiment 89 comprises a method for generating a plurality of tagged sequences from a plurality of DNA molecules, comprising: (a) binding said plurality of DNA molecules to a plurality of association molecules; (b) severing said plurality of DNA molecules to generate a plurality of DNA segments; (c) tagging at least a portion of said DNA segments to form a plurality of tagged DNA segments; and (d) sequencing said tagged DNA segments to obtain a plurality of tagged sequences; wherein said plurality of association molecules are not covalently modified with an affinity label prior to or during steps (a) and (b). Numbered embodiment 90 comprises the method of numbered embodiments 89, wherein less than 40% of DNA segments from said DNA molecules are linked to other DNA segments not having a common phosphodiester bond prior to step (b). Numbered embodiment 91 comprises the method of any one of numbered embodiments 89-90, wherein less than 20% of DNA segments from said DNA molecules are linked to other DNA segments not having a common phosphodiester bond prior to step (b). Numbered embodiment 92 comprises the method of any one of numbered embodiments 89-91, wherein said association molecules comprise amino acids. Numbered embodiment 93 comprises the method of any one of numbered embodiments 89-92, wherein said association molecules comprise polypeptides or proteins. Numbered embodiment 94 comprises the method of any one of numbered embodiments 89-93, wherein said association molecules comprise histone proteins. Numbered embodiment 95 comprises the method of any one of numbered embodiments 89-94, wherein said histone proteins are from a different source than said DNA molecules. Numbered embodiment 96 comprises the method of any one of numbered embodiments 89-95, wherein said association molecules comprise transposases. Numbered embodiment 97 comprises the method of any one of numbered embodiments 89-96, wherein said DNA molecules are non-covalently bound to said association molecules. Numbered embodiment 98 comprises the method of any one of numbered embodiments 89-97, wherein said DNA molecules are covalently bound to said association molecules. Numbered embodiment 99 comprises the method of any one of numbered embodiments 89-98, wherein said DNA molecules are crosslinked to said association molecules. Numbered embodiment 100 comprises the method of any one of numbered embodiments 89-99, wherein said DNA molecules are cross-linked using a fixative agent. Numbered embodiment 101 comprises the method of any one of numbered embodiments 89-100, wherein said fixative agent is formaldehyde. Numbered embodiment 102 comprises the method of any one of numbered embodiments 89-101, comprising immobilizing said plurality of association molecules on a plurality of solid supports. Numbered embodiment 103 comprises the method of any one of numbered embodiments 89-102, wherein said solid supports are beads. Numbered embodiment 104 comprises the method of any one of numbered embodiments 89-103, wherein said beads comprise a polymer. Numbered embodiment 105 comprises the method of any one of numbered embodiments 89-104, wherein said polymer comprise polystyrene or polyethylene glycol (PEG). Numbered embodiment 106 comprises the method of any one of numbered embodiments 89-103, wherein said beads comprise magnetic beads. Numbered embodiment 107 comprises the method of any one of numbered embodiments 89-103, wherein said beads comprise SPRI beads. Numbered embodiment 108 comprises the method of any one of numbered embodiments 89-102, wherein said solid support comprises a surface, and wherein said surface comprises a plurality of carboxyl groups. Numbered embodiment 109 comprises the method of any one of numbered embodiments 89-102, wherein said solid support is not covalently linked to any polypeptide. Numbered embodiment 110 comprises the method of any one of numbered embodiments 89-109, wherein said association molecule is not covalently linked to biotin prior to immobilization to said solid support. Numbered embodiment 111 comprises the method of any one of numbered embodiments 89-110, wherein said portion of said DNA segments are modified using an affinity label. Numbered embodiment 112 comprises the method of any one of numbered embodiments 89-111, wherein said affinity label comprises biotin. Numbered embodiment 113 comprises the method of any one of numbered embodiments 89-112, wherein said affinity label is a biotin-modified nucleoside triphosphate (dNTP). Numbered embodiment 114 comprises the method of any one of numbered embodiments 89-113, wherein said biotin-modified nucleoside triphosphate (dNTP) is a biotin-modified deoxyribocytosine triphosphate (dCTP). Numbered embodiment 115 comprises the method of any one of numbered embodiments 89-114, wherein a portion of said DNA segments are tagged at at least a first end using a first tag. Numbered embodiment 116 comprises the method of any one of numbered embodiments 89-115, wherein said DNA segments are tagged using a transposase. Numbered embodiment 117 comprises the method of any one of numbered embodiments 89-116, wherein a portion of said DNA segments are tagged by linking said DNA segments to at least one other DNA segment. Numbered embodiment 118 comprises the method of any one of numbered embodiments 89-117, wherein said portion of DNA segments are linked to said other DNA segments using a ligase. Numbered embodiment 119 comprises the method of any one of numbered embodiments 89-118, wherein said DNA molecules are severed using a nuclease enzyme. Numbered embodiment 120 comprises the method of any one of numbered embodiments 89-119, wherein said linked DNA segment is severed prior to step (c). Numbered embodiment 121 comprises the method of any one of numbered embodiments 89-120, wherein said linked DNA segment is severed using a physical method. Numbered embodiment 122 comprises the method of any one of numbered embodiments 89-121, comprising connecting said linked DNA segments to sequencing adaptors. Numbered embodiment 123 comprises the method of any one of numbered embodiments 89-122, wherein said DNA segments are washed for less than 10 times before said DNA segments are linked to form said linked DNA segments. Numbered embodiment 124 comprises the method of any one of numbered embodiments 89-123, wherein said DNA segments are washed for less than 6 times before said DNA segments are linked to form said linked DNA segments. Numbered embodiment 125 comprises the method of any one of any one of numbered embodiments 89 to 124, comprising assembling a plurality of contigs of said DNA molecules using said read-pairs. Numbered embodiment 126 comprises the method of any one of any one of numbered embodiments 89 to 124, comprising phasing said DNA segments using said read-pairs. Numbered embodiment 127 comprises the method of any one of any one of numbered embodiments 89 to 126, wherein the method is completed in no more than 2 days. Numbered embodiment 128 comprises the method of any one of numbered embodiments 89-127, where the amount of hands-on time required for steps (a)-(d) is no greater than 6 hours. Numbered embodiment 129 comprises the method of any one of numbered embodiments 89-128, wherein no dialysis is performed between steps (a)-(d). Numbered embodiment 130 comprises the method of any one of numbered embodiments 89-129, wherein the method is completed in less than 2 days. Numbered embodiment 131 comprises the method of any one of numbered embodiments 89-130, wherein said plurality of DNA molecules is no greater than about 5 micrograms. Numbered embodiment 132 comprises the method of any one of numbered embodiments 89-131, wherein said binding of said plurality of DNA molecules is conducted in vitro. Numbered embodiment 133 comprises the method of any one of numbered embodiments 89-132, wherein said binding of said plurality of DNA molecules is conducted in vivo.

Numbered embodiment 134 comprises a composition comprising a plurality of association molecules bound to a DNA fragment in an in vitro complex, wherein said in vitro complex is immobilized on a solid support, and wherein said solid support is not covalently linked to any polypeptides. Numbered embodiment 135 comprises the composition of any one of numbered embodiments 89-134, wherein said solid support is not covalently linked to streptavidin. Numbered embodiment 136 comprises the composition of any one of numbered embodiments 89-134, wherein said solid support comprise a bead. Numbered embodiment 137 comprises the composition of any one of numbered embodiments 89-136, wherein said bead comprises a polymer. Numbered embodiment 138 comprises the composition of any one of numbered embodiments 89-137, wherein said polymer comprise polystyrene or polyethylene glycol (PEG). Numbered embodiment 139 comprises the composition of any one of numbered embodiments 89-134, wherein said bead is an SPRI bead. Numbered embodiment 140 comprises the composition of any one of numbered embodiments 89-134, wherein said solid support is coated with a plurality of carboxyl groups. Numbered embodiment 141 comprises the composition of any one of numbered embodiments 89-134, wherein said solid support is not covalently linked to any polypeptide. Numbered embodiment 142 comprises the composition of any one of numbered embodiments 89-134, wherein said association molecules comprise amino acids. Numbered embodiment 143 comprises the composition of any one of numbered embodiments 89-134, wherein said association molecules comprise polypeptides or proteins. Numbered embodiment 144 comprises the composition of any one of numbered embodiments 89-143, wherein said association molecules comprise histone proteins. Numbered embodiment 145 comprises the composition of any one of numbered embodiments 89-144, wherein said histone proteins are from a different source than said DNA molecules. Numbered embodiment 146 comprises the composition of any one of numbered embodiments 89-134, wherein said association molecules comprise transposases. Numbered embodiment 147 comprises the composition of any one of numbered embodiments 89-134, wherein said first DNA molecule is non-covalently bound to said association molecules. Numbered embodiment 148 comprises the composition of any one of numbered embodiments 89-134, wherein said first DNA molecule is covalently bound to said association molecules. Numbered embodiment 149 comprises the composition of any one of numbered embodiments 89-148, wherein said first DNA molecule is crosslinked to said association molecules. Numbered embodiment 150 comprises the composition of any one of numbered embodiments 89-134, wherein said association molecules are cross-linked to said DNA fragment with a fixative agent. Numbered embodiment 151 comprises the composition of any one of numbered embodiments 89-150, wherein said fixative agent is formaldehyde. Numbered embodiment 152 comprises the composition of any one of numbered embodiments 89-134, wherein said DNA fragment is modified with an affinity label. Numbered embodiment 153 comprises the composition of any one of numbered embodiments 89-152, wherein said affinity label comprises biotin. Numbered embodiment 154 comprises the composition of any one of numbered embodiments 89-153, wherein said affinity label is a biotin-modified nucleoside triphosphate (dNTP). Numbered embodiment 155 comprises the composition of any one of numbered embodiments 89-154, wherein said nucleoside biotin-modified nucleoside triphosphate (dNTP) is a biotin-modified deoxyribocytosine triphosphate (dCTP). Numbered embodiment 156 comprises the method of any one of numbered embodiments 89-155, wherein said binding said plurality of DNA molecules is conducted in vitro. Numbered embodiment 157 comprises the method of any one of numbered embodiments 89-156, wherein said binding said plurality of DNA molecules is conducted in vivo.

Numbered embodiment 158 comprises a method for generating a plurality of tagged sequences from a plurality of DNA molecules, comprising: (a) obtaining a plurality of DNA molecules bound to a plurality of association molecules; (b) severing said DNA molecules to generate at least a plurality of DNA segments; (c) tagging at least a portion of said DNA segments to form a plurality of tagged DNA segments; and (d) sequencing said tagged DNA segments to obtain a plurality of tagged sequences; wherein a total amount of said plurality of DNA molecules is less than about 5 micrograms (μg). Number embodiment 159 comprises a method for generating a plurality of tagged sequences from a plurality of DNA molecules, comprising: (a) obtaining a plurality of DNA molecules bound to a plurality of association molecules; (b) severing said DNA molecules to generate at least a plurality of DNA segments; (c) tagging at least a portion of said DNA segments to form a plurality of tagged DNA segments; and (d) sequencing said tagged DNA segments to obtain a plurality of tagged sequences; wherein no dialysis is performed between step (a) and step (d). Number embodiment 160 comprises a method for generating a plurality of tagged sequences from a plurality of DNA molecules, comprising: (a) obtaining a plurality of DNA molecules bound to a plurality of association molecules; (b) severing said DNA molecules to generate at least a plurality of DNA segments; (c) tagging at least a portion of said DNA segments to form a plurality of tagged DNA segments; and (d) sequencing said tagged DNA segments to obtain a plurality of tagged sequences; wherein an amount of hands-on time required for steps (a)-(d) is less than 6 hours. Numbered embodiment 161 comprises the method of any one of numbered embodiments 158, 159, or 160, wherein less than 40% of DNA segments from said DNA molecules are linked to DNA segments from any other DNA molecule. Numbered embodiment 162 comprises the method of any one of numbered embodiments 158-161, wherein less than 20% of DNA segments from said DNA molecules are linked to DNA segments from any other DNA molecule. Numbered embodiment 163 comprises the method of any one of numbered embodiments 158-162, wherein said association molecules comprise amino acids. Numbered embodiment 164 comprises the method of any one of numbered embodiments 158-162, wherein said association molecules are polypeptides or proteins. Numbered embodiment 165 comprises the method of any one of numbered embodiments 158-164, wherein said association molecules are histone proteins. Numbered embodiment 166 comprises the method of any one of numbered embodiments 158-165, wherein said histone proteins are from a different source than said DNA molecules. Numbered embodiment 167 comprises the method of any one of numbered embodiments 158-166, wherein said association molecules are transposases. Numbered embodiment 168 comprises the method of any one of numbered embodiments 158-167, wherein said DNA molecules are non-covalently bound to said association molecules. Numbered embodiment 169 comprises the method of any one of numbered embodiments 158-168, wherein said DNA molecules are covalently bound to said association molecules. Numbered embodiment 170 comprises the method of any one of numbered embodiments 158-169, wherein said DNA molecules are crosslinked to said association molecules. Numbered embodiment 171 comprises the method of any one of numbered embodiments 158-170, wherein said DNA molecules are cross-linked using a fixative agent. Numbered embodiment 172 comprises the method of any one of numbered embodiments 158-171, wherein said DNA molecules are crosslinked using formaldehyde. Numbered embodiment 173 comprises the method of any one of numbered embodiments 158-172, comprising immobilizing said plurality of association molecules on a plurality of solid supports. Numbered embodiment 174 comprises the method of any one of numbered embodiments 158-173, wherein said solid supports are beads. Numbered embodiment 175 comprises the method of any one of numbered embodiments 158-174, wherein said beads comprise a polymer. Numbered embodiment 176 comprises the method of any one of numbered embodiments 158-175, wherein said polymer is polystyrene or polyethylene glycol (PEG). Numbered embodiment 177 comprises the method of any one of numbered embodiments 158-176, wherein said beads are magnetic beads. Numbered embodiment 178 comprises the method of any one of numbered embodiments 158-177, wherein said beads are SPRI beads. Numbered embodiment 179 comprises the method of any one of numbered embodiments 158-178, wherein said solid support comprises a surface, and wherein said surface comprises a plurality of carboxyl groups. Numbered embodiment 180 comprises the method of any one of numbered embodiments 158-179, wherein said solid support is not covalently linked to any polypeptide. Numbered embodiment 181 comprises the method of any one of numbered embodiments 158-180, wherein said association molecule is not covalently linked to biotin prior to immobilization to said solid support. Numbered embodiment 182 comprises the method of any one of numbered embodiments 158-181, wherein said portion of said DNA segments are modified with an affinity label. Numbered embodiment 183 comprises the method of any one of numbered embodiments 158-182, wherein said affinity label comprises biotin. Numbered embodiment 184 comprises the method of any one of numbered embodiments 158-183, wherein said affinity label is a biotin-modified nucleoside triphosphate (dNTP). Numbered embodiment 185 comprises the method of any one of numbered embodiments 158-184, wherein said biotin-modified nucleoside triphosphate (dNTP) is a biotin-modified deoxyribocytosine triphosphate (dCTP). Numbered embodiment 186 comprises the method of any one of numbered embodiments 158-185, wherein a portion of said DNA segments are tagged at at least a first end with a first tag. Numbered embodiment 187 comprises the method of any one of numbered embodiments 158-186, wherein said DNA segments are tagged using a transposase. Numbered embodiment 188 comprises the method of any one of numbered embodiments 158-187, wherein a portion of said DNA segments are tagged by linking each of said DNA segments to at least one other DNA segment. Numbered embodiment 189 comprises the method of any one of numbered embodiments 158-188, wherein said portion of DNA segments are linked to said other DNA segments using a ligase. Numbered embodiment 190 comprises the method of any one of numbered embodiments 158-189, wherein said DNA molecules are severed using a nuclease enzyme. Numbered embodiment 191 comprises the method of any one of numbered embodiments 158-190, wherein said linked DNA segment is severed prior to step (c). Numbered embodiment 192 comprises the method of any one of numbered embodiments 158-191, wherein said linked DNA segment is severed using a physical method. Numbered embodiment 193 comprises the method of any one of numbered embodiments 158-192, comprising connecting said linked DNA segments to sequencing adaptors. Numbered embodiment 194 comprises the method of any one of numbered embodiments 158-193, wherein said DNA segments are washed for less than about 10 times before said DNA segments are linked to form said linked DNA segments. Numbered embodiment 195 comprises the method of any one of numbered embodiments 158-194, wherein said DNA segments are washed for less than about 6 times before said DNA segments are linked to form said linked DNA segments. Numbered embodiment 196 comprises the method of any one of numbered embodiments 158-195, comprising assembling a plurality of contigs of said DNA molecules using said read-pairs. Numbered embodiment 197 comprises the method of any one of numbered embodiments 158-196, comprising phasing said DNA segments using said read-pairs. Numbered embodiment 198 comprises the method of any one of numbered embodiments 158-197, wherein the method is completed in no more than 2 days. Numbered embodiment 199 comprises the method of any one of numbered embodiments 158-198, wherein said obtaining in step (a) comprises binding said plurality of DNA molecules to said plurality of association molecules. Numbered embodiment 200 comprises the method of any one of numbered embodiments 158-199, wherein said obtaining in step (a) comprises collecting said plurality of DNA molecules bound to said plurality of association molecules. Numbered embodiment 201 comprises the method of any one of numbered embodiments 158-200, wherein the total amount of said plurality of DNA molecules is no greater than 4 μg. Numbered embodiment 202 comprises the method of any one of numbered embodiments 158-201, wherein the total amount of said plurality of DNA molecules is no greater than 3 μg. Numbered embodiment 203 comprises the method of any one of numbered embodiments 158-202, wherein the total amount of said plurality of DNA molecules is no greater than 2 μg. Numbered embodiment 204 comprises the method of any one of numbered embodiments 158-203, wherein the amount of hands-on time required for steps (a)-(d) is lesson greater than 5 hours. Numbered embodiment 205 comprises the method of any one of numbered embodiments 158-204, wherein the amount of hands-on time required for steps (a)-(d) is lesson greater than 4 hours. Numbered embodiment 206 comprises the method of any one of numbered embodiments 158-205, wherein no dialysis is performed between steps (a)-(d). Numbered embodiment 207 comprises the method of any one of numbered embodiments 158-206, wherein the method is completed in less than 2 days. Numbered embodiment 208 comprises the method of any one of numbered embodiments 158-207, wherein said binding of said plurality of DNA molecules is conducted in vitro. Numbered embodiment 209 comprises the method of any one of numbered embodiments 158-208, wherein said binding of said plurality of DNA molecules is conducted in vivo.

Numbered embodiment 210 comprises a method of detecting a pathogen in a host population, comprising: a) obtaining a stabilized sample from each of a plurality of individuals suspected of harboring a common pathogen; b) treating the stabilized sample to cleave double-stranded DNA in the stabilized sample; c) labeling exposed DNA ends; d) ligating labeled exposed DNA ends to form labeled paired ends; e) sequencing across labeled paired ends to generate a plurality of paired sequence reads; f) assigning each half of a paired sequence read of the plurality of sequence reads to a common organism of origin; wherein an organism of origin common to individuals suspected of harboring a common pathogen is the pathogen. Numbered embodiment 211 comprises the method of numbered embodiments 210, wherein the sequence reads of the organism of origin map to a known pathogen. Numbered embodiment 212 comprises the method of any one of numbered embodiments 210-211, wherein the sequence reads of the organism of origin identify a known pathogen in a sequence database search. Numbered embodiment 213 comprises the method of any one of numbered embodiments 210-212, wherein the sequence reads of the organism of origin are absent from a plurality of paired sequence reads obtained from stabilized samples obtained from each of a plurality of individuals not suspected of harboring a common pathogen. Numbered embodiment 214 comprises the method of any one of numbered embodiments 210-213, wherein the sequence reads of the organism of origin identify an organism not represented in sequence databases. Numbered embodiment 215 comprises the method of any one of numbered embodiments 210-214, wherein the stabilized sample has been cross-linked. Numbered embodiment 216 comprises the method of any one of numbered embodiments 210-215, wherein the stabilized sample has been contacted to formaldehyde. Numbered embodiment 217 comprises the method of any one of numbered embodiments 210-215, wherein the stabilized sample has been contacted to psoralen. Numbered embodiment 218 comprises the method of any one of numbered embodiments 210-215, wherein the stabilized sample has been exposed to UV radiation. Numbered embodiment 219 comprises the method of any one of numbered embodiments 210-218, wherein the sample has been contacted to a DNA binding moiety. Numbered embodiment 220 comprises the method of any one of numbered embodiments 210-219, wherein the DNA binding moiety comprises a histone. Numbered embodiment 221 comprises the method of any one of numbered embodiments 210-220, wherein treating the stabilized sample to cleave double-stranded DNA comprises contacting the sample to a restriction endonuclease. Numbered embodiment 222 comprises the method of any one of numbered embodiments 210-221, wherein treating the stabilized sample to cleave double-stranded DNA comprises sonicating the sample. Numbered embodiment 223 comprises the method of any one of numbered embodiments 210-22, wherein labeling exposed DNA ends comprises adding a biotin moiety to an exposed DNA end. Numbered embodiment 224 comprises the method of any one of numbered embodiments 210-223, wherein the sample is derived from blood, sweat, urine, or stool. Numbered embodiment 225 comprises the method of any one of numbered embodiments 210-224, wherein the method is completed in no more than 2 days. Numbered embodiment 226 comprises the method of any one of numbered embodiments 210-225, where the amount of hands-on time required to complete the method is no greater than 6 hours. Numbered embodiment 227 comprises the method of any one of numbered embodiments 210-226, wherein the method comprises using SPRI beads. Numbered embodiment 228 comprises the method of any one of numbered embodiments 210-227, wherein the stabilized sample comprises no greater than about 5 micrograms of DNA.

Numbered embodiment 229 comprises a method of identifying a microbial host of an antibiotic resistance gene comprising: a) obtaining a stabilized sample from an individual having a condition that demonstrates microbial antibiotic resistance; b) treating the stabilized sample to cleave double-stranded DNA in the stabilized sample; c) labeling exposed DNA ends; d) ligating labeled exposed DNA ends to form labeled paired ends; and e) sequencing across labeled paired ends to generate a paired sequence; wherein sequence adjacent to an antibiotic resistance gene sequence is indicative of a microbial host of an antibiotic resistance gene. Numbered embodiment 230 comprises the method of numbered embodiments 229, wherein the stabilized sample has been cross-linked. Numbered embodiment 231 comprises the method of any one of numbered embodiments 229-230, wherein the stabilized sample has been contacted to formaldehyde. Numbered embodiment 232 comprises the method of any one of numbered embodiments 229-230, wherein the stabilized sample has been contacted to psoralen. Numbered embodiment 233 comprises the method of any one of numbered embodiments 229-230, wherein the stabilized sample has been exposed to UV radiation. Numbered embodiment 234 comprises the method of any one of numbered embodiments 229-233, wherein the sample has been contacted to a DNA binding moiety. Numbered embodiment 235 comprises the method of any one of numbered embodiments 229-234, wherein the DNA binding moiety comprises a histone. Numbered embodiment 236 comprises the method of any one of numbered embodiments 229-235, wherein treating the stabilized sample to cleave double-stranded DNA comprises contacting the sample to a restriction endonuclease. Numbered embodiment 237 comprises the method of any one of numbered embodiments 229-236, wherein treating the stabilized sample to cleave double-stranded DNA comprises sonicating the sample. Numbered embodiment 238 comprises the method of any one of numbered embodiments 229-237, wherein labeling exposed DNA ends comprises adding a biotin moiety to an exposed DNA end. Numbered embodiment 239 comprises the method of any one of numbered embodiments 229-238, comprising searching the paired sequence against a DNA database. Numbered embodiment 240 comprises the method of any one of numbered embodiments 229-239, wherein the method is completed in no more than 2 days. Numbered embodiment 241 comprises the method of any one of numbered embodiments 229-240, where the amount of hands-on time required to complete the method is no greater than 6 hours. Numbered embodiment 242 comprises the method of any one of numbered embodiments 229-241, wherein the method comprises using SPRI beads. Numbered embodiment 243 comprises the method of any one of numbered embodiments 229-242, wherein the stabilized sample comprises no greater than about 5 micrograms of DNA.

Numbered embodiment 244 comprises a method of determining genomic linkage information for a heterogeneous nucleic acid sample comprising: (a) obtaining a stabilized heterogeneous nucleic acid sample; (b) treating the stabilized sample to cleave double-stranded DNA in the stabilized sample; (c) labeling exposed DNA ends; (d) ligating labeled exposed DNA ends to form labeled paired ends; (e) sequencing across labeled paired ends to generate a plurality of paired sequence reads; (f) assigning each half of a paired sequence read of the plurality of sequence reads to a common nucleic acid molecule of origin. Numbered embodiment 245 comprises the method of numbered embodiments 244, wherein the heterogeneous nucleic acid sample is obtained from blood, sweat, urine or stool. Numbered embodiment 246 comprises the method of any one of numbered embodiments 244-245, wherein the stabilized sample has been cross-linked. Numbered embodiment 247 comprises the method of any one of numbered embodiments 244-246, wherein the stabilized sample has been contacted to formaldehyde. Numbered embodiment 248 comprises the method of any one of numbered embodiments 244-246, wherein the stabilized sample has been contacted to psoralen. Numbered embodiment 249 comprises the method of any one of numbered embodiments 244-246, wherein the stabilized sample has been exposed to UV radiation. Numbered embodiment 250 comprises the method of any one of numbered embodiments 244-249, wherein the sample has been contacted to a DNA binding moiety. Numbered embodiment 251 comprises the method of any one of numbered embodiments 244-250, wherein the DNA binding moiety comprises a histone. Numbered embodiment 252 comprises the method of any one of numbered embodiments 244-251, wherein treating the stabilized sample to cleave double-stranded DNA comprises contacting the sample to a restriction endonuclease. Numbered embodiment 253 comprises the method of any one of numbered embodiments 244-252, wherein treating the stabilized sample to cleave double-stranded DNA comprises sonicating the sample. Numbered embodiment 254 comprises the method of any one of numbered embodiments 244-253, wherein labeling exposed DNA ends comprises adding a biotin moiety to an exposed DNA end. Numbered embodiment 255 comprises the method of any one of numbered embodiments 244-254, comprising searching the paired sequence against a DNA database. Numbered embodiment 256 comprises the method of any one of numbered embodiments 244-255, wherein the common nucleic acid molecule of origin maps to a single individual. Numbered embodiment 257 comprises the method of any one of numbered embodiments 244-256, wherein the common nucleic acid molecule of origin identifies a subset of a population. Numbered embodiment 258 comprises the method of any one of numbered embodiments 244-257, wherein the method is completed in no more than 2 days. Numbered embodiment 259 comprises the method of any one of numbered embodiments 244-258, where the amount of hands-on time required to complete the method is no greater than 6 hours. Numbered embodiment 260 comprises the method of any one of numbered embodiments 244-259, wherein the method comprises using SPRI beads. Numbered embodiment 261 comprises the method of any one of numbered embodiments 244260, wherein the stabilized sample comprises no greater than about 5 micrograms of DNA.

Numbered embodiment 262 comprises a method for meta-genomics assemblies, comprising: (a) collecting microbes from an environment; (b) obtaining a plurality of contigs from the microbes; (c) generating a plurality of read pairs from data produced by probing the physical layout of reconstituted chromatin; and (d) mapping the plurality of read pairs to the plurality of contigs thereby producing read-mapping data, wherein read pairs mapping to different contigs indicate that the different contigs are from a common species. Numbered embodiment 263 comprises the method of any one of numbered embodiments 262, wherein the microbes are collected from a human gut. Numbered embodiment 264 comprises a method for detecting a bacterial infectious agent, comprising: (a) obtaining a plurality of contigs from the bacterial infectious agent; (b) generating a plurality of read pairs from data produced by probing the physical layout of reconstituted chromatin; (c) mapping the plurality of read pairs to the plurality of contigs thereby producing read-mapping data; (d) arranging the contigs using the read-mapping data to assemble the contigs into a genome assembly; and (e) using the genome assembly to determine presence of the bacterial infectious agent.

Numbered embodiment 265 comprises a method of detecting a pathogen in a host population, comprising: a) obtaining a stabilized sample from each of a plurality of individuals suspected of harboring a common pathogen; b) treating the stabilized sample to cleave double-stranded DNA in the stabilized sample; c) tagging exposed DNA ends of a first portion of the stabilized sample using a first barcode tag and tagging exposed ends of a second portion of the stabilized sample using a second barcode tag; d) sequencing across barcode tagged ends to generate a plurality of barcode tagged sequence reads; and e) assigning commonly barcode tagged sequence read of the plurality of sequence reads to a common organism of origin; wherein an organism of origin common to individuals suspected of harboring a common pathogen is the pathogen. Numbered embodiment 266 comprises the method of numbered embodiments 265, wherein the sequence reads of the organism of origin map to a known pathogen. Numbered embodiment 267 comprises the method of any one of numbered embodiments 265-266, wherein the sequence reads of the organism of origin identify a known pathogen in a sequence database search. Numbered embodiment 268 comprises the method of any one of numbered embodiments 265-267, wherein the sequence reads of the organism of origin are absent from a plurality of paired sequence reads obtained from stabilized samples obtained from each of a plurality of individuals not suspected of harboring a common pathogen. Numbered embodiment 269 comprises the method of any one of numbered embodiments 265-268, wherein the sequence reads of the organism of origin identify an organism not represented in sequence databases. Numbered embodiment 270 comprises the method of any one of numbered embodiments 265-269, wherein the stabilized sample has been cross-linked. Numbered embodiment 271 comprises the method of any one of numbered embodiments 265-270, wherein the stabilized sample has been contacted to formaldehyde. Numbered embodiment 272 comprises the method of any one of numbered embodiments 265-271, wherein the stabilized sample has been contacted to psoralen. Numbered embodiment 273 comprises the method of any one of numbered embodiments 265-272, wherein the stabilized sample has been exposed to UV radiation. Numbered embodiment 274 comprises the method of any one of numbered embodiments 265-273, wherein the sample has been contacted to a DNA binding moiety. Numbered embodiment 275 comprises the method of any one of numbered embodiments 265-274, wherein the DNA binding moiety comprises a histone. Numbered embodiment 276 comprises the method of any one of numbered embodiments 265-275, wherein treating the stabilized sample to cleave double-stranded DNA comprises contacting the sample to a restriction endonuclease. Numbered embodiment 277 comprises the method of any one of numbered embodiments 265-276, wherein treating the stabilized sample to cleave double-stranded DNA comprises sonicating the sample. Numbered embodiment 278 comprises the method of any one of numbered embodiments 265-277, wherein tagging exposed DNA ends comprises adding a biotin moiety to an exposed DNA end. Numbered embodiment 279 comprises the method of any one of numbered embodiments 265-278, wherein the sample is derived from blood, sweat, urine, or stool. Numbered embodiment 280 comprises the method of any one of numbered embodiments 265-279, wherein the method is completed in no more than 2 days. Numbered embodiment 281 comprises the method of any one of numbered embodiments 265-280, where the amount of hands-on time required to complete the method is no greater than 6 hours. Numbered embodiment 282 comprises the method of any one of numbered embodiments 265-281, wherein the method comprises using SPRI beads. Numbered embodiment 283 comprises the method of any one of numbered embodiments 265-282, wherein the stabilized sample comprises no greater than about 5 micrograms of DNA.

Numbered embodiment 284 comprises a method of identifying a microbial host of an antibiotic resistance gene comprising: a) obtaining a stabilized sample from an individual having a condition that demonstrates microbial antibiotic resistance; b) treating the stabilized sample to cleave double-stranded DNA in the stabilized sample; c) tagging exposed DNA ends of a first portion of the stabilized sample using a first barcode tag and tagging exposed ends of a second portion of the stabilized sample using a second barcode tag; d) sequencing across barcode tagged ends to generate a plurality of barcode tagged sequence reads; wherein sequence having a barcode tag identical to a barcode tag of an antibiotic resistance gene sequence is indicative of a microbial host of an antibiotic resistance gene. Numbered embodiment 285 comprises the method of numbered embodiments 284, wherein the stabilized sample has been cross-linked. Numbered embodiment 286 comprises the method of any one of numbered embodiments 284-285, wherein the stabilized sample has been contacted to formaldehyde. Numbered embodiment 287 comprises the method of any one of numbered embodiments 284-285, wherein the stabilized sample has been contacted to psoralen. Numbered embodiment 288 comprises the method of any one of numbered embodiments 284-285, wherein the stabilized sample has been exposed to UV radiation. Numbered embodiment 289 comprises the method of any one of numbered embodiments 284-288, wherein the sample has been contacted to a DNA binding moiety. Numbered embodiment 290 comprises the method of any one of numbered embodiments 284-289, wherein the DNA binding moiety comprises a histone. Numbered embodiment 291 comprises the method of any one of numbered embodiments 284-290, wherein treating the stabilized sample to cleave double-stranded DNA comprises contacting the sample to a restriction endonuclease. Numbered embodiment 292 comprises the method of any one of numbered embodiments 284-291, wherein treating the stabilized sample to cleave double-stranded DNA comprises sonicating the sample. Numbered embodiment 293 comprises the method of any one of numbered embodiments 284-292, wherein tagging exposed DNA ends comprises adding a biotin moiety to an exposed DNA end. Numbered embodiment 294 comprises the method of any one of numbered embodiments 284-293, comprising searching the paired sequence against a DNA database. Numbered embodiment 295 comprises the method of any one of numbered embodiments 284-294, wherein the method is completed in no more than 2 days. Numbered embodiment 296 comprises the method of any one of numbered embodiments 284-295, where the amount of hands-on time required to complete the method is no greater than 6 hours. Numbered embodiment 297 comprises the method of any one of numbered embodiments 284-296, wherein the method comprises using SPRI beads. Numbered embodiment 298 comprises the method of any one of numbered embodiments 284-297, wherein the stabilized sample comprises no greater than about 5 micrograms of DNA.

Numbered embodiment 299 comprises a method of determining genomic linkage information for a heterogeneous nucleic acid sample comprising: (a) obtaining a stabilized heterogeneous nucleic acid sample; (b) treating the stabilized sample to cleave double-stranded DNA in the stabilized sample; (c) tagging exposed DNA ends of a first portion of the stabilized sample using a first barcode tag and tagging exposed ends of a second portion of the stabilized sample using a second barcode tag; (d) sequencing across barcode tagged ends to generate a plurality of barcode tagged sequence reads; (e) assigning commonly tagged sequence reads to a common nucleic acid molecule of origin. Numbered embodiment 300 comprises the method of numbered embodiments 299, wherein the heterogeneous nucleic acid sample is obtained from blood, sweat, urine or stool. Numbered embodiment 301 comprises the method of any one of numbered embodiments 299-300, wherein the stabilized sample has been cross-linked Numbered embodiment 302 comprises the method of any one of numbered embodiments 299-301, wherein the stabilized sample has been contacted to formaldehyde. Numbered embodiment 303 comprises the method of any one of numbered embodiments 299-301, wherein the stabilized sample has been contacted to psoralen. Numbered embodiment 304 comprises the method of any one of numbered embodiments 299-301, wherein the stabilized sample has been exposed to UV radiation. Numbered embodiment 305 comprises the method of any one of numbered embodiments 299-304, wherein the sample has been contacted to a DNA binding moiety. Numbered embodiment 306 comprises the method of any one of numbered embodiments 299-305, wherein the DNA binding moiety comprises a histone. Numbered embodiment 307 comprises the method of any one of numbered embodiments 299-306, wherein treating the stabilized sample to cleave double-stranded DNA comprises contacting the sample to a nuclease. Numbered embodiment 308 comprises the method of any one of numbered embodiments 299-307, wherein said nuclease is a restriction endonuclease. Numbered embodiment 309 comprises the method of any one of numbered embodiments 299-308, wherein treating the stabilized sample to cleave double-stranded DNA comprises sonicating the sample. Numbered embodiment 310 comprises the method of any one of numbered embodiments 299-309, wherein tagging exposed DNA ends comprises adding a biotin moiety to an exposed DNA end. Numbered embodiment 311 comprises the method of any one of numbered embodiments 299-310, comprising searching the paired sequence against a DNA database. Numbered embodiment 312 comprises the method of any one of numbered embodiments 299-311, wherein the common nucleic acid molecule of origin maps to a single individual. Numbered embodiment 313 comprises the method of any one of numbered embodiments 299-312, wherein the common nucleic acid molecule of origin identifies a subset of a population. Numbered embodiment 314 comprises the method of any one of numbered embodiments 299-313, wherein the heterogeneous sample comprises nucleic acids mapping to at least two individuals of a common species. Numbered embodiment 315 comprises the method of any one of numbered embodiments 299-314, wherein the heterogeneous sample comprises nucleic acids mapping to at least three individuals of a common species. Numbered embodiment 316 comprises the method of any one of numbered embodiments 299-315, wherein the heterogeneous sample comprises nucleic acids mapping to at least two species. Numbered embodiment 317 comprises the method of any one of numbered embodiments 299-316, wherein the heterogeneous sample comprises nucleic acids mapping to at least three species. Numbered embodiment 318 comprises the method of any one of numbered embodiments 299-317, wherein the heterogeneous sample comprises nucleic acids mapping to at least four species. Numbered embodiment 319 comprises the method of any one of numbered embodiments 299-318, wherein the sequence reads assemble into at least two nucleic acid scaffolds without reference to exogenous sequence information. Numbered embodiment 320 comprises the method of any one of numbered embodiments 299-319, wherein the sequence reads assemble into at least three nucleic acid scaffolds without reference to exogenous sequence information. Numbered embodiment 321 comprises the method of any one of numbered embodiments 299-320, wherein the sequence reads assemble into at least two nucleic acid scaffolds, such that at least 50% of a first genome and at least 50% of a second genome are represented in said at least two nucleic acid scaffolds. Numbered embodiment 322 comprises the method of any one of numbered embodiments 299-321, wherein the sequence reads assemble into at least two nucleic acid scaffolds, such that at least 60% of a first genome and at least 60% of a second genome are represented in said at least two nucleic acid scaffolds. Numbered embodiment 323 comprises the method of any one of numbered embodiments 299-322, wherein the sequence reads assemble into at least two nucleic acid scaffolds, such that at least 70% of a first genome and at least 70% of a second genome are represented in said at least two nucleic acid scaffolds. Numbered embodiment 324 comprises the method of any one of numbered embodiments 299-323, wherein the sequence reads assemble into at least two nucleic acid scaffolds, such that at least 80% of a first genome and at least 80% of a second genome are represented in said at least two nucleic acid scaffolds. Numbered embodiment 325 comprises the method of any one of numbered embodiments 299-324, wherein the method is completed in no more than 2 days. Numbered embodiment 326 comprises the method of any one of numbered embodiments 299-325, where the amount of hands-on time required to complete the method is no greater than 6 hours. Numbered embodiment 327 comprises the method of any one of numbered embodiments 299-326, wherein the method comprises using SPRI beads. Numbered embodiment 328 comprises the method of any one of numbered embodiments 299-327, wherein the stabilized sample comprises no greater than about 5 micrograms of DNA.

Numbered embodiment 329 comprises a method of detecting a pathogen in a host population, comprising: a) obtaining a stabilized sample from each of a plurality of subjects; b) treating the stabilized sample to cleave double-stranded DNA in the stabilized sample, thereby generating exposed DNA ends; c) labeling at least a portion of the exposed DNA ends; d) ligating the exposed DNA ends to form labeled paired ends; e) sequencing at least a recognizable portion of the labeled paired ends to generate a plurality of read-pairs; and f) assigning each half of a read-pair to a common organism of origin; wherein an organism of origin common to the subjects is detected as the pathogen. Numbered embodiment 330 comprises the method of numbered embodiments 329, wherein the read-pairs of the organism of origin map to a known pathogen. Numbered embodiment 331 comprises the method of any one of numbered embodiments 329-330, wherein the read-pairs of the organism of origin identify a known pathogen in a sequence database search. Numbered embodiment 332 comprises the method of any one of numbered embodiments 329-331, wherein the read-pairs of the organism of origin are absent from a plurality of read-pairs obtained from stabilized samples obtained from each of a plurality of subjects that do not harbor a common pathogen. Numbered embodiment 333 comprises the method of any one of numbered embodiments 329-332, wherein the read-pairs of the organism of origin identify an organism not represented in sequence databases. Numbered embodiment 334 comprises the method of any one of numbered embodiments 329-333, wherein the stabilized sample has been cross-linked. Numbered embodiment 335 comprises the method of any one of numbered embodiments 329-334, wherein the stabilized sample has been contacted to formaldehyde. Numbered embodiment 336 comprises the method of any one of numbered embodiments 329-334, wherein the stabilized sample has been contacted to psoralen. Numbered embodiment 337 comprises the method of any one of numbered embodiments 329-334, wherein the stabilized sample has been exposed to UV radiation. Numbered embodiment 338 comprises the method of any one of numbered embodiments 329-337, wherein a stabilized sample is obtained by contact a sample with a DNA binding moiety. Numbered embodiment 339 comprises the method of any one of numbered embodiments 329-338, wherein the DNA binding moiety comprises a histone. Numbered embodiment 340 comprises the method of any one of numbered embodiments 329-339, wherein treating the stabilized sample to cleave double-stranded DNA comprises contacting the stabilized sample to a restriction endonuclease. Numbered embodiment 341 comprises the method of any one of numbered embodiments 329-340, wherein treating the stabilized sample to cleave double-stranded DNA comprises sonicating the stabilized sample. Numbered embodiment 342 comprises the method of any one of numbered embodiments 329-341, wherein labeling exposed DNA ends comprises adding a biotin moiety to an exposed DNA end. Numbered embodiment 343 comprises the method of any one of numbered embodiments 329-342, wherein the stabilized sample is derived from blood, sweat, urine, or stool. Numbered embodiment 344 comprises the method of any one of numbered embodiments 329-343, wherein the method is completed in no more than 2 days. Numbered embodiment 345 comprises the method of any one of numbered embodiments 329-344, where the amount of hands-on time required to complete the method is no greater than 6 hours. Numbered embodiment 346 comprises the method of any one of numbered embodiments 329-345, wherein the method comprises using SPRI beads. Numbered embodiment 347 comprises the method of any one of numbered embodiments 329-346, wherein the stabilized sample comprises no greater than about 5 micrograms of DNA.

Numbered embodiment 348 comprises a method of identifying a microbial host of an antibiotic resistance gene comprising: a) obtaining a stabilized sample from a subject having a condition that demonstrates microbial antibiotic resistance; b) treating the stabilized sample to cleave double-stranded DNA in the stabilized sample, thereby generating exposed DNA ends; c) labeling at least a portion of the exposed DNA ends; d) ligating the labeled exposed DNA ends to form labeled paired ends; and e) sequencing at least a recognizable portion of the ligated paired ends to generate a paired sequence; wherein the paired sequence adjacent to an antibiotic resistance gene sequence is indicative of a microbial host of an antibiotic resistance gene. Numbered embodiment 349 comprises the method of numbered embodiments 348, wherein the stabilized sample has been cross-linked. Numbered embodiment 350 comprises the method of any one of numbered embodiments 348-349, wherein the stabilized sample has been contacted to formaldehyde. Numbered embodiment 351 comprises the method of any one of numbered embodiments 348-349, wherein the stabilized sample has been contacted to psoralen. Numbered embodiment 352 comprises the method of any one of numbered embodiments 348-349, wherein the stabilized sample has been exposed to UV radiation. Numbered embodiment 353 comprises the method of any one of numbered embodiments 348-352, wherein the sample has been contacted to a DNA binding moiety. Numbered embodiment 354 comprises the method of any one of numbered embodiments 348-353, wherein the DNA binding moiety comprises a histone. Numbered embodiment 355 comprises the method of any one of numbered embodiments 348-354, wherein treating the stabilized sample to cleave double-stranded DNA comprises contacting the sample to a restriction endonuclease. Numbered embodiment 356 comprises the method of any one of numbered embodiments 348-355, wherein treating the stabilized sample to cleave double-stranded DNA comprises sonicating the sample. Numbered embodiment 357 comprises the method of any one of numbered embodiments 348-356, wherein labeling exposed DNA ends comprises adding a biotin moiety to an exposed DNA end. Numbered embodiment 358 comprises the method of any one of numbered embodiments 348-357, comprising searching the paired sequence against a DNA database. Numbered embodiment 359 comprises the method of any one of numbered embodiments 348-358, wherein the method is completed in no more than 2 days. Numbered embodiment 360 comprises the method of any one of numbered embodiments 348-359, where the amount of hands-on time required to complete the method is no greater than 6 hours. Numbered embodiment 361 comprises the method of any one of numbered embodiments 348-360, wherein the method comprises using SPRI beads. Numbered embodiment 362 comprises the method of any one of numbered embodiments 348-361, wherein the stabilized sample comprises no greater than about 5 micrograms of DNA.

Numbered embodiment 363 comprises a method of determining genomic linkage information for a heterogeneous nucleic acid sample comprising: (a) stabilizing the heterogeneous nucleic acid sample; (b) treating the stabilized sample to cleave double-stranded DNA in the stabilized sample, thereby generating exposed DNA ends; (c) labeling at least a portion of the exposed DNA ends; (d) ligating the labeled exposed DNA ends to form labeled paired ends; (e) sequencing at least a recognizable portion of the labeled paired ends to generate a plurality of read-pairs; (f) assigning each half of a read-pair to a common nucleic acid molecule of origin. Numbered embodiment 364 comprises the method of numbered embodiments 363, wherein the heterogeneous nucleic acid sample is obtained from blood, sweat, urine or stool. Numbered embodiment 365 comprises the method of any one of numbered embodiments 363-364, wherein the stabilized sample has been cross-linked Numbered embodiment 366 comprises the method of any one of numbered embodiments 363-365, wherein the stabilized sample has been contacted to formaldehyde. Numbered embodiment 367 comprises the method of any one of numbered embodiments 363-365, wherein the stabilized sample has been contacted to psoralen. Numbered embodiment 368 comprises the method of any one of numbered embodiments 363-365, wherein the stabilized sample has been exposed to UV radiation. Numbered embodiment 369 comprises the method of any one of numbered embodiments 363-368, wherein the sample has been contacted to a DNA binding moiety. Numbered embodiment 370 comprises the method of any one of numbered embodiments 363-369, wherein the DNA binding moiety comprises a histone. Numbered embodiment 371 comprises the method of any one of numbered embodiments 363-370, wherein treating the stabilized sample to cleave double-stranded DNA comprises contacting the sample to a restriction endonuclease. Numbered embodiment 372 comprises the method of any one of numbered embodiments 363-371, wherein treating the stabilized sample to cleave double-stranded DNA comprises sonicating the sample. Numbered embodiment 373 comprises the method of any one of numbered embodiments 363-372, wherein labeling exposed DNA ends comprises adding a biotin moiety to an exposed DNA end. Numbered embodiment 374 comprises the method of any one of numbered embodiments 363-373, wherein searching the paired sequence against a DNA database. Numbered embodiment 375 comprises the method of any one of numbered embodiments 363-374, wherein the common nucleic acid molecule of origin maps to a single individual. Numbered embodiment 376 comprises the method of any one of numbered embodiments 363-375, wherein the common nucleic acid molecule of origin identifies a subset of a population. Numbered embodiment 377 comprises the method of any one of numbered embodiments 363-376, wherein the heterogeneous sample comprises nucleic acids mapping to at least two individuals of a common species. Numbered embodiment 378 comprises the method of any one of numbered embodiments 363-377, wherein the heterogeneous sample comprises nucleic acids mapping to at least three individuals of a common species. Numbered embodiment 379 comprises the method of any one of numbered embodiments 363-378, wherein the heterogeneous sample comprises nucleic acids mapping to at least two species. Numbered embodiment 380 comprises the method of any one of numbered embodiments 363-379, wherein the heterogeneous sample comprises nucleic acids mapping to at least three species. Numbered embodiment 381 comprises the method of any one of numbered embodiments 363-380, wherein the heterogeneous sample comprises nucleic acids mapping to at least four species. Numbered embodiment 382 comprises the method of any one of numbered embodiments 363-381, wherein the sequence reads assemble into at least two nucleic acid scaffolds without reference to exogenous sequence information. Numbered embodiment 383 comprises the method of any one of numbered embodiments 363-382, wherein the sequence reads assemble into at least three nucleic acid scaffolds without reference to exogenous sequence information. Numbered embodiment 384 comprises the method of any one of numbered embodiments 363-383, wherein the sequence reads assemble into at least two nucleic acid scaffolds, such that at least 50% of a first genome and at least 50% of a second genome are represented in said at least two nucleic acid scaffolds. Numbered embodiment 385 comprises the method of any one of numbered embodiments 363-384, wherein the sequence reads assemble into at least two nucleic acid scaffolds, such that at least 60% of a first genome and at least 60% of a second genome are represented in said at least two nucleic acid scaffolds. Numbered embodiment 386 comprises the method of any one of numbered embodiments 363-385, wherein the sequence reads assemble into at least two nucleic acid scaffolds, such that at least 70% of a first genome and at least 70% of a second genome are represented in said at least two nucleic acid scaffolds. Numbered embodiment 387 comprises the method of any one of numbered embodiments 363-386, wherein the sequence reads assemble into at least two nucleic acid scaffolds, such that at least 80% of a first genome and at least 80% of a second genome are represented in said at least two nucleic acid scaffolds. Numbered embodiment 388 comprises the method of any one of numbered embodiments 363-387, wherein the method is completed in no more than 2 days. Numbered embodiment 389 comprises the method of any one of numbered embodiments 363-388, where the amount of hands-on time required to complete the method is no greater than 6 hours. Numbered embodiment 390 comprises the method of any one of numbered embodiments 363-389, wherein the method comprises using SPRI beads. Numbered embodiment 391 comprises the method of any one of numbered embodiments 363-390, wherein the stabilized sample comprises no greater than about 5 micrograms of DNA.

Numbered embodiment 392 comprises a method for meta-genomics assemblies, comprising: (a) collecting microbes from an environment; (b) obtaining a plurality of contigs from the microbes; (c) generating a plurality of read pairs from data produced by probing the physical layout of reconstituted chromatin; and (d) mapping the plurality of read pairs to the plurality of contigs thereby producing read-mapping data, wherein read pairs mapping to different contigs indicate that the different contigs originate from a common individual. Numbered embodiment 393 comprises the method of any one of numbered embodiments 392, wherein the microbes are collected from a human gut. Numbered embodiment 394 comprises the method of numbered embodiments 392, wherein the microbes are collected from human skin. Numbered embodiment 395 comprises the method of any one of numbered embodiments 392-394, wherein the microbes are collected from toxic waste. Numbered embodiment 396 comprises the method of any one of numbered embodiments 392-395, wherein the microbes are collected from decomposing wood or cellulose. Numbered embodiment 397 comprises the method of any one of numbered embodiments 392-396, wherein the microbes are collected from an aquatic environment. Numbered embodiment 398 comprises the method of any one of numbered embodiments 392-397, wherein the microbes are collected from a sea floor. Numbered embodiment 399 comprises the method of any one of numbered embodiments 392-398, wherein the microbes are collected from a terrestrial environment. Numbered embodiment 400 comprises the method of any one of numbered embodiments 392-399, wherein the microbes are collected from a biological environment. Numbered embodiment 401 comprises the method of any one of numbered embodiments 392-400, wherein the heterogeneous sample comprises nucleic acids mapping to at least two individuals of a common species. Numbered embodiment 402 comprises the method of any one of numbered embodiments 392-401, wherein the heterogeneous sample comprises nucleic acids mapping to at least three individuals of a common species. Numbered embodiment 403 comprises the method of any one of numbered embodiments 392-402, wherein the heterogeneous sample comprises nucleic acids mapping to at least two species. Numbered embodiment 404 comprises the method of any one of numbered embodiments 392-403, wherein the heterogeneous sample comprises nucleic acids mapping to at least three species. Numbered embodiment 405 comprises the method of any one of numbered embodiments 392-404, wherein the heterogeneous sample comprises nucleic acids mapping to at least four species. Numbered embodiment 406 comprises the method of any one of numbered embodiments 392-405, wherein the sequence reads assemble into at least two nucleic acid scaffolds without reference to exogenous sequence information. Numbered embodiment 407 comprises the method of any one of numbered embodiments 392-406, wherein the sequence reads assemble into at least three nucleic acid scaffolds without reference to exogenous sequence information. Numbered embodiment 408 comprises the method of any one of numbered embodiments 392-407, wherein the sequence reads assemble into at least two nucleic acid scaffolds, such that at least 50% of a first genome and at least 50% of a second genome are represented in said at least two nucleic acid scaffolds. Numbered embodiment 409 comprises the method of any one of numbered embodiments 392-408, wherein the sequence reads assemble into at least two nucleic acid scaffolds, such that at least 60% of a first genome and at least 60% of a second genome are represented in said at least two nucleic acid scaffolds. Numbered embodiment 410 comprises the method of any one of numbered embodiments 392-409, wherein the sequence reads assemble into at least two nucleic acid scaffolds, such that at least 70% of a first genome and at least 70% of a second genome are represented in said at least two nucleic acid scaffolds. Numbered embodiment 411 comprises the method of any one of numbered embodiments 392-410, wherein the sequence reads assemble into at least two nucleic acid scaffolds, such that at least 80% of a first genome and at least 80% of a second genome are represented in said at least two nucleic acid scaffolds. Numbered embodiment 412 comprises the method of any one of numbered embodiments 392-411, wherein the method comprises using SPRI beads. Numbered embodiment 413 comprises the method of any one of numbered embodiments 392-412, wherein the stabilized sample comprises no greater than about 5 micrograms of DNA.

Numbered embodiment 414 comprises a method for detecting a bacterial infectious agent, comprising: (a) obtaining a plurality of contigs from the bacterial infectious agent; (b) generating a plurality of read pairs from data produced by probing the physical layout of reconstituted chromatin; (c) mapping the plurality of read pairs to the plurality of contigs thereby producing read-mapping data; (d) arranging the contigs using the read-mapping data to assemble the contigs into a genome assembly; and (e) using the genome assembly to determine presence of the bacterial infectious agent.

Numbered embodiment 415 comprises a method of obtaining genomic sequence information from an organism comprising: (a) obtaining a stabilized sample from said organism; (b) treating the stabilized sample to cleave double-stranded DNA in the stabilized sample, thereby generating exposed DNA ends; (c) tagging at least a portion of the exposed DNA ends to generate tagged DNA segments; (d) sequencing at least a recognizable portion of the tagged DNA segment and thereby obtaining tagged sequences; and (e) mapping said tagged sequences to generate genomic sequence information of said organism, wherein said genomic sequence information covers at least 75% of the genome of said organism. Numbered embodiment 416 comprises the method of numbered embodiments 415, wherein the heterogeneous sample comprises nucleic acids mapping to at least two individuals of a common species. Numbered embodiment 417 comprises the method of any one of numbered embodiments 415-416, wherein the heterogeneous sample comprises nucleic acids mapping to at least three individuals of a common species. Numbered embodiment 418 comprises the method of any one of numbered embodiments 415-417, wherein the heterogeneous sample comprises nucleic acids mapping to at least two species. Numbered embodiment 419 comprises the method of any one of numbered embodiments 415-418, wherein the heterogeneous sample comprises nucleic acids mapping to at least three species. Numbered embodiment 420 comprises the method of any one of numbered embodiments 415-419, wherein the heterogeneous sample comprises nucleic acids mapping to at least four species. Numbered embodiment 421 comprises the method of any one of numbered embodiments 415-420, wherein the sequence reads assemble into at least two nucleic acid scaffolds without reference to exogenous sequence information. Numbered embodiment 422 comprises the method of any one of numbered embodiments 415-421, wherein the sequence reads assemble into at least three nucleic acid scaffolds without reference to exogenous sequence information. Numbered embodiment 423 comprises the method of any one of numbered embodiments 415-422, wherein the sequence reads assemble into at least two nucleic acid scaffolds, such that at least 50% of a first genome and at least 50% of a second genome are represented in said at least two nucleic acid scaffolds. Numbered embodiment 424 comprises the method of any one of numbered embodiments 415-423, wherein the sequence reads assemble into at least two nucleic acid scaffolds, such that at least 60% of a first genome and at least 60% of a second genome are represented in said at least two nucleic acid scaffolds. Numbered embodiment 425 comprises the method of any one of numbered embodiments 415-424, wherein the sequence reads assemble into at least two nucleic acid scaffolds, such that at least 70% of a first genome and at least 70% of a second genome are represented in said at least two nucleic acid scaffolds. Numbered embodiment 426 comprises the method of any one of numbered embodiments 415-425, wherein the sequence reads assemble into at least two nucleic acid scaffolds, such that at least 80% of a first genome and at least 80% of a second genome are represented in said at least two nucleic acid scaffolds. Numbered embodiment 427 comprises the method of any one of numbered embodiments 415-426, wherein said organism is collected from a heterogeneous sample. Numbered embodiment 428 comprises the method of any one of numbered embodiments 415-427, wherein said heterogeneous sample comprises at least 1000 organisms each comprising a different genome. Numbered embodiment 429 comprises the method of any one of numbered embodiments 415-428, wherein said stabilized sample is obtained by contacting DNA from said organism to a DNA binding moiety. Numbered embodiment 430 comprises the method of any one of numbered embodiments 415-429, wherein said DNA binding moiety is a histone. Numbered embodiment 431 comprises the method of any one of numbered embodiments 415-429, wherein said DNA binding moiety is a nanoparticle. Numbered embodiment 432 comprises the method of any one of numbered embodiments 415-429, wherein said DNA binding moiety is a transposase. Numbered embodiment 433 comprises the method of any one of numbered embodiments 415-432, wherein said exposed DNA ends are tagged using a transposase. Numbered embodiment 434 comprises the method of any one of numbered embodiments 415-433, wherein said portion of exposed DNA ends are tagged by linking said exposed DNA ends to another exposed DNA end. Numbered embodiment 435 comprises the method of any one of numbered embodiments 415-434, wherein said portion of exposed DNA ends are linked to said other exposed DNA ends using a ligase. Numbered embodiment 436 comprises the method of any one of numbered embodiments 415-435, wherein said genomic sequence information is generated without using additional contig sequences obtained from said genome. Numbered embodiment 437 comprises the method of any one of numbered embodiments 415-436, wherein the method comprises using SPRI beads. Numbered embodiment 438 comprises the method of any one of numbered embodiments 415-437, wherein the stabilized sample comprises no greater than about 5 micrograms of DNA.

Numbered embodiment 439 comprises a method of analyzing a sample, comprising: (a) obtaining a stabilized sample comprising nucleic acids from a plurality of organisms; (b) treating the stabilized sample to cleave double-stranded DNA in the stabilized sample, thereby producing exposed DNA ends; (c) ligating said exposed DNA ends to form paired ends; (d) sequencing across said paired ends to generate a plurality of paired sequence reads; and (e) assigning each half of a paired sequence read of said plurality of sequence reads to a common organism of origin. Numbered embodiment 440 comprises the method of numbered embodiments 439, further comprising, prior to said ligating, labeling said exposed DNA ends. Numbered embodiment 441 comprises the method of any one of numbered embodiments 439-440, wherein sequence reads of an organism of origin identify an organism not represented in sequence databases. Numbered embodiment 442 comprises the method of any one of numbered embodiments 439-441, further comprising assembling said sequence reads into a genetic sequence not represented in sequence databases. Numbered embodiment 443 comprises the method of any one of numbered embodiments 439-442, further comprising generating a signature of said sample based on said assigning. Numbered embodiment 444 comprises the method of any one of numbered embodiments 439-443, wherein said signature is indicative of the microbial environment of said sample. Numbered embodiment 445 comprises the method of any one of numbered embodiments 439-444, further comprising identifying the presence of one or more individual organisms based on said assigning. Numbered embodiment 446 comprises the method of any one of numbered embodiments 439-445, wherein said one or more individual organisms are human. Numbered embodiment 447 comprises the method of any one of numbered embodiments 439-446, wherein the stabilized sample has been cross-linked Numbered embodiment 448 comprises the method of any one of numbered embodiments 439-447, wherein the stabilized sample has been contacted to formaldehyde. Numbered embodiment 449 comprises the method of any one of numbered embodiments 439-447, wherein the stabilized sample has been contacted to psoralen. Numbered embodiment 450 comprises the method of any one of numbered embodiments 439-447, wherein the stabilized sample has been exposed to UV radiation. Numbered embodiment 451 comprises the method of any one of numbered embodiments 439-450, wherein the sample has been contacted to a DNA binding moiety. Numbered embodiment 452 comprises the method of any one of numbered embodiments 439-451, wherein the DNA binding moiety comprises a histone. Numbered embodiment 453 comprises the method of any one of numbered embodiments 439-452, wherein said treating the stabilized sample to cleave double-stranded DNA comprises contacting the sample to a nuclease enzyme. Numbered embodiment 454 comprises the method of any one of numbered embodiments 439-453, wherein said nuclease enzyme is an endonuclease. Numbered embodiment 455 comprises the method of any one of numbered embodiments 439-454, wherein said endonuclease is a restriction endonuclease. Numbered embodiment 456 comprises the method of any one of numbered embodiments 439-455, wherein said nuclease enzyme is a nucleic acid-guided nuclease. Numbered embodiment 457 comprises the method of any one of numbered embodiments 439-456, wherein the heterogeneous sample comprises nucleic acids mapping to at least two individuals of a common species. Numbered embodiment 458 comprises the method of any one of numbered embodiments 439-457, wherein the heterogeneous sample comprises nucleic acids mapping to at least three individuals of a common species. Numbered embodiment 459 comprises the method of any one of numbered embodiments 439-458, wherein the heterogeneous sample comprises nucleic acids mapping to at least two species. Numbered embodiment 460 comprises the method of any one of numbered embodiments 439-459, wherein the heterogeneous sample comprises nucleic acids mapping to at least three species. Numbered embodiment 461 comprises the method of any one of numbered embodiments 439-460, wherein the heterogeneous sample comprises nucleic acids mapping to at least four species. Numbered embodiment 462 comprises the method of any one of numbered embodiments 439-461, wherein the sequence reads assemble into at least two nucleic acid scaffolds without reference to exogenous sequence information. Numbered embodiment 463 comprises the method of any one of numbered embodiments 439-462, wherein the sequence reads assemble into at least three nucleic acid scaffolds without reference to exogenous sequence information. Numbered embodiment 464 comprises the method of any one of numbered embodiments 439-463, wherein the sequence reads assemble into at least two nucleic acid scaffolds, such that at least 50% of a first genome and at least 50% of a second genome are represented in said at least two nucleic acid scaffolds. Numbered embodiment 465 comprises the method of any one of numbered embodiments 439-464, wherein the sequence reads assemble into at least two nucleic acid scaffolds, such that at least 60% of a first genome and at least 60% of a second genome are represented in said at least two nucleic acid scaffolds. Numbered embodiment 466 comprises the method of any one of numbered embodiments 439-465, wherein the sequence reads assemble into at least two nucleic acid scaffolds, such that at least 70% of a first genome and at least 70% of a second genome are represented in said at least two nucleic acid scaffolds. Numbered embodiment 467 comprises the method of any one of numbered embodiments 439-466, wherein the sequence reads assemble into at least two nucleic acid scaffolds, such that at least 80% of a first genome and at least 80% of a second genome are represented in said at least two nucleic acid scaffolds. Numbered embodiment 468 comprises the method of any one of numbered embodiments 439-467, wherein said treating the stabilized sample to cleave double-stranded DNA comprises sonicating the sample. Numbered embodiment 469 comprises the method of any one of numbered embodiments 439-468, wherein said labeling exposed DNA ends comprises adding a biotin moiety to an exposed DNA end. Numbered embodiment 470 comprises the method of any one of numbered embodiments 439-469, wherein the method comprises using SPRI beads. Numbered embodiment 471 comprises the method of any one of numbered embodiments 439-470, wherein the stabilized sample comprises no greater than about 5 micrograms of DNA.

EXAMPLES

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1. Methods to Generate Chromatin In Vitro

Two approaches to reconstitute chromatin are of particular attention: one approach is to use ATP-independent random deposition of histones onto DNA, while the other approach uses ATP-dependent assembly of periodic nucleosomes. The disclosure allows the use of either approach with one or more methods disclosed herein. Examples of both approaches to generate chromatin can be found in Lusser et al. ("Strategies for the reconstitution of chromatin," Nature Methods (2004), 1(1):19-26), which is incorporated herein by reference in its entirety, including the references cited therein.

A sample comprising genomic nucleic acids from a subject was used to prepare a nucleic acid library, and the library was subsequently sequenced. As an example, the genomic nucleic acids were collected from a sample of a human. A 50 kb sample from a human subject was used as a positive control. In general, multiple samples were prepared simultaneously to generate multiple libraries. In some cases, 4 samples and a 50 kb human control were prepared at a time. In some cases, 9 samples and a 50 kb human control were prepared at a time. In some cases, 12, 15, 20 or more samples were prepared.

The reaction parameters were as follows: A set of component from an Active Motif Chromatin assembly kit was mixed in a siliconized tube on ice. In some cases, a mixture of 1.25 times of a total volume of the reaction was prepared. In general, about 2.1 μl of h-Nap-1 were added to about 2.7 μl of Core Histones and about 15 μl of High Salt Buffer to generate a Solution A. The components of Solution A were mixed and incubated on ice for about 15 minutes. A mixture of 10×ATP Regeneration System was prepared by mixing on ice. Briefly, about 15 μl of 10×ATP Regen Buffer were added to about 0.45 μl of Creatine Kinase to generate a Solution B, and mixed on ice.

After incubation of Solution A on ice, about 96.45 μl of Low Salt Buffer to about 3.75 μl of Solution B to about 15 μl of 10×ATP Regen System to generate a Solution B. Solution B is mixed and about 135 μl of which were distributed to about 1.5 ng of DNA to generate a Solution C. Water was added to Solution 4 to yield a final volume of about 150 μl. Solution C was mixed and incubated at 27° C. overnight. In some examples, Solution C was mixed and incubated at 27° C. for at most, at least or about 12 hours, about 14 hours, about 18 hours, about 20 hours, or about 24 hours. In other examples, Solution C was mixed and incubated at 27° C. for 1 day, 2 days, 3 days, 4 days, 5 days, 6 days, 7 days, 8 days, 9 days, 10 days or more.

Approximately 10 μl of Solution C were collected and transferred to a siliconized tube after incubation at 27° C. overnight. The collected Solution C was saved for testing an efficiency of Chromatic Assembly. Typically, the testing is achieved by MNase digestion during MboI digestion.

Example 2. Buffers and Solutions

Buffers and solutions described herein can be prepared by the following parameters:

SPRI Reconstitution Buffer: The SPRI Reconstitution buffer was usually prepared by adding 9 g of PEG 8000 powder to about 10 ml of 1M NaCl. An amount of water to complete was added to the complete the mixture to 50 ml. Typically, the working concentration of PEG 8000 powder was about 18% and NaCl was about 1M.

Wash Buffer: The Wash Buffer was usually prepared by adding about 500 μl of 1M Tris-Cl pH8.0 to about 500 μl 5M NaCl. An amount of water was added to complete the mixture to 50 ml. In some cases, the working concentration of Tris-Cl pH8.0 was about 10 mM and for NaCl was about 100 mM.

LWB: The LWB was usually prepared by adding about 500 μl of 1M Tris-Cl pH8.0 to about 12.5 ml 4M LiCl, about 100 μl 0.5 M EDTA, and about 200 μl 10% Tween 20. An amount of water to was added to complete the mixture to 50 ml. In certain cases, the working concentration of Tris-Cl pH8.0 was 10 mM, LiCl was 1M, EDTA was 1 mM, and Tween 20 was 0.05%.

NWB: The NWB was usually prepared by adding about 500 μl of 1M Tris-Cl pH8.0 to about 10 ml of 56 M NaCl, about 100 μl of 0.5M EDTA, and about 200 μl of 10% Tween 20. An amount of water to was added to complete the mixture to 50 ml. In various cases, the working concentration of Tris-Cl pH8.0 was 10 mM, NaCl was 1M, EDTA was 1 mM, and Tween 20 was 0.05%.

Example 3. Methods for Capturing Read-Pairs Based on Chromatin Capture

A genome from a human subject was fragmented into pseudo-contigs having a size of 500 kb. Using a chromatin capture based method, a plurality of read pairs were generated by probing the physical layout of chromosomes within living cells. Any number of chromatin capture based methods can be used to generate read pairs, including the method presented in Lieberman-Aiden et al. ("Comprehensive mapping of long range interactions reveals folding principles of the human genome," *Science* (2009), 326(5950):289-293), which is incorporated herein in-full, including the references cited therein.

In various cases, the chromatic assembly was crosslinked with formaldehyde. In general, about 4.05 μl of about 37% Formaldehyde were added to the incubated Solution C the mixture was incubated at room temperature for about 15 minutes, followed by adding about 8.1 μl of 2.5 M Glycine to generate Solution D. Solution D was mixed and incubated on ice for about 10 minutes.

After formaldehyde crosslinking, the Solution D comprising crosslinked chromatin was added to about 330 μl of GE SPRI beads reconstituted in about 18% of PEG 8000/1M NaCl, mixed and left to sit for incubation. The supernatant was removed. The beads were washed at least two times with about 400 μl 1×10 mM Tris/50 mM NaCl. The supernatant was removed and the beads were left to dry. In one example, the beads were left for air dry.

Next, a solution for enzymatic digestion was prepared. To about 175 μl of water, about 20 μl of 10×NEB CutSmart Buffer and about 5 μl of NEB MboI added and mixed to generate a Solution E. Approximately 200 µl of Solution E were added to the dry beads and was incubated at 37° C. for about 60 minutes. In some examples, the incubation occurred at 37° C. for at most, at least, or about 30 minutes, about 60 minutes, about 90 minutes, about 120 minutes, about 180 minutes, or about 240 minutes. In certain examples, the incubation occurred at 4° C. for at most, at least, or about 1 hour, about 2 hours, about 6 hours, about 12 hours, about 14 hours, about 16 hours, or about 24 hours. In various examples, the incubation occurred at 4° C. for at most, at least, or about 1 hour, about 2 hours, about 6 hours, about 12 hours at 4° C. for at most, at least, or about 1 day, about 2 days, about 5 days, or about 10 days.

After enzymatic digestion, incubated beads were treated for buffer exchange. Briefly, a Magnet was put onto the mixture comprising Solution E and beads, and the supernatant was discarded. The precipitate was washed for at least two times with about 400 µl of 1×10 mM Tris/50 mM NaCl. In one example, the precipitates/washed beads were left to air dry.

A solution was prepared for End-Filling and adding Biotin to the beads. Briefly, about 160 µl water were added to about 20 µl of 10×NEB buffer #2, about 1 µl of 10 mM dATP, about 1 µl of 10 mM dTTP, about 1 µl 10 mM dGTP, about 8 µl 10 mM Biotin-dCTP, and about 2.5 µl NEB Klenow 5 U/µl to generate Solution F. Approximately about 200 µl of SolutionF were added to the beads, which was then incubated at 25° C. for about 40 minutes. In one example, mixture comprising Solution F and beads was incubated at 25° C. for at most, at least or about 30 minutes, about 60 minutes, about 120 minutes, or about 180 minutes.

The beads were then treated with buffer exchange. A magnet was added to the mixture of Solution F and beads, and the supernatant was discarded. The precipitate was washed for at least two times with about 400 µl 1×10 mM Tris/50 mM NaCl. In one example, the precipitates/washed beads were left to air dry.

The sample was then treated for intra-aggregate DNA end ligation. Briefly, about 870 µl of water was added to about 100 µl of 10×T4 Ligase Buffer, about 50 µl Thermo BSA 20 mg/ml, about 25 µl of 10% Triton X-100, and about 0.5 µl of NEB T4 DNA Ligase 400 U/µl to generate Solution G. The washed beads were then added with about 200 µl of Solution G and left to incubate at 16° C. for overnight with agitation set to about 1000 RPM (Thermo Block shaker). In one example, the washed beads and Solution G were incubated for at most, at least or about 12 hours, about 14 hours, about 16 hours, about 20 hours, about 24 hours, or about 48 hours.

The incubated beads were then treated for buffer exchange. A magnet was added to the mixture of Solution G and beads, and the supernatant was discarded. The precipitate/beads were then washed for at least twice with about 400 µl 10 mM Tris/50 mM NaCl. In one example, the precipitate/beads was left for air dry.

The DNA in the crosslinked assembly was released by treating with reverse crosslinking. A mixture was prepared for crosslink reversal. For instance, about 172 µl of water were added to about 10 µl 1M Tris pH8.0, about 10 µl 20% SDS, about 0.5 µl 0.1 M CaCl2 and about 5 µl NEB Proteinase K 20 mg/ml to generate Solution I. In one example, the final concentration each component in the solution was as follows: about 50 mM of Tris pH8.0, about 1% of 20% SDS, about 0.25 mM of CaCl2 and about 0.5 mg/ml of NEB Proteinase K. Approximately about 200 µl of Solution I were added to beads comprising crosslinked DNA, and the mixture was left to incubate at about 55° C. for about 15 minutes, then at about 68° C. for about 45 minutes.

The crosslinked reserved solution was subjected to magnet beads and the solution was transferred to a clean 1.5 ml tube. About 400 µl of Normal SPRI beads were added to the crosslinked reverse solution and the mixture was incubated at room temperature for about 5 minutes. Next, a magnet was added to the mixture and the supernatant was discarded. The precipitate/beads were washed for at least twice with about 400 µl of 80% ethanol. The supernatant was discarded and the precipitate/beads were left to air dry for about 10-15 minutes. Finally, the beads were resuspended with about 100 µl TE and incubated for about 2 minutes. The quantity of DNA from crosslink reversal was examined on a Qubit, and the DNA was expect to have at least about 30% to about 75% recovery compared to the starting point. In one example, more than 75% of DNA was recovered from crosslink reversal.

To quantify the quality of DNA and the efficiency of the DNA crosslink reversal, the DNA was analyzed on TapeStation. About 2 µl of genomic DNA sample buffer were distributed in an 8 tube PCR strip. Briefly, about 2 µl of genomic DNA molecular weight marker were added to the first tube. About 2 µl of Chicago DNA were added to the following tubes. The tubes were then closed and vortexed in TapeStation vortex. The genomic DNA tape was then loaded in the machine for analysis.

About 200 ng of DNA was subjected to fragmentation. The 200 ng DNA was added to a 100 µl solution. The solution with DNA was chilled on ice for at least 10 minutes. The BioRuptor was set at 4° C. and the solution with DNA was put on the BioRuptor, run for 7 cycles of 15 seconds ON/90 seconds OFF.

The fragmented DNA was analyzed in a TapeStation. About 1 µl of fragmented the fragmented DNA was diluted in about 4 µl of TE and 2 µl of the mixture was loaded on tape station using High Sensitivity D1000 chip. A broad distribution centered at about 350 nt was expected.

The fragmented DNA was then treated for end repair. A 100 µl solution was prepared by adding about 67.8 µl of water to about 20 µl of 10×NEB T4 Ligase Buffer, about 3.2 µl of dNTP 25 mM, about 1 µl of Klenow, large frag 5 U/µl, about 3 µl of T4 DNA Pol 5 U/µl (thermo), and about 5 µl of T4 PNK 10 U/µl (thermo) to generate Solution J. About 100 µl of Solution J was added to the tubes with fragment Chicago DNA and incubated at 20° C. for about 20 minutes to repair fragmented ends.

About 100 µl of C1 beads were collected and put on a magnet. The supernatant was removed and discarded. The precipitate/beads was washed for at least two times with about 400 µl of 1×TWB. The supernatant was removed and discarded. The precipitate/beads was then resuspended in about 200 µl of 2×NTB. Next, about 200 µl of end repair reaction was added to the beads and the mixture was incubated at room temperature for a period of time, with the tube rotated end over heal. A magnet was put on the solution and the supernatant was discarded. The precipitate/beads was washed for at least 1 time with about 400 µl LWB, followed by washing for at least two times with about 400 µl NWB, followed by washing at least two times with about 400 µl of 10 mM Tris/50 mM NaCl.

Example 4. Methods for Generating Read-Pairs Based on Chromatin Capture Methods

The precipitate/beads were then ligated with adapters. An adapter ligation solution was prepared by adding about 77.5

µl of water to about 20 µl of 5× Quick Ligase, about 1 µl of P5/P7 adapter, and about 2.5 µl of NEB T4 DNA Ligase 400 U/µl. The precipitate/beads were resuspended in about 100 µl of adapter ligation solution. The mixture was then incubated at 25° C. for about 30 minutes. A magnet was put onto the solution, and the supernatant was discarded. The precipitate/beads was washed for at least two times with about 400 µl 10 mM Tris/50 mM NaCl, followed by washing for at least two times with about 400 µl TE.

A solution for adapter fill-in was prepared by adding about 85.25 µl of water to about 10 µl of 10× Thermo Pol, about 1 µl of 25 mM dNTPs, and about 3.75 µl of NEB BST Pol 8 U/µl. The beads were resuspended in about 100 µl of adapter fill-in solution and incubated at 37° C. for about 20 minutes. A magnet was added to the mixture and the supernatant was discarded. The precipitate/beads was washed at least two times with about 400 µl of 10 mM Tris/50 mM NaCl.

A solution for indexing PCR was prepared by mixing about 48 µl of water with about 2 µl ISA Primer (10 mM) and about 50 µl of 2×KAPA MIX. The precipitate/beads was resuspended in about 98 µl of the indexing PCR solution. To each tube of the 8 strip tube, about 2 µl of indexing primer were added. The tubes were then covered and sent for PCR amplification with the following parameters: the PCR mixture for amplified for 13 cycles, each cycle comprises the steps of incubation at 98° C. for 3 minutes, denaturing at 98° C. for 20 seconds, annealing at 65° C. for 30 seconds, extension at 72° C. for 30 seconds, extended extension at 72° C. for 1 minute, and finally hold at 12° C. until the next step. In one example the PCR product was held at 12° C. for at most, at least, or about 1 hour, 2 hours, 5 hours, 10 hours, 15 hours, 20 hours, or 24 hours. In one example, the PCR product was stored at 4° C., at −20° C., at −80° C., in liquid nitrogen, in vitreous state, or dried at room temperature.

To purify amplified DNA or the PCR product, at least two PCR reactions were combined in a new clean tube and put on magnet. The solution was transferred to a clean 1.5 ml tube and added with about 200 µl of Normal SPRI beads. The mixture with beads was incubated at room temperature for about 5 minutes. A magnet was added to the mixture, and the supernatant was discarded. The precipitate/beads was washed for at least two times with about 400 µl 80% ethanol. The supernatant was discarded. The precipitate/beads was left for air dry for about 10-15 minutes. The precipitate/beads was then resuspended in about 20 µl TE and incubated for about 2 minutes. The resuspended DNA was quantified, for example on a broad range Qubit. Typically, a concentration was about 60 ng/µl was expected.

The DNA product of indexed PCR was analyzed. First, the DNA was diluted 1:10 by adding about 0.5 µl of PCR DNA in about 4.5 µl of TE. Approximately 2 µl of the mixture was loaded onto a tape station using High Sensitivity D1000 chip. In certain cases, a broad distribution centered at about 550 nt was expected. In some examples, the DNA product indexed PCR was selected by size. Briefly, the PCR DNA sample was completed to about 30 µl with TE (e.g. adding about 18 µl of TE). About 10 µl of the 1.5% DF Pippin Prep sample buffer was added to the mixture. The Pippin Prep instrument was prepared according to the manufacturer manual. Approximately about 40 µl of the prepared mixture was added into the cassette. The sizes of DNA were selected by a broad range of about 300 nt around the centered of the distribution observed in the TapeStation analysis. Typically, the size of DNA is about 400-700 nt. The DNA was then quantified by using Qubit High Sensitivity analysis, and recovery was expected to be about 5-10 ng/µl.

The DNA was then diluted 1:10 by adding about 0.5 µl in 4.5 TE. About 2 µl of the mixture was loaded on High Sensitivity D1000 Tape on the tape station. The concentration was then recorded into JIRA. Typically, the concentration was recorded in both pg/µl and molar.

In some cases, the quality of chromatin assembly was tested using enzymatic digestion. One example is the MNase digestion. Typically, the parameters used are listed as follows: an MNase solution was diluted 1:1000 by first diluting MNase 50 U/µl with water to 1:10. For example, about 1 µl of MNase 50 U/µl was added to 9 µl of water. The diluted MNase was further diluted to 1:1000 by adding 1 µl of 1:10 MNase to 99 µl of water.

A MNase digestion mixture was typically prepared in a solution, for example a 500 µl mixture, by adding about 480 µl water to about 5 µl 10 Mm Tris-Cl pH8.0, about 5 µl 1 mM CaCl, and about 1 µl MNase 5 mU. In general, the stock concentrations of each component was about 1M Tris-Cl pH8.0, 0.1 M CaCl, and 50 mU/µl MNase.

A Stop Buffer, for example, a solution of 500 µl, was prepared by adding about 362.5 µl of water to about 100 µl of 10 mM EDTA, about 25 µl of 1% SDS, and about 12.5 µl of 0.5 mg/ml Proteinase K. In certain cases, the stock concentration of each component in the mixture is about 0.5 M EDTA, about 20% SDS, and about 20 mg/ml Proteinase K.

The quality of Chromatin Assembly was tested by MNase digestion. In general, about 45 µl of MNase Digestion mixture was distributed in 1.5 ml Eppendorf tubes. The reaction was pre-warmed at 37° C. for about 2 minutes. Approximately 5 µl of the assembled chromatin was added to each tube, and incubated for about 15 seconds prior to adding the next sample. After about 5 minutes, about 50 µl of Stop Buffer were added to the samples, starting with first tube, waiting for about 15 seconds between tube so that every sample was typically digested for about 5 minutes. The samples were then left to incubate at 37° C. for about 30 minutes. About 300 µl of Qiagen Buffer ERC was added to the incubated samples prior to transferring the sample to MiniElute Reaction Cleanup columns. The following are typically manufacture suggested procedures. Typically, the columns were centrifuged for about 1 minute, and the flow through was discarded. About 700 µl of buffer PE were added to each column, which was then centrifuged for about 1 minute, and the flow through was discarded. The columns were usually centrifuge for an additional 30 seconds or 1 minute to elute residue PE buffer. About 10 µl of EB buffer was added to each column and usually incubated for about 1 minute. The columns were centrifuge to collect the purified DNA. To test the efficiency of MNase digestion, about 2 µl of eluted DNA were run on TapeStation.

Example 5. Genome Assembly Using Read Pairs

Read pairs were mapped to all pseudo-contigs and those pairs that mapped to two separate pseudo-contigs, were used to construct an adjacency matrix based upon the mapping data. At least about 50%, about 60%, about 70%, about 80%, about 90%, about 95% or about 99% of the read pairs were weighted by taking a function of the read's distance to the edge of the pseudo-contig so as to mathematically incorporate the empirically known higher probability of shorter contacts than longer contacts. Then, for each pseudo-contig, the adjacency matrix was analyzed to determine a path through the pseudo-contigs by finding the single best neighbor pseudo-contig, which was determined by having the highest sum-of-weights. By performing these methods, it was found that >97% of all pseudo-contigs identified their correct neighbor. Additional experiments can be performed to test the impact of shorter contigs and alternate weighting and path-finding schemes.

Alternatively, genome assembly using chromatin capture data can include computational methods that exploit the signal of genomic proximity in chromatin capture data sets for ultra-long scaffolding of de novo genome assemblies. Examples of such computational methods that can used with the methods disclosed herein, include the ligating adjacent chromatin method by Burton et al. (*Nature Biotechnology* 31:1119-1125 (2013)); and a DNA triangulation method by Kaplan et al. (*Nature Biotechnology* 31:1143-47 (2013)), which references are incorporated herein in-full, and any references cited therein. Further, it should be understood that these computational methods can be used in combination, including with the other genome assembly methods presented herein.

For example, a ligating adjacent chromatin method based on Burton et al. comprising the steps of (a) clustering contigs to chromosome groups, (b) ordering the contigs within one or more chromosome group, and then (c) assigning relative orientations to individual contigs, can be used with the methods disclosed herein. For step (a), contigs are placed into groups using hierarchical clustering. A graph is built, with each node initially representing one contig, and each edge between nodes having a weight equal to the number of chromatin capture read-pairs linking the two contigs. The contigs are merged together using hierarchical agglomerative clustering with an average-linkage metric, which is applied until the number of groups are reduced to the expected number of distinct chromosomes (counting only groups with more than one contig). Repetitive contigs (contigs whose average link density with other contigs, normalized by number of restriction fragment sites, is greater than two times the average link density) and contigs with too few restriction fragment sites are not clustered. However, after clustering, each of these contigs is assigned to a group if its average link density with that group is greater than four times its average link densities with any other group. For step (b), a graph is built as in the clustering step, but with the edge weights between nodes equal to the inverse of the number of chromatin capture links between the contigs, normalized by the number of restriction fragment sites per contig. Short contigs are excluded from this graph. A minimum spanning tree is calculated for this graph. The longest path in this tree, the "trunk", is found. The spanning tree is then modified so as to lengthen the trunk by adding to it contigs adjacent to the trunk, in ways that keep the total edge weight heuristically low. After a lengthened trunk is found for each group, it is converted into a full ordering as follows. The trunk is removed from the spanning tree, leaving a set of "branches" containing all contigs not in the trunk. These branches are reinserted into the trunk, the longest branches first, with the insertion sites chosen so as to maximize the number of links between adjacent contigs in the ordering. Short fragments are not reinserted; as a result, many small contigs that were clustered are left out of the final assembly. For step (c), the orientation of each contig within its ordering is determined by taking into account the exact position of the chromatin capture link alignments on each contig. It is assumed that the likelihood of a chromatin capture link connecting two reads at a genomic distance of x is roughly $1/x$ for $x \geq \sim 100$ Kb. A weighted, directed, acyclic graph (WDAG) is built representing all possible ways to orient the contigs in the given order. Each edge in the WDAG corresponds to a pair of adjacent contigs in one of their four possible combined orientations, and the edge weight is set to the log-likelihood of observing the set of chromatin capture link distances between the two contigs, assuming they are immediately adjacent with the given orientation. For each contig, a quality score for its orientation is calculated as follows. The log-likelihood of the observed set of chromatin capture links between this contig, in its current orientation, and its neighbors, is found. Then the contig is flipped and the log-likelihood is calculated again. The first log-likelihood is guaranteed to be higher because of how the orientations are calculated. The difference between the log-likelihoods is taken as a quality score.

An alternative DNA triangulation method similar to Kaplan et al. can also be used in the methods disclosed herein to assemble a genome from contigs and read pairs. DNA triangulation is based upon the use of high-throughput in vivo genome-wide chromatin interaction data to infer genomic location. For the DNA triangulation method, the CTR pattern is first quantified by partitioning a genome into 100-kb bins, each representing a large virtual contig, and calculating for each placed contig its average interaction frequency with each chromosome. To evaluate localization over long ranges, interaction data of a contig with its flanking 1 mb on each side is omitted. The average interaction frequency strongly separates inter- from intrachromosomal interactions, and is highly predictive of which chromosome a contig belongs to. Next, a simple multiclass model, a naive Bayes classifier, is trained to predict the chromosome of each contig based on its average interaction frequency with each chromosome. The assembled portion of the genome is used to fit a probabilistic single-parameter exponential decay model describing the relationship between chromatin capture interaction frequency and genomic distance (the DDD pattern). In each turn, a contig is removed from the chromosome, along with a flanking region of 1 Mb on each side. It is then estimated the most likely position for each contig based upon the interaction profile and decay model. The prediction error is quantified as the absolute value of the distance between the predicted position and the actual position.

By combining the DNA triangulation method with long-insert libraries the predictability for each contig can be further improved. By knowing the chromosomal assignment and approximate location of each contig could significantly reduce the computational complexity of long-insert scaffolding, as each contig need only be paired with contigs in its vicinity; thereby resolving ambiguous contig joining, and reduce assembly errors where contigs which are located at distant regions of a chromosome or on different chromosomes, are incorrectly joined.

Example 6. Methods for Haplotype Phasing

Because the read pairs generated by the methods disclosed herein are generally derived from intra-chromosomal contacts, any read pairs that contain sites of heterozygosity will also carry information about their phasing. Using this information, reliable phasing over short, intermediate and even long (megabase) distances can be performed rapidly and accurately. Experiments designed to phase data from one of the 1000 genomes trios (a set of mother/father/offspring genomes) have reliably inferred phasing. Additionally, haplotype reconstruction using proximity-ligation similar to Selvaraj et al. (*Nature Biotechnology* 31:1111-1118 (2013)) can also be used with haplotype phasing methods disclosed herein.

For example, a haplotype reconstruction using proximity-ligation based method can also be used in the methods disclosed herein in phasing a genome. A haplotype reconstruction using proximity-ligation based method combines a proximity-ligation and DNA sequencing with a probabilistic algorithm for haplotype assembly. First, proximity-ligation sequencing is performed using a chromosome capture protocol, such as chromatin capture protocol. These methods can capture DNA fragments from two distant genomic loci that looped together in three-dimensional space. After shotgun DNA-sequencing of the resulting DNA library, paired-end sequencing reads have 'insert sizes' that range from several hundred base pairs to tens of millions of base pairs. Thus, short DNA fragments generated in a chromatin capture experiment can yield small haplotype blocks, long fragments ultimately can link these small blocks together. With enough sequencing coverage, this approach has the potential to link variants in discontinuous blocks and assemble every such block into a single haplotype. This data is then combined with a probabilistic algorithm for haplotype assembly. The probabilistic algorithm utilizes a graph in which nodes correspond to heterozygous variants and edges correspond to overlapping sequence fragments that may link the variants. This graph might contain spurious edges resulting from sequencing errors or trans interactions. A max-cut algorithm is then used to predict parsimonious solutions that are maximally consistent with the haplotype information provided by the set of input sequencing reads. Because proximity ligation generates larger graphs than conventional genome sequencing or mate-pair sequencing, computing time and number of iterations are modified so that the haplotypes can be predicted with reasonable speed and high accuracy. The resulting data can then be used to guide local phasing using Beagle software and sequencing data from the genome project to generate chromosome-spanning haplotypes with high resolution and accuracy.

Example 7. Methods for Meta-Genomic Assembly

Microbes are collected from an environment and fixed with a fixative agent, such as formaldehyde, in order to form cross-links within the microbial cells. A plurality of contigs from the microbes is generated by using high-throughput sequencing. A plurality of read pairs are generated by using chromatin capture based techniques. Read pairs that map to different contigs indicate which contigs are from the same species.

Example 8. Methods for Producing Extremely Long-Range Read Pairs (XLRPs)

Using commercially available kits, DNA is extracted to fragments sizes up to 150 kbp. The DNA is assembled into a reconstituted chromatin structure in vitro using a commercial kit from Active Motif. The chromatin is fixed with formaldehyde, and immobilized onto SPRI beads. The DNA fragments are digested with a restriction enzyme and incubated overnight. The resulting sticky ends are filled-in with an alpha-thio-dGTP and a biotinylated dCTP to generate blunt ends. The blunt ends are ligated with T4 ligase. The reconstituted chromatin is digested with a proteinase to recover the ligated DNA. The DNA is extracted from the beads, sheared, and the ends are repaired with dNTPs. The fragments are purified by a pull-down with SPRI beads. In some cases, adaptors are ligated and the fragments are PCR amplified for high-throughput sequencing.

Example 9. Methods for Producing a High Quality Human Genome Assembly

With the knowledge that read pairs spanning considerable genomic distances can be generated by the disclosure, the utilization of this information for genomic assembly can be tested. The disclosure can significantly improve the linkage of de novo assemblies, potentially to chromosome-length scaffolds. An assessment can be performed on how complete an assembly can be produced and how much data will be required using the disclosure. To evaluate the efficacy of the present method for producing data that is valuable for assembly, a standard Illumina shotgun library and XLRP libraries can be built and sequenced. In one case, data from 1 Illumina HiSeq lane each of a standard shotgun library and an XLRP library are used. The data generated from each method is tested and compared with various existing assemblers. Optionally, a new assembler is also written to specifically tailor to the unique data produced by the disclosure. Optionally, a well-characterized human sample is used to provide a reference to compare the assembly produced by the present method against to assess its accuracy and completeness. Using the knowledge gained in the previous analyses, an assembler is produced to increase efficient and effective utilization the XLRP and shotgun data. A genome assembly of the quality of the December 2002 mouse genome draft, or better is generated using methods described herein.

One sample that can be used for this analysis is NA12878. DNA from sample cells are extracted using a variety of published techniques designed to maximize DNA fragment length. A standard Illumina TruSeq shotgun library and an XLRP library are each built. A single HiSeq lane of 2×150 bp sequence is obtained for each library, which may yield approximately 150 million read pairs per library. The shotgun data are assembled into contigs using algorithms for whole genome assembly. Examples of such algorithms include: Meraculous as described in Chapman et al. (PLOS ONE 6(8):e2350 (2011)) or SGA as described in Simpson et al. (Genome research 22(3):549-56 (2012)). The XLRP library reads are aligned to the contigs produced by the initial assembly. The alignments are used to further link the contigs. Once the effectiveness of the XLRP library for connecting contigs is ascertained, the Meraculous assembly is extended to integrate both the shotgun and XLRP libraries simultaneously into a single assembly process. Meraculous provides a strong foundation for the assembler. Optionally, an all-in-one assembler is produced to suit the specific needs of the disclosure. The human genome assembled by the disclosure is compared to any known sequence to evaluate the quality in the assembly of the genome.

Example 10. Methods for Phasing of Heterozygous SNPs for a Human Sample at High Accuracy from a Small Data Set In one experiment, approximately 44% of the heterozygous variants in a test human sample dataset are phased. All or nearly all phasing variants that are within one read-length's distance of a restriction site are captured. By using in silico analysis, more variants for phasing can be captured by using longer read lengths and using one or more combinations restriction enzymes for digestion. Using a combination of restriction enzymes with different restriction sites increases the proportion of the genome (and therefore heterozygous sites) that is within range of one of the two restriction sites that participate in each read pair. In silico analysis shows that the methods of the disclosure can phase more than 95% of known heterozygous positions using various combinations of two restriction enzymes. Additional enzymes and greater read lengths further increase the fraction of heterozygous sites that are observed and phased, up to a complete coverage and phasing.

Heterozygous site coverages achievable with various combinations of two restriction enzymes are calculated. The top three combinations, in terms of heterozygous sites in read proximity, are tested with the protocol. For each of these combinations, an XLRP library is produced and sequenced. The resulting reads are aligned to a human reference genome and compared to the known haplotypes of the sample to determine the accuracy of the protocol. Up to 90% or more of the heterozygous SNPs for a human sample are phased at an accuracy of 99% or greater using only 1 lane of Illumina HiSeq data. In addition, further variants are captured by increasing the read length to 300 bp. The read area around the observable restriction sites is effectively doubled. Additional restriction enzyme combinations are implemented increasing the coverage and accuracy.

Example 11. Extraction and Effects of High Molecular Weight DNA

Figure 7:
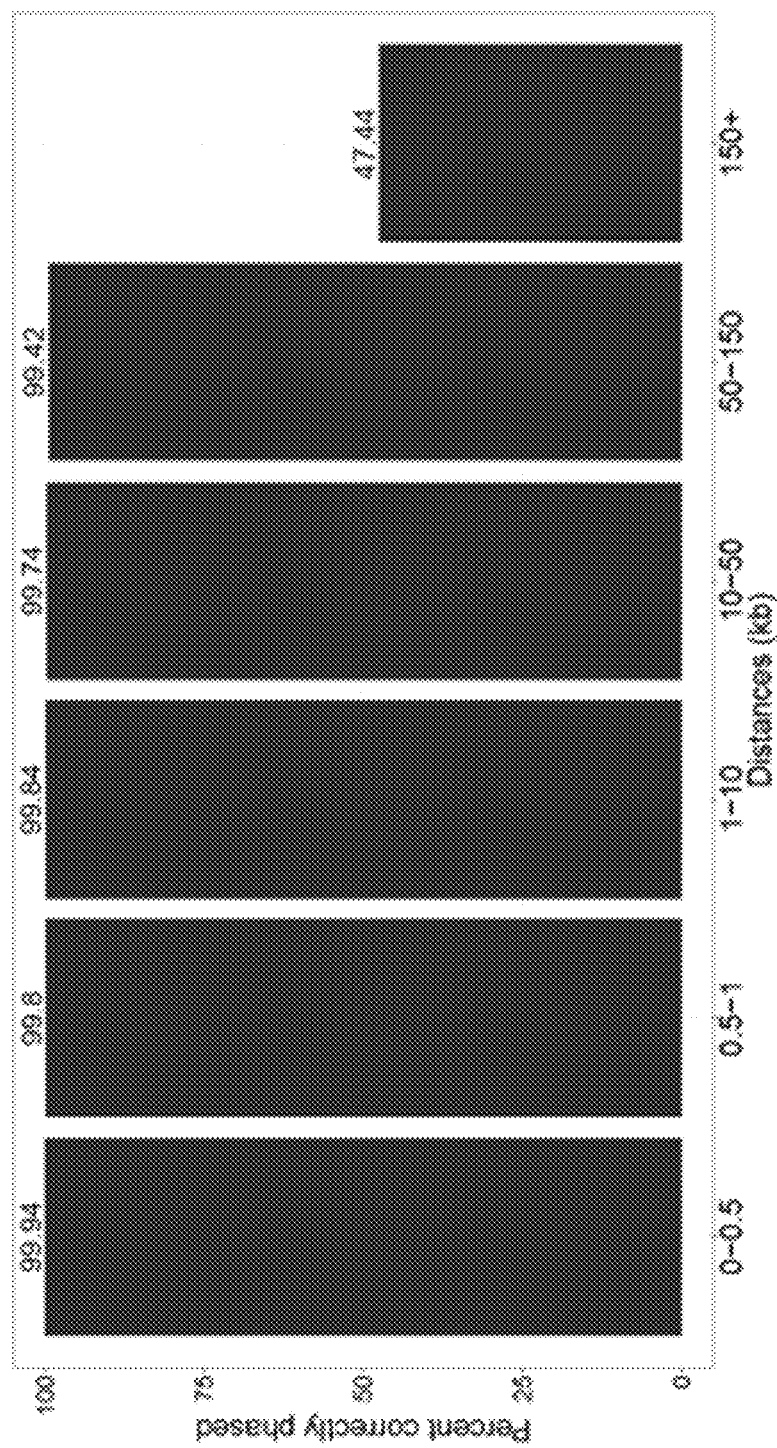
FIG. 7 illustrates the phasing accuracy for a sample with well-characterized haplotypes, NA12878. Indicated distances are those between the SNPs being phased.

DNA up to 150 kbp was extracted with commercially available kits. FIG. 7 demonstrates that XLRP libraries can be generated from capture read pairs up to maximum fragment lengths of the extracted DNA. Accordingly, the methods disclosed herein can be expected to be capable of generating read pairs from even longer stretches of DNA. There are numerous well-developed processes for high molecular weight DNA recovery, and these methods can be used with the methods or protocols disclose herein. Using an extraction method to produce large fragment lengths of DNA, an XLRP library is created from these fragments and the read pairs that are produced can be evaluated. For example, large molecular weight DNA can be extracted by, (1) gentle lysis of the cells according to Teague et al. (Proc. Nat. Acad. Sci. USA 107(24): 10848-53 (2010)) or Zhou et al. (PLOS Genetics, 5(11):e1000711 (2009)); and (2) agarose gel plugs according to Wing et al. (The Plant Journal: for Cell and Molecular Biology, 4(5):893-8 (1993)), which references are incorporated herein in-full, including any references cited therein, or by using the Aurora System from Boreal Genomics. These methods are capable of generating long DNA fragments beyond what is routinely required for next generation sequencing; however, any other suitable methods known in the art can be substituted for achieving similar results. The Aurora System provides exceptional results and can separate and concentrate DNA from tissue or other preparations up to, and beyond, a megabase in length. DNA extractions are prepared using each of these methodologies, beginning from a single GM12878 cell culture to control for possible differences at the sample level. The size distribution of the fragments can be evaluated by pulsed field gel electrophoresis according to Herschleb et al. (*Nature Protocols* 2(3):677-84 (2007)). Using the foregoing methods, extremely large stretches of DNA can be extracted and used to build XLRP libraries. The XLRP library is then sequenced and aligned. The resulting read data are analyzed by comparing the genomic distance between read pairs to the fragment sizes observed from the gel.

Example 12. Reducing Read-Pairs from Undesired Genomic Regions

RNA complementary to the undesired genomic regions is produced by in vitro transcription and added to the reconstructed chromatin prior to crosslinking. As the supplemented RNA binds to one or more undesired genomic regions, RNA binding decreases the crosslinking efficiency at these regions. The abundance of DNA from these regions in the cross-linked complexes is thereby reduced. The reconstructed chromatin is immobilized, and used as described above. In some cases, the RNA is designed to target repetitive regions in the genome.

Example 13. Increasing Read-Pairs from Desired Chromatin Regions

DNA from desired chromatin regions is produced in double stranded form for gene assembly or haplotyping. Representation of DNA from undesired regions is accordingly reduced. Double-stranded DNA from desired chromatin regions is generated by primers that tile at such regions in multi-kilobase intervals. In other implementations of the method, the tiling intervals are varied to address desired regions of different sizes with desired replication efficiency. Primer binding sites across the desired regions are contacted with primers, optionally by melting the DNA. New strands of DNA are synthesized using the tiled primers. Undesired regions are reduced or eliminated, for example by targeting these regions with an endonuclease specific to single-stranded DNA. The remaining desired regions can be optionally amplified. The prepared sample is subjected to the sequencing library preparation methods as described elsewhere herein. In some implementations, read-pairs spanning distances up to the length of each desired chromatin regions are generated from each such desired chromatin region.

Example 14. Rapid Chicago Library Preparation Protocol

This protocol is performed over only two days and produces high-quality libraries for determining contiguity information in a nucleic acid sample.

On Day 1 the following steps are performed.

Chromatin Assembly.

Thaw Active Motif kit components on ice. Meanwhile, Qubit (Broad Range) quantitate 1 µl of the gDNAs to be assembled; include size standards for accuracy. Heat especially high molecular weight/viscous samples before pipetting to ensure even resuspension.

In a siliconized tube, mix together in order on ice the following Active Motif Chromatin assembly kit components (Make a master mix with 0.25× extra):

| | |
|---|---|
| h-NAP-1 | 0.7 µl |
| HeLa Core Histones | 0.9 µl |
| High Salt Buffer | 5 µl |

Incubate 15 mins on ice.

Meanwhile, prepare the 10×ATP Regeneration System by mixing on ice:

| | |
|---|---|
| 10 × ATP Regeneration System | 5 µl |
| Creatine Kinase | 0.15 µl |

After incubation on ice, add the following in order to the histones mix:

| Low Salt Buffer | 32.15 µl |
|---|---|
| ACF | 1.25 µl |
| 10 × ATP Regen System | 5 µl |

Distribute 45 µl of the master mix to:

| DNA | 0.5 µg |
|---|---|
| H₂O | final volume of DNA + H2O is 5 µl |

Incubate 1 hrs at 27° C.

The DNA concentration in the histone mix to which the ACF/10×ATP Regen System is to be added should be at least 100 ng/µl in some cases. However, the method is performed successfully to assemble chromatin that gave successful Chicago libraries using DNA as low as 50 ng/µl, by adding 45 µl of the master mix on top of 10 µl of the DNA sample. This increase of 10% in total volume does not impact the overall quality of the assembled chromatin.

Optionally, 5 µl are saved to a siliconized tube for testing chromatin assembly by MNase digestion (during DpnII digest, below).

Formaldehyde Crosslink.

Add 1.35 µl of 37% Formaldehyde tube (White Cap 2 ml tubes @R/T). Flick mix and spin down. Incubate 15 minutes at room temperature (RT). Add 2.7 µl of 2.5M Glycine tube (Green Cap 2 ml tubes @R/T). Incubate 10 minutes on ice.

Bind Chromatin to SPRI Beads.

Add 100 µl of SPRI beads; mix by pipetting ~10 times. Incubate 5 mins RT. Clarify the tubes on a Magnet for 5 mins and then discard supernatant (SN). Wash 2× with 250 µl Wash Buffer (10 mM Tris/50 mM NaCl).

The digestion master mix (below) can be prepared during these incubations.

DpnII Digest.

Before binding to SPRI beads, thaw on ice one tube of DpnII Digest mix (Purple cap 2 ml tubes @−30° C.). After Removing the wash, resuspend the beads with 50 ul of DpnII Digest Mix. Discard the remainder of the mix. Digest in thermomixer at >1000 rpm for one hour at 37° C.

Buffer Exchange.

Put the samples on magnet to separate the supernatant, and discard supernatant. Wash 1× with 250 µl Wash Buffer.

The master mix (below) can be prepared during these incubations.

End Fill-In.

15 minutes before the end of the Dpn II digest, thaw on ice one tube of End Fill-In Mix (Green cap 2 ml tubes @−30° C.). After removing the wash, resuspend the beads with 50 ul of End Fill-In Mix. Discard the remainder of the mix.

Incubate in thermomixer at >1000 rpm for 30 minutes at 25° C.

Buffer Exchange.

Put the samples on magnet to separate the supernatant, and discard supernatant. Wash 1× with 250 µl Wash Buffer.

The master mix (below) can be prepared during these incubations.

Intra-Aggregate DNA End Ligation.

30 minutes before the end of the End Fill-In reaction, thaw on ice one tube of Intra-Aggregate Ligation Mix (false bottom 3 ml tubes @−30° C.). After removing the wash, resuspend the beads with 250 ul of the Intra-Aggregate Mix. Discard the remainder of the mix.

Incubate in thermomixer at >1000 rpm for at least 1 hours at 16° C.

Terminal Nucleotide Exchange.

5 minutes before the end of the Intra-Aggregate Ligation reaction, thaw on ice one tube of Terminal Nucleotide Exchange Mix (Yellow cap 2 ml tubes @−30° C.). Add 5 ul of the Terminal Nucleotide Exchange Mix directly to the reaction. Discard the remainder of the mix.

Incubate in thermomixer at >1000 rpm for 15 mins at 16° C.

Buffer Exchange.

Put the samples on magnet to separate the supernatant, and discard supernatant. Wash 1× with 250 µl Wash Buffer.

The master mix (below) can be prepared during these incubations.

Crosslink Reversal.

5 minutes before the end of the Terminal Nucleotide Exchange reaction, add 11 µl of NEB Proteinase K (20 mg/ml @−30° C.) to one full Crosslink Reversal Buffer tube (Red Cap 2 ml tubes @R/T). After removing the supernatant, resuspend the beads with 50 ul of the Crosslink Reversal/Proteinase K Mix. Discard the remainder of the mix.

Incubate in thermomixer at >1000 rpm for 15 mins at 55° C.

Incubate in thermomixer at >1000 rpm for 45 mins at 68° C.

Purify DNA on SPRI.

Put the Crosslink Reversal reaction on magnet to separate the supernatant. Transfer the SUPERNATANT to a clean 1.5 ml tube. Add 100 µl of SPRI beads; mix by pipetting ~10 times. Incubate 5 mins RT. Place the samples on Magnet for 5 mins, then draw off and discard the supernatant.

Wash 3× with 250 µl freshly made 80% EtOH. Air dry 5 mins, taking care not to over-dry. Resuspend beads with 78 µl TE, wait 2 mins. Put on magnet, transfer 75 µl of the SUPERNATANT to a Bioruptor 0.65 ml tube. Quantify 1 ul DNA with Qubit HS; expected recovery is 30%-75% of input.

On Day 2 the following steps are performed

Fragmentation.

A Bioruptor is cooled down to 4° C. DNAs are chilled on ice for a minimum of 10 mins. Vortex, spin samples. Put tubes in the Bioruptor carrousel, taking care not to splash the DNA. Run 4 cycles of 15 sec ON/90 sec OFF. Remove from carousel. Vortex, spin tubes down. Run 3 cycles of 15 sec ON/90 sec OFF. Remove from carousel. Vortex, spin tubes down.

Analyze Chicago DNA on TapeStation.

Load 2 ul of fragmented DNA on TapeStation using the High Sensitivity D1000 tape. Expect a broad distribution centered at ~350 nt.

End Repair.

Transfer 55.5 µl of fragmented DNA to a PCR tube containing the following NEBNext Ultra reagents (Green Cap): End Prep Enzyme Mix 3.0 µl, End Repair Reaction Buffer 6.5 µl. Incubate in PCR machine, using the NEB-END protocol: 30 mins at 20° C., 30 mins at 65° C., Hold at 4° C.

Adapter Ligation.

Add the following NEBNext Ultra reagent (Red Cap) to the reactions: Blunt/TA Ligase Master Mix 15 µl, Ligation Enhancer 1.0 µl, Home Made Y-Adapter 15 µM 2.5 µl.

Incubate in PCR machine, using the NEB-Ligate protocol: 15 mins at 20° C.

Capture of Ligation Events.

Prepare a master mix of 25 µl of C1 beads for each Chicago reaction. Put the samples on magnet to separate the supernatant, and discard supernatant. Wash twice with 250

µl of 1×TWB (see buffer recipes page). Resuspend the beads in 85 µl times the number of Chicago reaction of 2×NTB. Distribute 85 µl of the beads in 2×NTB to a set of clean 1.5 µl tubes. Transfer the 85 µl end repair reaction to the beads. Incubate at RT for 30 mins on LabQuake rotator.

Put the samples on magnet to separate the supernatant, and discard supernatant. Wash 1× with 250 µl LWB. Wash 2× with 250 µl NWB. Wash 2× with 250 µl Wash Buffer.

Indexing PCR.

Resuspend the beads in 49 µl of the mix below—(master mix+0.25% Rx): H2O 23 µl; IS4 Primer (10 uM) 1.0 µl; 2×KAPA MIX 25 µl.

Transfer to PCR strip tubes. To each tube, add 1 µl of 10 µM indexing primer; making sure to record the indexing IDs for each sample.

Amplify for 13 cycles with these steps: 3 mins @98° C.; 20 sec @98° C.; 30 sec @65° C.; 30 sec @72° C.; Repeat 12 more times from step 2; 1 min @72° C.; hold @12° C.

Purify Amplified DNA on SPRI.

Put the samples on magnet to separate the supernatant. Transfer the SUPERNATANT to a clean 1.5 ml tube. Add 100 µl of SPRI beads; mix by pipetting ~10 times. Incubate 5 mins RT. Put the samples on magnet to separate the supernatant for 5 mins; discard the supernatant. Wash 2× with 250 µl freshly made 80% EtOH. Air dry 5 mins, taking care not to over-dry. Resuspend beads with 32 µl TE, wait 2 mins. Concentrate on magnet. Transfer eluted DNA to a new 1.5 ml tube. Quantify DNA on broad range Qubit; expected concentration ~30 ng/ul.

Analyze Indexed PCR DNA on TapeStation.

Dilute 1:10 by adding 0.5 ul of the purified PCR to 4.5 µl of TE. Load 2 µl on TapeStation High Sensitivity D1000 tape. Expect a broad distribution centered at ~550 nt.

Size Select Indexed PCR DNA on Pippin Prep.

Add 10 µl of the 1.5% DF Pippin Prep sample buffer (marker K). Prepare the instrument and gel according to the manufacturer protocol. Size select using a broad range window of 300 nt around the center of the distribution observed on the TapeStation analysis; usually 400-700 nt. Quantify the DNA using Qubit High Sensitivity; recovery should be around 5-10 ng/ul.

Analyze Size Selected DNA on TapeStation.

Dilute 1:5 by adding 1 ul to 4 ul TE. Load 2 ul on TapeStation High Sensitivity D1000 tape. Record the concentration (both pg/ul and molar) into JIRA.

Example 15

Pursuant to the generation of the Chicago Library, a Micrococcal Nuclease (MNase) digestion is performed to test for Chromatin Assembly.

Master Mix Preparations.

Digestion and Stop master mixes are prepared at Room Temperature Dilute MNase to 1:1000 as follows: Make a 1:10 dilution in H2O (1 µl of MNase 50 U/µl+9 µl of H2O); Make a 1:1000 dilution in H2O (1 µl of 1:10 dilution+99 µl of H2O); Prepare MNase Digestion Mix by adding 1 µl of the MNase 1:1000 to one tube of MNase Digestion Buffer (Yellow Cap Tubes @R/T); Prepare Stop Buffer Mix by adding 11 µl of NEB Proteinase K 20 mg/ml to one full tube of Stop Buffer (Blue Cap Tubes @R/T).

MNase Digestion.

Pre-warm the MNase Digestion Mix at 37° C. for 2 mins. Add 45 ul to the 5 µl of assembled chromatin per tube, waiting 30 secs between each sample. Start the timer at the first sample addition, and keep the samples in order. After 5 mins, add 50 µl of Stop Buffer Mix, starting with first tube. Again, wait 30 secs between each tube so that each sample is digested for 5 mins precisely. Incubate for an additional 30 mins at 37° C.

Purify using the Qiagen MinElute kit: Add 300 ul of Qiagen Buffer ERC, mix well; transfer to MinElute Reaction Cleanup column; Centrifuge 1 min, discard the flow through; Add 700 µl of buffer PE (make sure ethanol has been added); Centrifuge 1 mM, discard the flow through; Centrifuge 1 min to make sure no PE buffer is left; Transfer columns to 1.5 ml tubes; Add 10 ul of EB buffer, wait 1 min; Centrifuge 1 min to recover DNA.

Run 2 ul of MNase digested samples on HS DNA 1000 TapeStation tape.

Example 16

Amplification Adapter Preparation by Annealing.

Making the 15 µM partially double-stranded amplification Adapter is accomplished as follows. Mix together in a 1.5 ml tube: 37.5 µl of 200 µM P5_full_A in TE+50 mM NaCl (oligo #111); 37.5 µl of 200 µM P7_Y_Rev in TE+50 mM NaCl (oligo #132); 420 µl of TE; 5 µl of NaCl 5M. Aliquot into two PCR tubes in thermocycler, run the Anneal program: 95° C. 2 min; Ramp down to 25° C. at 0.1° C./sec.

Oligo that are suitable for the amplification adapter are indicated below (* is phosphorothioate bond)

| SEQ ID NO | Position | Sequence (5' to 3') |
| --- | --- | --- |
| 1 | P5_full | ACACTCTTTCCCTACACGACGCTCTTCCGATG*T |
| 2 | P7_rev | /5Phos/CATCGGAAGAGCACACGTCTGAACTCCAGTCA*/3ddC/ |
| 3 | P5_full | ACACTCTTTCCCTACACGACGCTCTTCCGACC*T |
| 4 | P7_rev | /5Phos/GGTCGGAAGAGCACACGTCTGAACTCCAGTCA*/3ddC/ |
| 5 | P5_full | ACACTCTTTCCCTACACGACGCTCTACCGATC*T |
| 6 | P7_rev | /5Phos/GATCGGTAGAGCACACGTCTGAACTCCAGTCA*/3ddC/ |
| 7 | P5_full | ACACTCTTTCCCTACACGACGCTATTCCGATC*T |
| 8 | P7_rev | /5Phos/GATCGGAATAGCACACGTCTGAACTCCAGTCA*/3ddC/ |
| 9 | P5_full | ACACTCTTTCCCTACACGACGCTCTTCGGATC*T |
| 10 | P7_rev | /5Phos/GATCCGAAGAGCACACGTCTGAACTCCAGTCA*/3ddC/ |

-continued

| SEQ ID NO | Position | Sequence (5' to 3') |
|---|---|---|
| 11 | P5_full | ACACTCTTTCCCTACACGACCCTCTTCCGATC*T |
| 12 | P7_rev | /5Phos/GATCGGAAGAGGACACGTCTGAACTCCAGTCA*/3ddC/ |
| 13 | P5_full | ACACTCTTTCCCTACACGACGCACTTCCGATC*T |
| 14 | P7_rev | /5Phos/GATCGGAAGTGCACACGTCTGAACTCCAGTCA*/3ddC/ |
| 15 | P5_full | ACACTCTTTCCCTACACGACGCTCTTCCGATC*T |
| 16 | P7_rev | /5Phos/GATCGGAAGAGCACACGTCTGAACTCCAGTCA*/3ddC/ |

Example 17

Making SPRI Beads.

Measure into a 50 ml tube: PEG-8000 powder 9 g. Then add:

| Stock Concentration | Final Concentration |
|---|---|
| 1M Tris-Cl pH 8.0 | 500 μl 10 mM |
| 0.5M EDTA | 100 μl 1 mM |
| NaCl | 1M |
| H₂O | to ~48 mL |

Shake to dissolve the PEG. Then add Tween and mix gently: 10% Tween 20 250 μl 0.05%.

Meanwhile, resuspend Sera-Mag beads. Transfer 1 ml to a 1.5 ml tube. Clarify the tubes on a Magnet and then discard supernatant (SN). Wash beads 4× with 1 ml TE. Resuspend in 1 ml TE. Transfer all to PEG solution and mix by inverting. Bring up to 50 mls with H$_2$O. Store at 4° C. Calibrate each batch with 50 bp ladder (e.g., GeneRuler or Hyperladder) at various ratios.

Example 18. Human Fecal Metagenomic Assembly Using Sequence Reads Generated from In Vitro Assembled Chromatin Aggregates Derived from Nucleic Acids in the Fecal Sample DNA for fecal metagenomic assembly was prepared with the MoBio Powerfecal kit. Fecal sub-samples (sub-samples of a sample collected from a single individual at a single timepoint), were prepared according to the protocol for DNA isolation provided in the kit. Four sub-samples of ~250 mg were prepared. The DNA yield for each sample was as follows: (1) 4.28 μg; (2) 7.28 μg; (3) 6.48 μg; and (4) 5.56 μg.

Figure 13A:
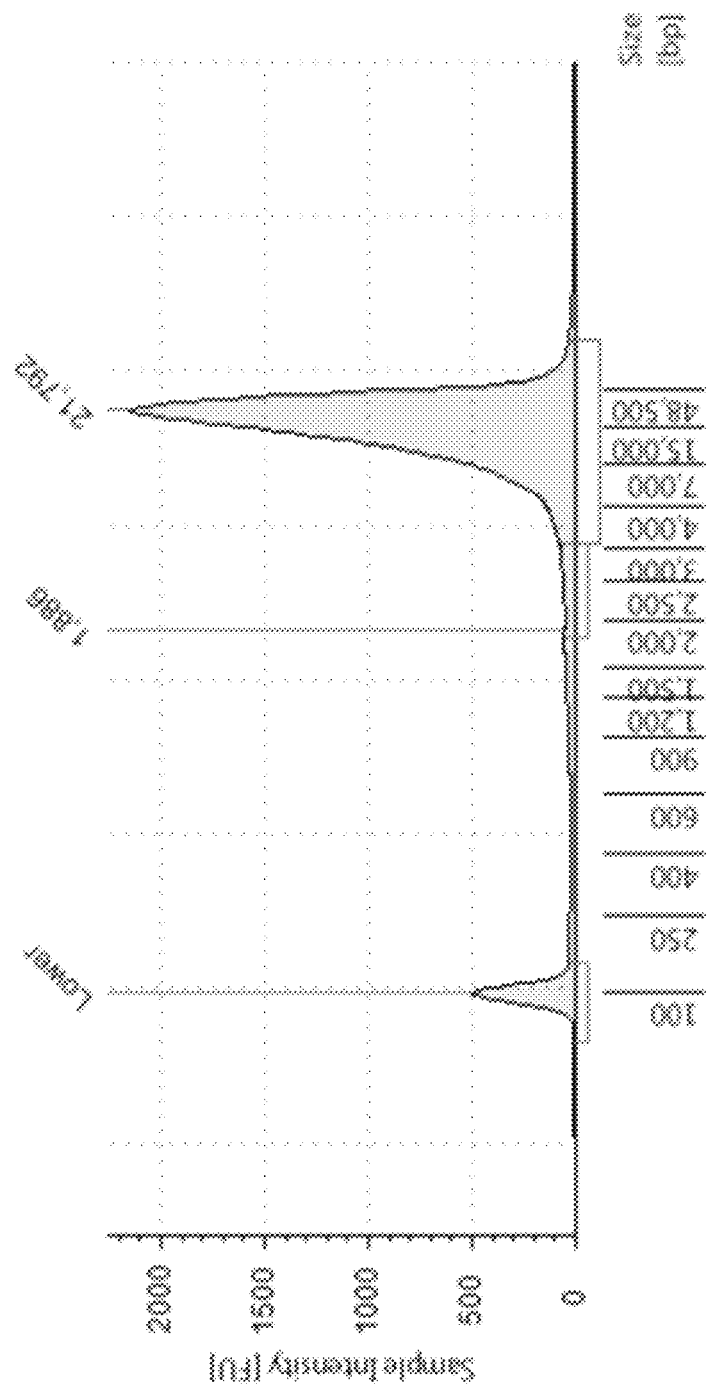
FIG. 13A shows size analysis of DNA fragments from a fecal DNA sample, in accordance with an aspect of the present disclosure.

Sample (2) was selected for further processing since it had the highest DNA yield of the four sub-samples. DNA fragments in sample (2) were analyzed for size using a TapeStation (Agilent). As shown in FIG. 13A, the median fragment size of the sample was approximately 22 kb and small fragments were absent. Two libraries were prepared for metagenomic assembly—the first library was prepared using in vitro assembled chromatin aggregates and proximity ligation, and the second library was prepared for shotgun sequencing.

Figure 13B:
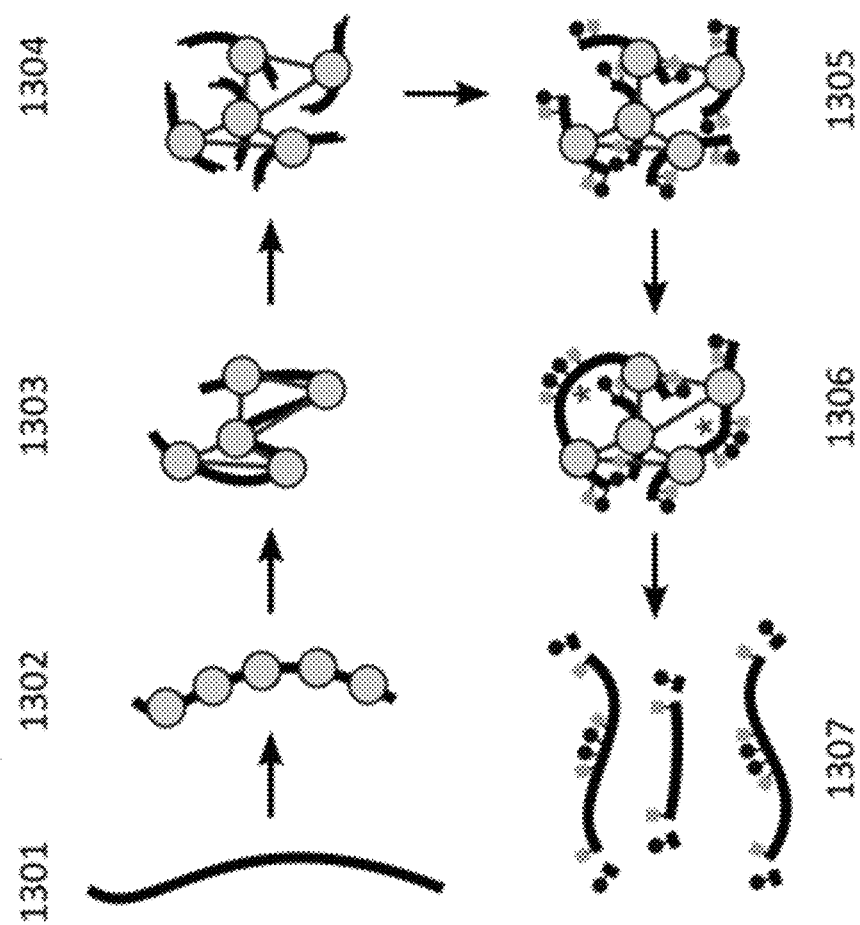
FIG. 13B shows a method for generating a sequencing library using in vitro assembled chromatin aggregates.

A first library was prepared using 500 ng of DNA from sample (2) and in vitro assembled chromatin as shown in FIG. 13B. Chromatin was reconstituted in vitro 1302 upon naked DNA 1301 from sample (2). Chromatin was then fixed with formaldehyde to form chromatin aggregates as shown in 1303. The fixed chromatin was digested with a restriction enzyme to generate free sticky ends as shown in 1304. The free ends were filled in with biotinylated (circle) and thiolated (square) nucleotides as shown in 1305. The free blunt ends were ligated (ligations indicated by asterisks) as shown in 1306. The cross-links were reversed and the chromatin associated proteins were removed to yield library fragments as shown in 1307. The library was sequenced on a MiSeq (Illumina, 2×75 bp). 5,026,934 read pairs were generated.

A second library was prepared for shotgun sequencing. The second library was a TrueSeq PCR-free library prepared from 2 μg of sample (2) using a library preparation kit. The shotgun library was sequenced on a MiSeq (Illumina, 2×150 bp). The reads were trimmed and merged using SeqPrep before a metagenome assembly was generated using Omega (overlap-graph metagenome assembler, Haider et al. Bioinformatics (2014) doi: 10.1093/bioinformatics/btu39). There were 15,758,635 read pairs, and 1,810,877 of the read pairs merged into a single read.

Figure 14:
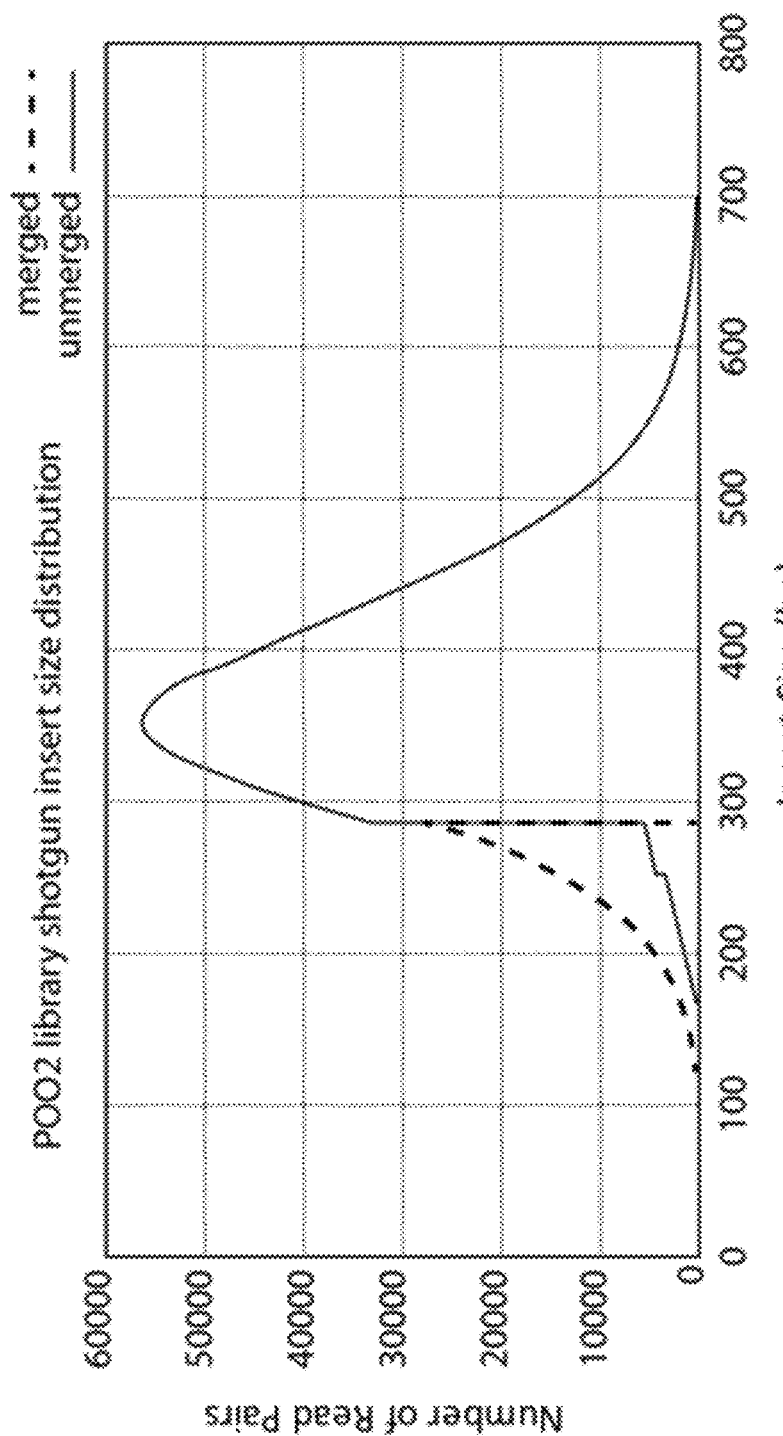
FIG. 14 shows insert size distribution of a shotgun library, in accordance with an aspect of the present disclosure.

The shotgun reads were mapped to the assembly to assess insert length distributions and coverage as shown in FIG. 14. In FIG. 14, the x-axis shows insert length in bp, and the y-axis shows the number of read pairs. Merged read pairs are shown as a dashed line, and unmerged read pairs are shown as a solid line.

Figure 15:
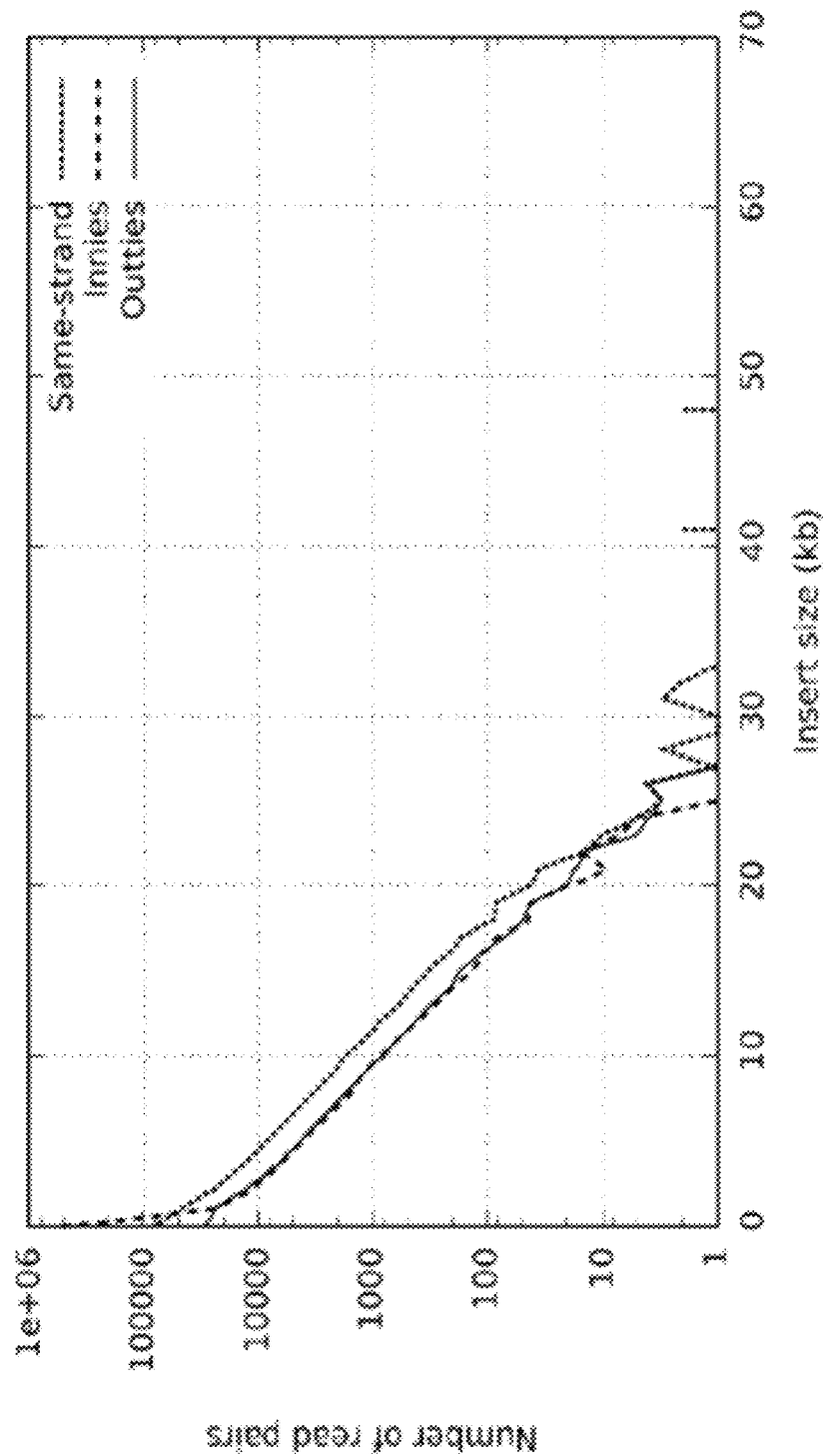
FIG. 15 shows size distribution of reads from a library prepared using in vitro assembled chromatin mapped to the same scaffold.

Reads from the library prepared with in vitro chromatin aggregates were mapped to the assembly to assess the insert length distribution. 819,566 read pairs mapped to the same scaffold. Insert distribution between map positions is shown in FIG. 15. In FIG. 15, the x-axis shows the insert size in kb, and the y-axis shows the number of read pairs. Same-strand read pairs are shown in a short dashed line. Two read pair categories are also shown—"innies" are shown in a long dashed line, and "outties" are shown in a solid line. Of the read pairs, 1,358,770 mapped to different scaffolds. Remaining pairs did not map or did not map uniquely.

Figure 16:
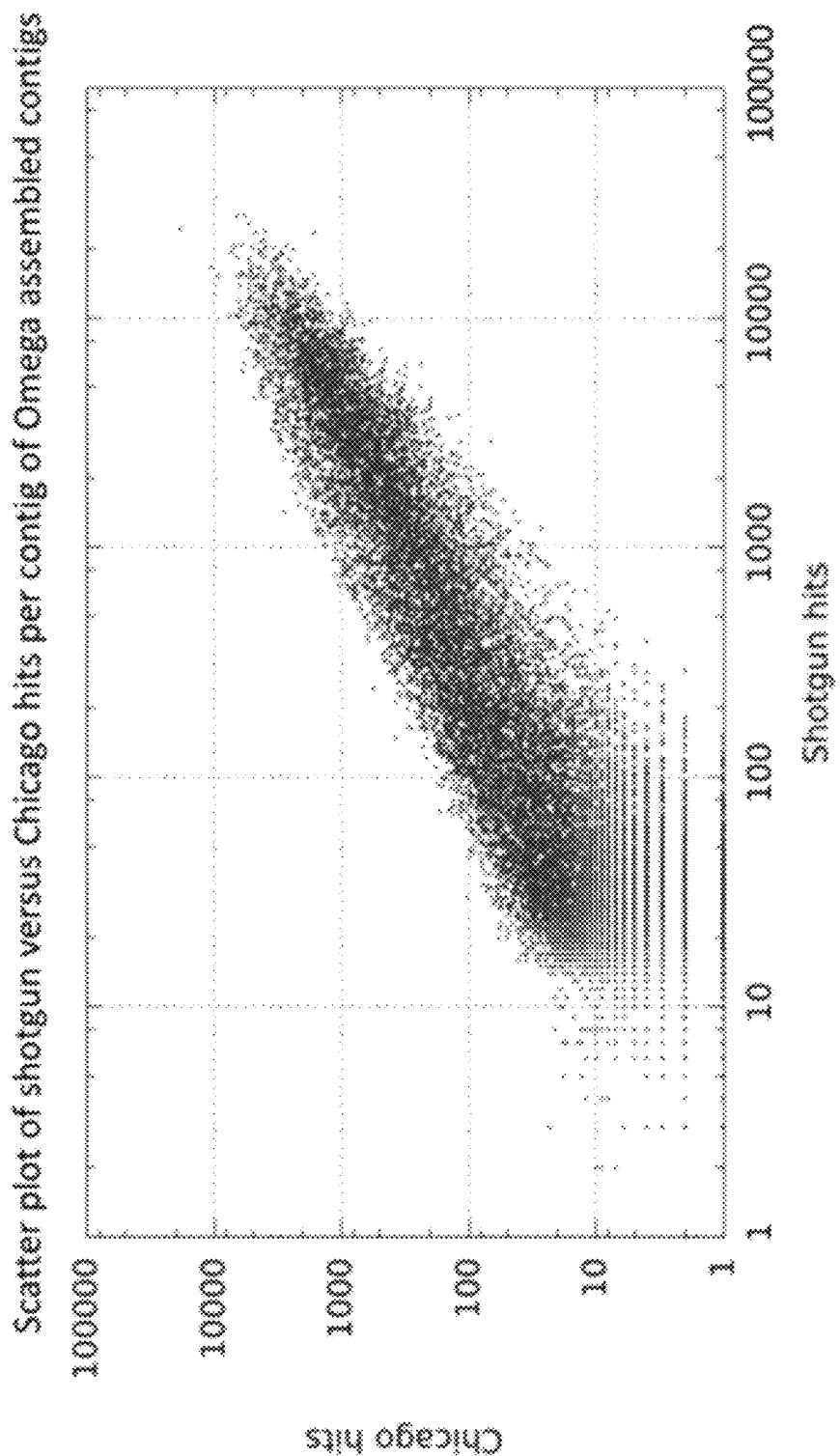
FIG. 16 shows a scatter plot of hits from a library prepared for shotgun sequencing and a library prepared using in vitro assembled chromatin aggregates.
Figure 17:
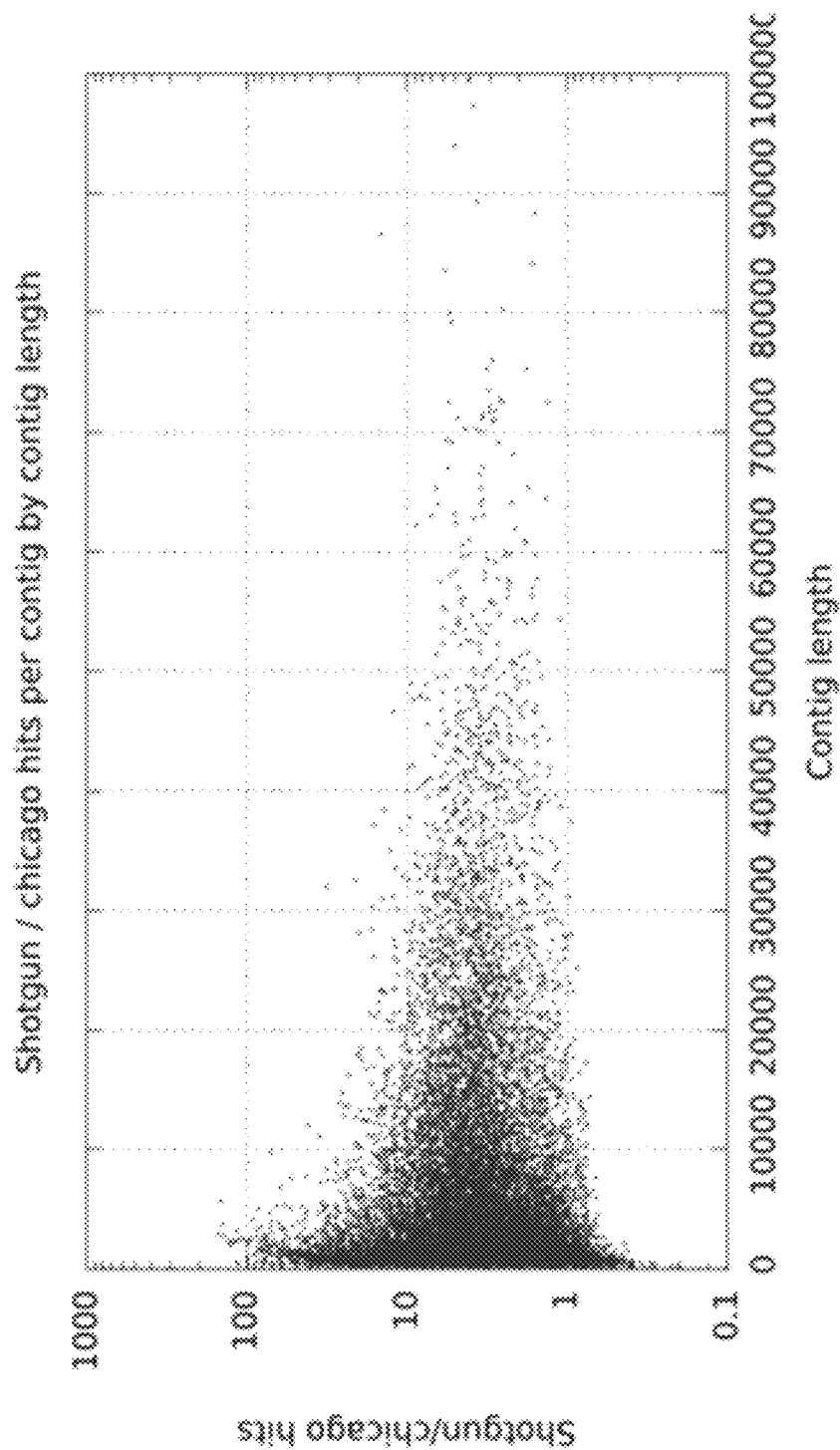
FIG. 17 shows a scatter plot of shotgun hits/in vitro assembled chromatin hits per contig by contig length.

FIG. 16 and FIG. 17 show a comparison of the hit coverage using two methods of library of preparation. FIG. 16 shows a scatter plot of hits from a library prepared for shotgun sequencing versus a library prepared using in vitro assembled chromatin aggregates ("Chicago"). FIG. 17 shows a scatter plot of shotgun hits/in vitro assembled chromatin hits ("Chicago") per contig by contig length. The reads were analyzed with HiRise software which applies a likelihood model to build scaffolds and also breaks input scaffolds which appear to be incorrect. The final scaffold N50 is about 53.4 kb compared to 15.7 kb in the Omega output.

Example 19. Detection and Sequencing of an Unknown Pathogen in a Human Population De novo genome assembly of read data from fecal samples is used to identify an unknown pathogen in a subject. As international health improves, it is becoming increasingly common to find outbreaks of diseases having no known cause or pathogen source. Efforts to isolate a pathogen re often time consuming and challenging, because the pathogen is difficult to isolate or culture.

Fecal specimens and/or urine specimens are collected from suspected or confirmed patients suffering from an unknown ailment. DNA for fecal metagenomic assembly is prepared with the fecal DNA extraction methods, such as the MetaHIT (Metagenomics of the Human Intestinal Tract) method or HMP (Human Microbiome Project) method, fecal DNA extraction kits, such as a MoBio Powerfecal kit from MO BIO, QIAmp DNA Stool Mini Kit from Qiagen, or ZR Fecal DNA MiniPrep kit from Zymo Research. DNA from urine is extracted with DNA extraction methods or DNA extract kits such as QIAamp DNA Micro Kit from Qiagen; i-genomic Urine DNA Extraction Mini Kit from Intron Biotechnology; ZR Urine DNA Isolation Kit from Zymo Research; Norgen RNA/DNA/Protein Purification Kit from Norgen Biotek; and Abcam Urine Isolation Kit from Abcam.

A library is prepared with in vitro assembled chromatin aggregates and 500 ng of DNA from a fecal DNA sample or a urine DNA. Chromatin is reconstituted in vitro upon naked DNA from the fecal or urine sample, and the chromatin and DNA are fixed with formaldehyde to form chromatin aggregates. The fixed chromatin is digested with a restriction enzyme to generate free sticky ends. The free ends are filled in with biotinylated and thiolated nucleotides, and the free blunt ends are then ligated. The cross-links are reversed and the chromatin associated proteins are removed to yield library fragments. The library is sequenced and the read pairs are assembled.

De novo genome assembly of read data from fecal samples is then used to identify nucleic acid molecules that correspond to ill or diseased individuals in a subject population. The nucleic acid information is assembled into genome-sized contigs so that sequence information is grouped into chromosome or genome-sized units.

Genomes corresponding to organisms likely to be present in healthy individuals are de-emphasized in analysis. Genomes corresponding to organisms likely to be opportunistically more abundant in individuals demonstrating symptoms of the disorder are also de-emphasized in analysis.

A genome corresponding to a previously uncharacterized organism is identified. The genome is analyzed to determine metabolic pathways encoded therein, and a culture regimen is designed to facilitate host-independent culturing of the microbe having the genome. Analysis of metabolic pathways is continued to identify potential drug targets that selectively block microbial replication. The drug targets are tested on the microbial cultures generated in light of the genomic information generated herein, and are shown to block replication. The drugs are administered to individuals demonstrating symptoms of the outbreak, and the drug treatment is demonstrated to alleviate symptoms.

Example 20. Detection and Sequencing of an Unknown Pathogen in a Human Population Using Shotgun Sequencing De novo shotgun sequencing of read data from fecal samples is used to identify genomic sequence of an unknown pathogen in a subject. Nucleic acids are isolated as in the example above, and are subjected to shotgun sequencing only.

Sequencing reads corresponding to known and unknown microbes are identified. It is determined that an unknown organism or organisms are present in individuals suffering from the ailment. Metabolic pathway information cannot be determined, however, and the shotgun sequence information does not provide insight as to how the microbe may be cultured or which drugs may be useful in blocking growth or proliferation of the microbe in a human host. No treatment regimen is suggested from the results.

Example 21. Detection of an Antibiotic Resistance Gene in a Patient

A patient suffers from an infection that is resistant to antibiotic treatment. A stool sample from the patient is obtained, and nucleic acids are extracted from the sample.

The nucleic acids are subjected to shotgun sequence analysis, and a number of sequence reads are generated. Some individual sequence reads are sufficiently long to allow them to be mapped with confidence to putative host organisms. Some reads map to putative antibiotic resistance loci, and it is suspected that nucleic acids encoding gene products conveying antibiotic resistance are present in the patient.

The sequence information is not sufficient to allow the determination of which antibiotic resistance loci map to which host microbes.

Example 22. Detection of an Antibiotic Resistance Gene Host in a Patient

A patient suffers from an infection that is resistant to multiple antibiotic treatment. A stool sample from the patient is obtained, and nucleic acids are extracted from the sample.

The nucleic acids are subjected to shotgun sequence analysis, and a number of sequence reads are generated. Some individual sequence reads are sufficiently long to allow them to be mapped with confidence to putative host organisms. Some reads map to putative antibiotic resistance loci, and it is suspected that nucleic acids encoding gene products conveying antibiotic resistance are present in the patient.

The nucleic acids are subjected to analysis as disclosed herein. Linkage information is determined such that nucleic acid sequence arising from a common nucleic acid molecule relative to the antibiotic resistance genes is determined. The shotgun sequence information is assembled into contigs corresponding to microbial genomes.

It is determined that multiple antibiotic resistance genes map to a single microbial host. It is also determined that the microbial host of the antibiotic resistance genes is likely to be vulnerable to a previously unadministered antibiotic based upon analysis of the metabolic pathways present and absent from the assembled microbial genome.

The patient is administered the previously unadministered antibiotic, and the infection symptoms are alleviated.

Example 23. Detection of an Antibiotic Resistance Gene Host in a Patient

A patient suffers from an infection that is resistant to treatment of multiple antibiotics administered in series. A stool sample from the patient is obtained, and nucleic acids are extracted from the sample.

The nucleic acids are subjected to shotgun sequence analysis, and a number of sequence reads are generated.

Some individual sequence reads are sufficiently long to allow them to be mapped with confidence to putative host organisms. Some reads map to putative antibiotic resistance loci, and it is suspected that nucleic acids encoding gene products conveying antibiotic resistance are present in the patient.

The nucleic acids are subjected to analysis as disclosed herein. Linkage information is determined such that nucleic acid sequence arising from a common nucleic acid molecule relative to the antibiotic resistance genes is determined. The shotgun sequence information is assembled into contigs corresponding to microbial genomes.

It is determined that multiple antibiotic resistance genes map to a multiple microbial hosts, and that no microbial host possesses more than one microbial resistance gene.

The patient is administered the previously administered antibiotic treatment, but the antibiotics are administered in parallel rather than in series. That is, the antibiotics that were previously found to be ineffective when administered on at a time are administered concurrently and the infection symptoms are alleviated.

Example 24. Detection of an Individuals' Sequence in a Heterogeneous Sample

An individual of interest is sought. The individual's genome information is reasonably inferred from nucleic acid samples provided by the individual's parents. A SNP (single nucleotide polymorphism) pattern expected in the individual is determined. The SNP pattern on a given chromosome comprises a number of SNPs that are individually common but which, collectively, are unlikely to occur in combination in any single individual.

The individual is suspected to have been present at a location. The location is investigated and a heterogeneous DNA sample is obtained from the location. The DNA is subjected to shotgun sequencing, and a large number of reads are determined. Each SNP expected to be present in the individual of interest's genome are identified. However, linkage information among the SNPs is unavailable, and investigators are unable to determine whether the SNPs detected arise from a single individual or correspond to a single nucleic acid molecule.

Example 25. Detection of an Individuals' Genomic Signature in a Heterogeneous Sample An individual of interest is sought as in Example 24, above. The DNA is subjected to shotgun sequencing, and a large number of reads are determined. Each SNP expected to be present in the individual of interest's genome are identified.

A second sample of the heterogeneous DNA obtained from the site is subjected to analysis as disclosed herein. Sequence reads spanning the SNPs of interest are identified, and mapped to specific nucleic acid molecules along with other reads that share common tag information. Phase information for SNPs is determined, and it is determined that an individual having the SNP pattern predicted for the individual of interested was recently at the location investigated.

Concurrently, SNP patterns for other individuals at the location are determined based upon the shotgun and linkage information derived from the heterogeneous DNA sample obtained from the site.

Example 26. Novel Organism Assay

A termite known to harbor a gut biome of interest is selected for sequencing. The termite is known to lack genes encoding enzymes necessary for the degradation of wood. It is suspected that the gut of the termite harbors a microbe or microbes that alone or in combination encode the enzymes necessary to metabolize cellulose.

Nucleic acids are obtained from a termite population and are subjected to shotgun sequencing. Isolated reads are obtained indicative of a capacity to metabolize cellulose. However, the sequence reads cannot be assembled into higher-order scaffolds so as to identify the number or identity of organisms inhabiting the termite gut.

Example 27. Novel Organism Discovery

A termite known to harbor a gut biome of interest is selected for sequencing. The termite is known to lack genes encoding enzymes necessary for the degradation of wood. It is suspected that the gut of the termite harbors a microbe or microbes that alone or in combination encode the enzymes necessary to metabolize cellulose.

Nucleic acids are obtained from a termite population and are subjected to shotgun sequencing as in Example 16, above, while a second sample of the same nucleic acids is subjected to analysis using the methods disclosed herein. The shotgun sequence reads are mapped to distinct clusters corresponding to substantially complete genomes of a number of distinct organisms, including anaerobic bacteria and novel alveolate species.

Analysis of the genomes generated hereby indicates that at least some of the genomes lack biosynthetic pathways necessary for the organisms to be cultured aerobically or in the absence of complex metabolite combinations produced by other members of the gut microflora. Thus, genomes are determined for organisms that are previously unknown and that are unlikely to be culturable using standard approaches.

Example 28. Spike-In Experiment in Fecal Metagenomics Assembly

De novo assembly of genomes from complex metagenomics communities presents a special challenge Unlike typical de novo assembly projects of single organisms, the input DNA is derived from up to hundreds or thousands or more of unrelated organisms of wildly varying abundances. Additionally, individual species may be represented in different strains with small or large allelic variation. We describe a new approach to whole-genome metagenomics assembly that leverages the long-range contact information available by proximity ligation. We perform a set of control experiments wherein we add DNA from a bacterial species whose genome is well-characterized, *Streptomyces coelicolor*, but is absent from fecal samples. We prepare two libraries: a standard, short-insert shotgun library and a proximity-ligation library and sequence both. Using these data, we show it is possible to generate a complete assembly of the known genome of *Streptomyces coelicolor*. Thus, using this approach it is possible to accurately reconstruct the genomes of microbes from complex metagenomics samples.

Figure 18:
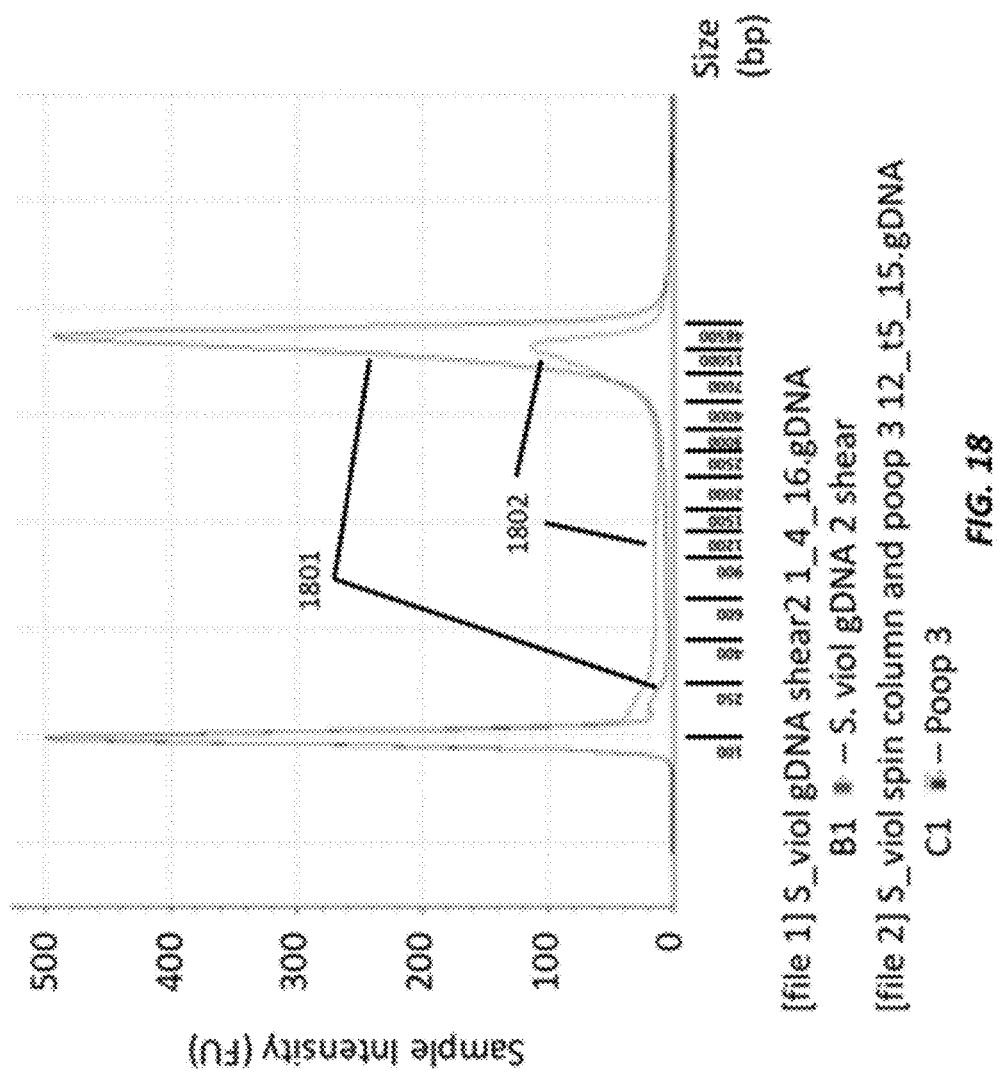
FIG. 18 Shows a TapeStation trace indicating fragment size distribution in the fecal DNA preparation (blue, spiking near the top of the y-axis at 100 and 15000 bp on the x axis) and the *Streptomyces coelicolor* DNA (green, spiking at a sample intensity of 100 at 15000 bp) were of similar lengths.

DNA Collection:

Using the MoBio PowerFecal collection kit, according to protocol, we collected 2 micrograms of DNA from a 250 mg fecal sample. We ordered from ATCC a genomic DNA prep from *Streptomyces coelicolor*. To mimic the size distribution of DNA fragments after PowerFecal purification, we ran the *Streptomyces coelicolor* DNA through the spin-column supplied in the PowerFecal kit. As shown in FIG. 18 in the TapeStation trace, the fragment size distribution in the fecal DNA preparation (1801, blue, spiking near the top of the y-axis at 100 and 15000 bp on the x axis) and the *Streptomyces coelicolor* DNA (1802, green, spiking at a sample intensity of 100 at 15000 bp) were of similar lengths. The x-axis shows size in bp, with marks from left to right of 100, 250, 400, 600, 900, 1200, 1500, 2000, 2500, 3000, 4000, 7000, 15000, and 48500. The y-axis shows sample intensity in fluorescence units (FU).

Preparation of Sequencing Libraries:

We prepared three mixes of fecal DNA with *Streptomyces coelicolor* added in a 1%, 5%, and 10% of the total. This is meant to approximate the difficulty of correctly assembling a genome when it comprises 1%, 5%, and 10% of a total metagenomics sample. For each mix, we prepared an Illumina shotgun library and a proximity-ligation library using in vitro reconstituted chromatin as described previously (Putnam et al. Genome Research, 2016). We then sequenced these libraries on the Illumina MySeq sequencer.

Figure 19:
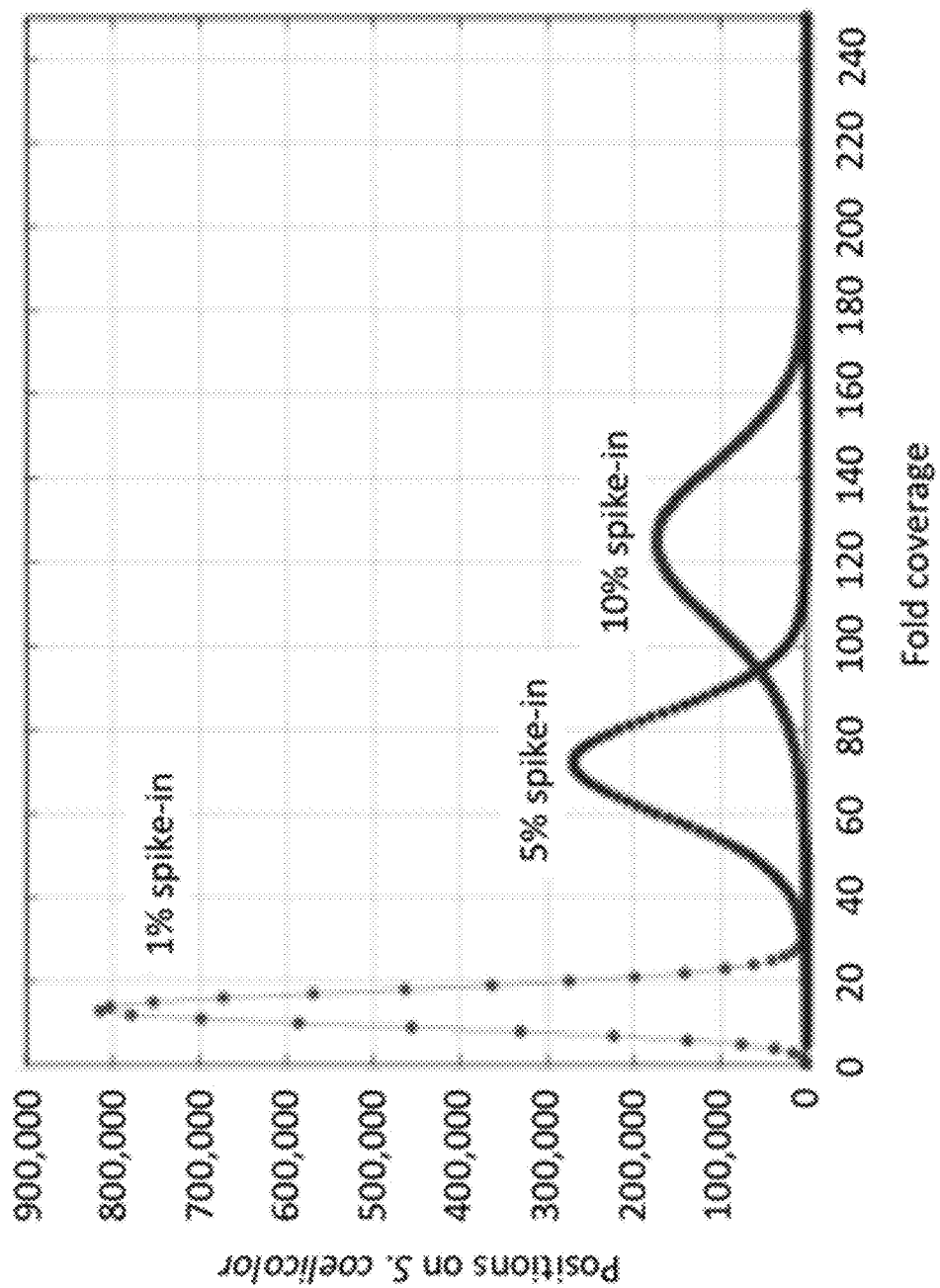
FIG. 19 shows the fold-coverage distribution in these shotgun data for each level of spiked-in *Streptomyces coelicolor* DNA.

Analysis of shotgun reads and contig assembly: We assessed the coverage of the *Streptomyces coelicolor* genome in the shotgun data by aligning the shotgun reads to the known genome sequence of *Streptomyces coelicolor* (GenBank ID: NC_003888.3). Shown in FIG. 19 is the fold-coverage distribution in these shotgun data for each level of spiked-in *Streptomyces coelicolor* DNA. The x-axis shows fold coverage, and the y-axis shows the number of positions on *S. coelicolor*. As shown, the fold genome coverage of the 1% spike-in (left-most peak) experiment (13-fold median) is not high-enough to support accurate contig assembly which typically requires at least 30-fold genome coverage. On the other hand, the 5% (middle peak) and 10% (right-most peak) spike-in experiments are not likely to be coverage-limited for contig assembly.

Figure 20:
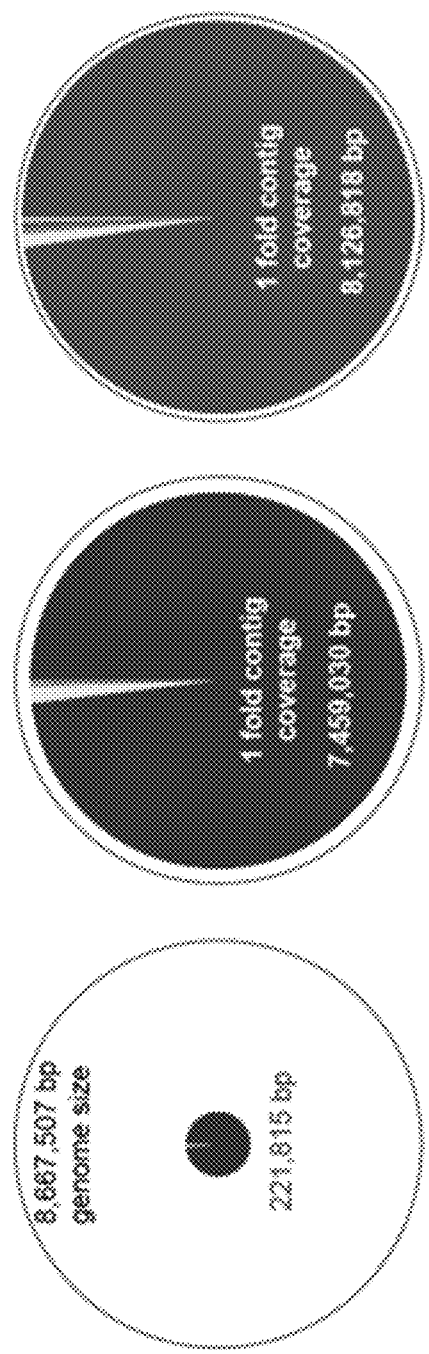
FIG. 20 shows the total amount of the *Streptomyces coelicolor* genome present as contigs for the 1% (red, left) 5% (green, center) and 10% (blue, right) shotgun datasets.

We used Omega (Haider et al, 2014 *Bioinformatics*) to assemble contigs for each dataset. We then mapped these contigs to the known genome sequence of *Streptomyces coelicolor* to assess the completeness and fragmentation of assembly in these data. Shown in FIG. 20 is the total amount of the *Streptomyces coelicolor* genome present as contigs for the 1% (red, left) 5% (green, center) and 10% (blue, right) shotgun datasets. The outer black circle surrounding each is proportional to the total genome size of *Streptomyces coelicolor*. As expected, the 1% spike-in experiment failed to assemble much of the genome into contigs, whereas the 5% and 10% experiment assembled most of the genome into contigs. The total number of contigs for each experiment is given in Table 2.

TABLE 2

Total number of contigs.

| Experiment | Total number of contigs of Streptomyces coelicolor | Total contigs in the OMEGA assembly |
|---|---|---|
| 1% | 297 | 24,333 |
| 5% | 2,647 | 26,567 |
| 10% | 1,524 | 25,347 |

These results are typical for some approaches to de novo assembly from metagenomics: most of the constituent genomes can be assembled into small contigs. In a typical case, one would not know, for example, that the 1,524 contigs in the 10% spike-in experiment are all from *Streptomyces coelicolor*.

Figure 21:
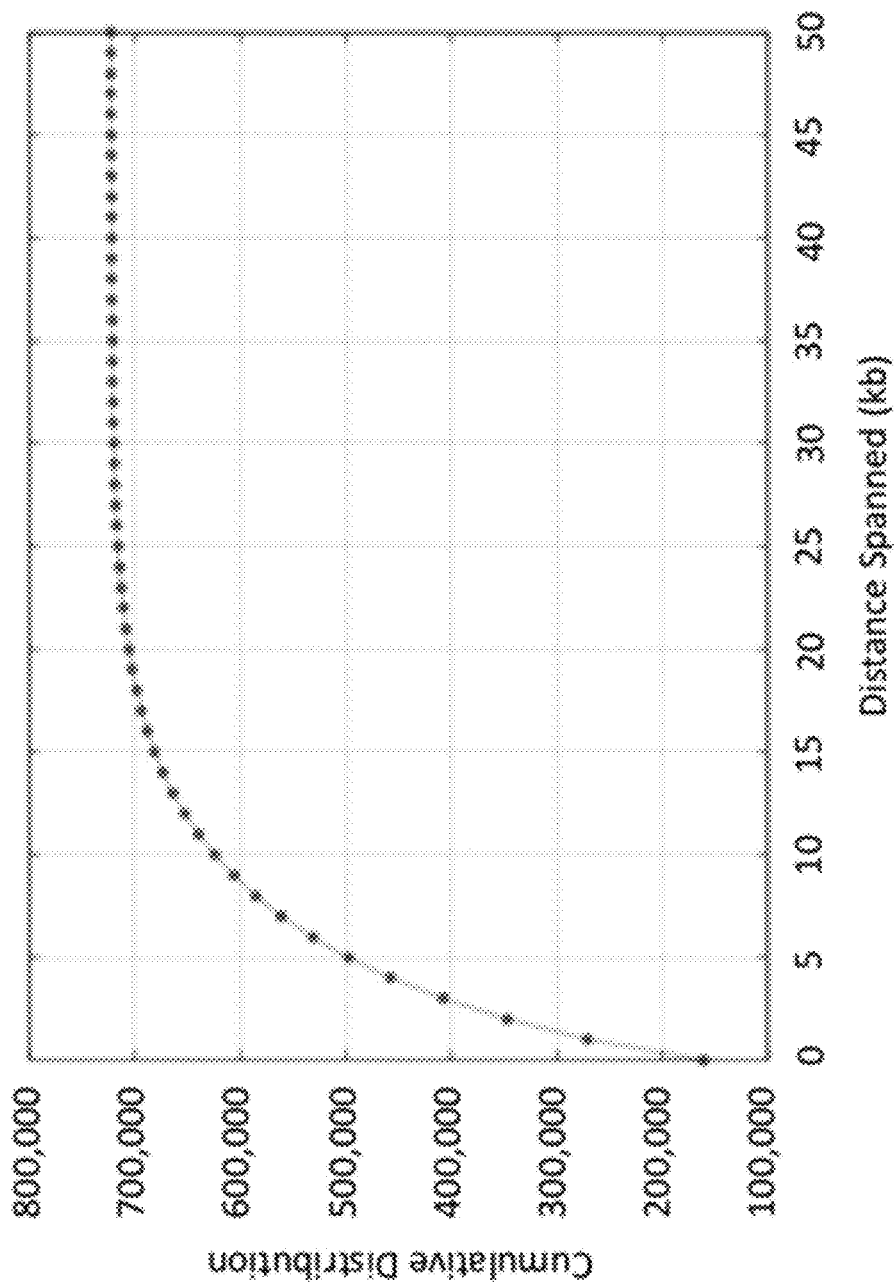
FIG. 21 shows the read pairs from the proximity ligation libraries mapped to the known genome sequence of *Streptomyces coelicolor*; the x-axis shows the distance spanned in kilobase units and the y-axis is a cumulative distribution over all read-pairs.

Assessment of Linkage Information in the Proximity-Ligation Library:

To determine if the proximity ligation libraries contain information useful for correctly scaffolding these contigs, we mapped the read pairs from these libraries to the known genome sequence of *Streptomyces coelicolor*. See FIG. 21, which shows the distance spanned by each read pair, where the x-axis shows the distance spanned in kilobase (kb) units and the y-axis is a cumulative distribution over all read-pairs. As is typical for a proximity-ligation library, the distance-spanned by read pairs covers all distances out to the size of the input DNA fragments used to generate the library. This indicates that the in vitro proximity ligation library preparation worked, even for these bacterial DNA preps and contains information useful for genome scaffolding and assembly.

Genome Scaffolding:

We used the proximity ligation library data to scaffold all the contigs. Then, we assessed the scaffolding accuracy and completeness by identifying genome scaffolds that correspond to *Streptomyces coelicolor* in the 5% and 10% experiments where there are contigs that represent most of the *Streptomyces coelicolor* genome. Note that scaffolding of *Streptomyces coelicolor* in the 1% experiment is not possible under the parameters chosen for this experiment because there is too little contig coverage to be scaffolded. Alternative parameters may yield separate results. Note also that generating more shotgun data for any of these experiments is likely to increase the contig coverage for all genomes present, including *Streptomyces coelicolor*.

Figure 22A:
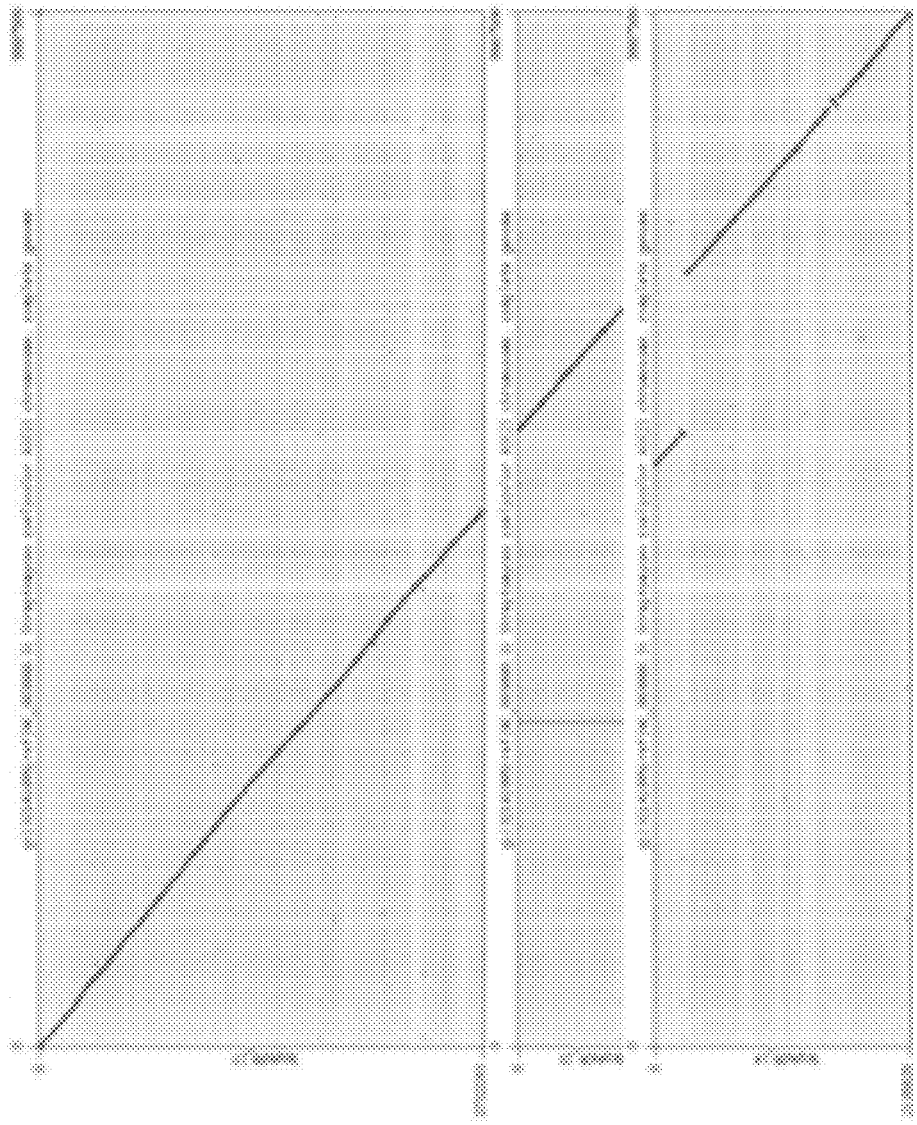
FIG. 22A depicts a dot-plot of the known *Streptomyces coelicolor* genome (x-axis) versus three scaffolds generated as described here in the 5% experiment.
Figure 22B:
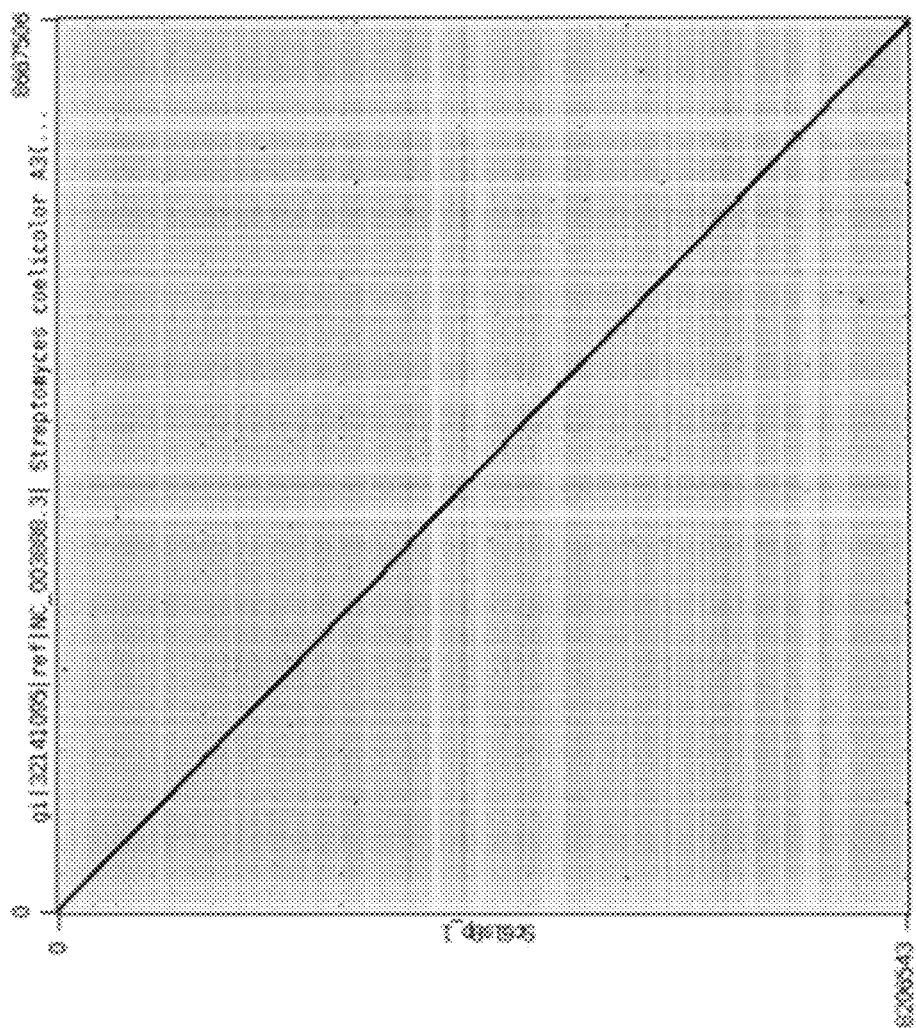
FIG. 22B depicts a dot-plot of the known *Streptomyces coelicolor* genome (x-axis) versus the one scaffold generated as described here in the 10% experiment.

Shown in FIG. 22A and FIG. 22B are the scaffolds that represent the *Streptomyces coelicolor* in the 5% and 10% experiments. FIG. 22A depicts a Dot-plot of the known *Streptomyces coelicolor* genome (x-axis) versus three scaffolds generated as described here in the 5% experiment. In the 5% experiment, the *Streptomyces coelicolor* is present in 3 large scaffolds as opposed to 2,647 contigs before scaffolding with the proximity-ligation data. FIG. 22B depicts a dot-plot of the known *Streptomyces coelicolor* genome (x-axis) versus the one scaffold generated as described here in the 10% experiment. In the 10% experiment, the *Streptomyces coelicolor* genome is present in 1 large scaffold.

Example 29. Human Fecal DNA

A series of experiments were conducted to assess the approach to de novo metagenome sequencing and assembly described above. Shotgun and "Chicago" in vitro proximity ligation libraries were generated from human fecal DNA extracts, and "HiRise" de novo contig assembly and scaffolding were performed. These proof-of-concept experiments were designed to determine: (1) how to quickly and reliably extract DNA of high-molecular weight from fecal samples; (2) how to use the Chicago laboratory protocol to generate in vitro chromatin proximity ligation libraries from DNA recovered from fecal samples, which is primarily from prokaryotic organisms; (3) if Chicago data can be used to effectively scaffold metagenomics contigs from the same DNA prep; (4) if a known genome whose DNA is spiked into a metagenomics sample, and thus is processed the same way, can be reliably assembled; and (5) in what ways the HiRise genome assembly strategy may be adapted for the special challenges of metagenomics assembly.

Figures 23A, 23B:
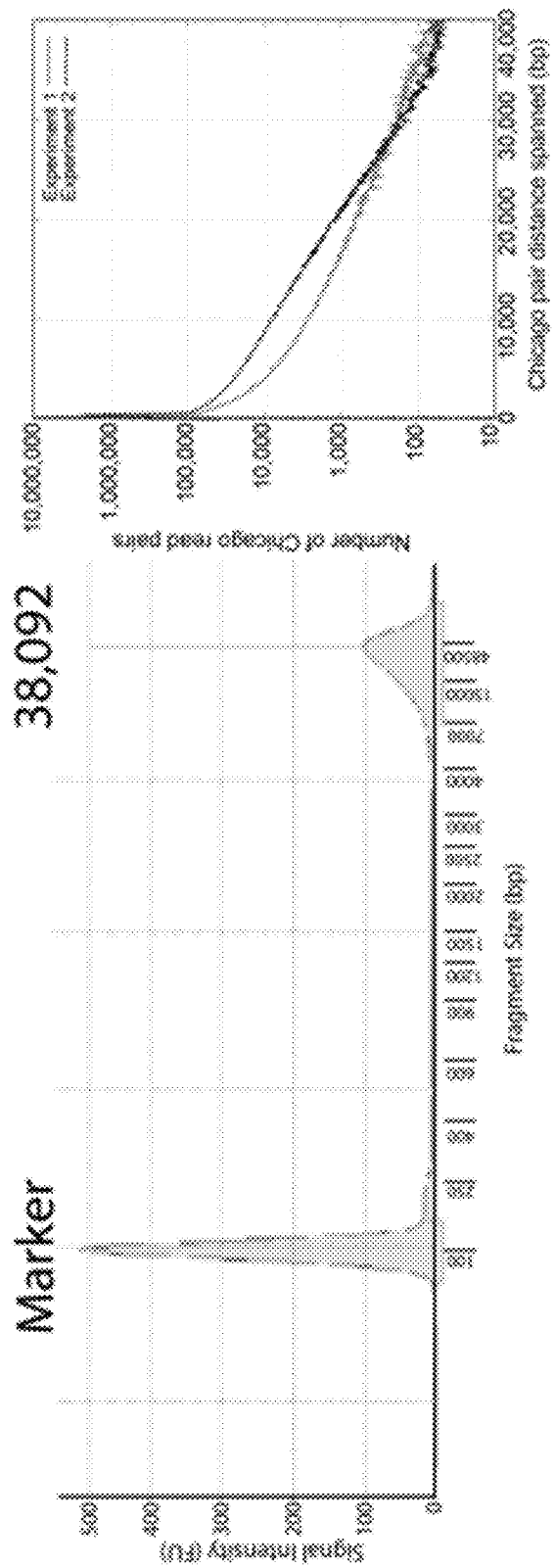
FIG. 23A depicts a graph of DNA fragment size from a fecal DNA prep kit.
FIG. 23B depicts a graph of the number of read pairs versus read pair distance spanned.

Several commercially available kits were tested for DNA extraction from fecal DNA. The Qiagen fecal DNA kit consistently yielded DNA of 30-40 kilobases, the longest of any tested kit, with few shorter fragments (see FIG. 23A, where DNA fragment size from a Qiagen Fecal prep kit used to collect DNA from a healthy donor is shown to be a single mode distribution, with most fragments between 30 and 40 kb). Following assembly (described below), the proximity ligation libraries were assessed by mapping the reads against several of our largest assembly scaffolds and measuring the distribution of inferred distances between proximity ligation events (see FIG. 23B, where after assembly and scaffolding, Chicago pairs from this library (Experiment 2, shown in dashed lines) were mapped to the scaffolds). In a typical Chicago library, read pairs can span distances up to the size of the input DNA. This analysis can be part of the standard quality-control procedure for "Chicago" libraries in a pipeline, and can provide an effective assessment of the distribution of proximity ligation products in a standard Chicago library. Note that this analysis can require a genome assembly against which the reads can be mapped. For this analysis, a metagenomic version of HiRise was used to scaffold these data, modified for metagenomics data as described below. From this analysis it can be shown that the Chicago procedure performs as expected for at least some fraction of the DNA in fecal samples.

Also tested was the ability to accurately assemble the genome of a prokaryotic organism when it is a known component of a mixture, present at low abundance. In this experiment, DNA from *Streptomyces coelicolor* was used, whose complete genome is known. DNA from *S. coelicolor* was added to a fecal DNA prep such that it was 1% of the total DNA mass. Importantly, the input *S. coelicolor* DNA was fragmented to a size comparable to the fecal DNA by running it through the Qiagen column used in the fecal prep. In this experiment, a single scaffold of 7.68 Mb was recovered, comprising 89% of the 8.67 Mb *S. coelicolor* genome. This single scaffold (see FIG. 24) is devoid of any large structural differences versus the known genome. The *S. coelicolor* genome is on the x-axis and the scaffold generated herein is along the y-axis. Because the new scaffold does not begin at the same start point as the reference sequence, the dotplot wraps. Note that the assembly is without mis-joins and nearly complete. The "missing" segment is a single region that is itself assembled nearly completely as another large scaffold, and the two scaffolds provide a nearly complete assembly of *S. coelicolor*. From this analysis, it is shown that this assembly strategy can accurately scaffold a known genome, even when it is a minor component of the overall community −1% in this test case.

Given the correct and nearly complete assembly of the spike-in, next assessed was the contiguity of the assemblies before and after scaffolding. For the contig assembly step, a version of the Meraculous assembler was used, modified to allow a broad range of coverage as is expected in metagenomic data. Other metagenome assemblers were also successfully used (not shown). Then the contigs were scaffolded using a metagenomics version of HiRise (meta-HiRise) that relaxes assumptions about coverage uniformity across scaffolds made in standard HiRise approaches.

For this analysis, a metric called Metagenomics Community N50 (MGC N50) was employed, which is calculated by (1) ordering scaffolds, from largest to smallest, and (2) mapping shotgun reads to all scaffolds. The MGC N50 is the size of the scaffold at which a cumulative count of all shotgun reads reaches 50% of the total. Under the assumption that the shotgun reads represent a census of the community abundance of each OTU, this metric describes the overall contiguity of a metagenome assembly as it relates to the abundance of OTUs present in the sample. Note that if less than 50% of reads can be reliably mapped to the assembly then the MGC N50 is undefined. With the data collected herein, improvements in MGC N50 ranging from 1.5-25 fold were achieved. Furthermore, in each experiment, several multi-megabase scaffolds were generated.

These results show that the in vitro chromatin assembly framework disclosed herein for efficiently generating long-range contiguity information is applicable in a metagenomic context. This procedure can require about 1 microgram of high molecular weight DNA. This amount can be reliably extracted from normal fecal samples using standard, commercial fecal DNA prep kits. This DNA is suitable for the in vitro chromatin assembly methods employed herein. The proximity ligation libraries generated can be used to accurately scaffold genomes in metagenomic samples as shown from the spike-in positive control experiment with *S. coelicolor*.

Example 30. Minimization of Representational Bias

As disclosed herein, it has been shown that the Chicago protocol can be used with DNA from fecal samples as input. Exemplary approaches to expand upon the protocol are discussed herein.

Figure 25:
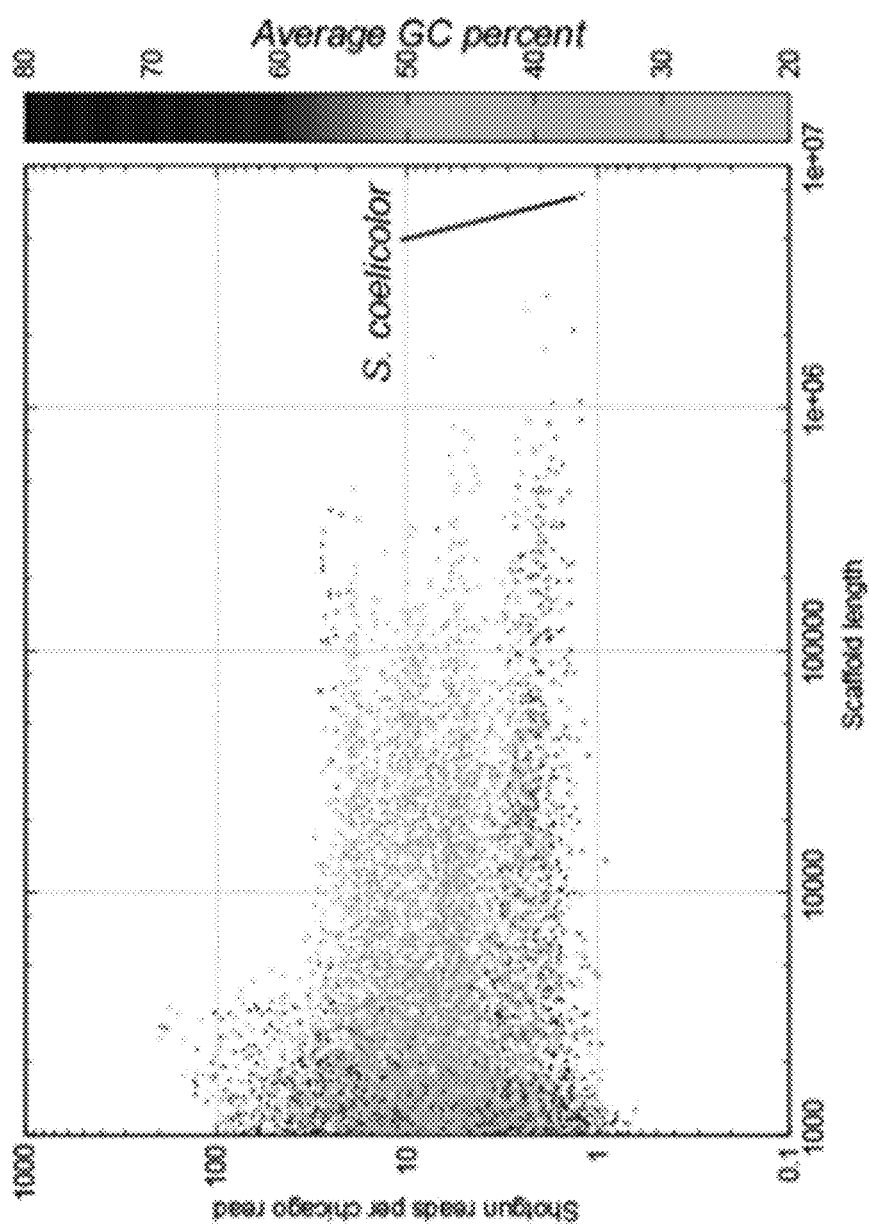
FIG. 25 depicts an exemplary plot of the ratio of read coverage in Chicago assembly data versus shotgun data in a spike-in experiment.

The Chicago protocol can rely on digestion of in vitro chromatin aggregates with a specific restriction enzyme, MboI, whose cut site is GATC. The protocol can be modified to use other restriction enzymes, such a methylation insensitive isoschizomer of MboI (e.g., DpnII). Varying base composition of the metagenomic community members can result in uneven cutting and therefore uneven representation in assembly libraries. FIG. 25 shows an exemplary plot of the ratio of read coverage in Chicago assembly data versus shotgun data in a spike-in experiment. As shown in FIG. 25, shotgun coverage per basepair of scaffold is taken to be proportional to the abundance in the sample. The ratio of shotgun coverage to Chicago coverage varies over about one order of magnitude. Large scaffolds are produced in many cases even when this ratio is low. This ratio ranges over ten-fold for most scaffold lengths. Note that scaffolds with intermediate GC fractions have intermediate levels of Chicago coverage, consistent with base composition being a factor in Chicago library efficiency on a per OTU basis. To reduce this bias, various strategies can be employed.

Test Use of a Combination of Restriction Enzymes:

For projects with extremely high A/T content, an alternate restriction enzyme can be used whose restriction site is more A/T rich that MboI (GATC). Metagenomic communities have genomes with a wide variety of G/C content; thus a single restriction enzyme may not be ideal for producing efficient Chicago library generation for all community OTUs. A combination of enzymes can be employed in Chicago library prep with diverse fecal samples.

Adapt a Restriction Enzyme-Free Protocol for Metagenomics Use:

Restriction enzyme-free protocols can also be employed for Chicago libraries. Such methods can employ a nuclease that cuts DNA in a sequence-independent manner A biotinylated adapter, for example, is then used to bridge the blunt ends and to mark ligated regions.

Example 31. Metagenome Assembly Software Platform

A two-step process was used to analyze data. First, paired-end fragment shotgun data were assembled into scaffolds using ad hoc modifications to Meraculous. These assembled sequences, plus Chicago data from the same sample, were used as input to HiRise. For these experiments, both Meraculous and HiRise were modified ad hoc to allow for (1) varying sequence coverage (i.e., abundance) in scaffolds representing different species, and (2) inter-strain polymorphism within species. Experiments with other metagenome assemblers (e.g., Omega and metaSpades) did not provide substantial improvement over the modified Meraculous for the first stage (not shown). HiRise was originally developed for diploid genome assembly and thus assumes uniform Chicago and shotgun coverage. This feature was modified for metagenomes in the scaffolding step. Remarkable scaffold sizes were achievable with the Chicago data by this assembly methodology. These two steps can also be integrated for improved assemblies and separate assembly of divergent strains.

Improved Assembly of Polymorphic Regions:

In the spike-in control experiment, the longest scaffold was from *S. coelicolor* (a 1% spike-in) despite that fact that many other OTUs were present in higher abundance in the fecal sample. Importantly, we note that the (clonal) spike-in control was categorically different from the other OTUs present in that it had no strain variation. Thus, an effective method for detecting and assembling through strain variation can improve species-level contiguity.

The original Meraculous algorithm was designed for assembling diploid genomes. In that setting, polymorphism appears as two allelic variants of equal frequency, such that their sum is the (uniform) depth of coverage of the diploid genome. These allelic variants can easily be differentiated from sequencing error, which occurs at a low level (e.g., <1% in Illumina data). In contrast, in a metagenome (1) haplotypes can occur at differing frequencies depending on strain abundance; (2) total depth across all haplotypes of a strain represents the abundance of the species, which varies from species-to-species (and therefore scaffold-to-scaffold); and (3) in very abundant species, even low error rates can produce recurrent errors that can be easily confused for bona fide variants.

Thus for metagenomes, Meraculous can be adapted to (1) allow for haplotypes of differing frequency (appearing as forks in a deBruijn graph), (2) allow depth to be a local rather than global constraint, and (3) filter errors relative to local depth, rather than with a global cutoff. These changes can be made to the open-source Meraculous code, and empirically validated with test data generated with spike-ins of two or more closely related strains. There is an element of self-consistency to these adjustments to Meraculous, as local depth (abundance of each species) can be learned from the data. These approaches can be tested for a variety of fecal samples to ensure that our algorithms are robust.

As shown in FIG. 15A and FIG. 15B, preliminary assemblies indicate that Chicago data contain residual unexploited information for further scaffolding. For example, the current assembly strategy can generate many unlinked scaffolds with similar GC content and depths of coverage that are more likely to represent scaffolds form the same species than scaffolds with widely differing GC content or depth. Grouping these scaffolds in an ad hoc manner is the basis of the original binning strategies, which can be thought of as hypotheses for further linkages.

Figure 26A:
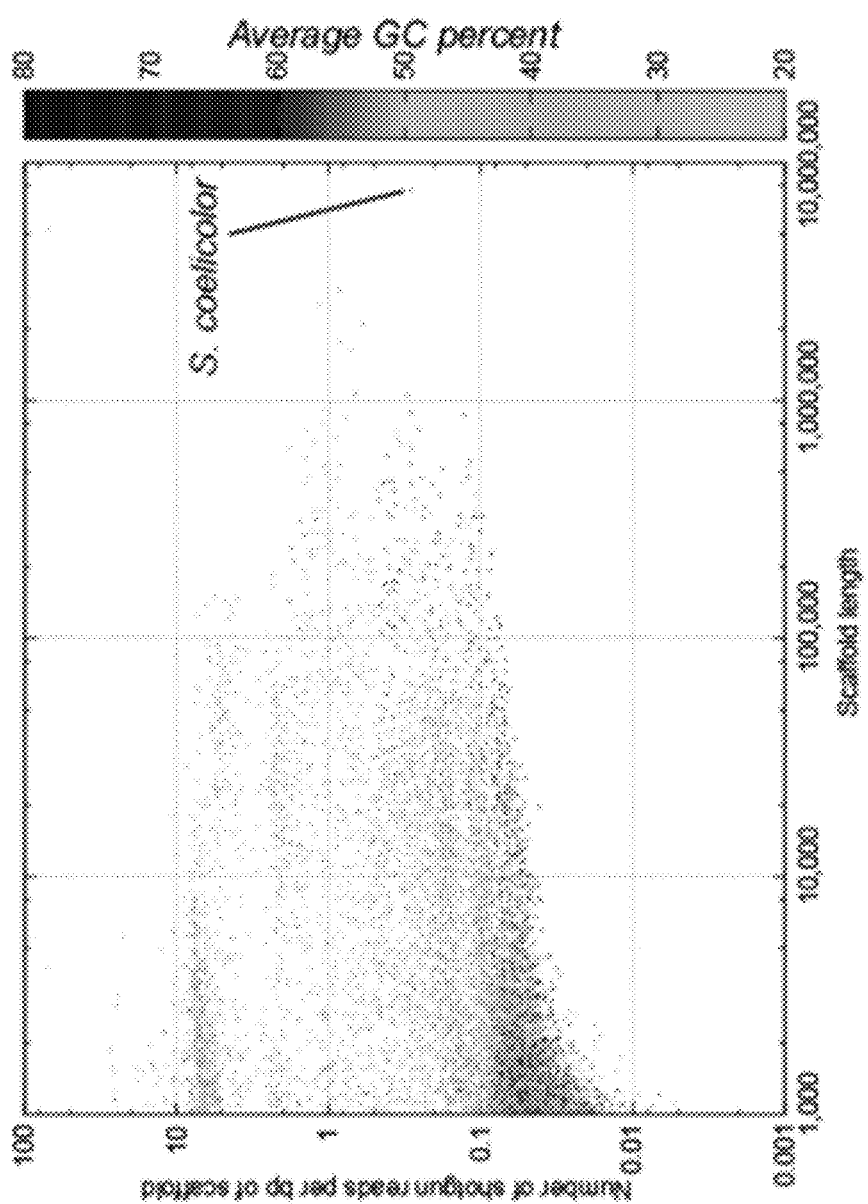
FIG. 26A depicts a graph of coverage depth and GC content for scaffolds in a spike-in experiment.
Figure 26B:
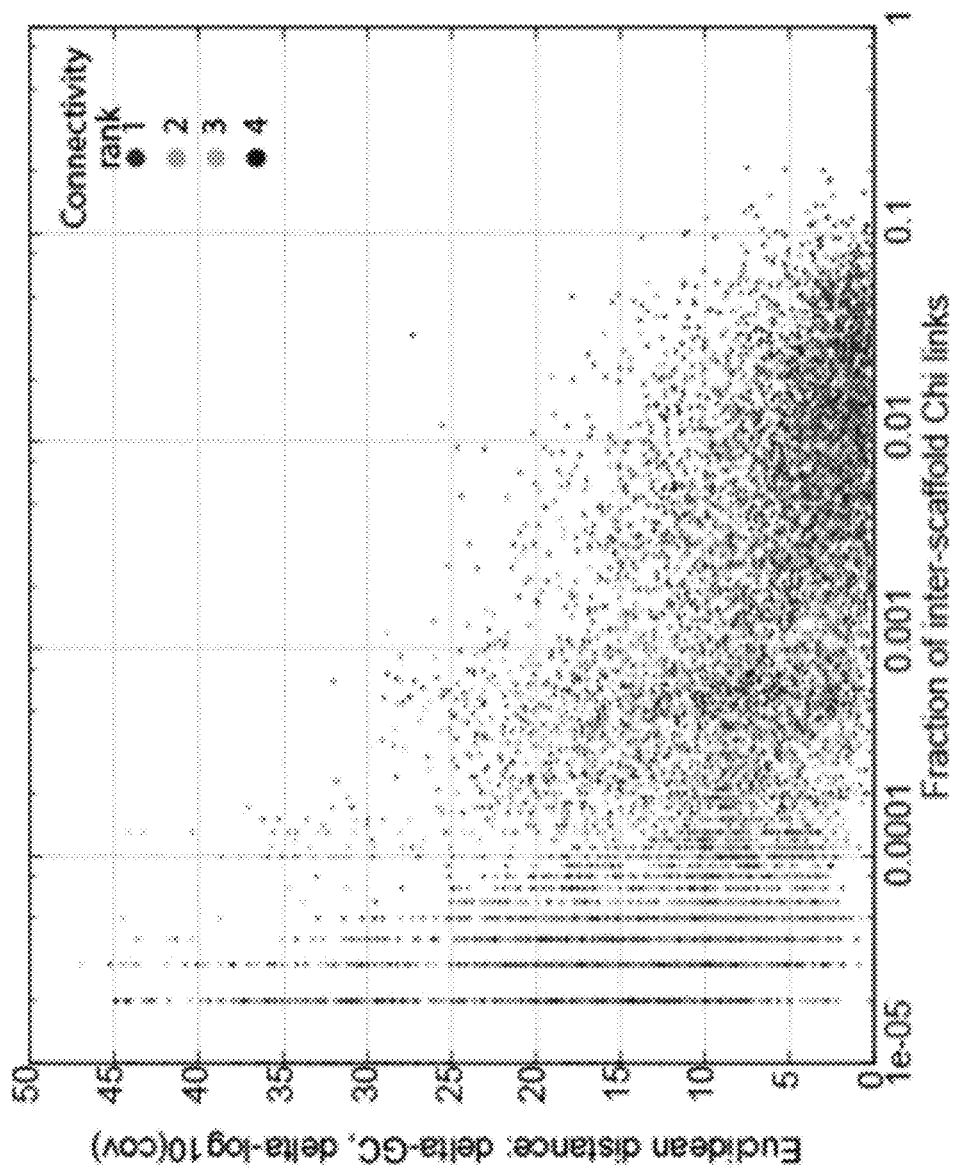
FIG. 26B depicts a graph of in vitro chromatin assembly connectivity for each scaffold on as a fraction of all links to its $1^{st}$-$4^{th}$ most connected scaffold, and the Euclidean distance in GC+fold coverage space between scaffold pairs.

Further investigation was performed into whether Chicago data could provide independent experimental corroboration of these hypotheses. FIG. 26A and FIG. 26B show that shotgun scaffolds that are highly connected by Chicago read pairs are far more likely to be similar in GC content and depth of coverage. FIG. 26A shows coverage depth (y-axis) and GC content (color scale) for all scaffolds in the spike-in experiment; streaks of scaffolds at similar coverage and GC content that are likely from the same OTU. FIG. 26B shows the Chicago connectivity for each scaffold on the x-axis as a fraction of all Chicago links to its $1^{st}$-$4^{th}$ most connected scaffold, and the y-axis shows the Euclidean distance in GC+fold coverage space between scaffold pairs; scaffold pairs that are highly connected with Chicago linkages tend to be similar in GC content and fold coverage. Comparison with the known genomes of microbial isolates further supports that these are joins that are supported by Chicago read pairs but are not made by the current HiRise algorithm. Multiple methods can be employed in correcting for this. First, the internal weights given by HiRise to these unmade joins can be analyzed, and improved heuristics can be employed, guided by either the ground truth of spike-ins or external support from known genomes. Second, heuristics can be employed that explicitly take into account GC content and depth.

GC content and depth are ways to partition scaffolds into hypothesized linkage groups. More elaborate methods have been developed since the original Tyson report, and there are multiple approaches to this problem based on different statistical features of scaffolds features (e.g., tetramer frequencies). Full linkage information can also be extracted from Chicago data.

Figure 27:
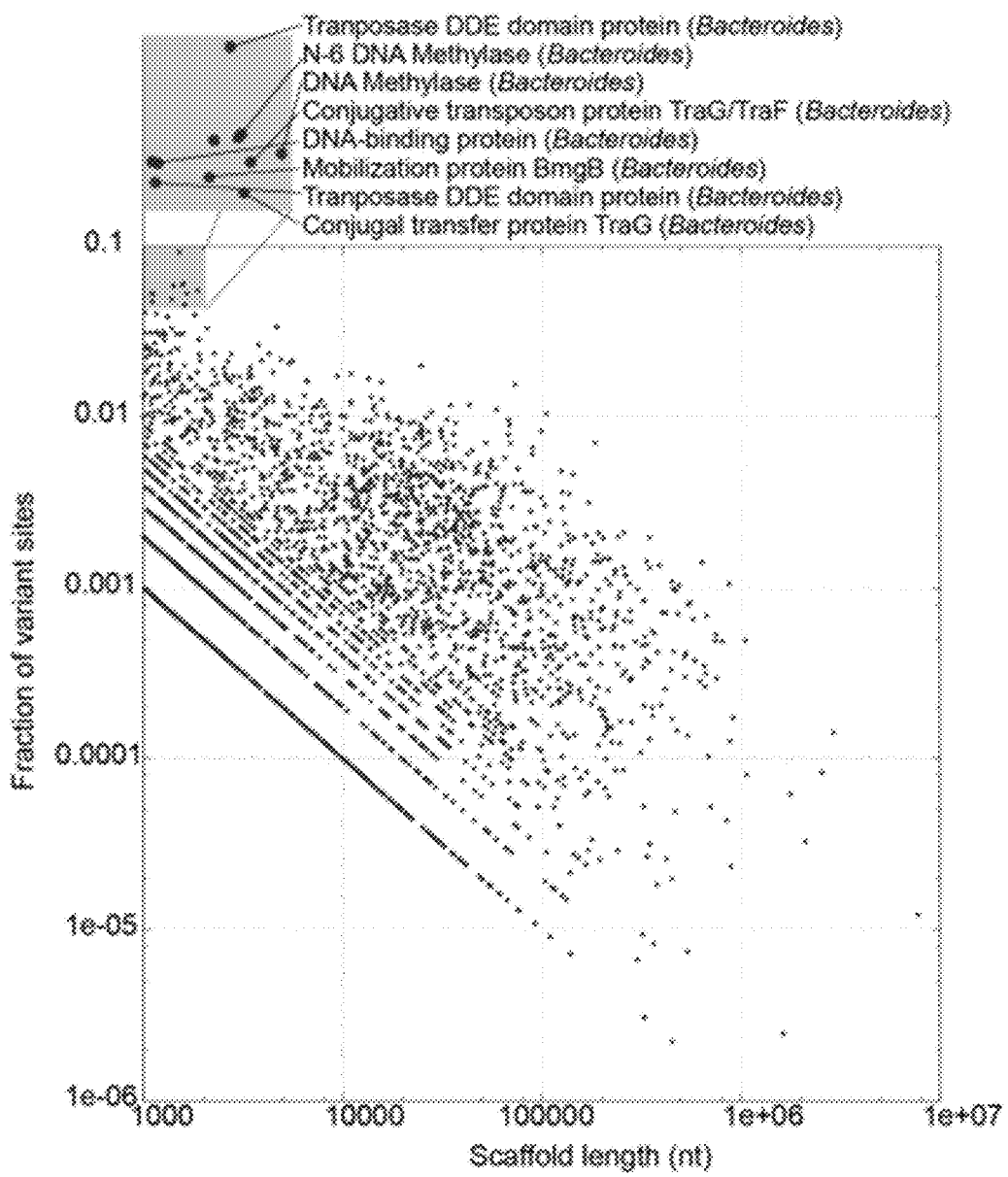
FIG. 27 depicts a graph of the effect of strain variation on scaffolding performance.

In order to achieve the goal of separately assembling strains, software modules can be employed that implement the following iterative approach:

(1) map all reads back to the initial Meraculous/HiRise assembly. BWA-MEM is a general purpose aligner that can easily align sequences that are up to 3-4% divergent, as expected for strain variation;

(2) identify variable positions in these alignments and "phase" them to extract haplotypes. Existing methods, including GATK and HapCut can be adapted for use with metagenomes, notably anticipating the possibility of more than two haplotypes and unequal frequencies. Identification of haplotypes from shotgun sequence can be limited by read length, since phasing requires reads/read-pairs to map onto multiple variants; and (3) finally, with haplotypes identified in suitably polymorphic regions, Chicago reads matching these haplotypes can be identified, and Chicago pairs can be used to produce strain-specific scaffolding. Strain-aware assembly can dramatically improve assembly quality, since different strains often show structural variability; if multiple such strains are collapsed to one "consensus" species assembly, scaffolding will terminate at structural differences (see FIG. 27). FIG. 27 shows a graph of the effect of strain variation on scaffolding performance; the length of each scaffold is shown versus its fraction of sites that show evidence of strain variation (alternate bases), with the most variant scaffolds identified at top.

While preferred embodiments of the disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

What is claimed is:

1. A method of assaying for nucleic acid species diversity in a heterogeneous sample comprising at least two species, comprising
   a) obtaining a stabilized nucleic acid sample comprising a diverse plurality of nucleic acids from at least two species stabilized such that, for at least a first member of the plurality, a first nucleic acid segment and a second nucleic acid segment are held together independent of their common phosphodiester backbone, wherein said phosphodiester backbone is cleaved between said first nucleic acid segment and said second nucleic acid segment, and for at least a second member of the plurality, a third nucleic acid segment and a fourth nucleic acid segment are held together independent of their common phosphodiester backbone, wherein said phosphodiester backbone is cleaved between said third nucleic acid segment and said fourth nucleic acid segment;
   b) tagging said first nucleic acid segment with a first tag and said second nucleic acid segment with a second tag, such that said first nucleic acid segment and said second nucleic acid segment are identifiable as arising from a common nucleic acid of the diverse plurality of nucleic acids, and tagging said third nucleic acid segment with a third tag and said fourth nucleic acid segment with a fourth tag, such that said third nucleic acid segment and said fourth nucleic acid segment are identifiable as arising from a common nucleic acid of the diverse plurality of nucleic acids;
   c) sequencing at least an identifiable portion of said first nucleic acid segment and said first tag, of said second nucleic acid segment and said second tag, of said third nucleic acid segment and said third tag, and of said fourth nucleic acid segment and said fourth tag;
   d) constructing at least a first sequence scaffold comprising said first nucleic acid segment and said second nucleic acid segment and a second sequence scaffold comprising said third nucleic acid segment and said fourth nucleic acid segment; such that a plurality of segments of said diverse plurality of nucleic acids are assigned to at least one of the first or second sequence scaffold; and
   e) counting a plurality of sequence scaffolds constructed, wherein nucleic acid segments tagged such that they are identifiable as arising from a common nucleic acid of the diverse plurality of nucleic acids are assigned to a common scaffold; and
   wherein the number of scaffolds generated indicates the species diversity in the heterogeneous sample.

2. The method of claim 1, wherein tagging said first nucleic acid segment and said second nucleic acid segment comprises adding a first oligo to the first nucleic acid segment and adding a second oligo to the second segment, said first oligo and said second oligo sharing a common oligo sequence.

3. The method of claim 2, wherein nucleic acid segments having said common oligo sequence are assigned to a common scaffold.

4. The method of claim 3, comprising mapping said identifiable portion of said first nucleic acid segment to a contig dataset, and including any matching contig of said contig dataset into said common scaffold.

5. The method of claim 4, wherein the contig dataset is concurrently generated.

6. The method of claim 4, wherein the contig dataset is obtained from a database.

7. The method of claim 1, wherein tagging said first nucleic acid segment and said second nucleic acid segment comprises ligating said first nucleic acid segment to said second nucleic acid segment, and wherein said first nucleic acid segment and said second nucleic acid segment are assigned to a common scaffold.

8. The method of claim 7, comprising mapping said identifiable portion of said first nucleic acid segment to a contig dataset, and including any matching contig of said contig dataset into said common scaffold.

9. The method of claim 8, wherein the contig dataset is concurrently generated.

10. The method of claim 8, wherein the contig dataset is obtained from a database.

11. The method of claim 1, wherein said phosphodiester backbone is cleaved subsequent to said obtaining said stabilized nucleic acid sample.

12. The method of claim 1, wherein said stabilized nucleic acid sample is contacted to a crosslinking agent.

13. The method of claim 1, wherein said stabilized nucleic acid sample is an FFPE sample.

14. The method of claim 1, comprising contacting said heterogeneous sample to a reverse transcriptase.

15. The method of claim 1, comprising categorizing said common scaffold as corresponding to a sample condition when a plurality of samples correlating to said condition have said common scaffold and if a plurality of samples lacking said condition lack said sample.

16. The method of claim 1, wherein sequence reads from the nucleic acid segments assemble into at least two nucleic acid scaffolds without reference to exogenous sequence information.

17. The method of claim 1, wherein sequence reads from the nucleic acid segments assemble into at least two nucleic acid scaffolds, such that at least 50% of a first genome and at least 50% of a second genome are represented in said at least two nucleic acid scaffolds.

18. The method of claim 1, wherein the method comprises using SPRI beads.

19. The method of claim 1, wherein the stabilized nucleic acid sample comprises no greater than about 5 micrograms of DNA.

20. The method of claim 1, wherein said first tag and said second tag are the same.

21. The method of claim 1, wherein said third tag and said fourth tag are the same.

22. The method of claim 1, wherein said first tag comprises a covalently-linked DNA segment from said second nucleic acid segment and said second tag comprises a covalently-linked DNA segment from said first nucleic acid segment.

23. The method of claim 1, wherein said third tag comprises a covalently-linked DNA segment from said fourth nucleic acid segment and said fourth tag comprises a covalently-linked DNA segment from said third nucleic acid segment.

* * * * *

SEQUENCE LISTING

<160> NUMBER OF SEQ ID NOS: 18

<210> SEQ ID NO 1
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
acactctttc cctacacgac gctcttccga tgt                33

<210> SEQ ID NO 2
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
catcggaaga gcacacgtct gaactccagt ca                 32

<210> SEQ ID NO 3
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
acactctttc cctacacgac gctcttccga cct                33

<210> SEQ ID NO 4
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
ggtcggaaga gcacacgtct gaactccagt ca                 32

<210> SEQ ID NO 5
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
acactctttc cctacacgac gctctaccga tct                33

<210> SEQ ID NO 6
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
gatcggtaga gcacacgtct gaactccagt ca                 32

```
<210> SEQ ID NO 7
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
acactctttc cctacacgac gctattccga tct                               33

<210> SEQ ID NO 8
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
gatcggaata gcacacgtct gaactccagt ca                                32

<210> SEQ ID NO 9
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
acactctttc cctacacgac gctcttcgga tct                               33

<210> SEQ ID NO 10
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
gatccgaaga gcacacgtct gaactccagt ca                                32

<210> SEQ ID NO 11
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
acactctttc cctacacgac cctcttccga tct                               33

<210> SEQ ID NO 12
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
gatcggaaga ggacacgtct gaactccagt ca                                32
```

```
<210> SEQ ID NO 13
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
acactctttc cctacacgac gcacttccga tct                                 33

<210> SEQ ID NO 14
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
gatcggaagt gcacacgtct gaactccagt ca                                  32

<210> SEQ ID NO 15
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
acactctttc cctacacgac gctcttccga tct                                 33

<210> SEQ ID NO 16
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
gatcggaaga gcacacgtct gaactccagt ca                                  32

<210> SEQ ID NO 17
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
aagctagctt                                                           10

<210> SEQ ID NO 18
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: a, c, t, g, unknown or other
<220> FEATURE:
<221> NAME/KEY: modified_base
```

```
<222> LOCATION: (8)..(10)
<223> OTHER INFORMATION: a, c, t, g, unknown or other

<400> SEQUENCE: 18 nnngatcnnn                                                          10
```